(12) United States Patent
Plaschkes et al.

(10) Patent No.: US 11,872,375 B2
(45) Date of Patent: Jan. 16, 2024

(54) ELECTRONIC AUTO-INJECTION DEVICE

(71) Applicant: E3D AGRICULTURAL COOPERATIVE ASSOCIATION LTD., Merom Hagalil (IL)

(72) Inventors: Ran Plaschkes, Moshav BenAmi (IL); Ziv Naftalovitz, West Galilee (IL); Roman Plut, Merom Hagalil (IL); Amotz Porat, DN Oshrat (IL); Michael Segev, Lower Galilee (IL); Menachem Zucker, Haifa (IL); Lior Raday, MP Hof Ashkelon (IL); David Daily, Herzliya (IL)

(73) Assignee: E3D AGRICULTURAL COOPERATIVE ASSOCIATION LTD., Merom Hagalil (IL)

( * ) Notice: Subject to any disclaimer, the term of this patent is extended or adjusted under 35 U.S.C. 154(b) by 1127 days.

(21) Appl. No.: 14/423,834

(22) PCT Filed: Sep. 3, 2013

(86) PCT No.: PCT/IL2013/050752
§ 371 (c)(1),
(2) Date: Feb. 25, 2015

(87) PCT Pub. No.: WO2014/037946
PCT Pub. Date: Mar. 13, 2014

(65) Prior Publication Data
US 2015/0202367 A1  Jul. 23, 2015

Related U.S. Application Data

(60) Provisional application No. 61/697,216, filed on Sep. 5, 2012.

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/1452* (2013.01); *A61M 5/20* (2013.01);
(Continued)

(58) Field of Classification Search
CPC .......... A61M 5/00; A61M 5/178; A61M 5/20; A61M 5/24; A61M 5/28; A61M 5/30;
(Continued)

(56) References Cited

U.S. PATENT DOCUMENTS 3,702,608 A * 11/1972 Tibbs ................. A61M 5/2033
604/136
3,880,163 A *  4/1975 Ritterskamp ....... A61M 5/2033
604/136
(Continued)

FOREIGN PATENT DOCUMENTS

EP        855922      4/1997
EP       1087808     12/1999
(Continued)

*Primary Examiner* — Scott J Medway
(74) *Attorney, Agent, or Firm* — Sughrue Mion, PLLC

(57) ABSTRACT

An electronic automatic injection device including a housing configured to receive an injection module containing a material to be injected, an electric motor having a rotary drive output, at least one forward driving spring and a multifunctional electric motor driven drive assembly responsive to the rotary drive output of the electric motor and being operative in a first mode of operation, when the injection module includes a prefilled syringe, to enable the at least one forward driving spring to displace the prefilled syringe in a forward direction and in a second mode of operation, when the injection module includes a needleless cartridge, to eject the injectable liquid from the prefilled syringe through a needle.

18 Claims, 147 Drawing Sheets

(51) Int. Cl.
*A61M 5/46* (2006.01)
*A61M 5/145* (2006.01)
*A61M 5/32* (2006.01)
*A61M 5/50* (2006.01)
*A61M 5/315* (2006.01)
*A61M 5/31* (2006.01)
*A61M 5/142* (2006.01)

(52) U.S. Cl.
CPC ............ *A61M 5/24* (2013.01); *A61M 5/3202* (2013.01); *A61M 5/46* (2013.01); *A61M 5/5086* (2013.01); *A61M 5/3129* (2013.01); *A61M 5/3146* (2013.01); *A61M 5/31511* (2013.01); *A61M 5/31541* (2013.01); *A61M 5/31561* (2013.01); *A61M 5/3204* (2013.01); *A61M 5/326* (2013.01); *A61M 2005/14208* (2013.01); *A61M 2005/206* (2013.01); *A61M 2005/2073* (2013.01); *A61M 2005/2407* (2013.01); *A61M 2005/2481* (2013.01); *A61M 2005/2485* (2013.01); *A61M 2005/2492* (2013.01); *A61M 2005/314* (2013.01); *A61M 2005/3125* (2013.01); *A61M 2005/3126* (2013.01); *A61M 2005/3142* (2013.01); *A61M 2005/3152* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/6018* (2013.01)

(58) Field of Classification Search
CPC .......... A61M 5/31; A61M 5/315; A61M 5/32; A61M 2005/3247; A61M 5/3245; A61M 5/3271; A61M 5/3158; A61M 2205/581; A61M 2205/582; A61M 5/31555; A61M 5/3157; A61M 5/326; A61M 5/31585; A61M 2005/206; A61M 5/2033
See application file for complete search history.

(56) References Cited

U.S. PATENT DOCUMENTS

| | | | |
|---|---|---|---|
| 4,333,459 A * | 6/1982 | Becker | A61M 5/20 604/117 |
| 5,026,343 A * | 6/1991 | Holzer | A61M 5/30 604/72 |
| 5,505,697 A | 4/1996 | Mckinnon, Jr. et al. | |
| 5,569,190 A * | 10/1996 | D'Antonio | A61D 7/00 604/71 |
| 5,582,598 A * | 12/1996 | Chanoch | A61M 5/31551 222/309 |
| 6,056,716 A * | 5/2000 | D'Antonio | A61M 5/30 604/134 |
| 6,146,109 A | 11/2000 | Davis et al. | |
| 6,171,276 B1 | 1/2001 | Lippe et al. | |
| 6,277,098 B1 | 8/2001 | Klitmose et al. | |
| 6,362,591 B1 | 3/2002 | Moberg | |
| 6,482,185 B1 | 11/2002 | Hartmann | |
| 6,547,755 B1 | 4/2003 | Lippe et al. | |
| 6,555,986 B2 | 4/2003 | Moberg | |
| 6,585,698 B1 | 7/2003 | Packman et al. | |
| 6,589,210 B1 * | 7/2003 | Rolfe | A61M 5/2033 604/136 |
| 6,595,962 B1 * | 7/2003 | Perthu | A61M 5/3287 604/157 |
| 6,599,272 B1 * | 7/2003 | Hjertman | A61M 5/315 604/209 |
| 6,685,678 B2 | 2/2004 | Evans et al. | |
| 6,743,202 B2 | 6/2004 | Hirschman et al. | |
| 6,854,620 B2 | 2/2005 | Ramey | |
| 6,929,619 B2 | 8/2005 | Fago et al. | |
| 6,942,646 B2 | 9/2005 | Langley et al. | |
| 6,997,906 B2 | 2/2006 | Langley et al. | |
| 7,029,459 B2 | 4/2006 | Reilly | |
| 7,052,484 B2 | 5/2006 | Veasey et al. | |
| 7,074,211 B1 | 7/2006 | Heiniger et al. | |
| 7,194,749 B2 | 3/2007 | Hatazawa | |
| 7,322,955 B2 | 1/2008 | Azizi et al. | |
| 7,397,730 B2 | 7/2008 | Skyggebjerg et al. | |
| 7,416,540 B2 | 8/2008 | Edwards et al. | |
| 7,462,166 B2 | 12/2008 | Cowan et al. | |
| 7,465,290 B2 | 12/2008 | Reilly | |
| 7,597,682 B2 | 10/2009 | Moberg | |
| 7,621,893 B2 | 11/2009 | Moberg et al. | |
| 7,648,482 B2 | 1/2010 | Edwards et al. | |
| 7,648,483 B2 | 1/2010 | Edwards et al. | |
| 7,686,789 B2 | 3/2010 | Nemoto et al. | |
| 7,704,231 B2 | 4/2010 | Pongpairochana et al. | |
| 7,740,612 B2 | 6/2010 | Hochman | |
| 7,749,194 B2 * | 7/2010 | Edwards | A61M 5/2046 604/131 |
| 7,794,429 B2 | 9/2010 | Niehoff | |
| 7,828,776 B2 | 11/2010 | Nemoto et al. | |
| 7,833,196 B2 | 11/2010 | Estes et al. | |
| 7,854,726 B2 | 12/2010 | Fago et al. | |
| 7,859,473 B2 | 12/2010 | Gibson | |
| 7,871,393 B2 | 1/2011 | Monroe et al. | |
| 7,898,416 B2 | 3/2011 | Fago et al. | |
| 7,975,922 B2 | 7/2011 | Fago et al. | |
| 7,993,300 B2 | 8/2011 | Nyholm et al. | |
| 8,035,517 B2 | 10/2011 | Gibson et al. | |
| 8,044,778 B2 | 10/2011 | Monroe | |
| 8,128,603 B2 | 3/2012 | Langley et al. | |
| 8,141,417 B2 | 3/2012 | Gibson et al. | |
| 8,149,111 B2 | 4/2012 | Monroe | |
| 8,177,747 B2 | 5/2012 | Pinedjian | |
| 8,177,749 B2 | 5/2012 | Slate et al. | |
| 8,211,062 B2 | 7/2012 | Estes et al. | |
| 8,226,610 B2 | 7/2012 | Edwards et al. | |
| 8,231,573 B2 | 7/2012 | Edwards et al. | |
| 8,313,466 B2 | 11/2012 | Edwards et al. | |
| 8,333,752 B2 | 12/2012 | Veit et al. | |
| 8,361,026 B2 | 1/2013 | Edwards et al. | |
| 8,366,680 B2 * | 2/2013 | Raab | A61M 5/31555 604/207 |
| 8,376,993 B2 * | 2/2013 | Cox | A61M 5/24 604/110 |
| 8,381,029 B2 | 2/2013 | Koshiyama | |
| 8,500,692 B2 | 8/2013 | Yodfat et al. | |
| 8,544,645 B2 | 10/2013 | Edwards et al. | |
| 8,632,511 B2 | 1/2014 | Dos Santos et al. | |
| 8,641,669 B2 | 2/2014 | Renz et al. | |
| 8,647,296 B2 | 2/2014 | Moberg et al. | |
| 8,663,201 B2 | 3/2014 | Hill et al. | |
| 8,690,827 B2 | 4/2014 | Edwards et al. | |
| 8,715,224 B2 | 5/2014 | Kamen et al. | |
| 8,784,378 B2 | 7/2014 | Weinandy | |
| 8,827,962 B2 | 9/2014 | Giambattista et al. | |
| 8,834,420 B2 | 9/2014 | Estes et al. | |
| 8,858,508 B2 | 10/2014 | Lavi et al. | |
| 8,870,827 B2 | 10/2014 | Young et al. | |
| 8,920,374 B2 | 12/2014 | Bokelman et al. | |
| 8,926,594 B2 | 1/2015 | Edwards et al. | |
| 8,932,254 B2 | 1/2015 | Eaton | |
| 8,936,565 B2 | 1/2015 | Chawla | |
| 8,968,256 B2 * | 3/2015 | Raab | A61M 5/31543 604/211 |
| 9,011,371 B2 | 4/2015 | Moberg et al. | |
| 9,283,325 B2 * | 3/2016 | Karlsson | A61M 5/20 |
| 9,345,841 B2 * | 5/2016 | Plumptre | A61M 5/24 |
| 9,421,334 B2 * | 8/2016 | Quinn | A61M 5/31541 |
| 9,457,154 B2 * | 10/2016 | Moller | A61M 5/20 |
| 2001/0005781 A1 * | 6/2001 | Bergens | A61M 5/2033 604/208 |
| 2003/0114836 A1 * | 6/2003 | Estes | A61M 5/14244 604/890.1 |
| 2003/0120209 A1 * | 6/2003 | Jensen | A61M 5/326 604/110 |
| 2004/0054318 A1 | 3/2004 | Langley et al. | |
| 2004/0054319 A1 | 3/2004 | Langley et al. | |

(56) References Cited

U.S. PATENT DOCUMENTS

| | | | |
|---|---|---|---|
| 2004/0054328 | A1 | 3/2004 | Langley et al. |
| 2005/0020979 | A1* | 1/2005 | Westbye ............ A61M 5/2033 604/151 |
| 2005/0197650 | A1* | 9/2005 | Sugimoto ......... A61M 5/31541 604/890.1 |
| 2005/0254348 | A1 | 11/2005 | Niemiec et al. |
| 2007/0167920 | A1* | 7/2007 | Hommann ........ A61M 5/31583 604/206 |
| 2007/0197974 | A1 | 8/2007 | Gibson |
| 2008/0015512 | A1 | 1/2008 | D' Antonio et al. |
| 2008/0031259 | A1 | 2/2008 | Zampiello |
| 2008/0059133 | A1* | 3/2008 | Edwards ................ G06Q 10/00 703/7 |
| 2008/0125724 | A1 | 5/2008 | Monroe |
| 2009/0076458 | A1 | 3/2009 | Nielsen et al. |
| 2010/0211005 | A1 | 8/2010 | Edwards et al. |
| 2010/0318035 | A1 | 12/2010 | Edwards et al. |
| 2011/0004165 | A1* | 1/2011 | Iio .......................... A61M 5/24 604/197 |
| 2011/0009821 | A1 | 1/2011 | Jespersen et al. |
| 2011/0033832 | A1 | 2/2011 | Baba et al. |
| 2011/0062703 | A1* | 3/2011 | Lopez ................... A61J 1/2062 285/129.1 |
| 2011/0118694 | A1 | 5/2011 | Yodfat et al. |
| 2011/0166521 | A1 | 7/2011 | Marshall et al. |
| 2011/0201998 | A1* | 8/2011 | Pongpairochana ..... A61M 5/20 604/67 |
| 2011/0224614 | A1 | 9/2011 | Moberg et al. |
| 2011/0224616 | A1* | 9/2011 | Slate ................... A61M 5/3134 604/154 |
| 2011/0270214 | A1 | 11/2011 | Jrgensen et al. |
| 2011/0279271 | A1 | 11/2011 | Monroe et al. |
| 2011/0284577 | A1 | 11/2011 | Nemoto et al. |
| 2011/0288481 | A1 | 11/2011 | Mudd et al. |
| 2011/0301534 | A1 | 12/2011 | Renz et al. |
| 2011/0301566 | A1* | 12/2011 | Schaefer ............. A61M 5/1452 604/500 |
| 2012/0022458 | A1 | 1/2012 | Oh et al. |
| 2012/0029349 | A1 | 2/2012 | Bruce et al. |
| 2012/0044070 | A1 | 2/2012 | Putrino |
| 2012/0056019 | A1 | 3/2012 | Renz et al. |
| 2012/0101439 | A9 | 4/2012 | Slate et al. |
| 2012/0101470 | A1 | 4/2012 | Rasmussen et al. |
| 2012/0107783 | A1 | 5/2012 | Julian et al. |
| 2012/0116311 | A1* | 5/2012 | Bruggemann .... A61M 5/14244 604/154 |
| 2012/0179016 | A1 | 7/2012 | Iio et al. |
| 2012/0226226 | A1 | 9/2012 | Edwards et al. |
| 2012/0233834 | A1* | 9/2012 | Szechinski ............. B23P 19/04 29/407.01 |
| 2012/0265142 | A1 | 10/2012 | Slate et al. |
| 2012/0280815 | A1 | 11/2012 | Edwards et al. |
| 2012/0323176 | A1 | 12/2012 | Watanabe et al. |
| 2013/0046246 | A1* | 2/2013 | Cross ................... A61M 5/326 604/189 |
| 2013/0053692 | A1 | 2/2013 | Barron et al. |
| 2013/0067416 | A1 | 3/2013 | Barron et al. |
| 2013/0123685 | A1 | 5/2013 | Jespersen et al. |
| 2013/0138040 | A1 | 5/2013 | Weinandy |
| 2013/0146615 | A1 | 6/2013 | Gaudet |
| 2013/0184649 | A1 | 7/2013 | Edwards et al. |
| 2013/0190692 | A1 | 7/2013 | Edwards et al. |
| 2013/0261563 | A1* | 10/2013 | Zachek ................ A61M 5/326 604/263 |
| 2013/0274655 | A1 | 10/2013 | Jennings et al. |
| 2013/0317324 | A1 | 11/2013 | Yodfat et al. |
| 2014/0012229 | A1* | 1/2014 | Bokelman ............ A61M 5/2033 604/154 |
| 2014/0039404 | A1* | 2/2014 | Young ................ A61M 5/2448 604/192 |
| 2014/0039407 | A1* | 2/2014 | Schoonmaker ..... A61M 5/3202 604/198 |
| 2014/0114258 | A1 | 4/2014 | Day |
| 2014/0142499 | A1 | 5/2014 | Moberg et al. |
| 2014/0148785 | A1 | 5/2014 | Moberg et al. |
| 2014/0155827 | A1 | 6/2014 | Ostrander et al. |
| 2014/0163339 | A1 | 6/2014 | Goldstein et al. |
| 2014/0188048 | A1 | 7/2014 | Edwards et al. |
| 2014/0228763 | A1 | 8/2014 | Kondoh et al. |
| 2014/0243749 | A1 | 8/2014 | Edwards et al. |
| 2014/0257185 | A1 | 9/2014 | Bechmann et al. |
| 2014/0296782 | A1 | 10/2014 | Ulrich et al. |
| 2014/0296824 | A1 | 10/2014 | Edwards et al. |
| 2014/0303560 | A1 | 10/2014 | Yates et al. |
| 2014/0309616 | A1 | 10/2014 | Edwards et al. |
| 2014/0323982 | A1 | 10/2014 | Lumme et al. |
| 2014/0330203 | A1* | 11/2014 | McLoughlin ......... A61M 5/172 604/131 |
| 2014/0336587 | A1 | 11/2014 | McLoughlin et al. |
| 2014/0350470 | A1 | 11/2014 | Gyory et al. |
| 2014/0358072 | A1 | 12/2014 | McLoughlin et al. |
| 2014/0358084 | A1 | 12/2014 | McLoughlin et al. |
| 2014/0358085 | A1 | 12/2014 | McLoughlin et al. |
| 2014/0378911 | A1 | 12/2014 | Dolk et al. |
| 2015/0011944 | A1 | 1/2015 | Young et al. |
| 2015/0011973 | A1 | 1/2015 | Edwards et al. |
| 2015/0025375 | A1 | 1/2015 | Pollard |
| 2015/0025457 | A1 | 1/2015 | Moberg et al. |
| 2015/0250954 | A1* | 9/2015 | Keitzmann ......... A61M 5/3271 604/198 |

FOREIGN PATENT DOCUMENTS

| | | |
|---|---|---|
| EP | 1001821 | 5/2000 |
| EP | 1349591 | 7/2002 |
| EP | 1349592 | 7/2002 |
| EP | 1349593 | 7/2002 |
| EP | 1349594 | 7/2002 |
| EP | 1353713 | 7/2002 |
| EP | 1349595 | 8/2002 |
| EP | 1349596 | 8/2002 |
| EP | 1240913 | 9/2002 |
| EP | 0921828 B1 | 2/2003 |
| EP | 1461099 | 7/2003 |
| EP | 1467785 | 7/2003 |
| EP | 1551480 | 4/2004 |
| EP | 1349591 | 8/2005 |
| EP | 1353713 | 4/2006 |
| EP | 1880330 | 10/2006 |
| EP | WO2007079016 | 7/2007 |
| EP | 2083887 | 5/2008 |
| EP | 2051755 | 2/2009 |
| EP | 2229201 | 7/2009 |
| EP | 2298391 | 3/2011 |
| EP | 2359884 | 8/2011 |
| EP | 2468338 | 6/2012 |
| EP | 2469437 | 6/2012 |
| EP | 2609949 | 7/2013 |
| EP | 2311510 B1 | 5/2014 |
| EP | 1461099 | 8/2014 |
| EP | 2007450 | 12/2014 |
| JP | 2014-012214 A | 1/2014 |
| WO | WO1999065548 | 12/1999 |
| WO | WO2005077441 | 8/2005 |
| WO | WO2005084732 | 9/2005 |
| WO | WO2006045524 | 5/2006 |
| WO | WO2006078400 | 7/2006 |
| WO | WO2007032341 | 3/2007 |
| WO | WO2007062315 | 5/2007 |
| WO | WO2007126851 | 11/2007 |
| WO | WO2008024595 | 2/2008 |
| WO | WO2008064092 | 5/2008 |
| WO | WO2008091838 | 7/2008 |
| WO | WO2009032400 | 3/2009 |
| WO | WO2009081399 | 7/2009 |
| WO | WO2009140251 | 11/2009 |
| WO | WO2009143255 | 11/2009 |
| WO | WO2009144726 | 12/2009 |
| WO | WO2010056712 | 5/2010 |
| WO | WO2010076275 | 7/2010 |
| WO | WO2010117923 | 10/2010 |
| WO | WO2011067187 | 6/2011 |

(56) References Cited

FOREIGN PATENT DOCUMENTS

| | | |
|---|---|---|
| WO | WO2011091246 | 7/2011 |
| WO | WO2011108225 | 9/2011 |
| WO | WO2012066767 | 5/2012 |
| WO | WO2012085031 | 6/2012 |
| WO | WO2012145685 | 10/2012 |
| WO | WO2012160164 | 11/2012 |
| WO | WO2012164389 | 12/2012 |
| WO | WO2012164390 | 12/2012 |
| WO | WO2012164394 | 12/2012 |
| WO | WO2012164402 | 12/2012 |
| WO | WO2012164403 | 12/2012 |
| WO | WO2012164404 | 12/2012 |
| WO | WO2012164406 | 12/2012 |
| WO | WO2013004844 | 1/2013 |
| WO | WO2013034985 | 3/2013 |
| WO | WO2013034986 | 3/2013 |
| WO | WO2013038639 | 3/2013 |
| WO | 2013045617 | 4/2013 |
| WO | WO2013045617 | 4/2013 |
| WO | WO2013070715 | 5/2013 |
| WO | 2013093059 | 6/2013 |
| WO | WO2013079643 | 6/2013 |
| WO | 2013126318 | 8/2013 |
| WO | WO2014008393 | 1/2014 |
| WO | WO2014083343 | 6/2014 |

* cited by examiner

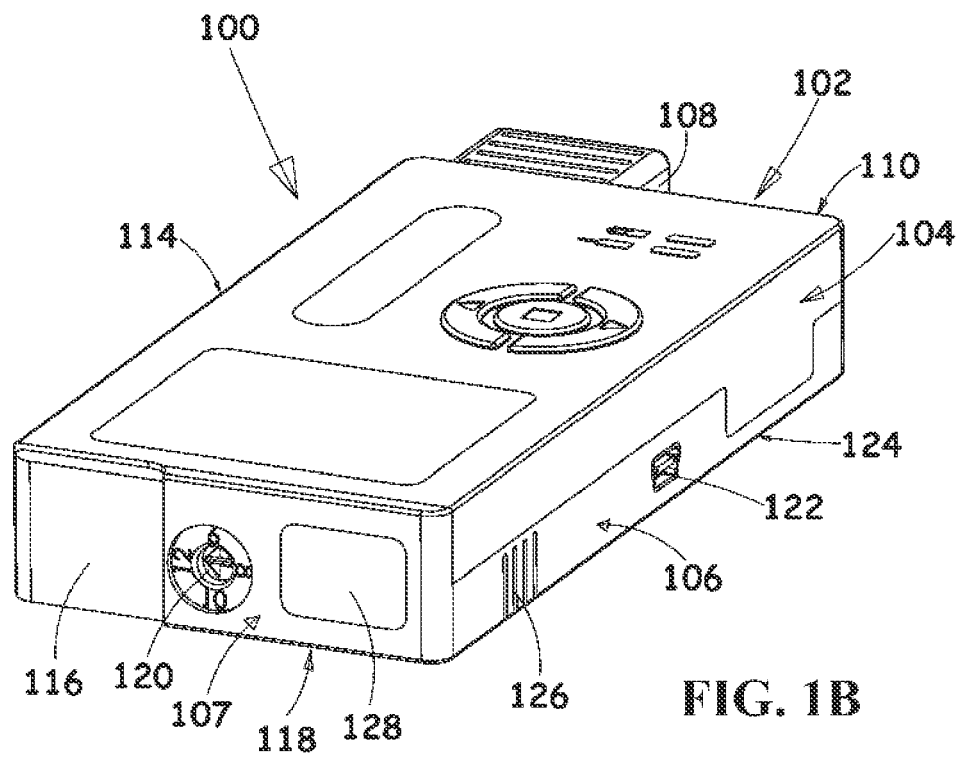
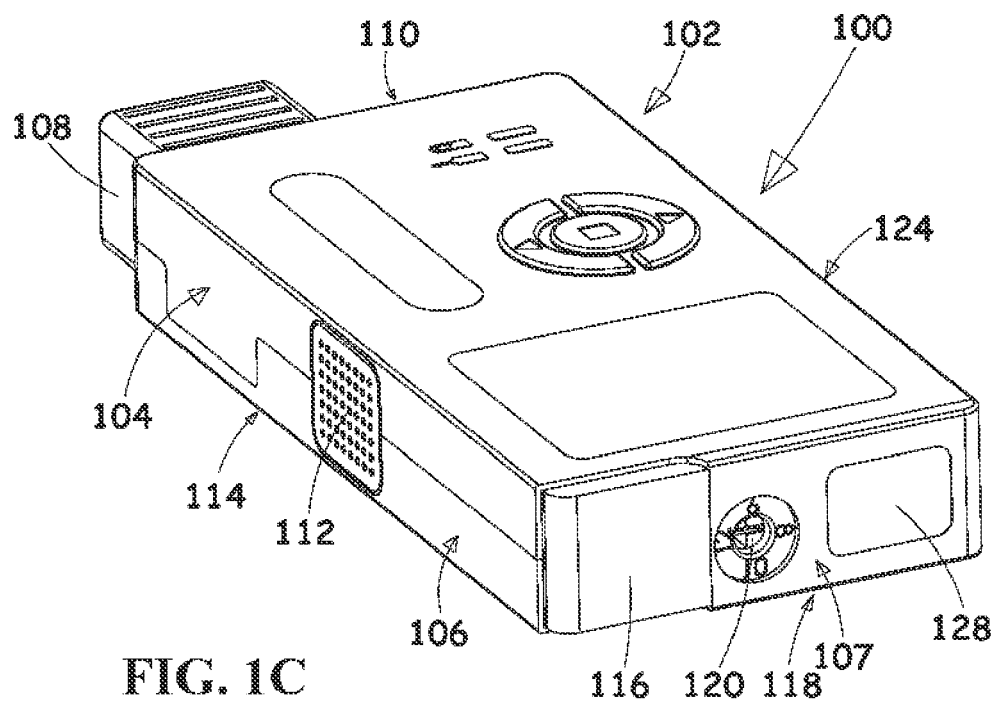

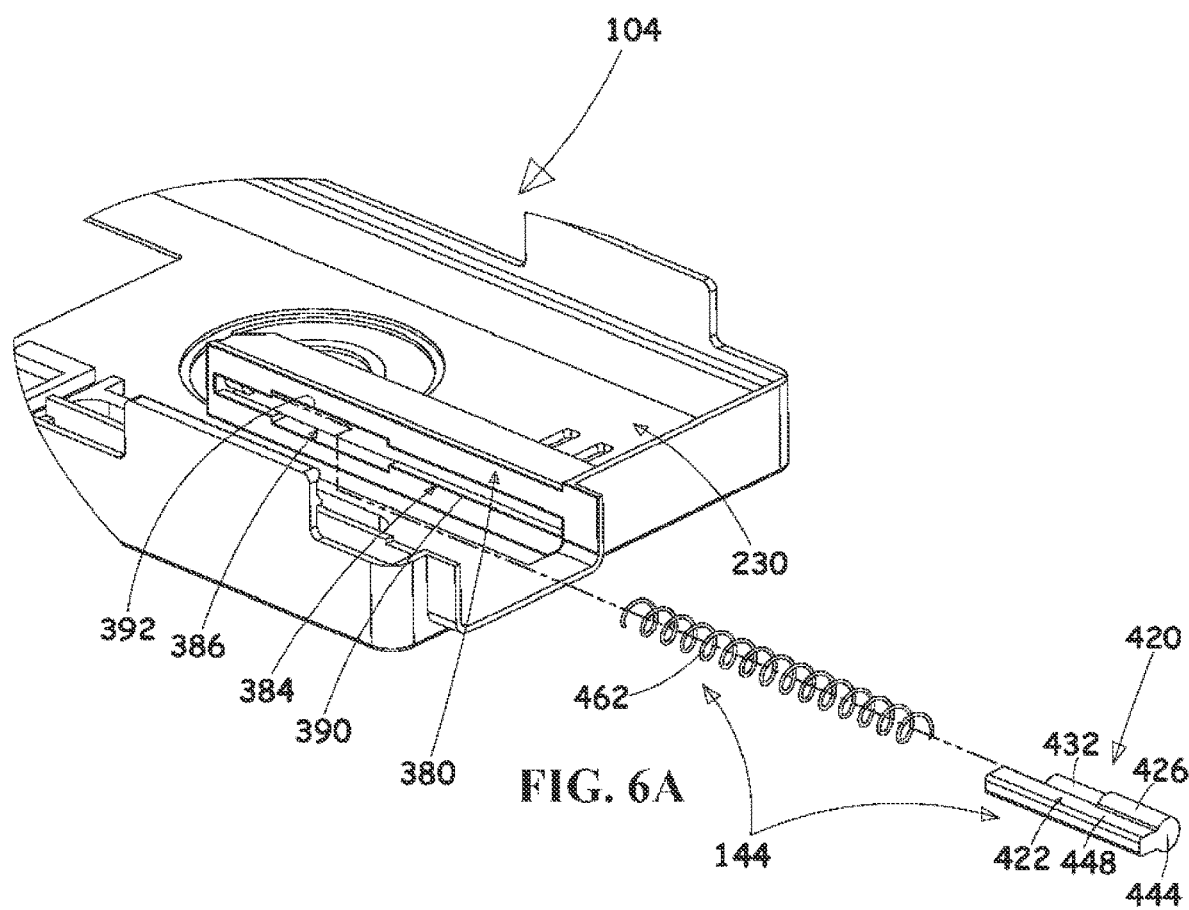

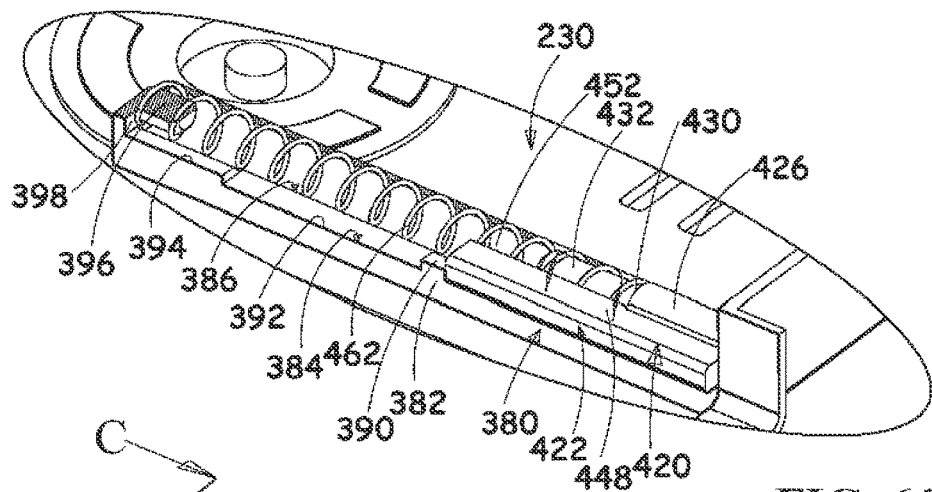
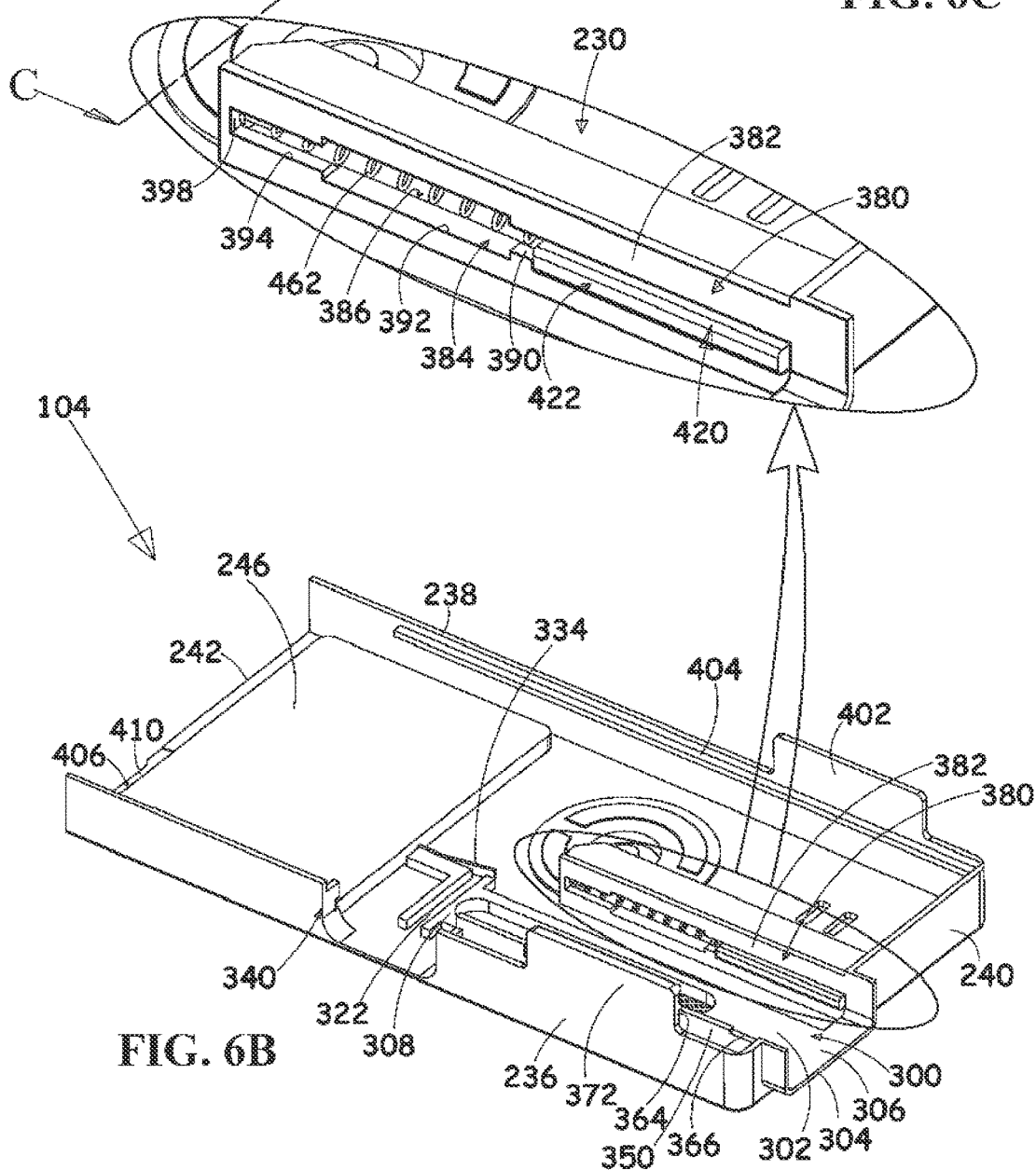
FIG. 6C
FIG. 6B

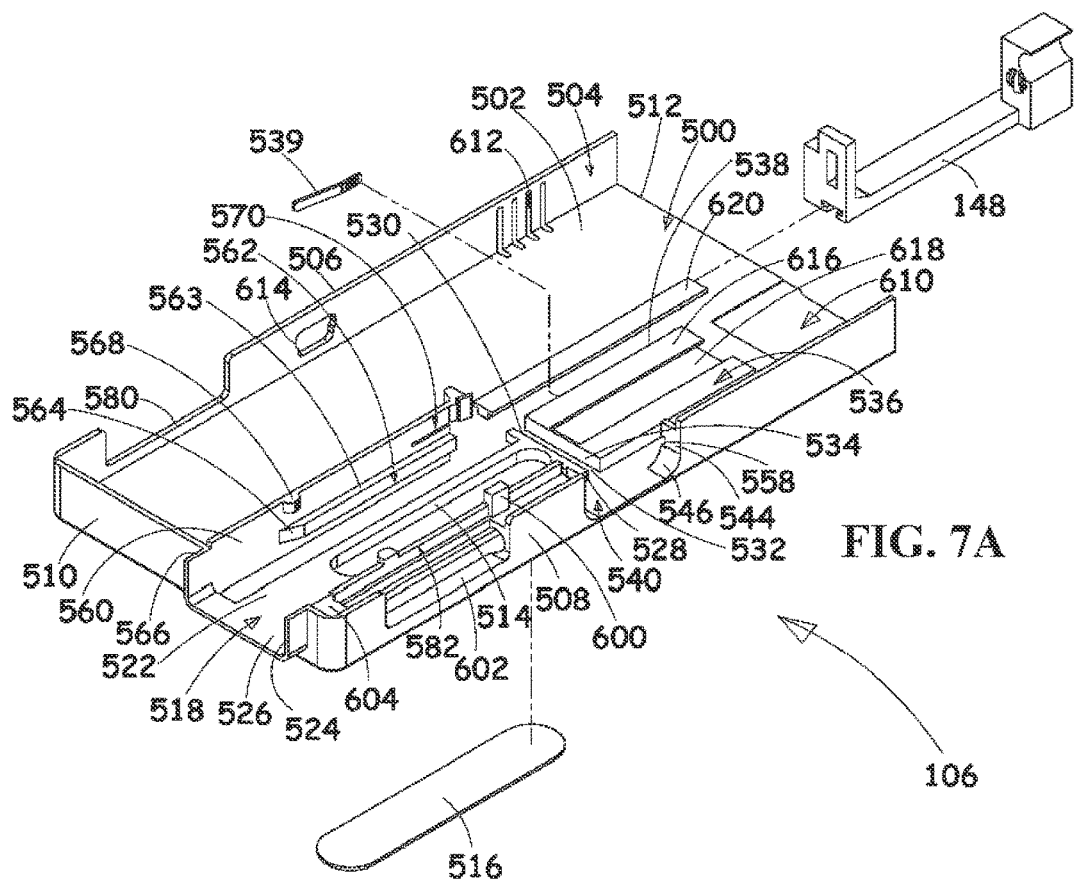
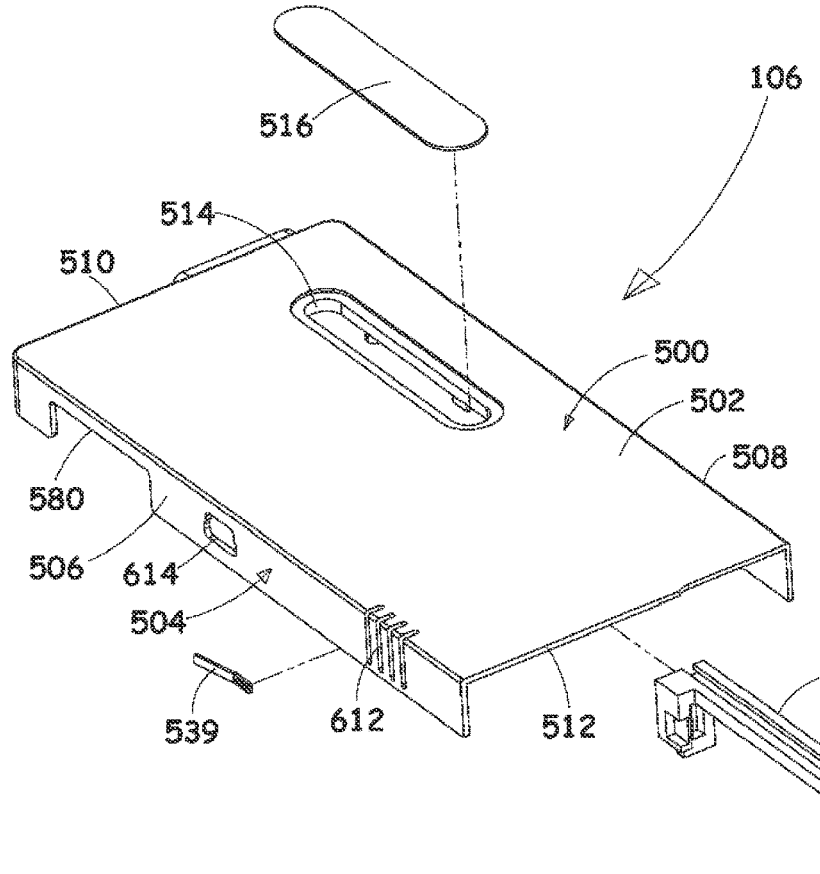

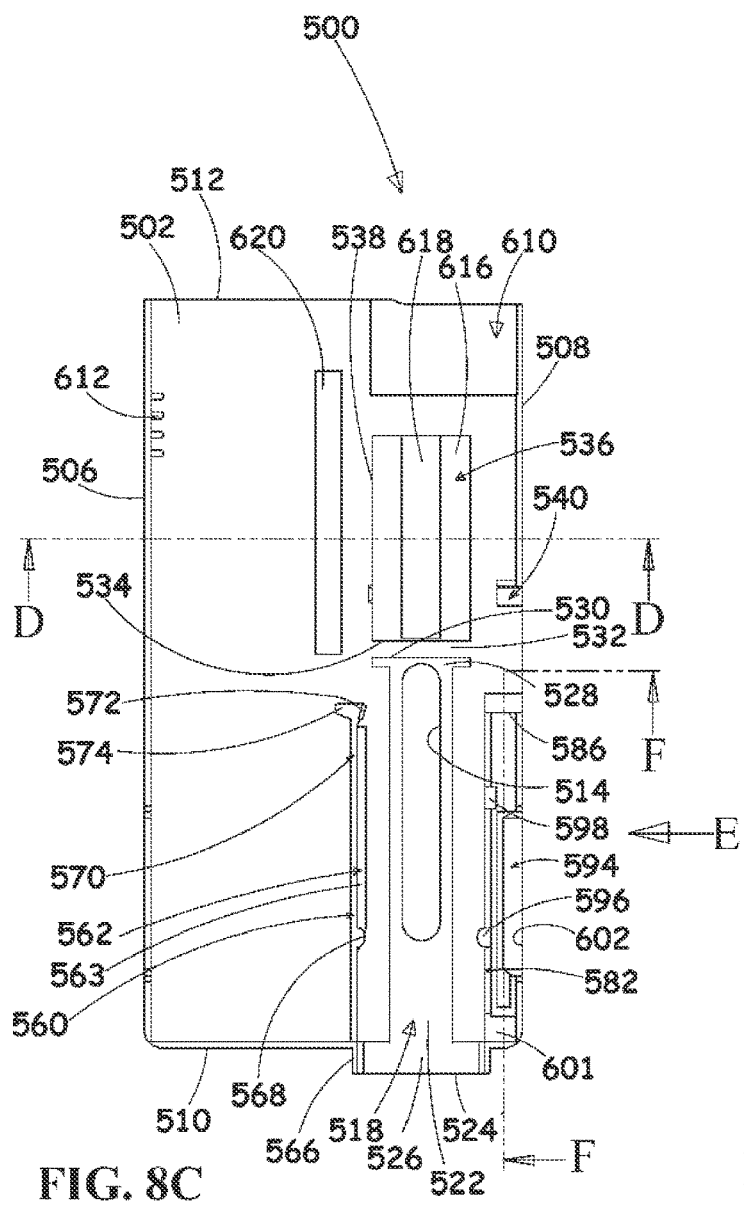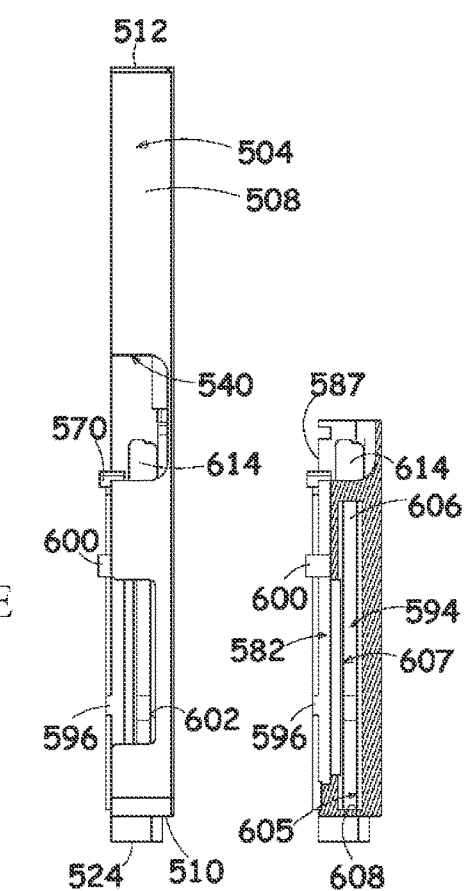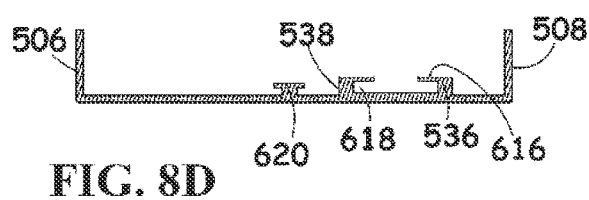

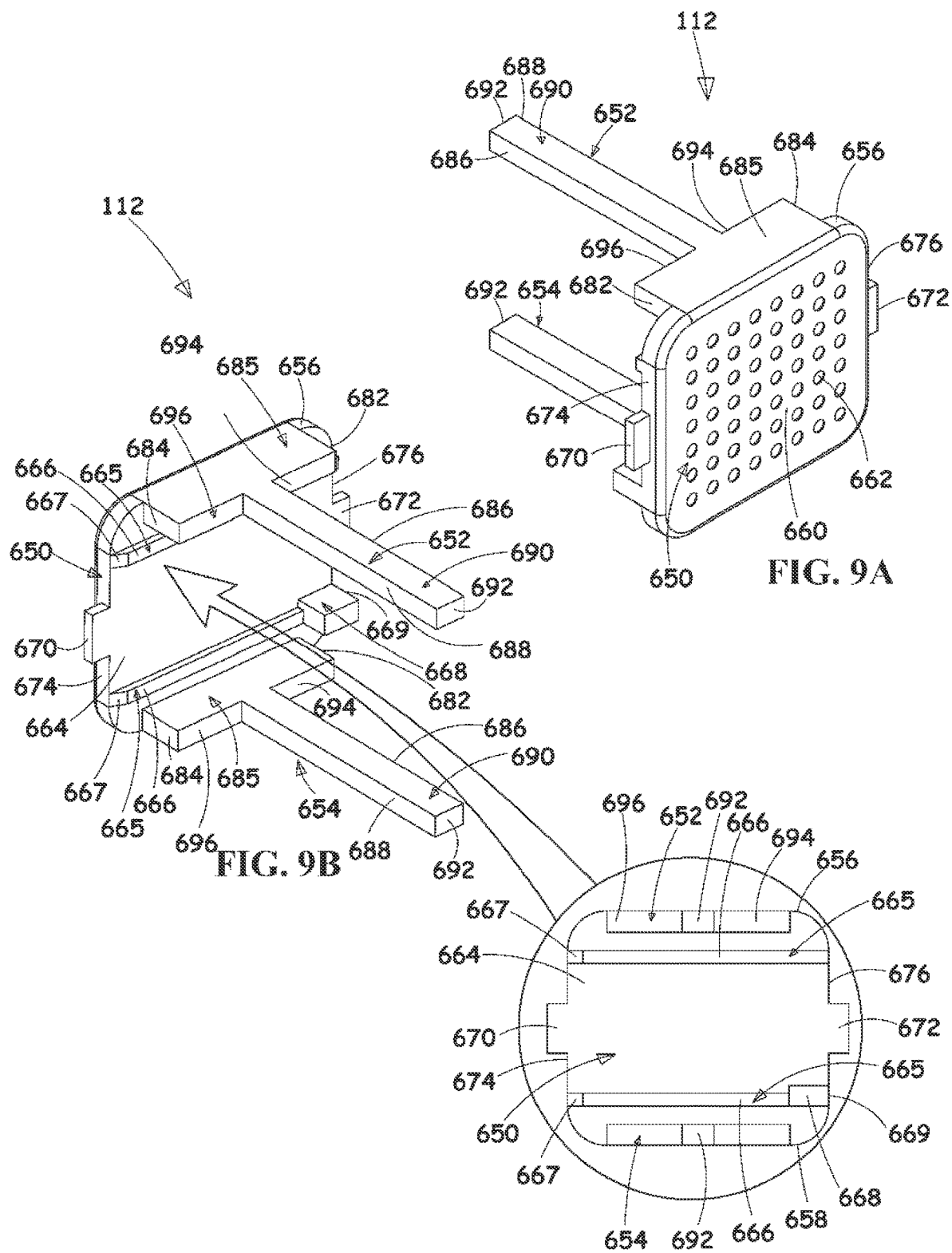

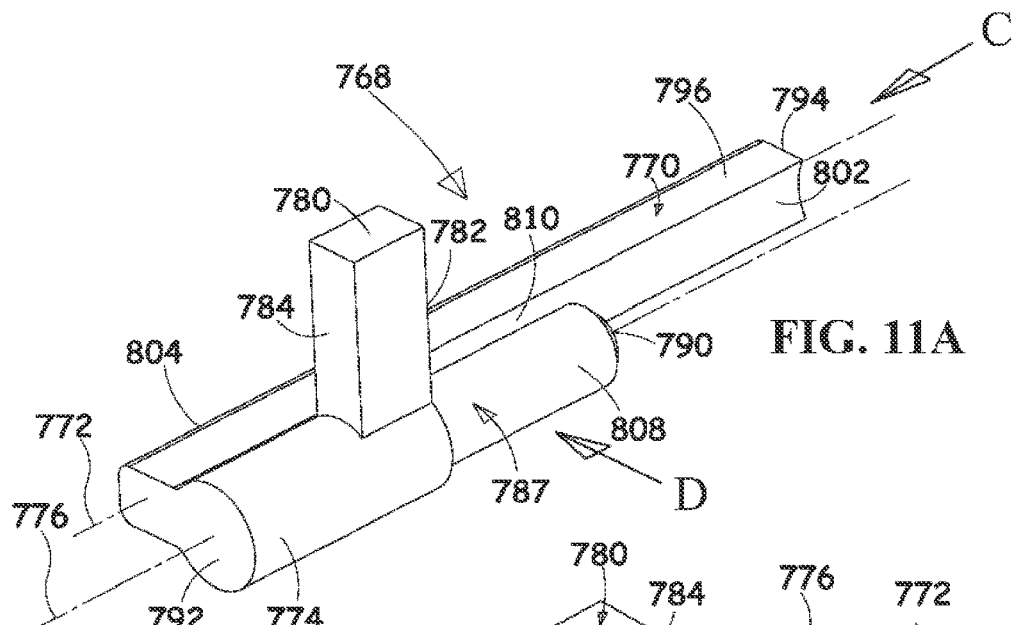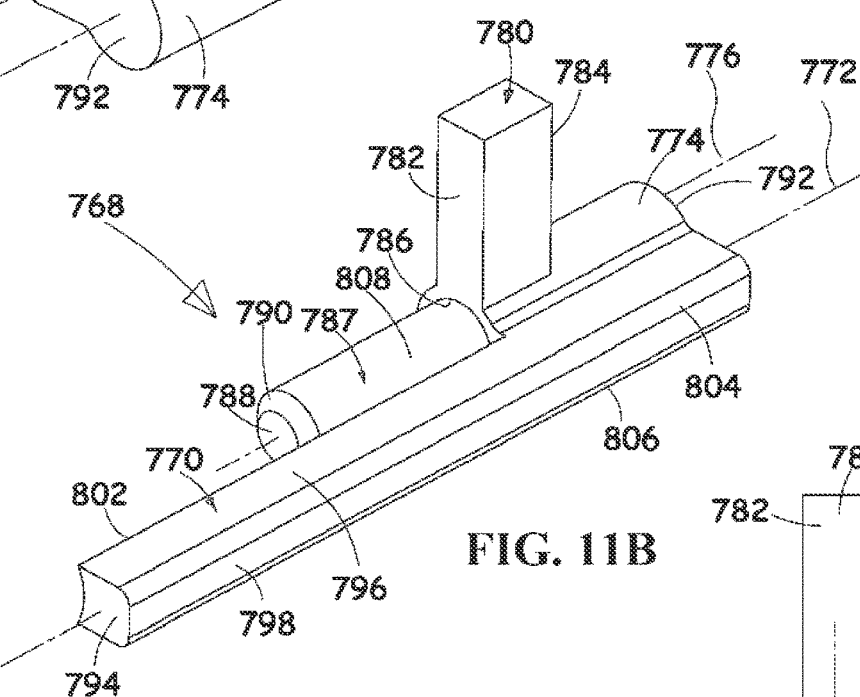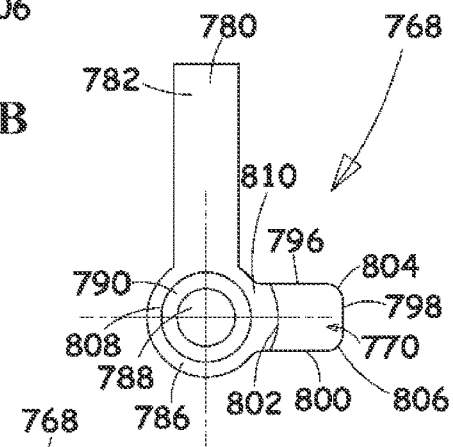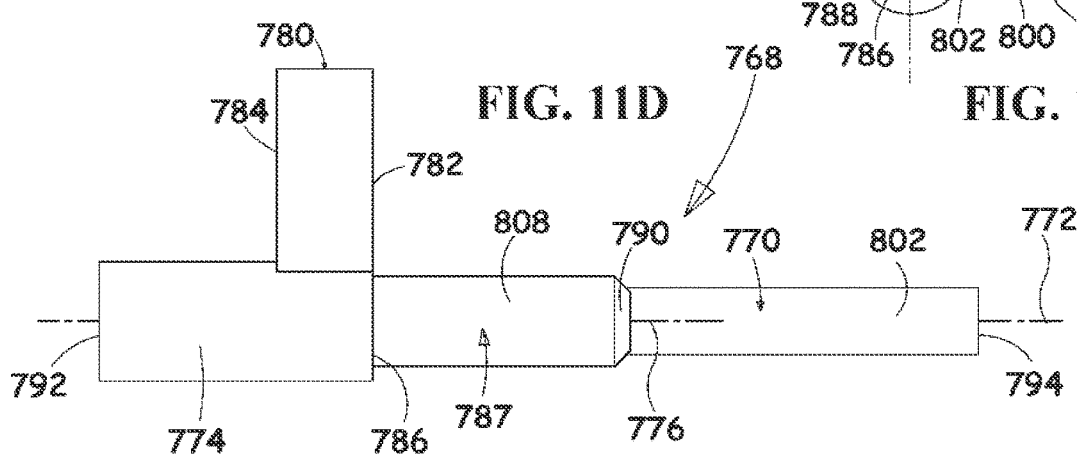

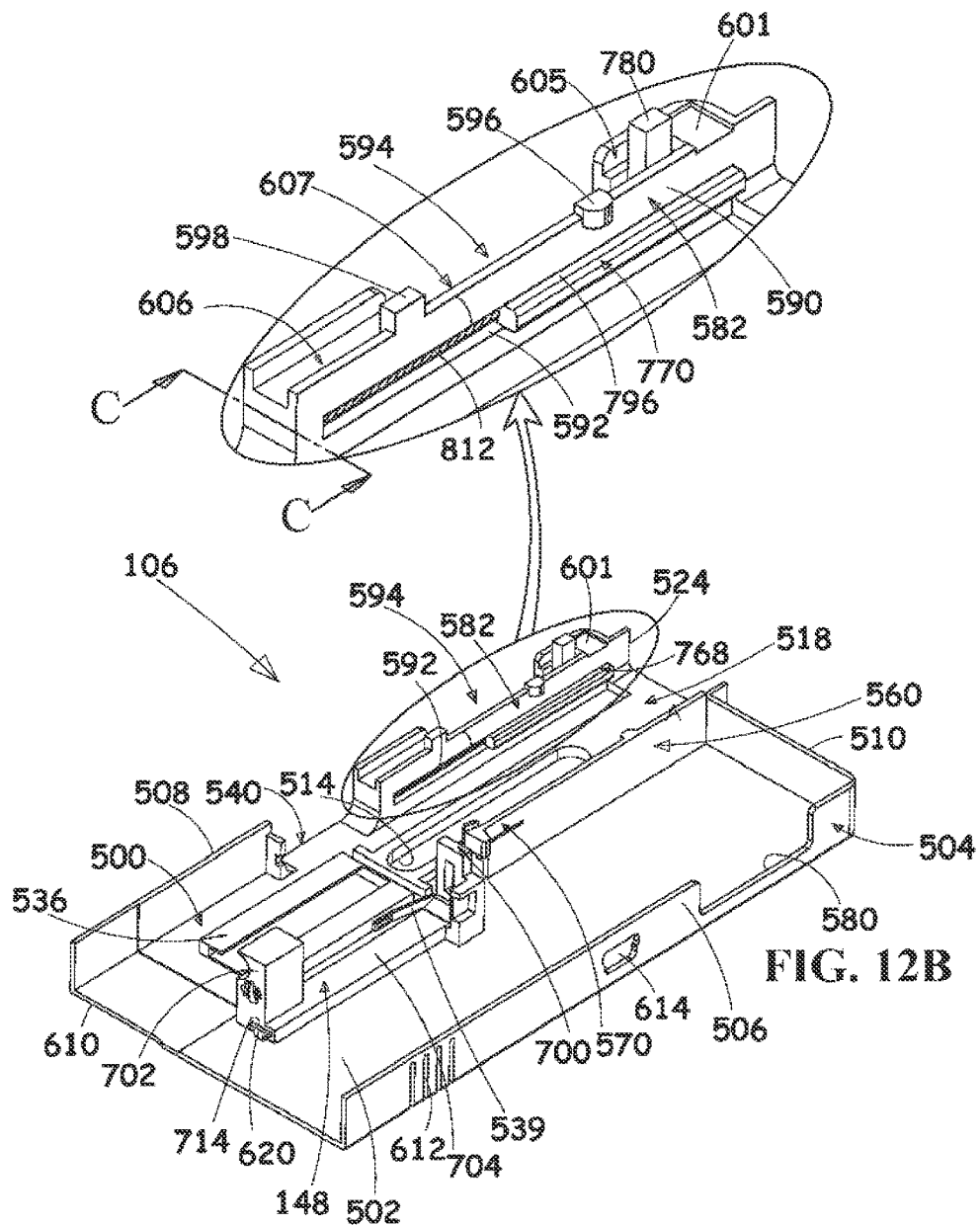
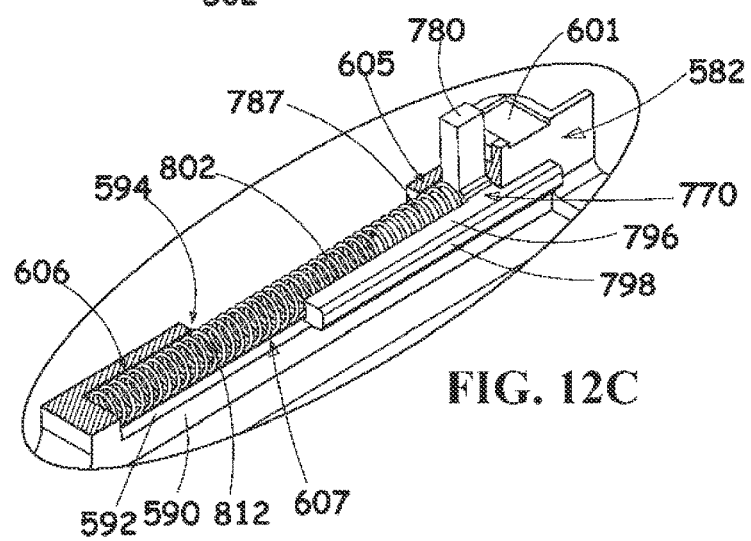
FIG. 12B
FIG. 12C

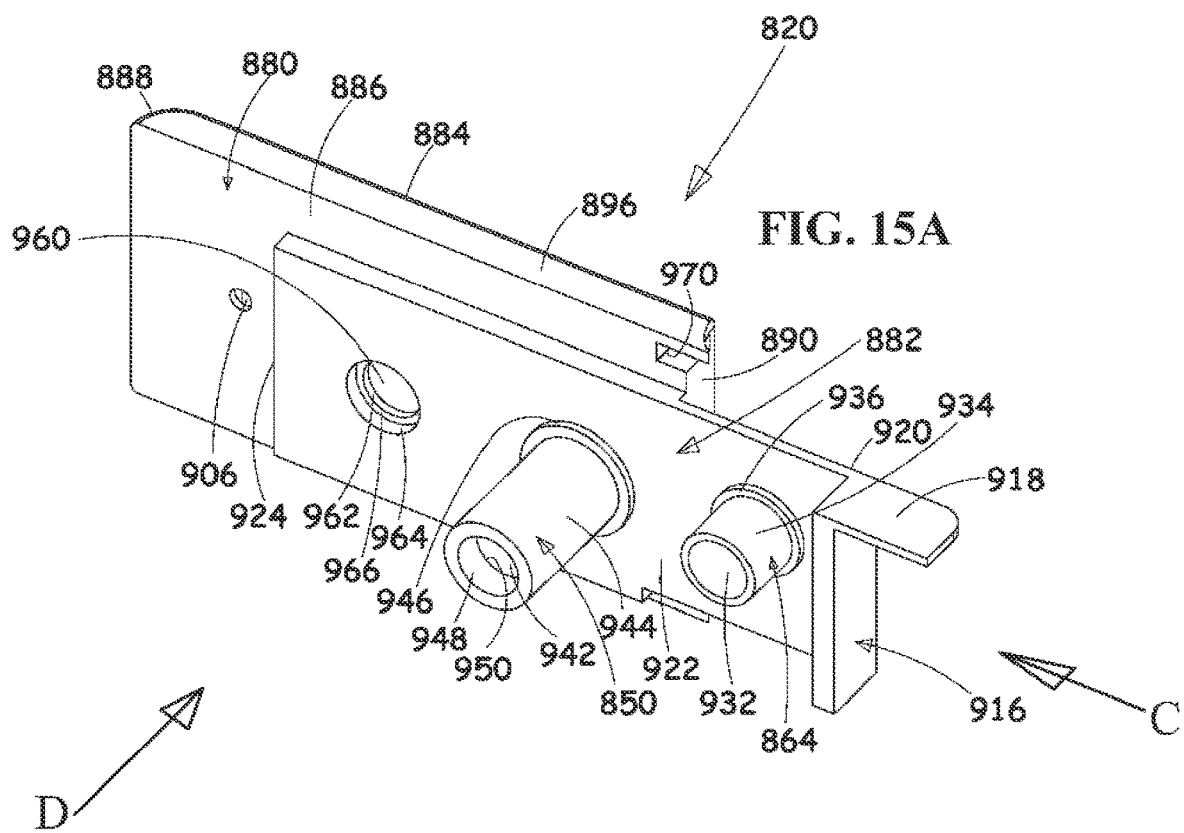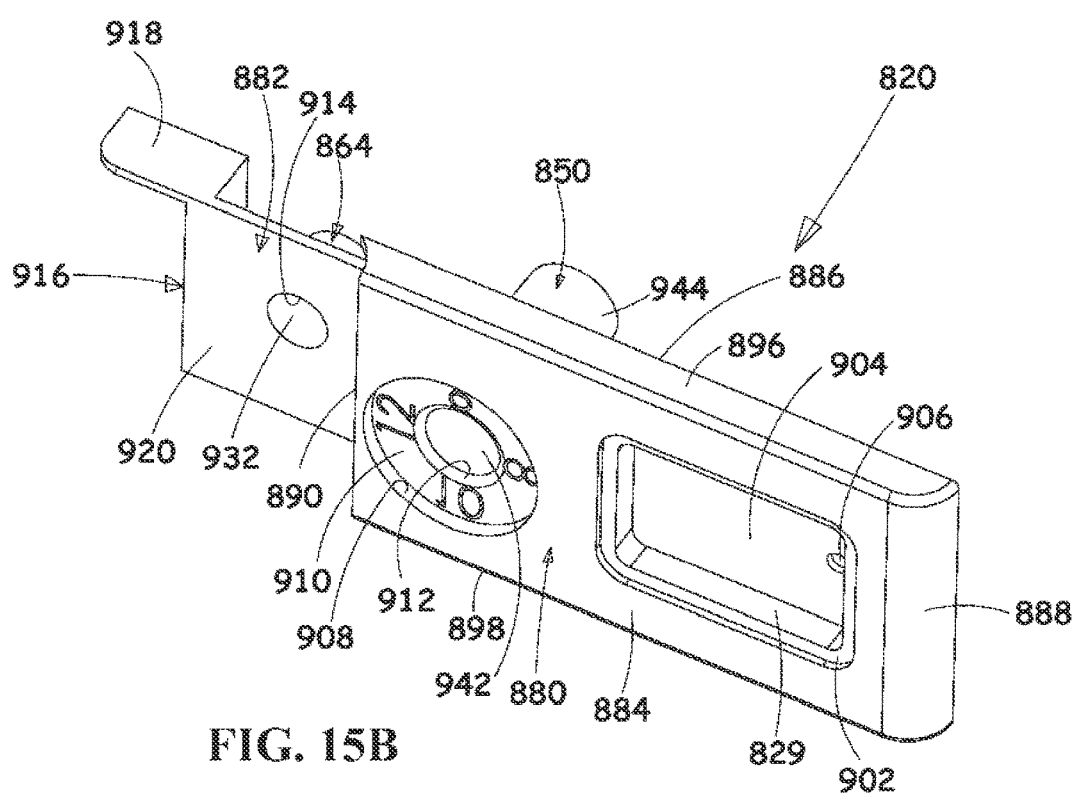

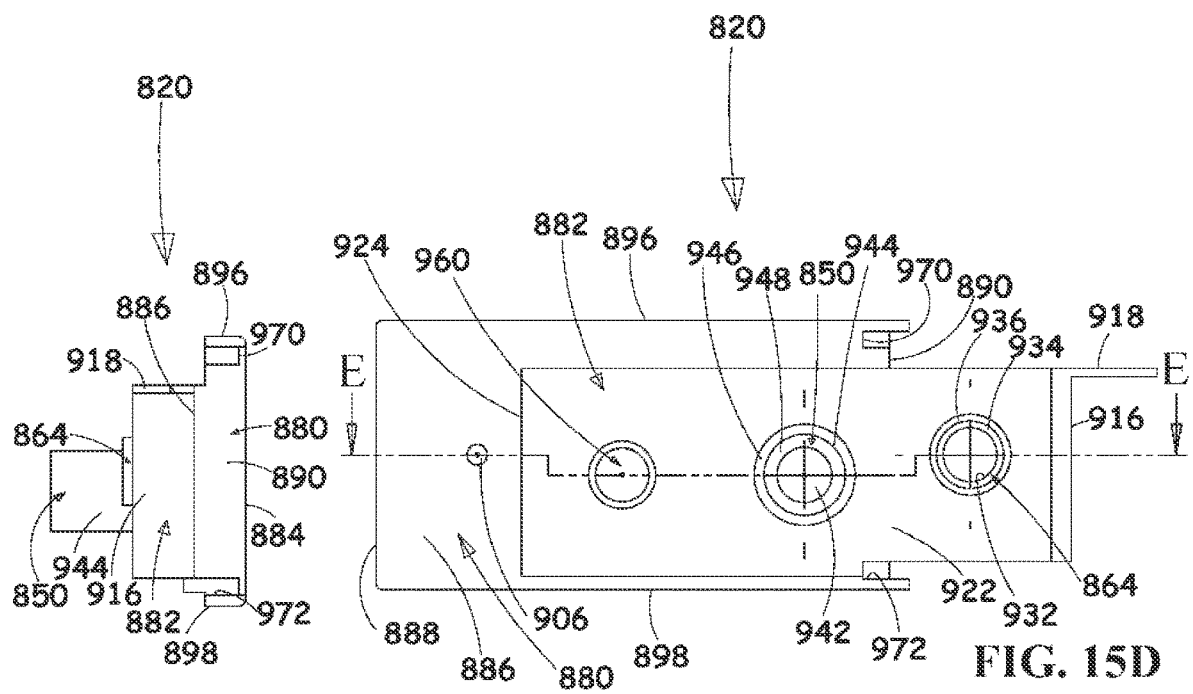
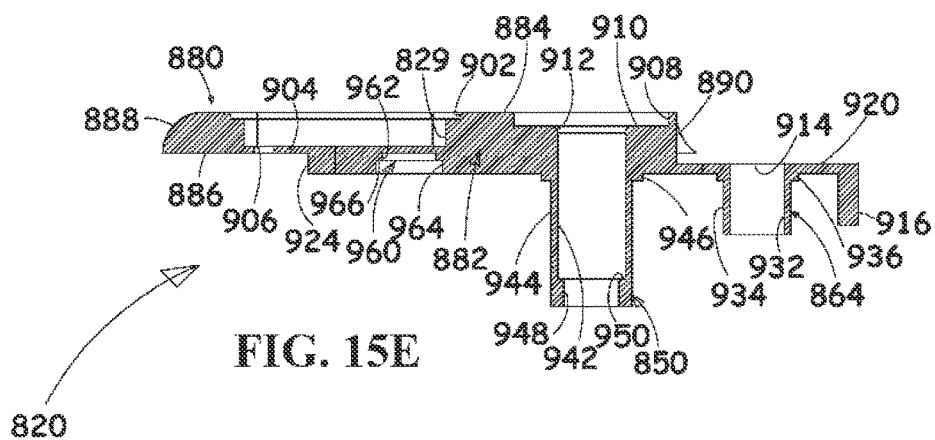

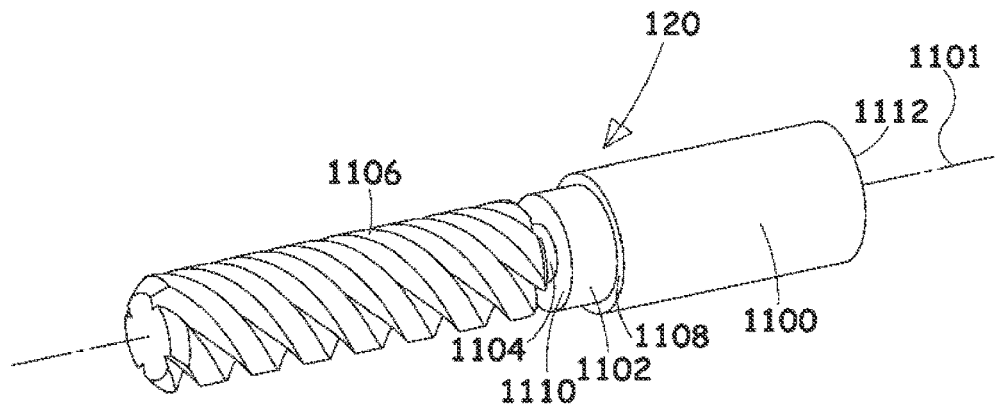
FIG. 18A
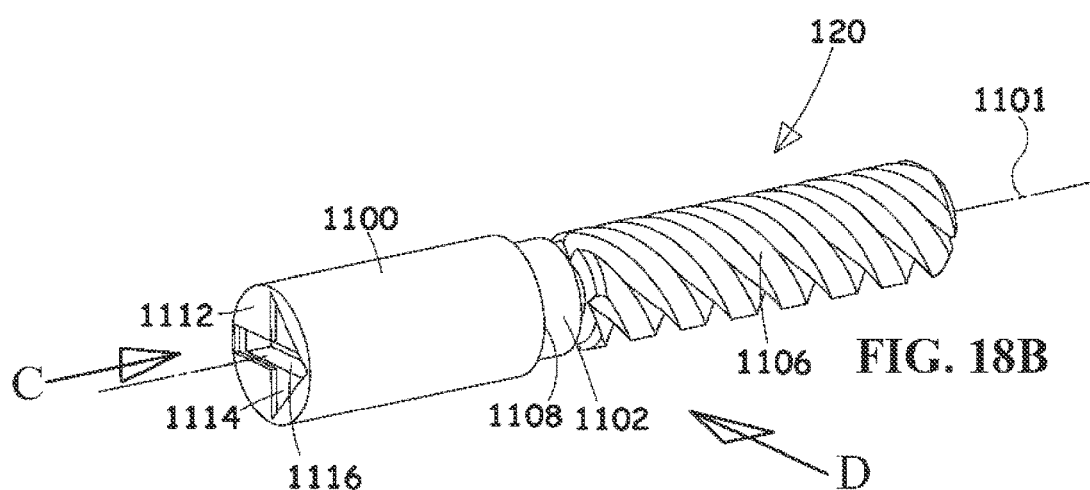
FIG. 18B
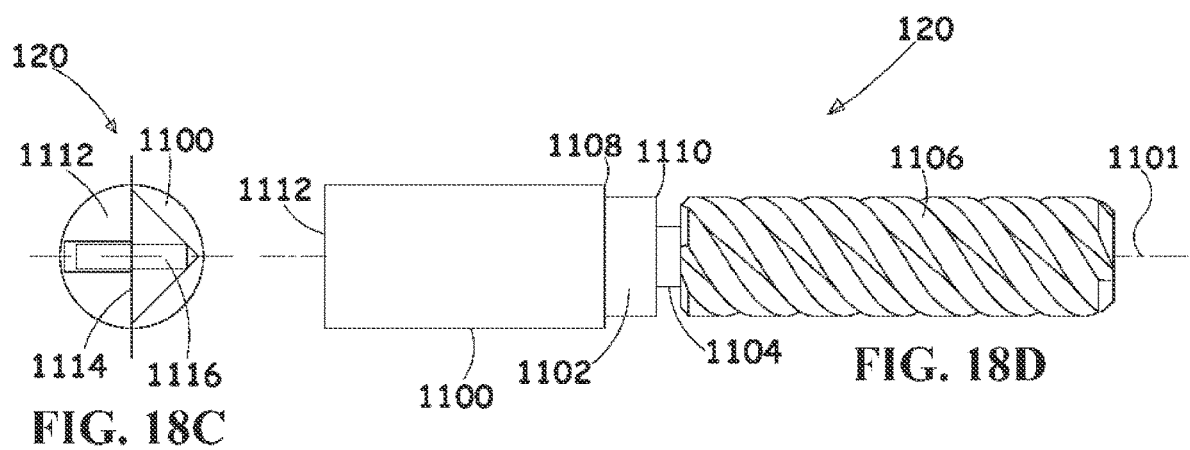
FIG. 18C
FIG. 18D

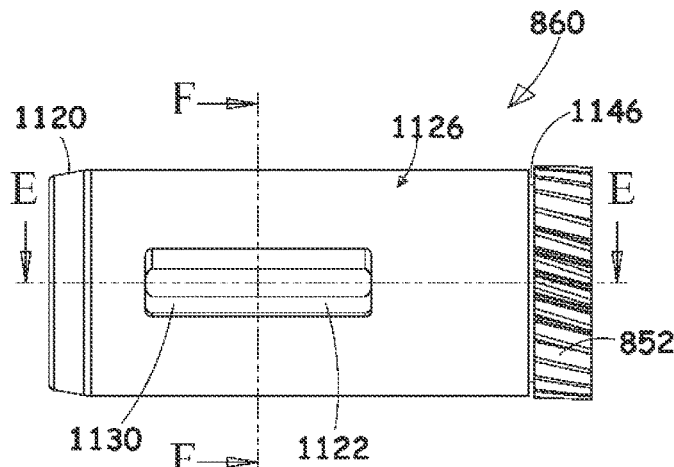
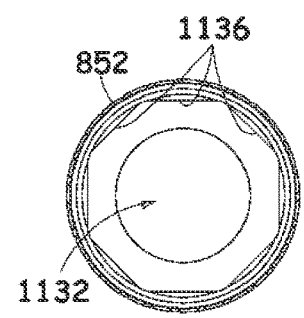
FIG. 19C
FIG. 19D
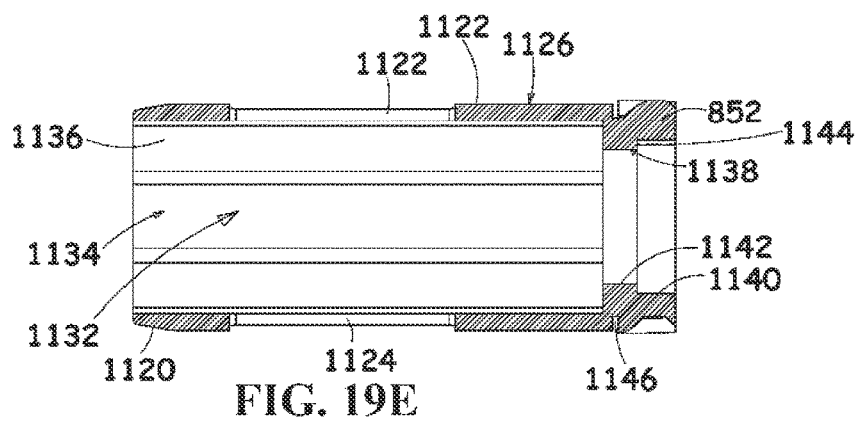
FIG. 19E
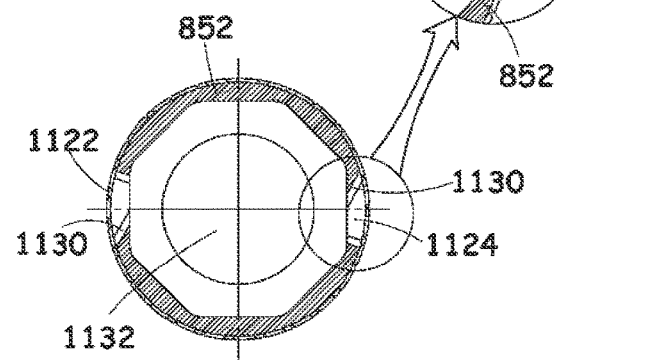
FIG. 19F

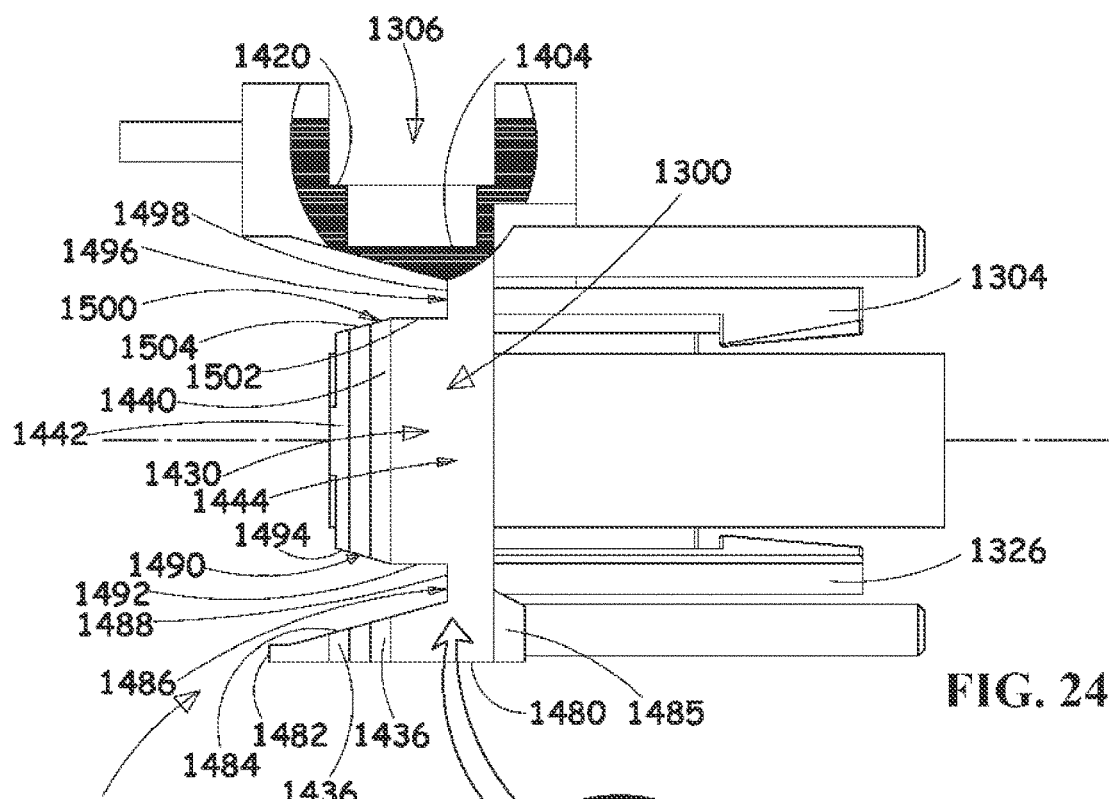
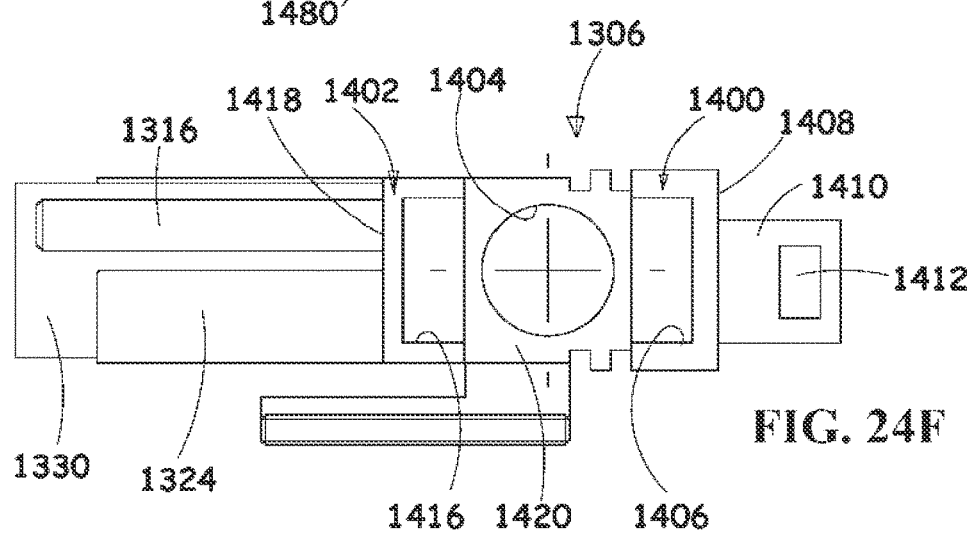
FIG. 24E
FIG. 24F

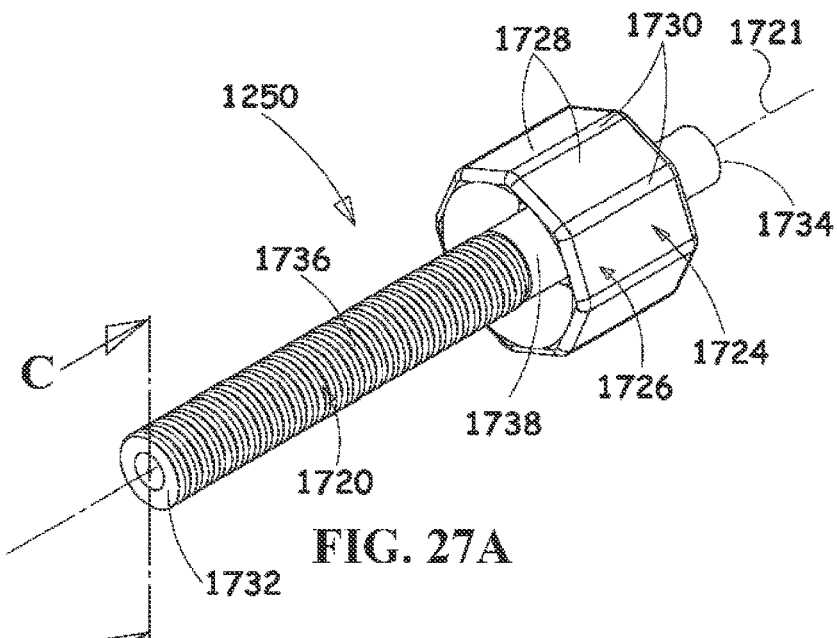
FIG. 27A
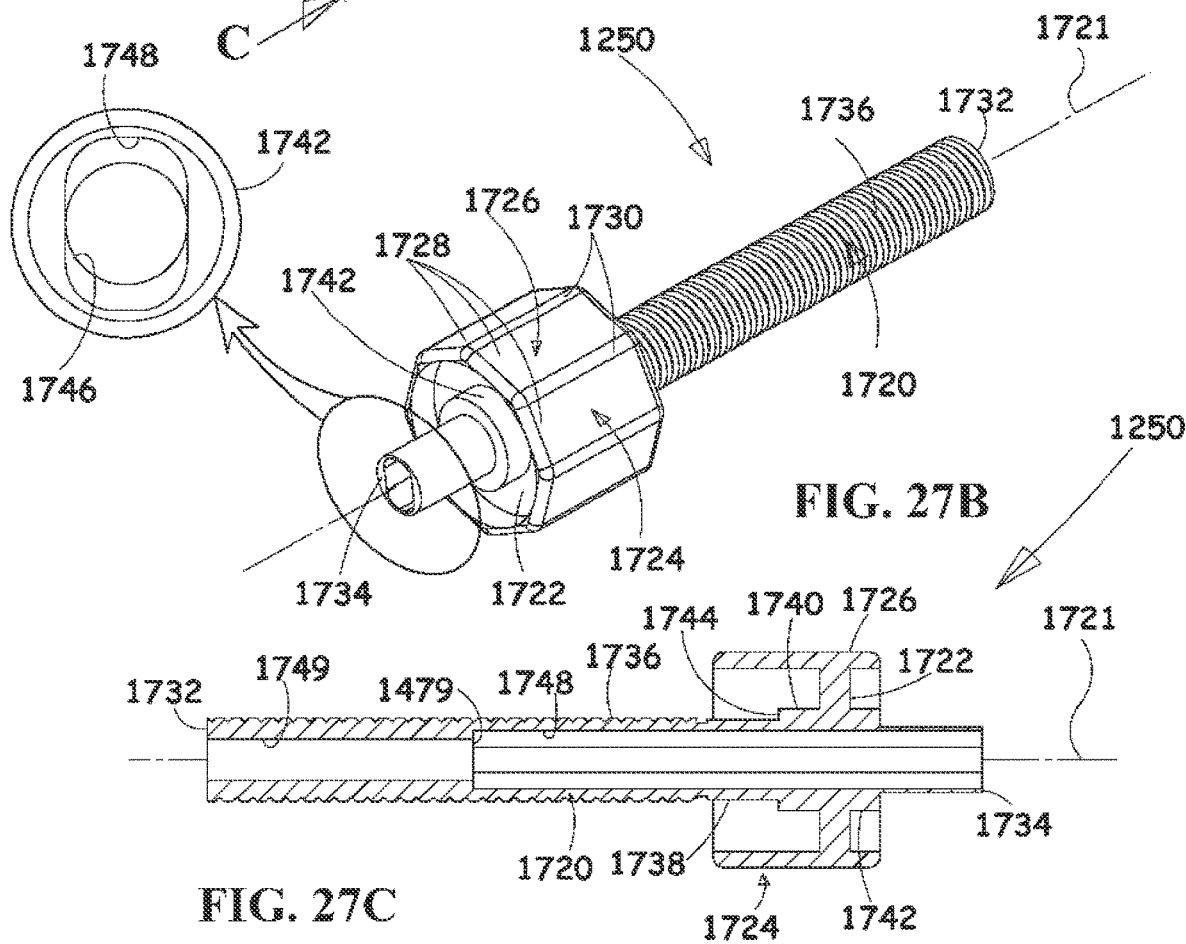
FIG. 27B
FIG. 27C

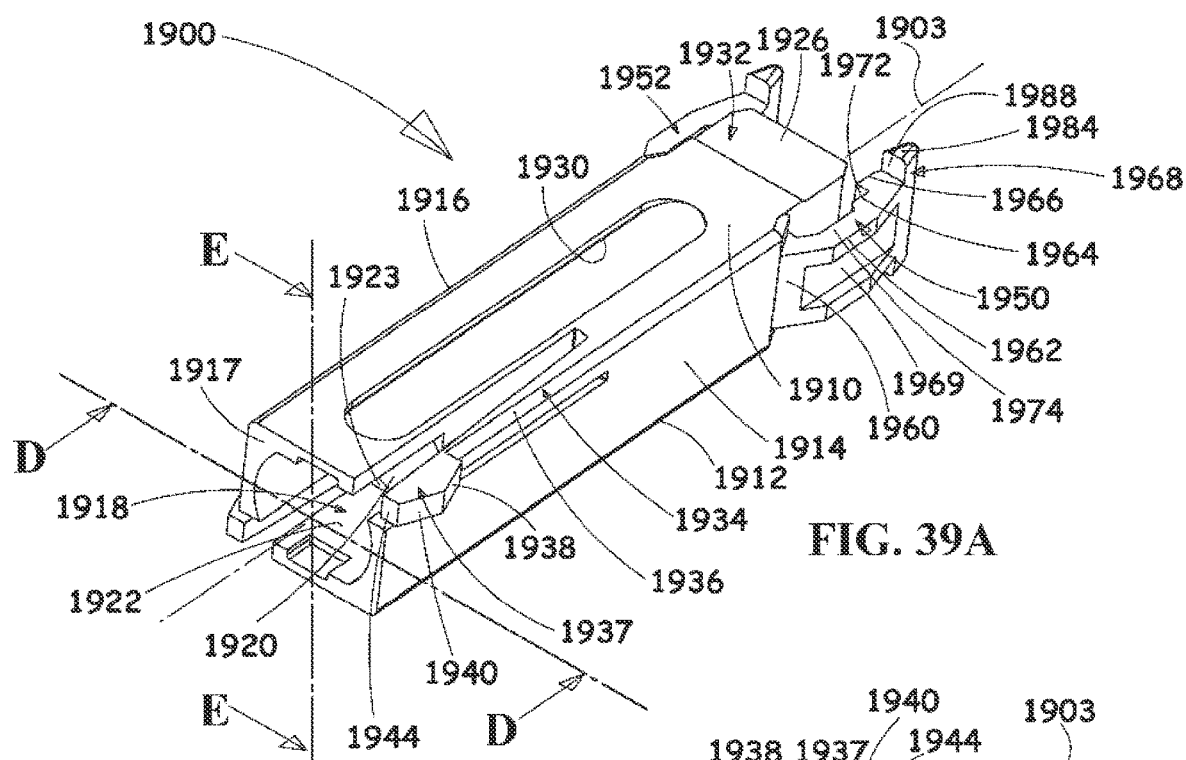
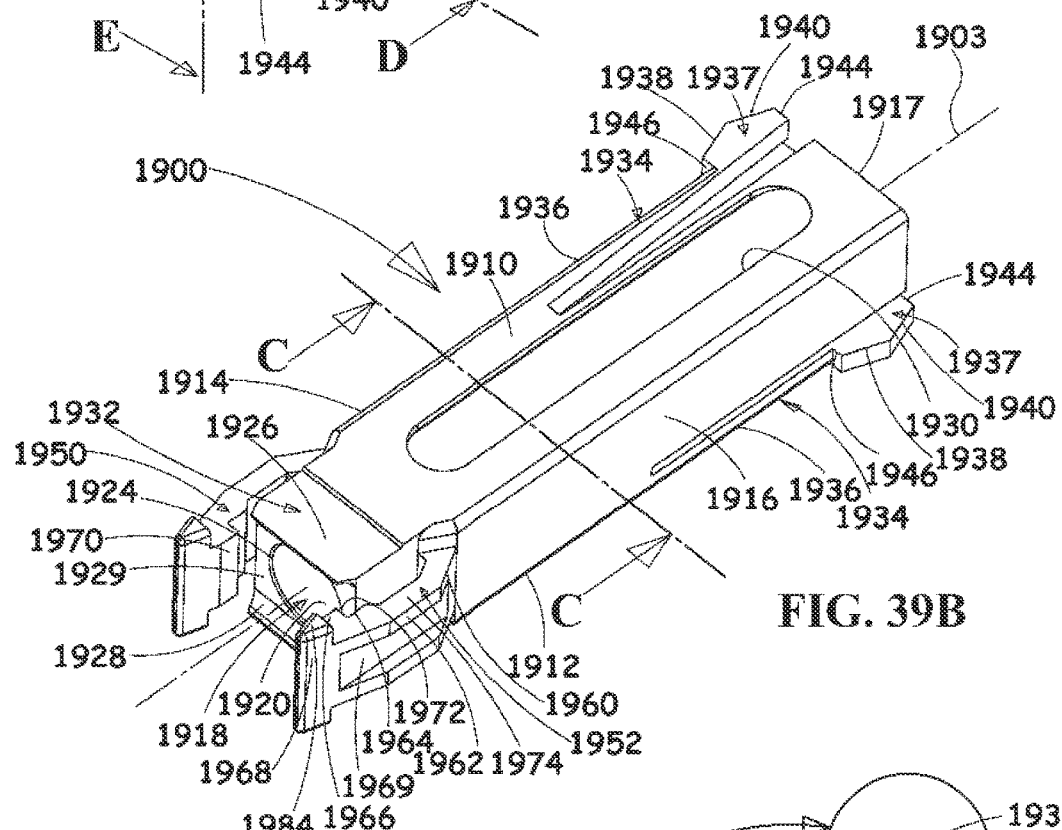
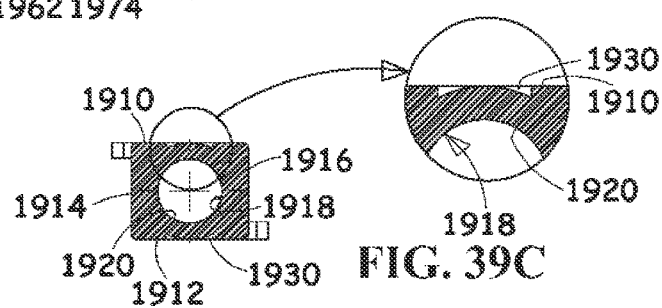

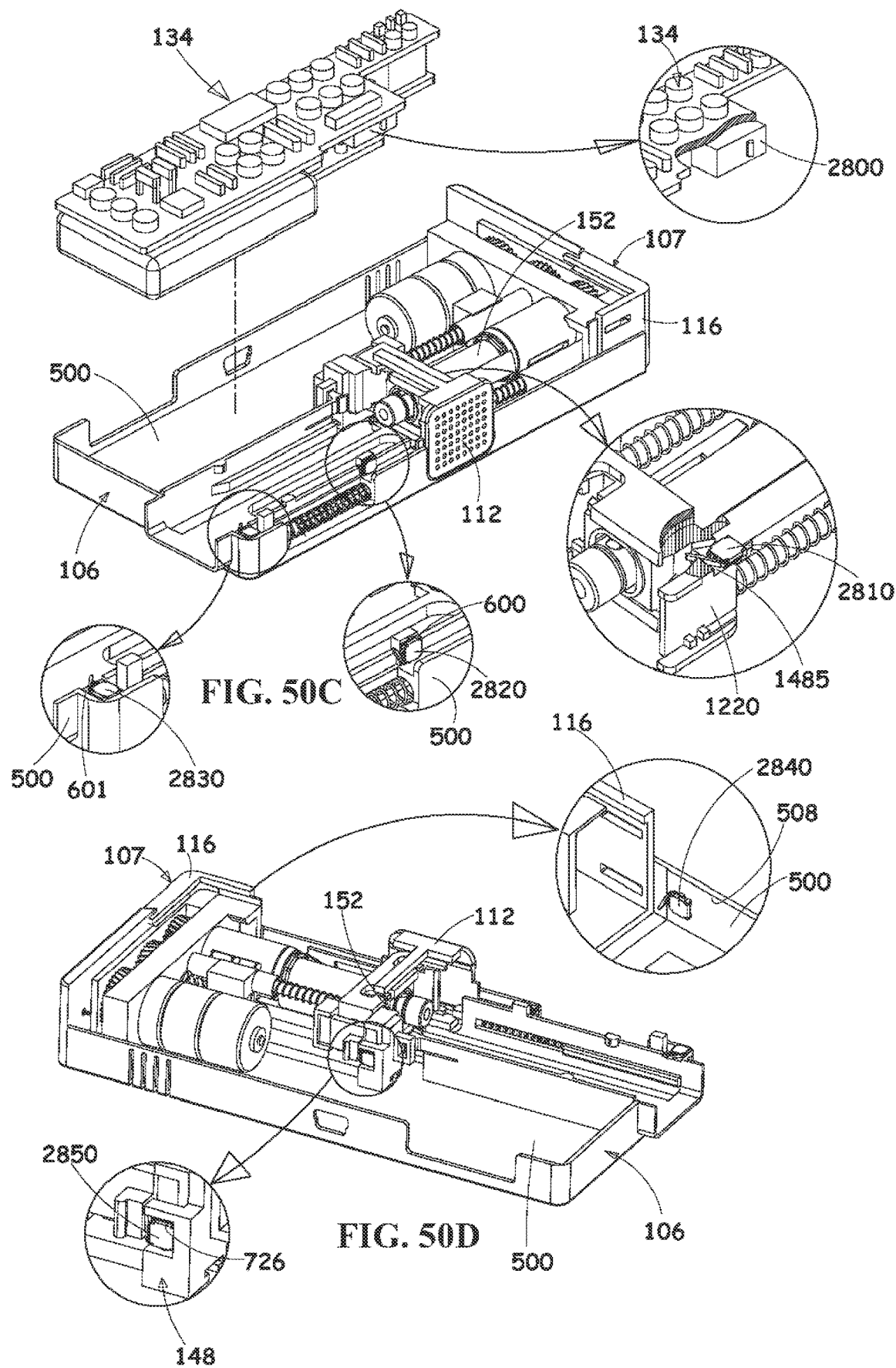

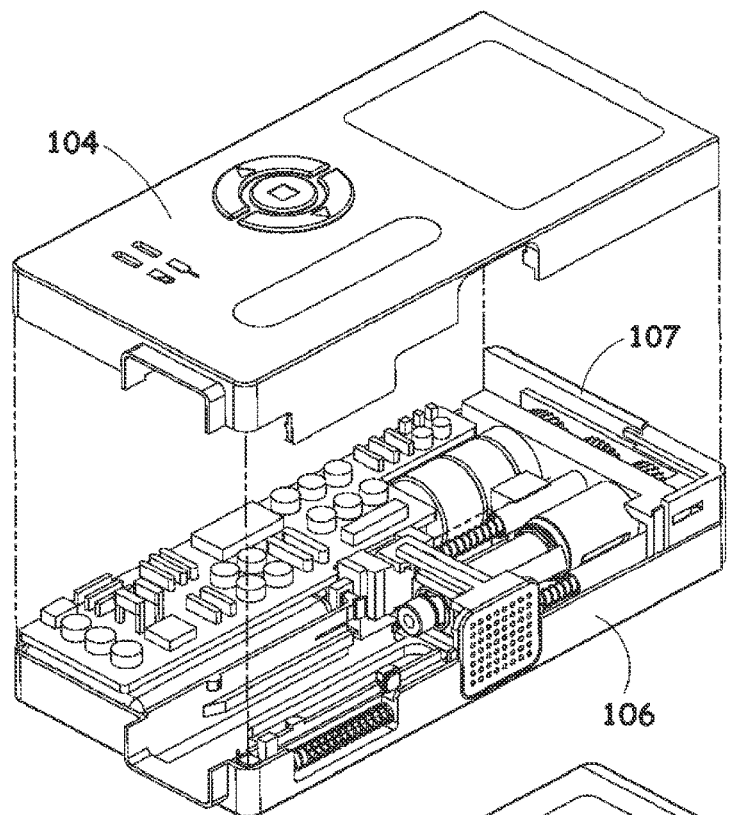
FIG. 51A
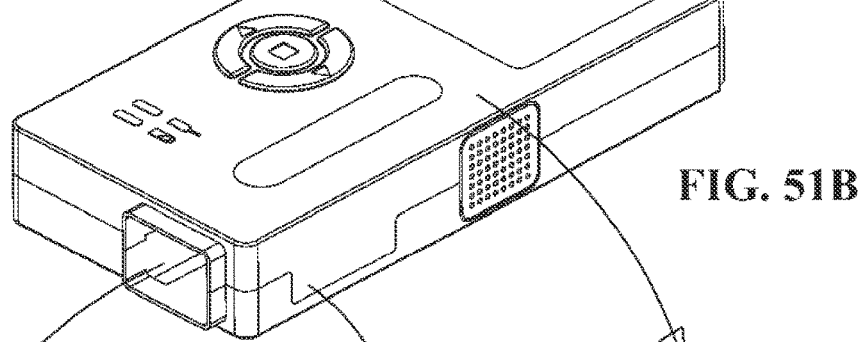
FIG. 51B
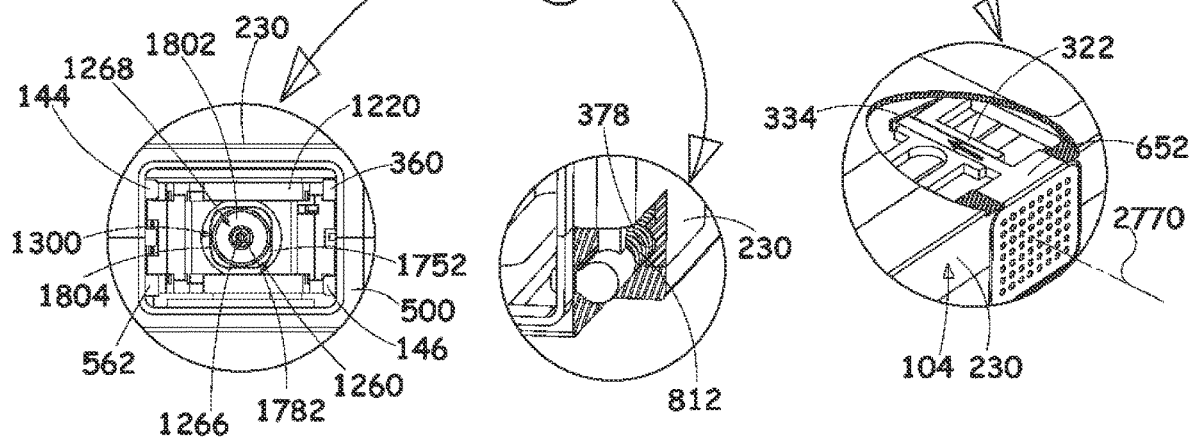

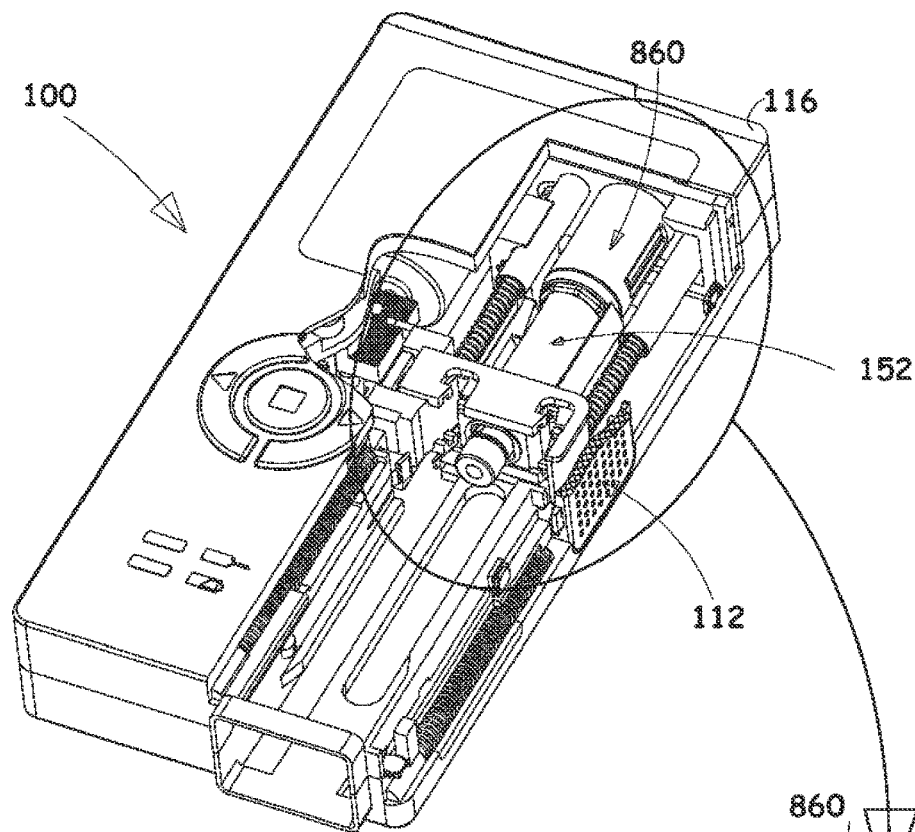
FIG. 52B
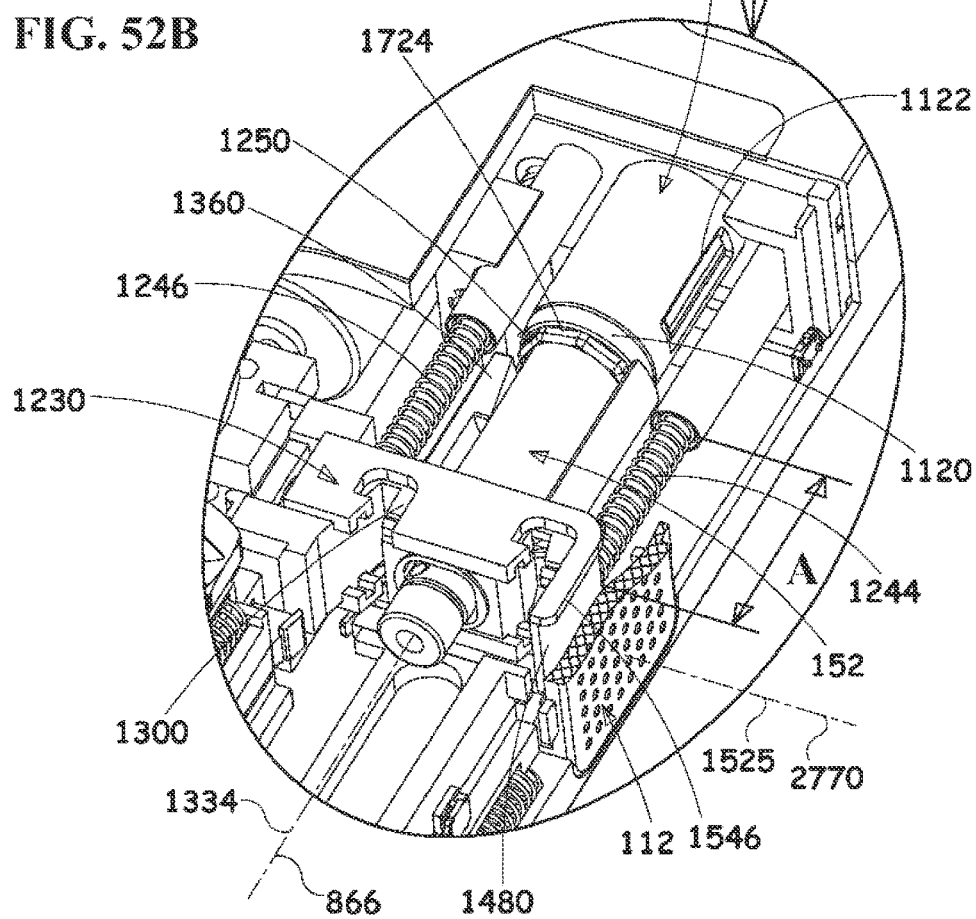

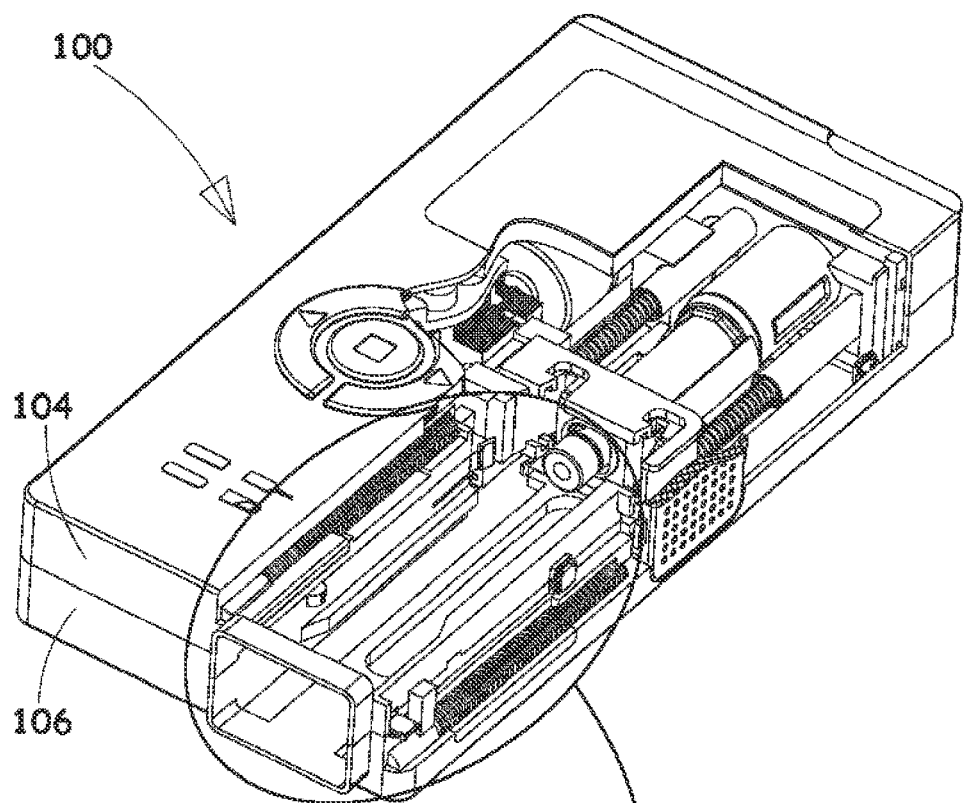
FIG. 52C
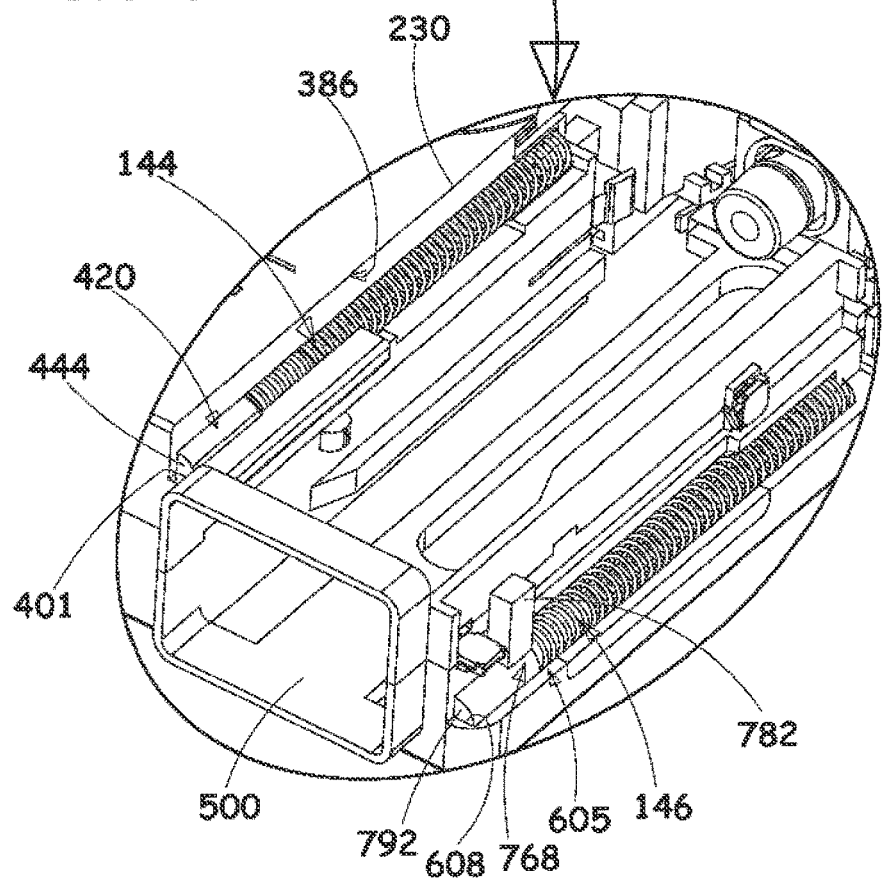

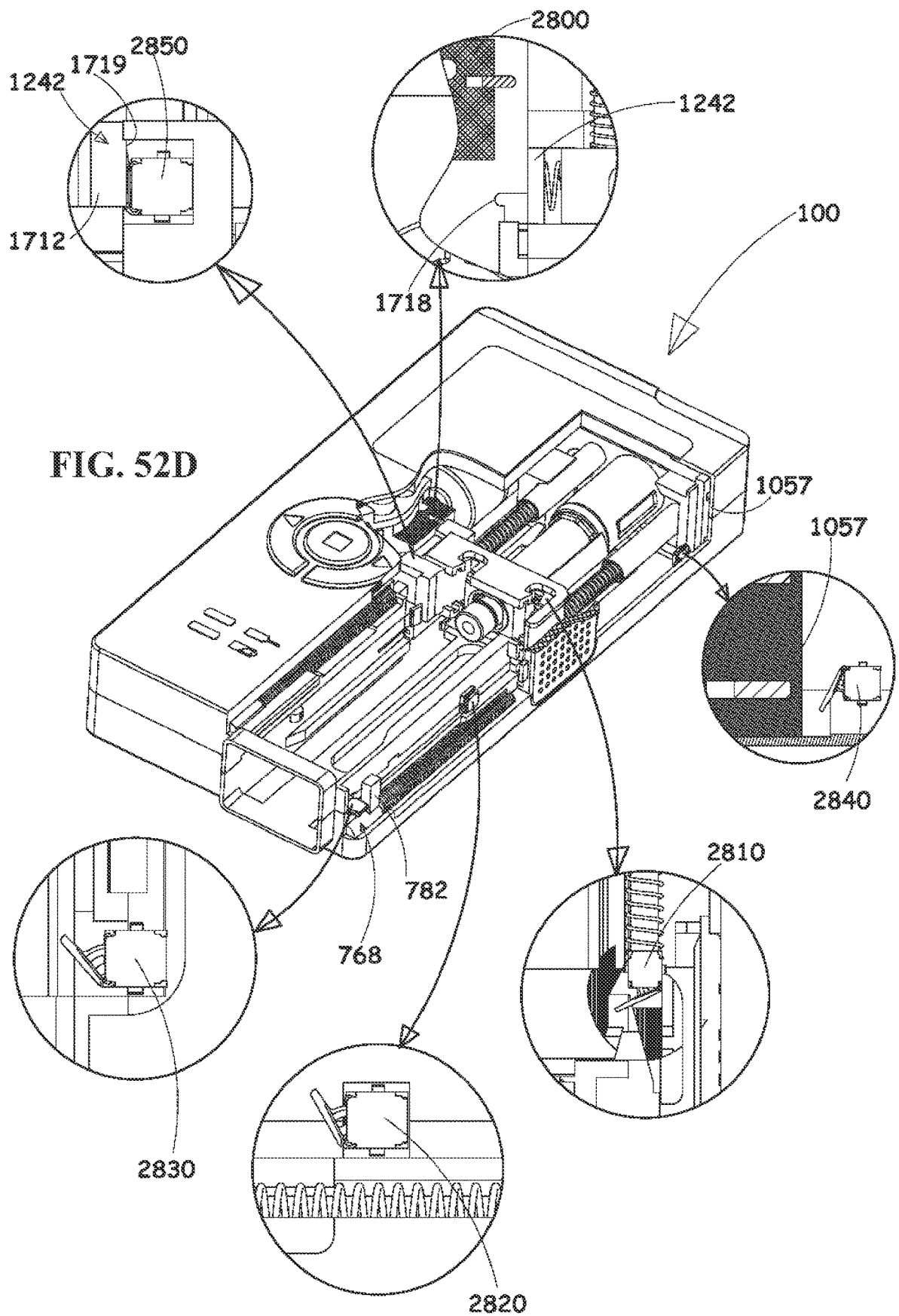

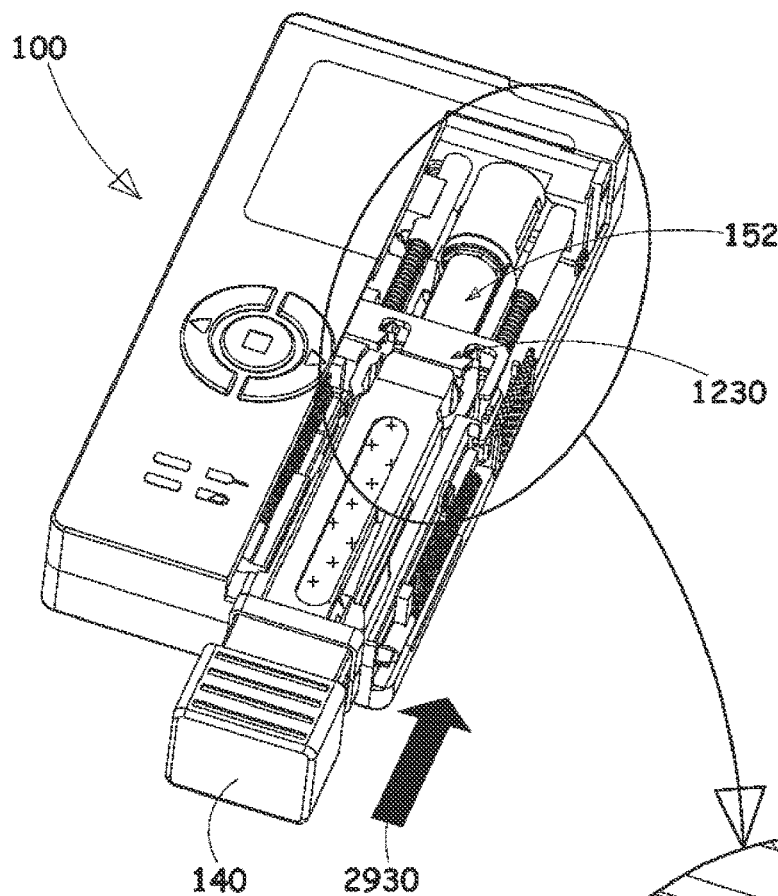
FIG. 57B
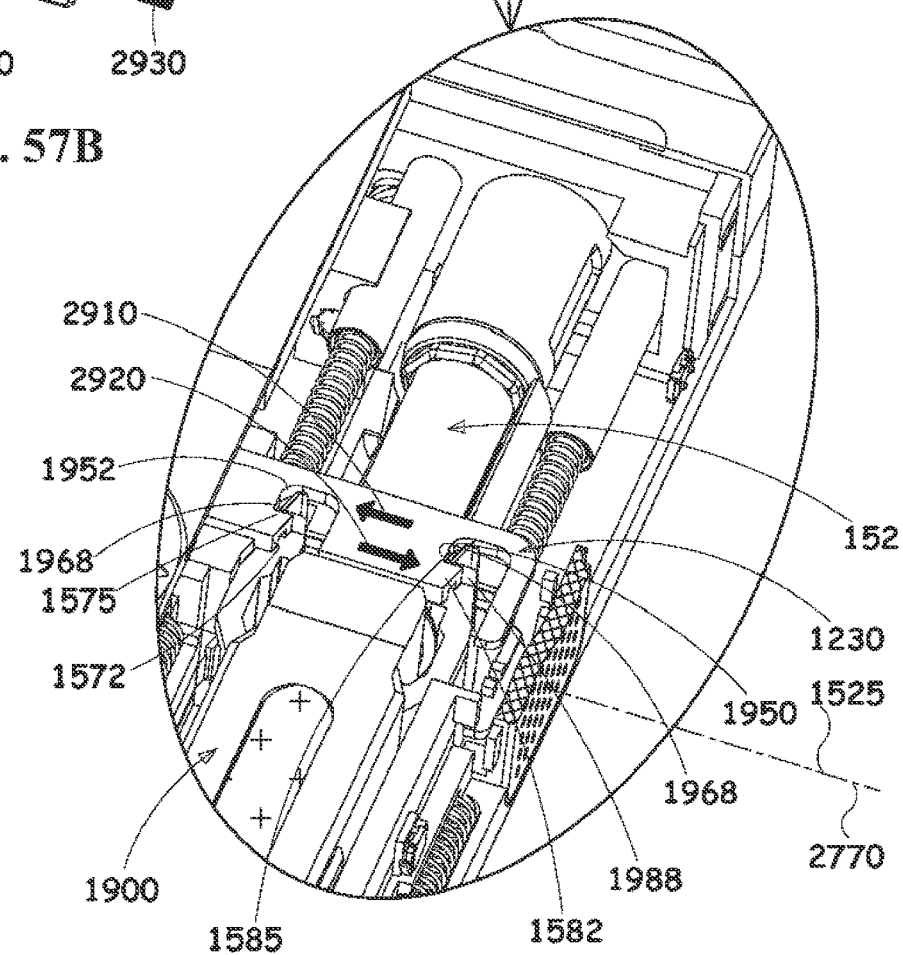

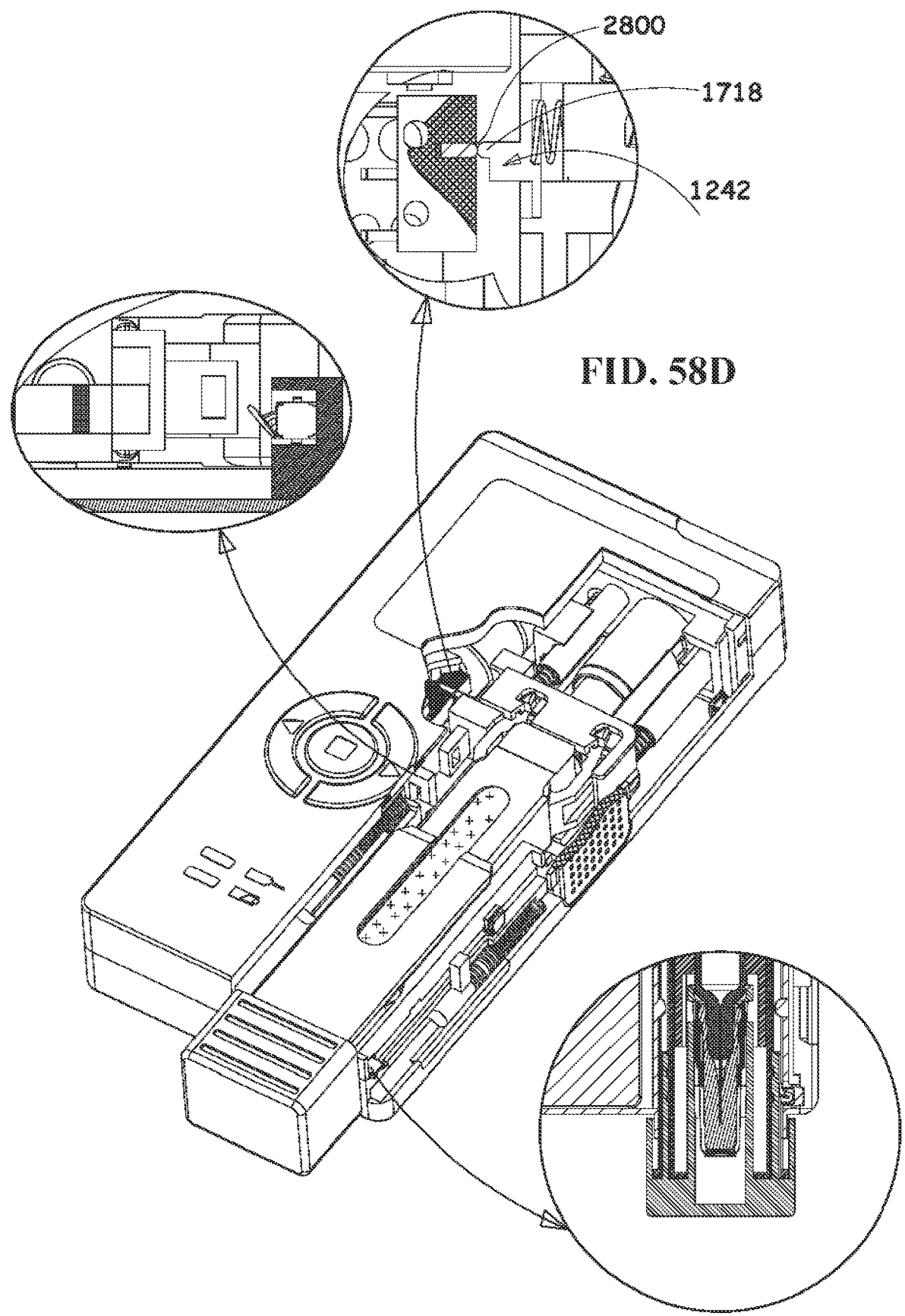
FID. 58D

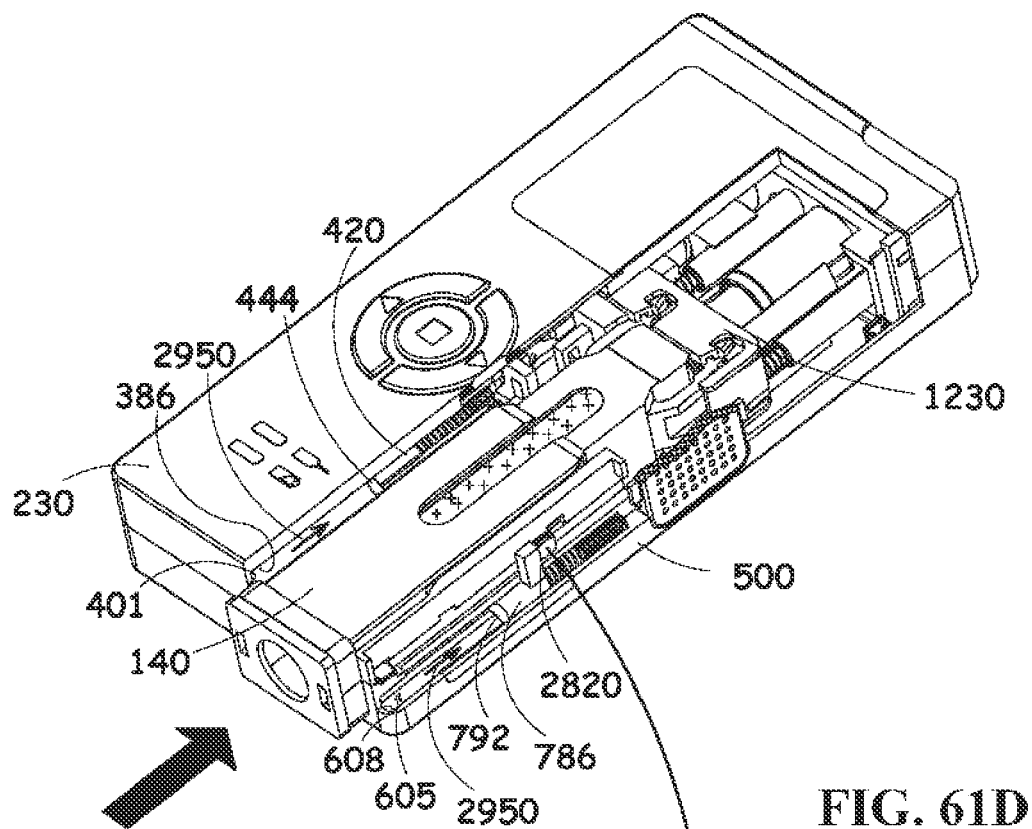
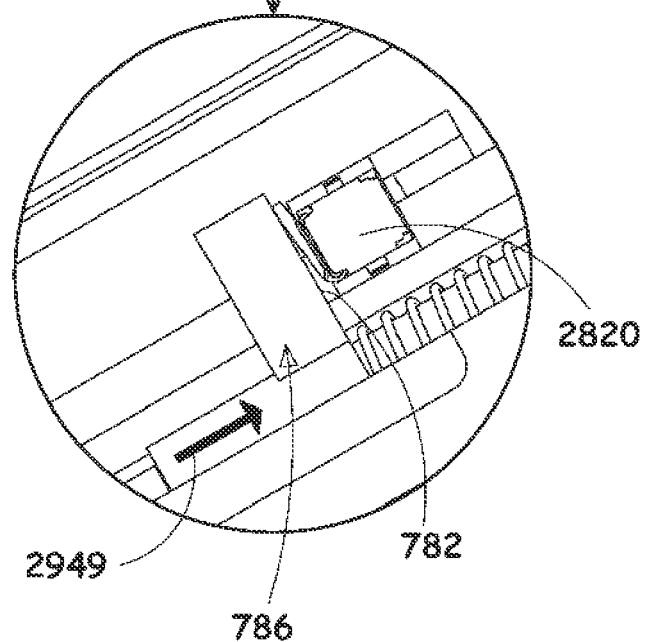
FIG. 61D

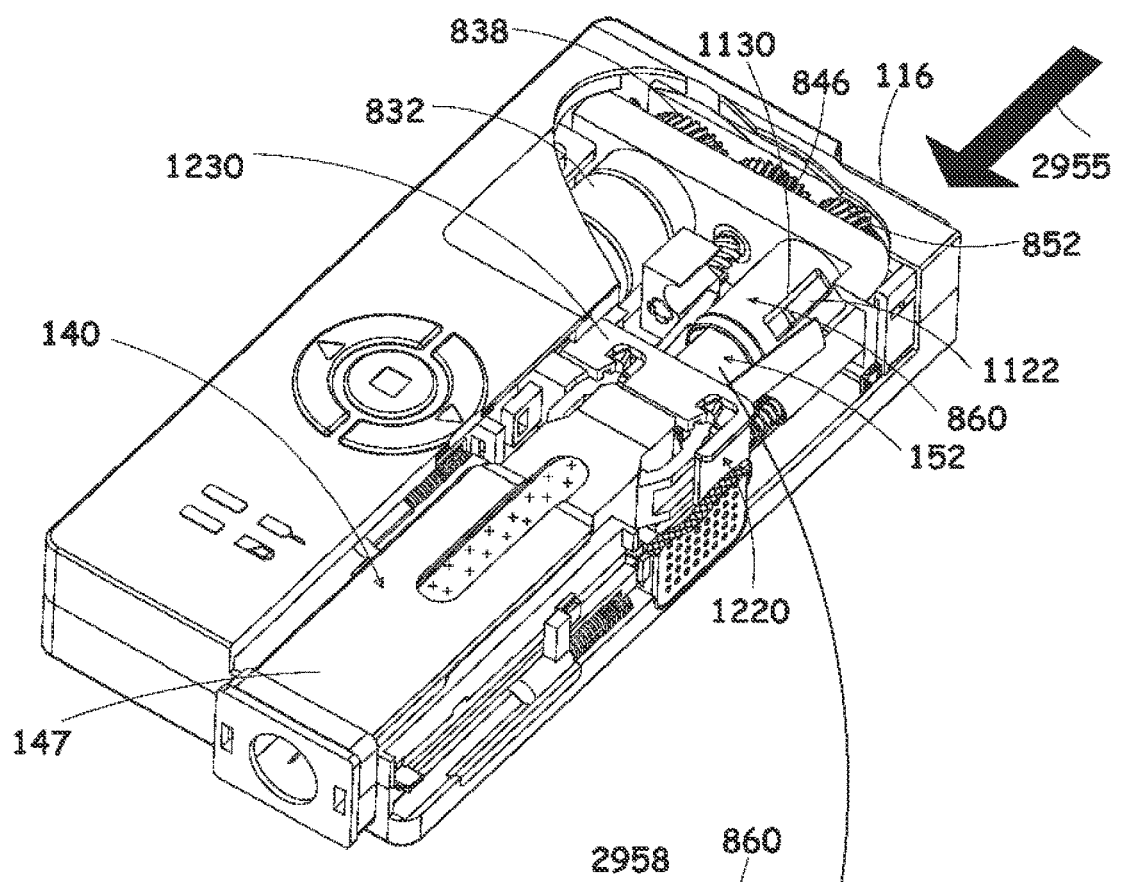
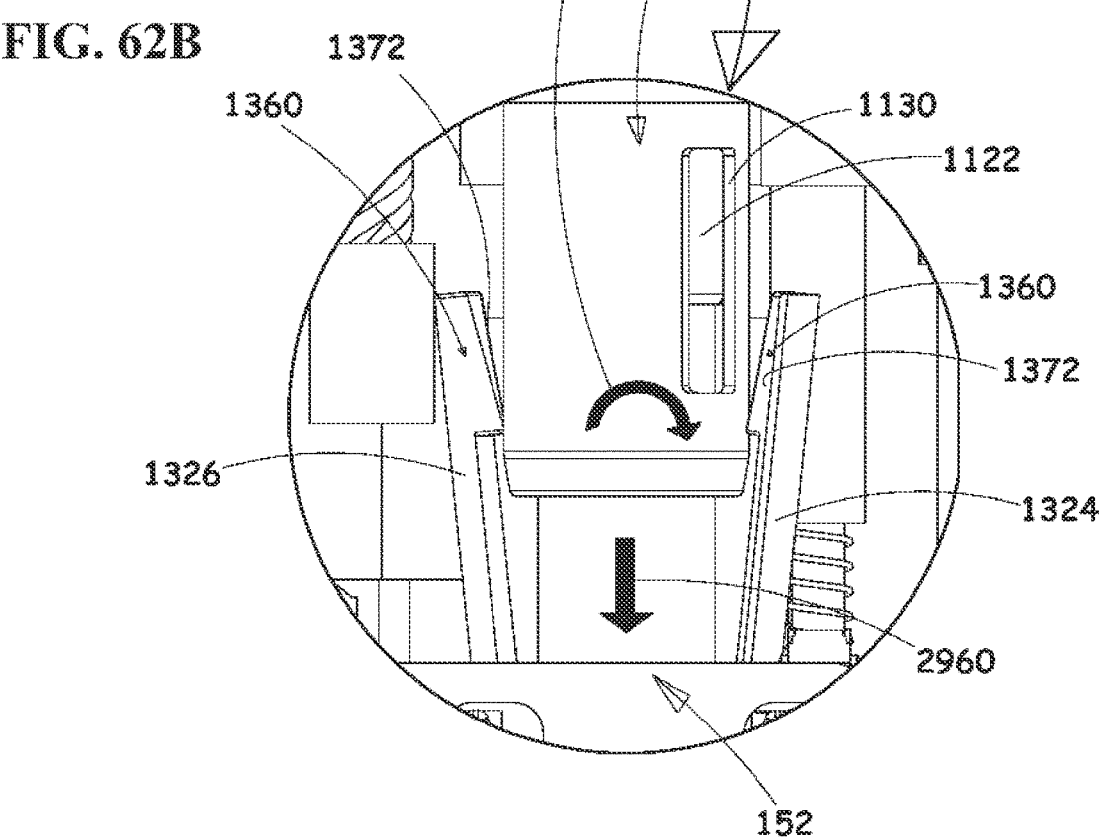
FIG. 62B

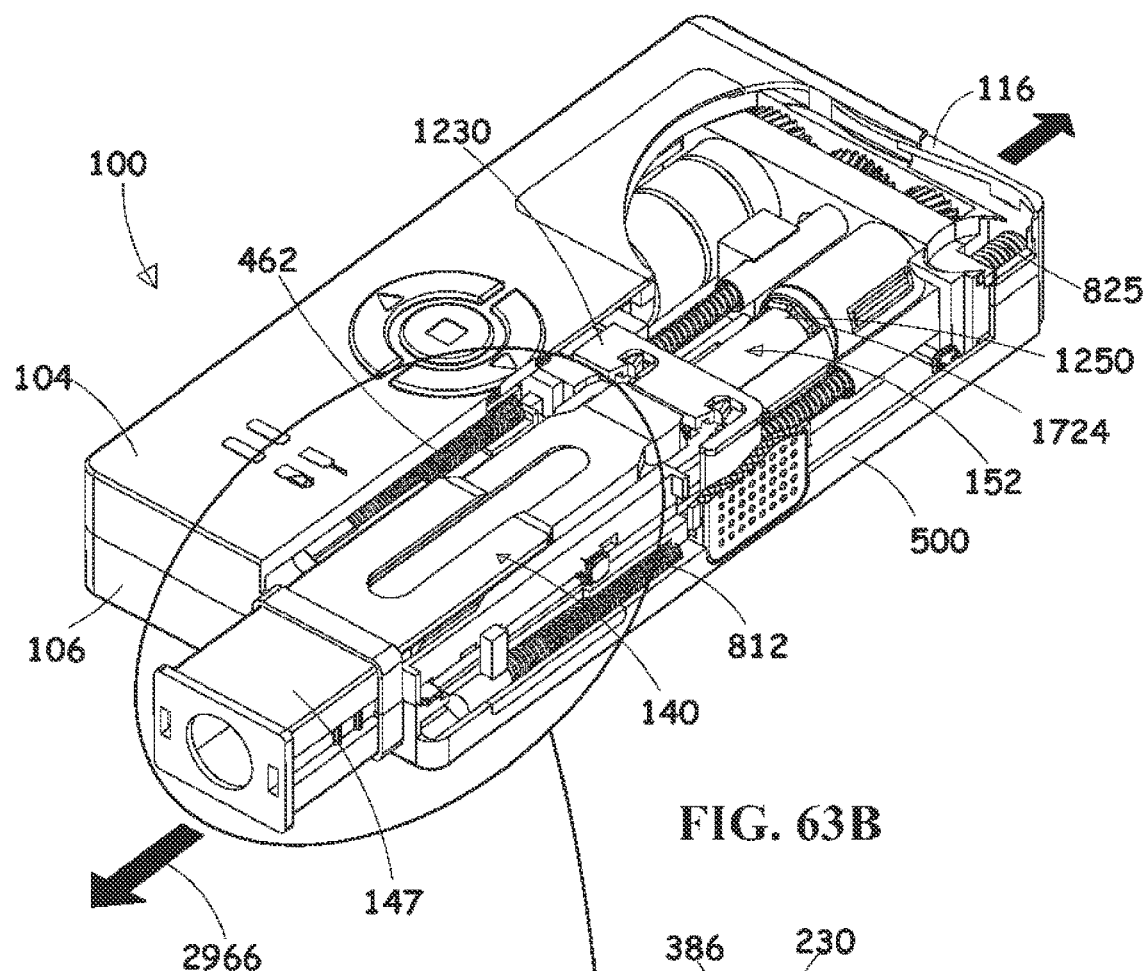
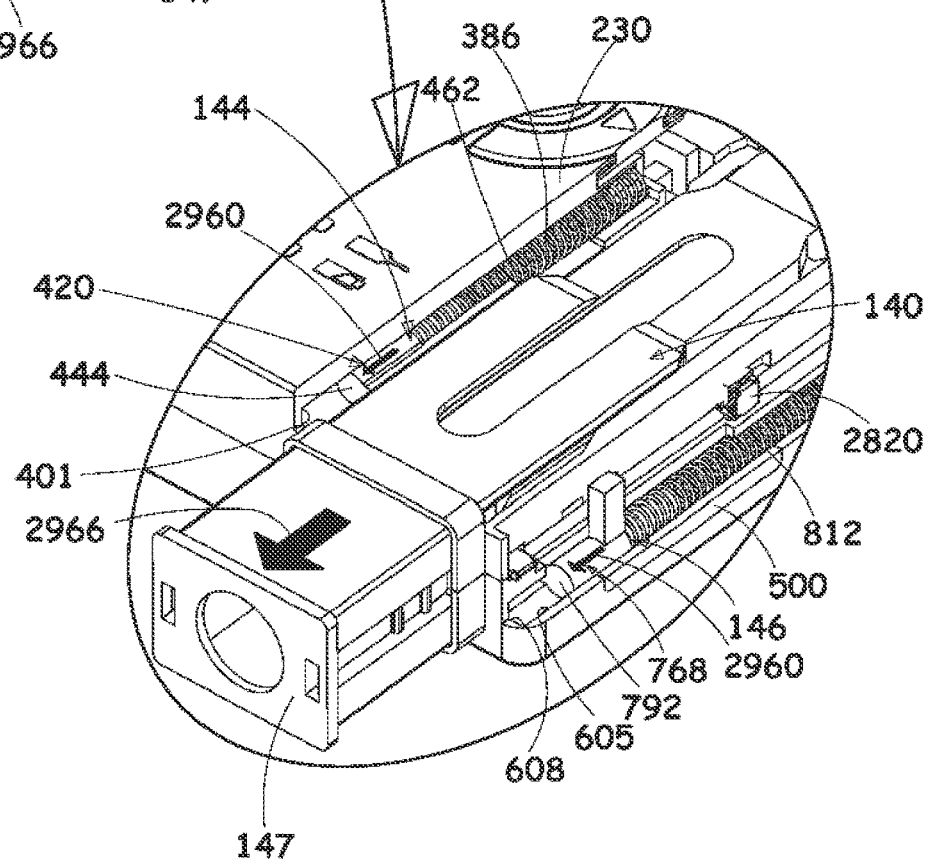
FIG. 63B

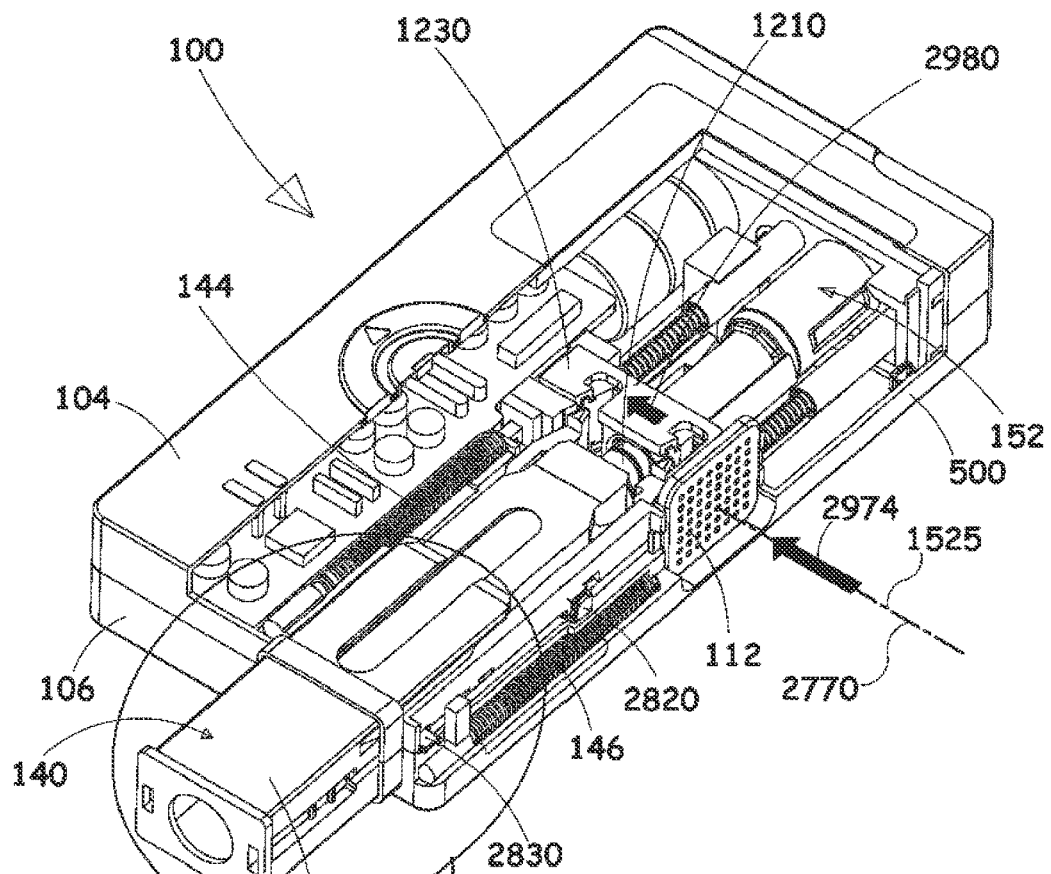
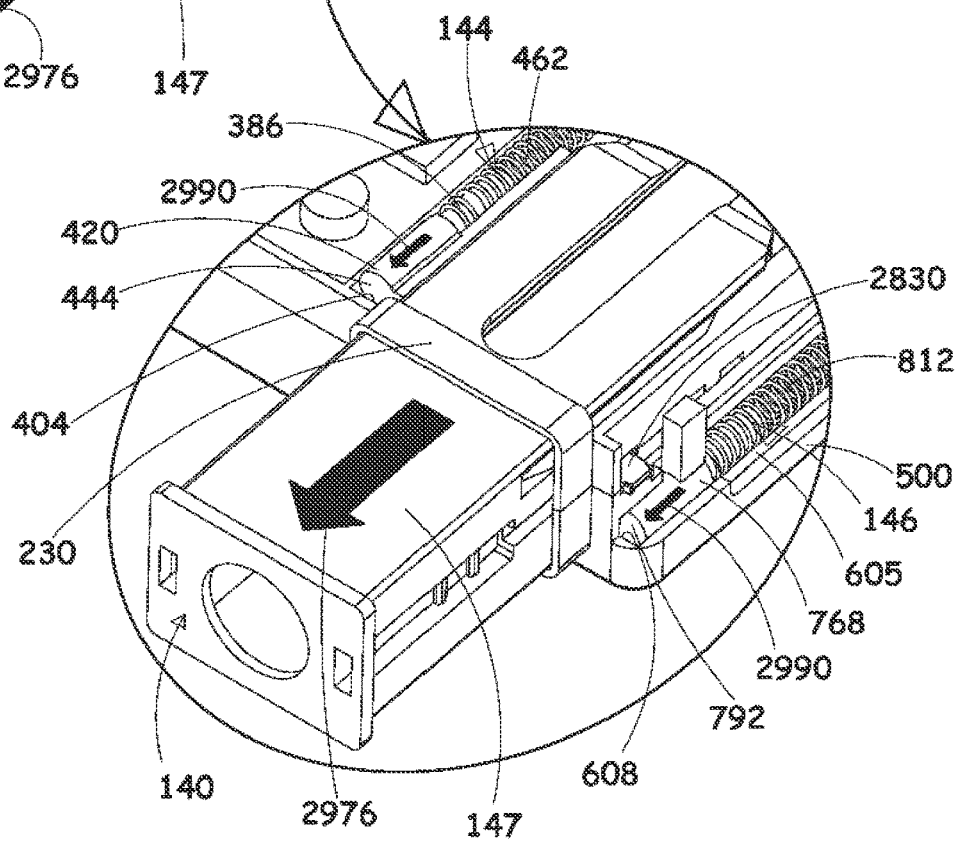
FIG. 64B

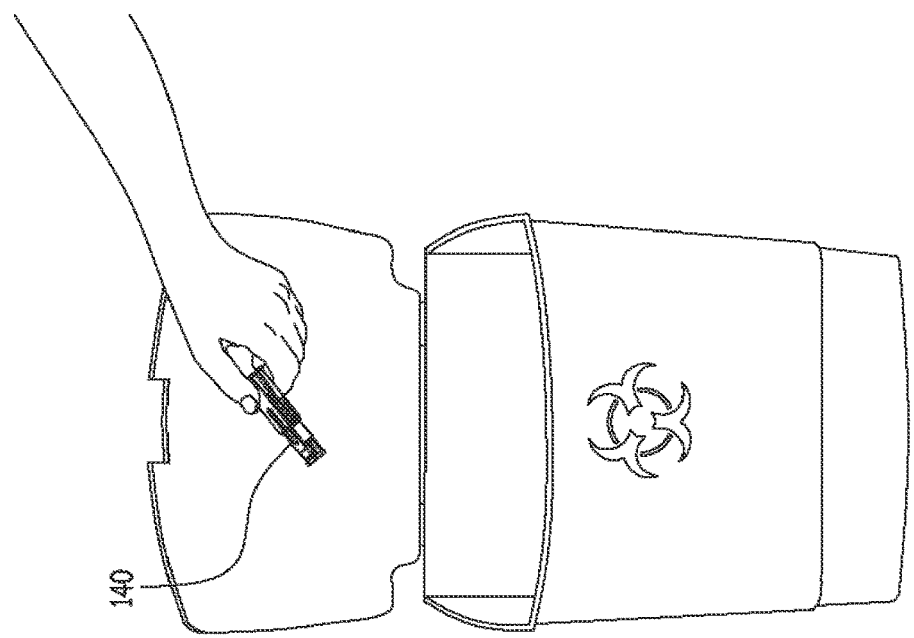
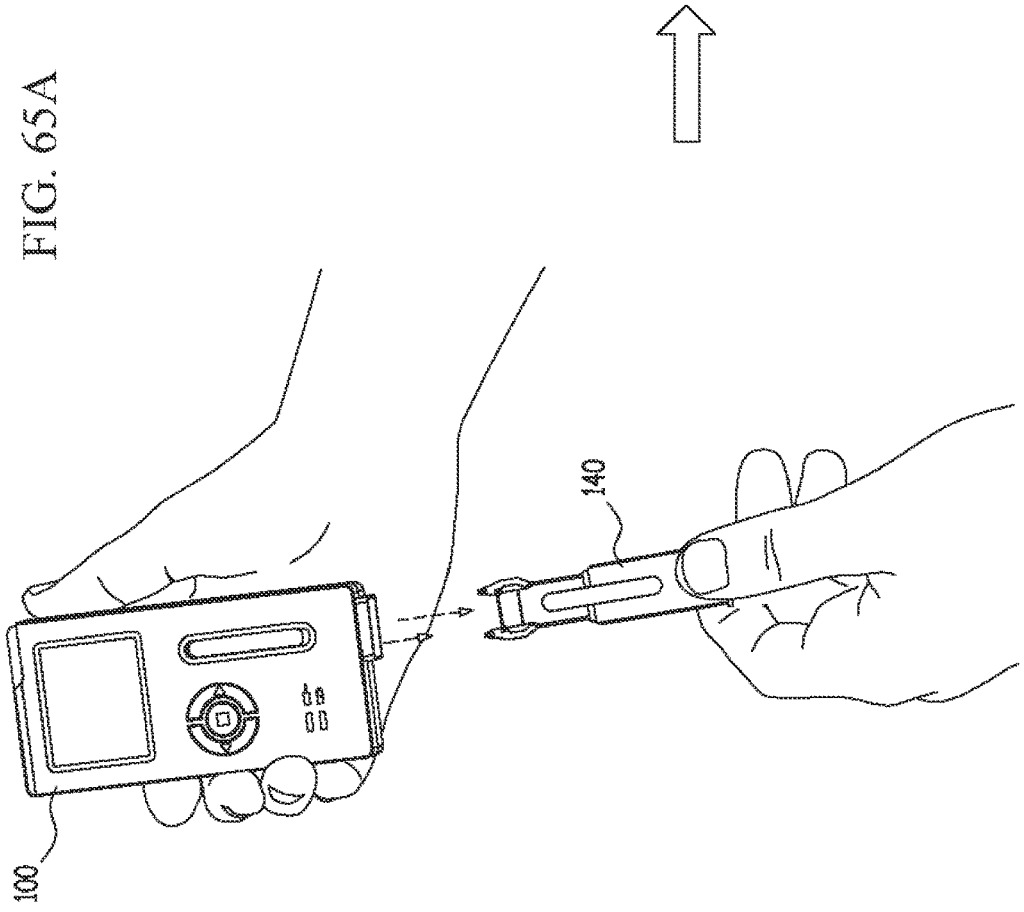
FIG. 65A

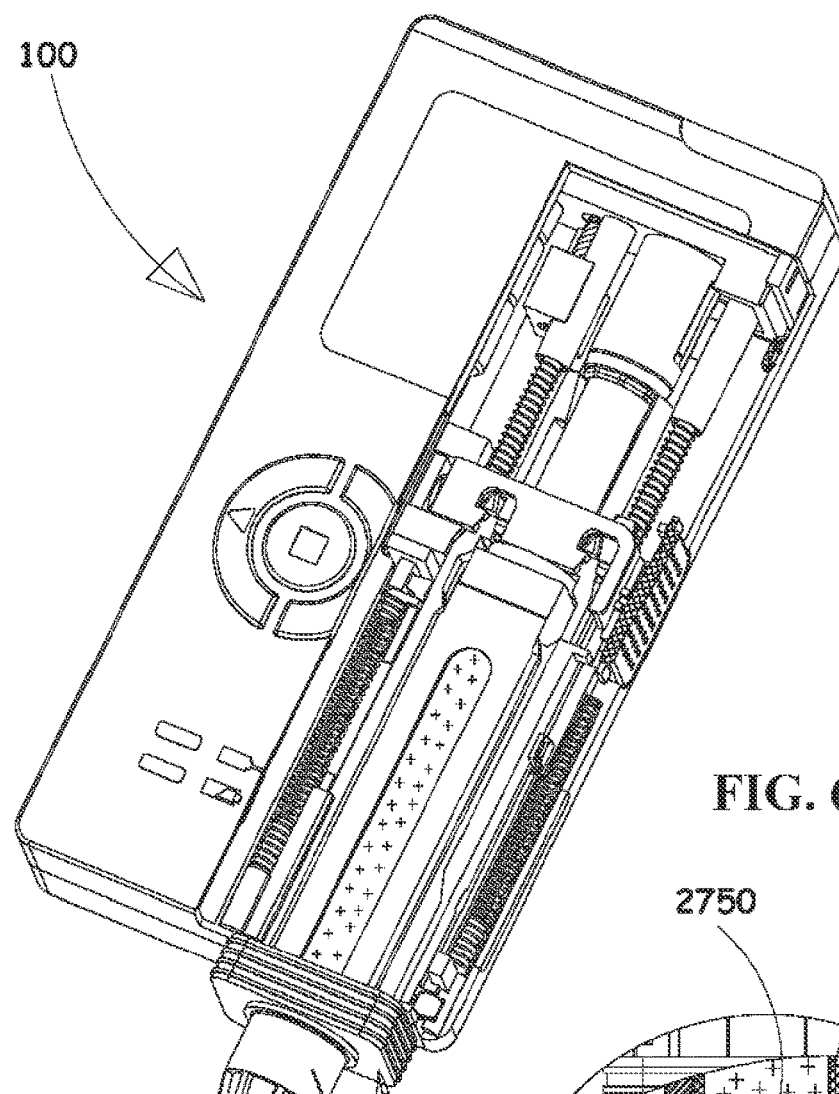
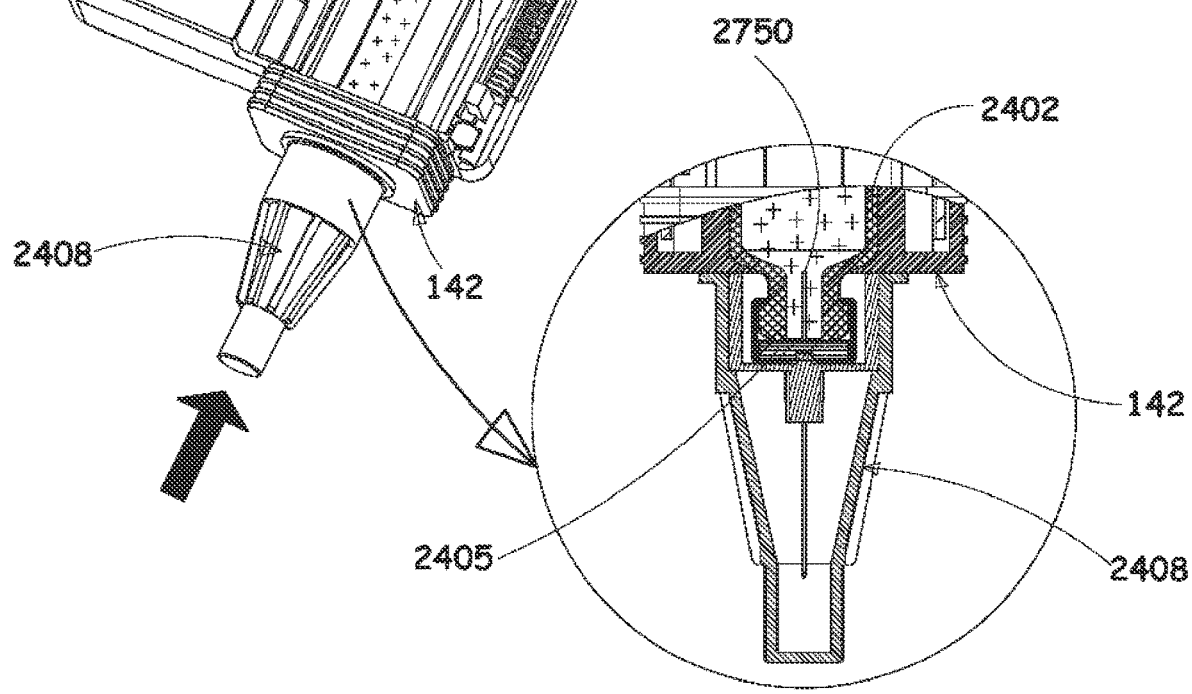
FIG. 68B

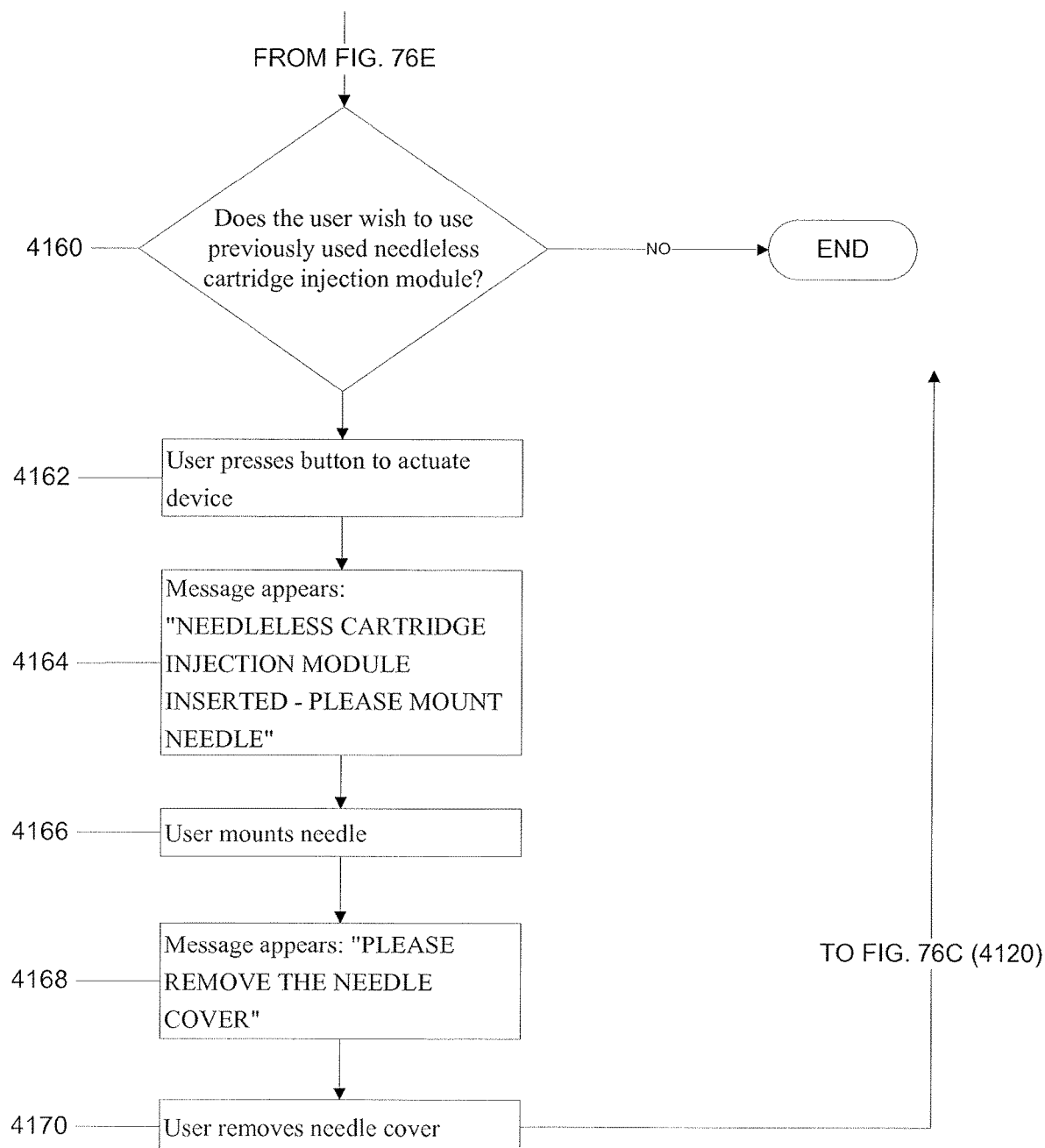

ELECTRONIC AUTO-INJECTION DEVICE

CROSS REFERENCE TO RELATED APPLICATIONS

This application is a National Stage of International Application No. PCT/IL2013/050752 filed Sep. 3, 2013, claiming priority based on U.S. Provisional Application No. 61/697,216 filed Sep. 5, 2012, the contents of all of which are incorporated herein by reference in their entirety.

REFERENCE TO RELATED APPLICATIONS

Reference is hereby made to U.S. Provisional Patent Application Ser. No. 61/697,216, filed Sep. 5, 2012 and entitled "AUTO INJECTION DEVICE", the disclosure of which is incorporated by reference in its entirety and priority of which is hereby claimed pursuant to 37 CFR 1.78(a) (4) and (5)(i).

FIELD OF THE INVENTION

The present invention generally relates to an automatic injection device, and more specifically to a partially-disposable automatic injection device adapted for administration of medication to a patient.

BACKGROUND OF THE INVENTION

Many automatic injection devices adapted for administration of medication to a patient are known.

SUMMARY OF THE INVENTION

The present invention seeks to provide an improved electronic automatic injection device.

There is thus provided in accordance with a preferred embodiment of the present invention an electronic automatic injection device including a housing configured to receive an injection module containing a material to be injected, an electric motor having a rotary drive output, at least one forward driving spring and a multifunctional electric motor driven drive assembly responsive to the rotary drive output of the electric motor and being operative in a first mode of operation, when the injection module includes a prefilled syringe, to enable the at least one forward driving spring to displace the prefilled syringe in a forward direction and in a second mode of operation, when the injection module includes a needleless cartridge, to eject the injectable liquid from the prefilled syringe through a needle.

Preferably, the electronic automatic injection device also includes a forward driving spring compression assembly operative in response to insertion of the injection module into the housing for automatically compressing the forward driving spring.

There is also provided in accordance with another preferred embodiment of the present invention an electronic automatic injection device including a housing configured to receive a prefilled syringe including a needle and containing a material to be injected, an electric motor having a rotary drive output, at least one forward driving spring and a multifunctional electric motor driven drive assembly responsive to the rotary drive output of the electric motor and being operative in an initial mode of operation to enable the at least one forward driving spring to displace the prefilled syringe in a forward direction and in a subsequent mode of operation to eject the injectable liquid from the prefilled syringe through the needle without employing the at least one forward driving spring.

In accordance with a preferred embodiment of the present invention the electronic automatic injection device also includes a forward driving spring compression assembly operative in response to insertion of the prefilled syringe into the housing for automatically compressing the forward driving spring. Additionally or alternatively, in the initial mode of operation, the at least one forward driving spring drives the needle into injection engagement with a target subsequent to an actuation produced by operation of the electric motor.

There is further provided in accordance with yet another preferred embodiment of the present invention an electronic automatic injection device including a housing configured to receive an injection module containing a material to be injected, an electric motor having a rotary drive output, at least one forward driving spring, a forward driving spring compression assembly operative in response to insertion of the injection module into the housing for automatically compressing the forward driving spring and a multifunctional electric motor driven drive assembly responsive to the rotary drive output of the electric motor being operative to eject the injectable liquid from the injection module through a needle.

There is even further provided in accordance with still another preferred embodiment of the present invention an electronic automatic injection device including a housing configured to receive an injection module containing a material to be injected, at least one forward driving assembly and a telescopic plunger assembly driven by the at least one forward driving assembly being operative to eject the material from the injection module through a needle.

Preferably, the telescopic plunger assembly includes a forward plunger assembly and a rearward plunger assembly which operate together in a telescopic manner.

There is also provided in accordance with yet another preferred embodiment of the present invention an electronic automatic injection device including a housing configured to receive an injection module containing a material to be injected, a multifunctional drive assembly operative for lockingly engaging the injection module upon insertion of the injection module into the housing and a locking element slidably coupled to the housing and configured to lockingly engage the injection module.

There is still further provided in accordance with a further preferred embodiment of the present invention an electronic automatic injection device including a housing configured to receive an injection module containing a material to be injected, a needle shield, an injection module release button and at least one biasing element, the at least one biasing element being configured to prevent actuation of the injection module release button when the needle shield is pressed against an injection site.

There is yet further provided in accordance with yet a further preferred embodiment of the present invention an electronic automatic injection device including a housing configured to receive an injection module containing a material to be injected, the injection module including a mounting element and a needle shield, a multifunctional drive assembly connectable to the mounting element of the injection module and a multiple drive element connectable to the multifunctional drive assembly, the needle shield being displaceable relative to the injection module only following engagement of the multifunctional drive assembly with the multiple drive element.

There is even further provided in accordance with another preferred embodiment of the present invention an electronic automatic injection device including a housing configured to receive an injection module containing a material to be injected, the injection module including a needle shield including at least one needle shield protrusion, the housing including at least one housing protrusion and a multiple motion output subassembly including a locking element for locking the injection module relative thereto; the at least one needle shield protrusion and the at least one housing protrusion being configured to engage the injection module and to prevent ejection of the injection module from the housing when the injection module is unlocked from the locking element.

Preferably, the electronic automatic injection device also includes a computerized controller for governing the operation of at least the electric motor. In accordance with a preferred embodiment of the present invention the injection module includes at least one machine readable message and the computerized controller is responsive at least partially to the at least one machine readable message. Additionally or alternatively, the electronic automatic injection device also includes a touch screen user interface. Additionally or alternatively, the electronic automatic injection device also includes wireless communications functionality associated with the computerized controller.

Preferably, the electronic automatic injection device also includes injection history logging functionality associated with the computerized controller. Additionally or alternatively, the electronic automatic injection device also includes injection reminder functionality associated with the computerized controller.

In accordance with a preferred embodiment of the present invention the electronic automatic injection device also includes defective injection alarm functionality associated with the computerized controller. Additionally or alternatively, the electronic automatic injection device also includes encoder functionality cooperating with the computerized controller for indicating quantities of ejected liquid. Preferably, the electric motor cooperates with an encoder to provide a validated indication of quantity of ejected liquid. Additionally, the computerized controller is responsive to the validated indication of quantity of ejected liquid for operating the electric motor in an injection completion mode of operation.

Preferably, the electronic automatic injection device also includes a voice annunciator associated with the computerized controller. Additionally or alternatively, the electronic automatic injection device also includes user-responsive ejection rate control functionality associated with the computerized controller.

In accordance with a preferred embodiment of the present invention the injection module includes one of a prefilled syringe injection module (PFS) and a needleless cartridge injection module.

Preferably, the electronic automatic injection device also includes a needle shield, a first needle shield biasing assembly and a second needle shield biasing assembly, the first and second needle shield biasing assemblies providing automatic displacement of the needle shield. Additionally, each of the first and second needle shield biasing assemblies includes an elongate compression spring and a biasing element.

In accordance with a preferred embodiment of the present invention the electronic automatic injection device also includes an injection depth selector and an injection depth selector travel track slidably mounted on the housing for operative engagement with the injection depth selector. Additionally, the electronic automatic injection device also includes a needle penetration depth adjusting element travel track protrusion for engaging the injection depth selector travel track. Additionally or alternatively, the injection depth selector includes a forward-facing threaded portion.

Preferably, the injection depth selector is formed with a rearward-facing end surface in which is formed a recessed indicator arrow, which includes a further recessed elongate portion for receiving a screwdriver. Additionally or alternatively, the injection depth selector is retained in rotatable engagement with the housing in a manner which permits rotation thereof but does not permit displacement thereof.

In accordance with a preferred embodiment of the present invention the electronic automatic injection device also includes an injection module travel track. Additionally, the injection module travel track includes an upper injection module travel track protrusion formed on an underside of an upper housing portion and a lower injection module travel track protrusion formed on an upper-facing side of a lower housing portion.

Preferably, the electronic automatic injection device also includes an audio transducer.

There is also provided in accordance with another preferred embodiment of the present invention an electronic automatic injection device including an injection module operating assembly, the injection module operating assembly including, a rotational motion output subassembly and a multiple motion output subassembly driven by the rotational motion output subassembly to simultaneously produce both axial and rotational motion.

Preferably, the rotational motion output subassembly includes an electric motor and an encoder mounted onto an output shaft of the electric motor, the encoder providing a rotary drive output. Additionally, the rotational motion output subassembly also includes a static sleeve fixedly mounted to the housing, a first gear; a first bearing rotatably fixed to the static sleeve; a second gear fixedly mounted to a second bearing, the first gear drivingly engaging the second gear and a multiple drive element, having a gear portion drivingly engaged with at least one if the first and second gears.

In accordance with a preferred embodiment of the present invention the multiple drive element includes an integrally formed, generally hollow, generally cylindrical element, having a toothed portion at a rearward end thereof and an inwardly tapered outer surface at a forward end thereof. Additionally or alternatively, the multiple drive element includes first and second windows located in mutually oppositely located regions of a cylindrical wall thereof.

Preferably, the multiple motion output subassembly includes a base element; a rearward plunger assembly, partially inserted into the base element; a forward plunger assembly partially inserted into the base element; a locking element slidably mounted onto the base element and first and second compression springs. Additionally the multiple motion output subassembly also includes an intermediate screw, slidably at least partially inserted into the base element and a rearward driving screw threadably inserted into the intermediate screw, the rearward driving screw rotatably mounted onto the base element.

In accordance with a preferred embodiment of the present invention the rearward driving screw in non-rotatably connected to a multiple drive element of the rotational motion output subassembly. Additionally, the multiple motion output subassembly also includes a forward driven element, rotatably mounted onto the intermediate screw, a piston engaging element, rotatably mounted onto a forward end of the forward driven element, a driving rod, axially slidably inserted through the rearward driving screw, the intermediate screw and at least partially through the forward driven element.

Preferably, the multiple motion output subassembly is configured to allow axial movement of the driving rod relative to the rearward driving screw, the intermediate screw and the forward driven element, and to prevent rotational movement of the driving pin relative to rearward driving screw.

In accordance with a preferred embodiment of the present invention the multiple motion output subassembly is configured to prevent axial relative movement between the base element and the rearward driving screw. Additionally or alternatively, the multiple motion output subassembly is configured to prevent relative rotational movement between the intermediate screw and a plunger assembly receiving cylinder of the base element and the rearward driving screw and to provide relative axial movement between the intermediate screw and the base element when the rearward driving screw is rotated.

Preferably, the multiple motion output subassembly is configured such that rotational movement of the rearward driving screw relative to the base element produces rotational movement of the driving pin, axial movement of the intermediate screw relative to the base element, rotational movement of the forward element relative to the base element and axial movement between the forward element and the intermediate screw.

In accordance with a preferred embodiment of the present invention the locking element is configured for locking engagement with the injection module.

Preferably, the electronic automatic injection device also includes at least one microswitch providing an output indication. Additionally, the output indication includes at least one of an indication of if the multiple motion output subassembly is in a fully retracted position, an indication of if a injection module is fully inserted and locked with respect to the multiple motion output subassembly, an indication of if the injection module is in a second operative orientation, an indication of if an RNS remover is engaged with the needle shield; an indication of if an injection actuation button has been actuated and an indication of if the multiple motion output subassembly is in a fully extended position.

Preferably, the housing includes a window and the device also includes a light disposed adjacent the window.

There is yet further provided in accordance with still another preferred embodiment of the present invention an injection module containing a material to be injected using an injection device, the injection module including a mounting element, a needleless cartridge including a piston, the needleless cartridge being retained in the mounting element and a piston extension element associated with the piston.

Preferably, the piston extension element includes a retaining portion which is mounted onto the needleless cartridge and a piston extending portion which lies rearwardly of the piston in operative engagement therewith and which is interconnected with the first portion by at least one frangible connection portion.

There is still further provided in accordance with another preferred embodiment of the present invention an injection module containing a material to be injected using an injection device, the injection module including a mounting element, a prefilled syringe fixedly retained in the mounting element and a needle shield located outside of the mounting element and arranged in slidable relationship therewith.

In accordance with a preferred embodiment of the present invention the injection module also includes a wireless transmitter and data storage assembly mounted on the needle shield and containing information to be displayed to a user of the injection module. Additionally or alternatively, the needle shield has formed on at least one elongate surface thereof at least one travel track suitable for interaction with an injector. In accordance with a preferred embodiment of the present invention at least three travel tracks are provided on each of at least two opposite-facing elongate surfaces thereof.

There is also provided in accordance with still another preferred embodiment of the present invention an injection module containing a material to be injected using a reusable injector, the injection module including a mounting element including an engagement locking portion for selectably removable axial engagement with the reusable injector and a prefilled container fixedly retained in the mounting element.

There is further provided in accordance with yet another preferred embodiment of the present invention a syringe including a syringe body, a telescopic plunger slidably and sealably displaceable in the syringe body and including at least a first element, an intermediate element slidably connected to the at least first element and a second element slidably connected to the intermediate element, the at least a first element being operative to drive the second element.

There is yet further provided in accordance with another preferred embodiment of the present invention a method for injecting a material including providing an injection device configured to receive an injection module containing a material to be injected and including, at least one forward driving spring and a forward driving spring compression assembly operative in response to insertion of the injection module into the device for automatically compressing the forward driving spring, inserting the injection module into device, thereby automatically compressing the forward driving spring and without any further manipulation of the injection device, thereafter pressing an injection actuation button, which immediately provides injection of the material.

BRIEF DESCRIPTION OF THE DRAWINGS

The present invention will be understood and appreciated more fully from the following detailed description, taken in conjunction with the drawings in which:

FIGS. 1B & 1C are simplified partial pictorial illustrations of two different views of the fully assembled electronic automatic injection device of FIG. 1A seen from a rearward end;

FIGS. 6A and 6B are simplified respective partially exploded and assembled view illustrations of an upper biasing assembly mounted in elongate needle shield biasing spring enclosure forming part of the upper housing assembly of the electronic automatic injection device of FIGS. 1A-4D;

FIG. 6C is a simplified partially sectional illustration of the upper biasing assembly of FIGS. 6A & 6B taken along the lines C-C of FIG. 6B;

FIG. 7A is a simplified exploded view illustration of the lower housing assembly of the electronic automatic injection device of FIGS. 1A-2 shown from a normally upward facing side thereof;

FIG. 7B is a simplified exploded illustration of the lower housing assembly of the electronic automatic injection device of FIGS. 1A-2 shown from a normally downward facing side thereof;

FIGS. 8B & 8C are simplified illustrations showing various views of the lower housing portion of the lower housing assembly of the electronic automatic injection device of FIGS. 1A-2 seen from a upward facing side;

FIG. 8D is a simplified pictorial illustration of the lower housing portion of the lower housing assembly of the electronic automatic injection device of FIGS. 1A-2 seen from a downward facing side thereof;

FIGS. 8E & 8F are simplified illustrations showing various views of the lower housing portion of the lower housing assembly of the electronic automatic injection device of FIGS. 1A-2 seen from a side thereof;

FIGS. 9A & 9B are simplified pictorial illustrations of an injection module release button forming part of the electronic automatic injection device of FIGS. 1A-2 as seen from mutually opposite directions;

FIGS. 11A & 11B are simplified pictorial illustrations of a biasing element forming part of the lower housing assembly of the electronic automatic injection device of FIGS. 1A-2 shown from a forward end and a rearward end respectively;

FIGS. 11C & 11D are simplified respective side view and end view illustrations of the biasing element of FIGS. 11A & 11B, taken in directions indicated by arrows C and D respectively in FIG. 11A;

FIGS. 12B & 12C are simplified assembled view illustrations corresponding to FIG. 12A and particularly showing the biasing assembly of FIG. 2 mounted in an elongate needle shield biasing spring enclosure forming part of the lower housing assembly of the electronic automatic injection device of FIGS. 7A-8D;

FIGS. 15A and 15B are simplified pictorial illustrations of a rearward portion of the end housing assembly of the electronic automatic injection device of FIGS. 1A-2 seen from respective forward and rearward ends thereof;

FIGS. 15C & 15D are elevation view illustrations of the rearward portion of the end housing assembly of FIGS. 15A-15B, taken along respective directions indicated by arrows C and D in FIG. 15A;

FIG. 15E is a sectional illustration of the rearward portion of the end housing assembly, taken along lines E-E in FIG. 15D;

FIGS. 18A and 18B are simplified pictorial illustrations of an injection depth selector of the end housing assembly of the electronic automatic injection device of FIGS. 1A-2 seen from respective forward and rearward ends thereof;

FIGS. 18C & 18D are elevation view illustrations of the injection depth selector of FIGS. 18A-18B, taken along respective directions indicated by arrows C and D in FIG. 18A;

FIGS. 19C & 19D are elevation view illustrations of the multiple drive element of FIGS. 19A & 19B, taken along respective directions indicated by arrows C and D in FIG. 19A;

FIGS. 19E & 19F are sectional illustrations of the multiple drive element of FIGS. 19A & 19B, taken along respective lines E-E and F-F in FIG. 19C;

FIGS. 24E, 24F, 24G & 24H are simplified, partially cut away elevation view illustrations of the base element of FIGS. 24A-24D, taken along lines E, F, G and H in FIGS. 24A & 24B;

FIGS. 27A & 27B are simplified pictorial illustrations of a rearward driving screw, forming part of the multiple motion output subassembly of FIG. 23, seen from respective forward and rearward ends thereof;

FIG. 27C is a simplified sectional illustration of the rearward driving screw of FIGS. 27A & 27B, taken along the line C in FIG. 27A;

FIGS. 39A and 39B are simplified pictorial illustrations of a mounting element forming part of the prefilled syringe injection module of FIG. 38, seen from a forward end and a rearward end respectively;

FIGS. 39C, 39D and 39E are respective simplified sectional illustrations of the mounting element of FIGS. 39A & 39B, taken along respective lines C-C, D-D and E-E;

FIG. 50C is a simplified partially cut away illustration of the electronic automatic injection device of FIGS. 1A-2 seen from the first direction and showing in various enlargements the mounting of the electronic control assembly and four micro switches;

FIG. 50D is a simplified partially cut away illustration of the electronic automatic injection device of FIGS. 1A-2 seen from the second direction and showing in various enlargements the mounting of two additional microswitches;

FIGS. 51A & 51B are illustrations of the electronic automatic injection device of FIGS. 1A-2 in respective open and closed operative states;

FIGS. 52A, 52B, 52C, 52D, 52E & 52F are simplified illustrations of the electronic automatic injection device of FIGS. 1A-51B in a first illustrative operative state, which is a typical "out of the box" state;

FIGS. 57A, 57B, 57C & 57D are simplified illustrations of the electronic automatic injection device of FIGS. 1A-51B in a third illustrative operative state, which is a typical "partial insertion of a prefilled syringe injection module" state;

FIGS. 58A, 58B, 58C & 58D are simplified illustrations of the electronic automatic injection device of FIGS. 1A-51B in a fourth illustrative operative state, which is a typical "full insertion of a prefilled syringe injection module" state;

FIGS. 61A, 61B, 61C & 61D are simplified illustrations of the electronic automatic injection device employing a prefilled syringe injection module of FIGS. 1A-51B in a sixth illustrative operative state, which is a typical injection site engagement state;

FIGS. 62A, 62B, 62C, 62D & 62E are simplified illustrations of the electronic automatic injection device employing a prefilled syringe injection module of FIGS. 1A-51B in a seventh illustrative operative state, which is a typical needle penetration and injection state;

FIGS. 63A, 63B, 63C & 63D are simplified illustrations of the electronic automatic injection device employing a prefilled syringe injection module of FIGS. 1A-51B in a eighth illustrative operative state, which is a typical injection site disengagement state;

FIGS. 64A, 64B, 64C & 64D are simplified illustrations of the electronic automatic injection device employing a prefilled syringe injection module of FIGS. 1A-51B in a ninth illustrative operative state, which is a typical prefilled syringe injection module release state;

FIGS. 65A, 65B & 65C are simplified illustrations of the electronic automatic injection device employing a prefilled syringe injection module of FIGS. 1A-51B in a tenth illustrative operative state, which is a typical prefilled syringe injection module removal state;

FIGS. 68A & 68B are simplified illustrations of the electronic automatic injection device employing a needleless cartridge of FIGS. 1A-51B in a third operative state, which is a needle attachment state;

Figure 1A:
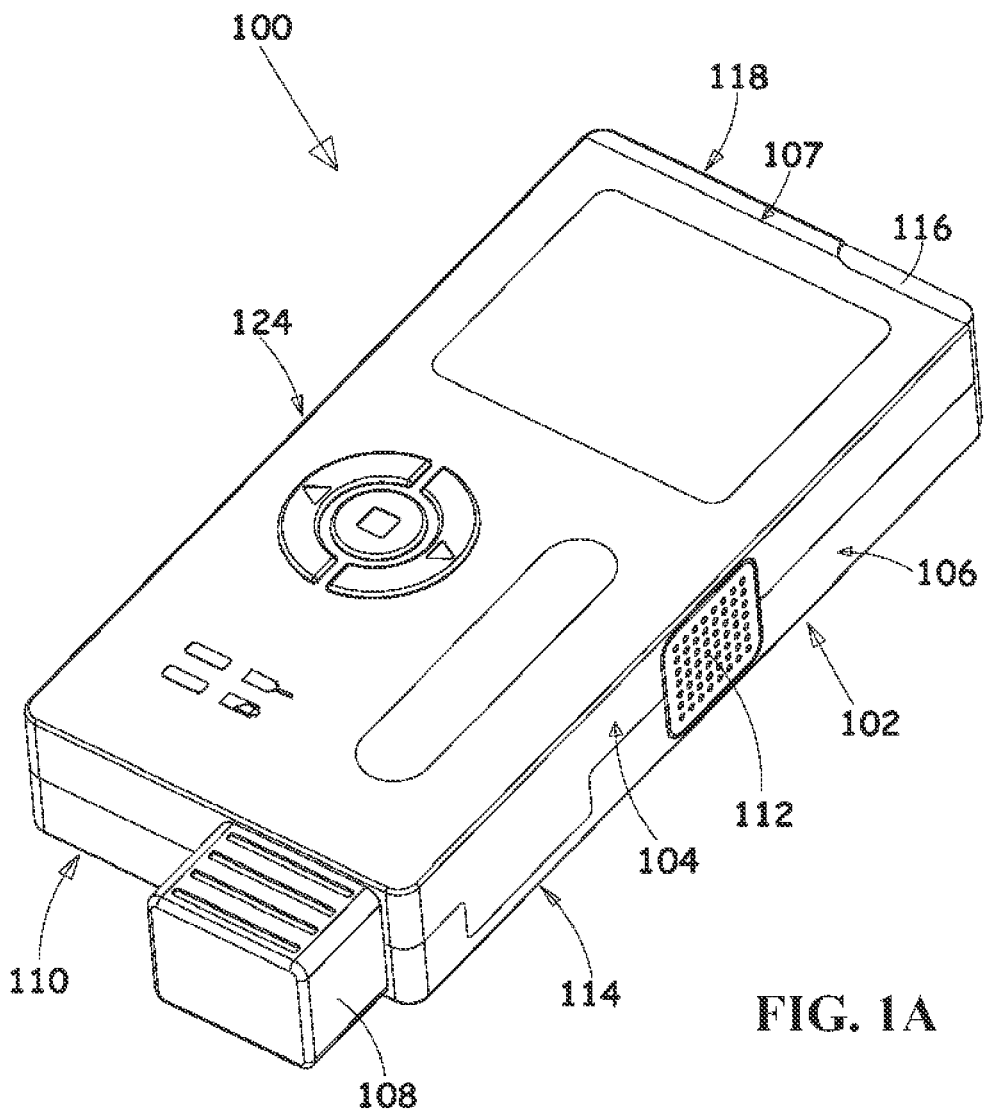
FIG. 1A is a simplified pictorial illustration of a fully assembled electronic automatic injection device shown from a forward end, constructed and operative in accordance with an embodiment of the present invention in a ready-to-use operational state.
Figure 71A:
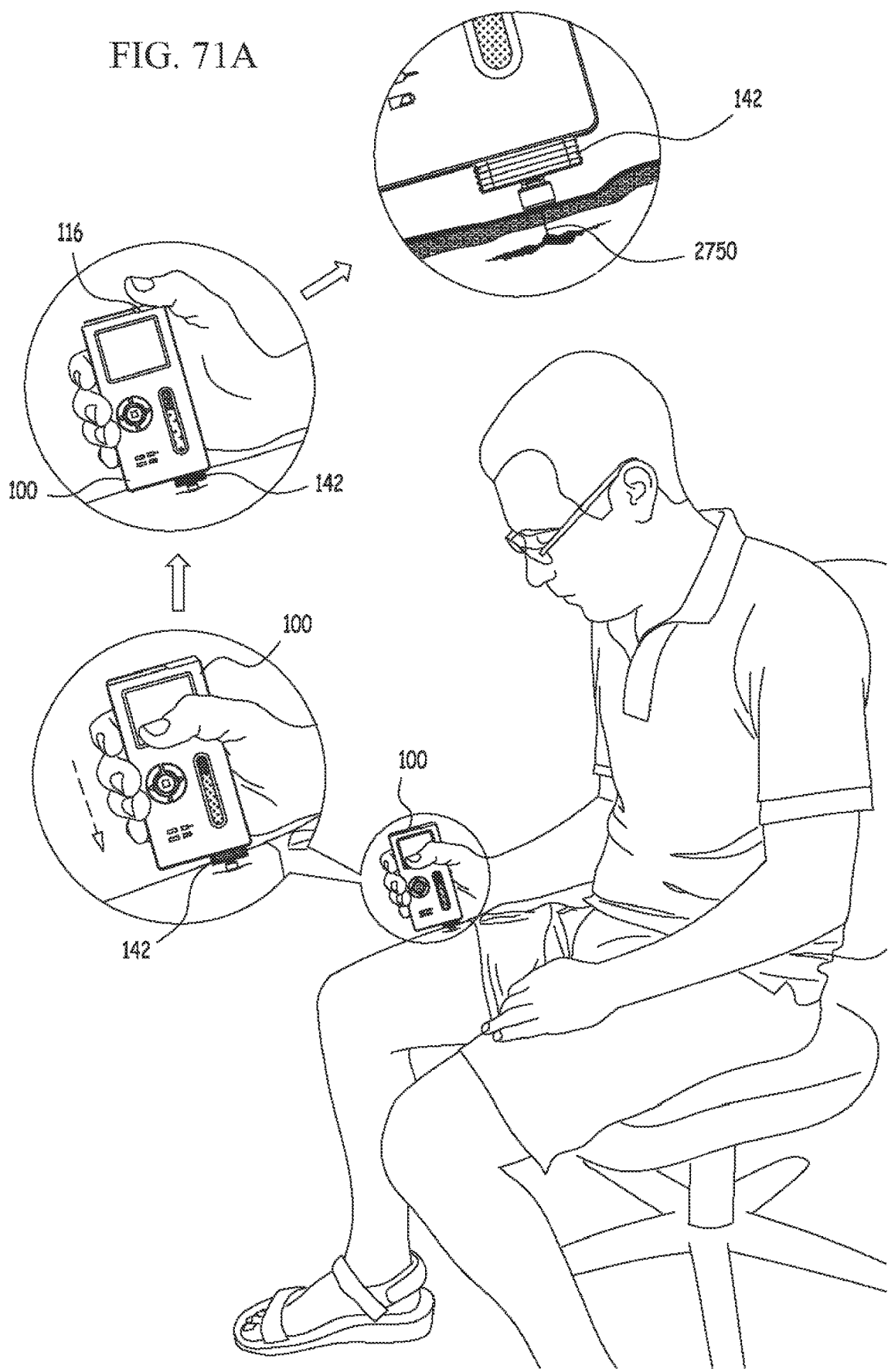
Figure 71B:
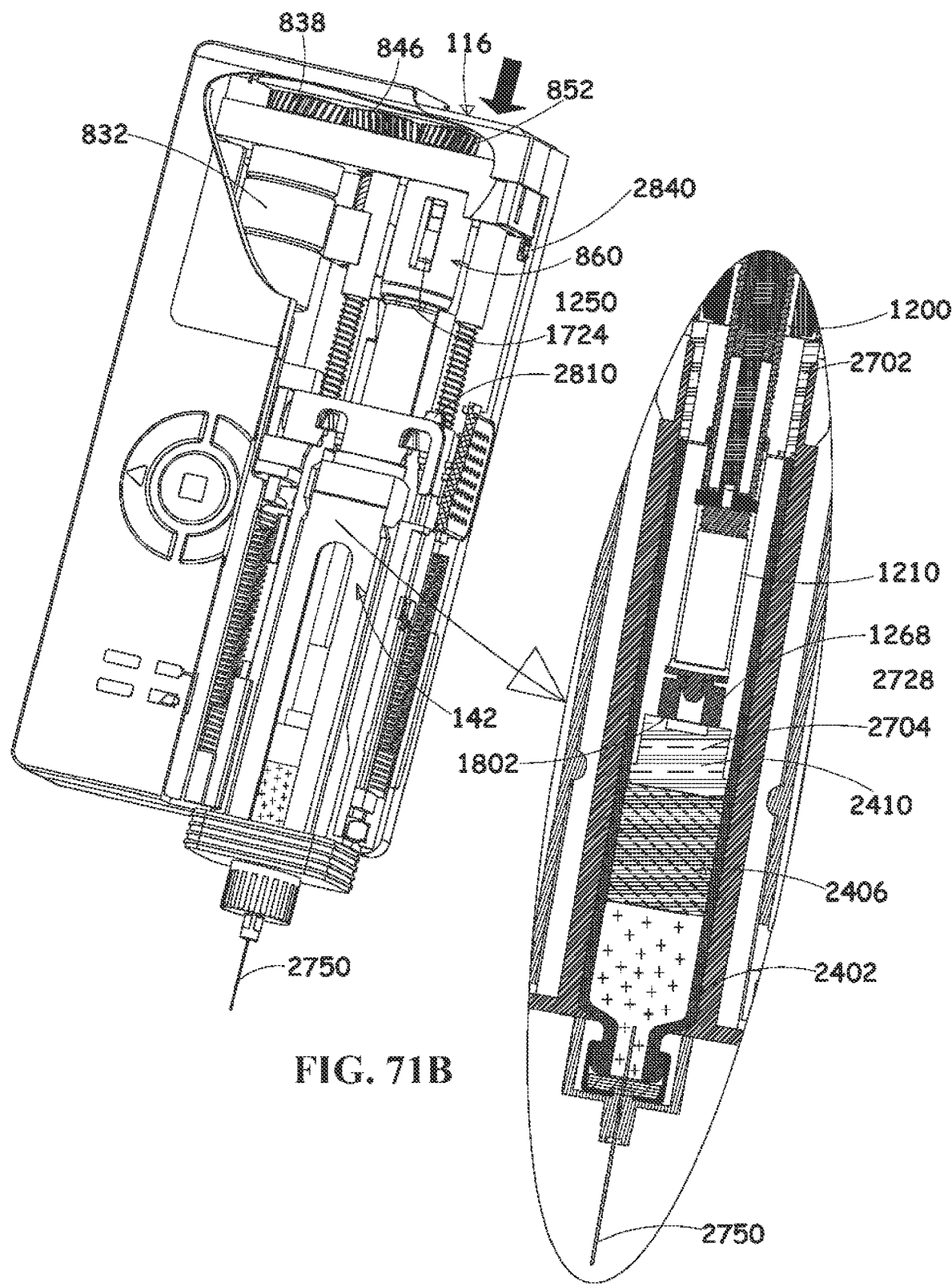
Figure 71C:
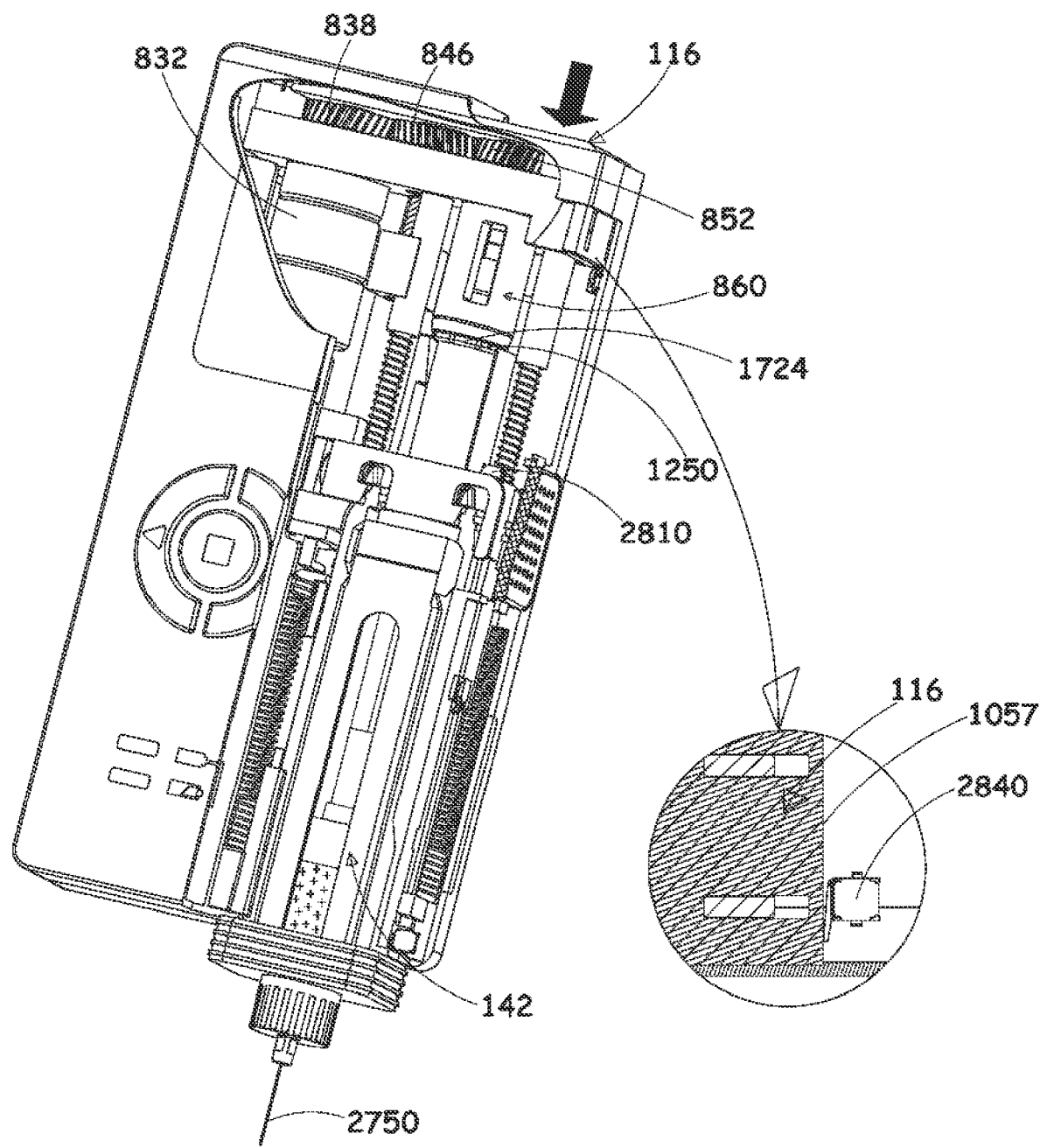
Figure 72A:
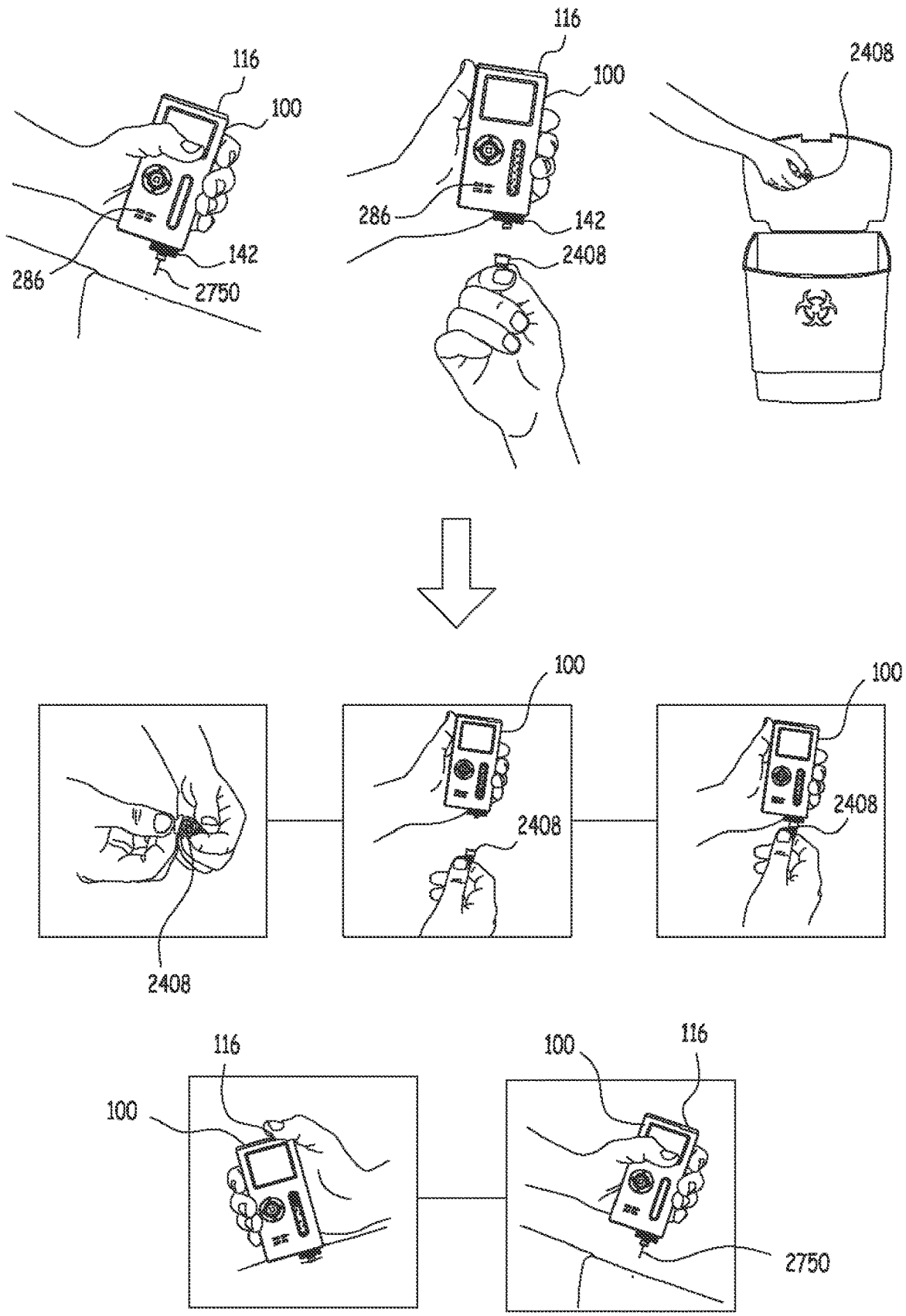
Figure 72B:
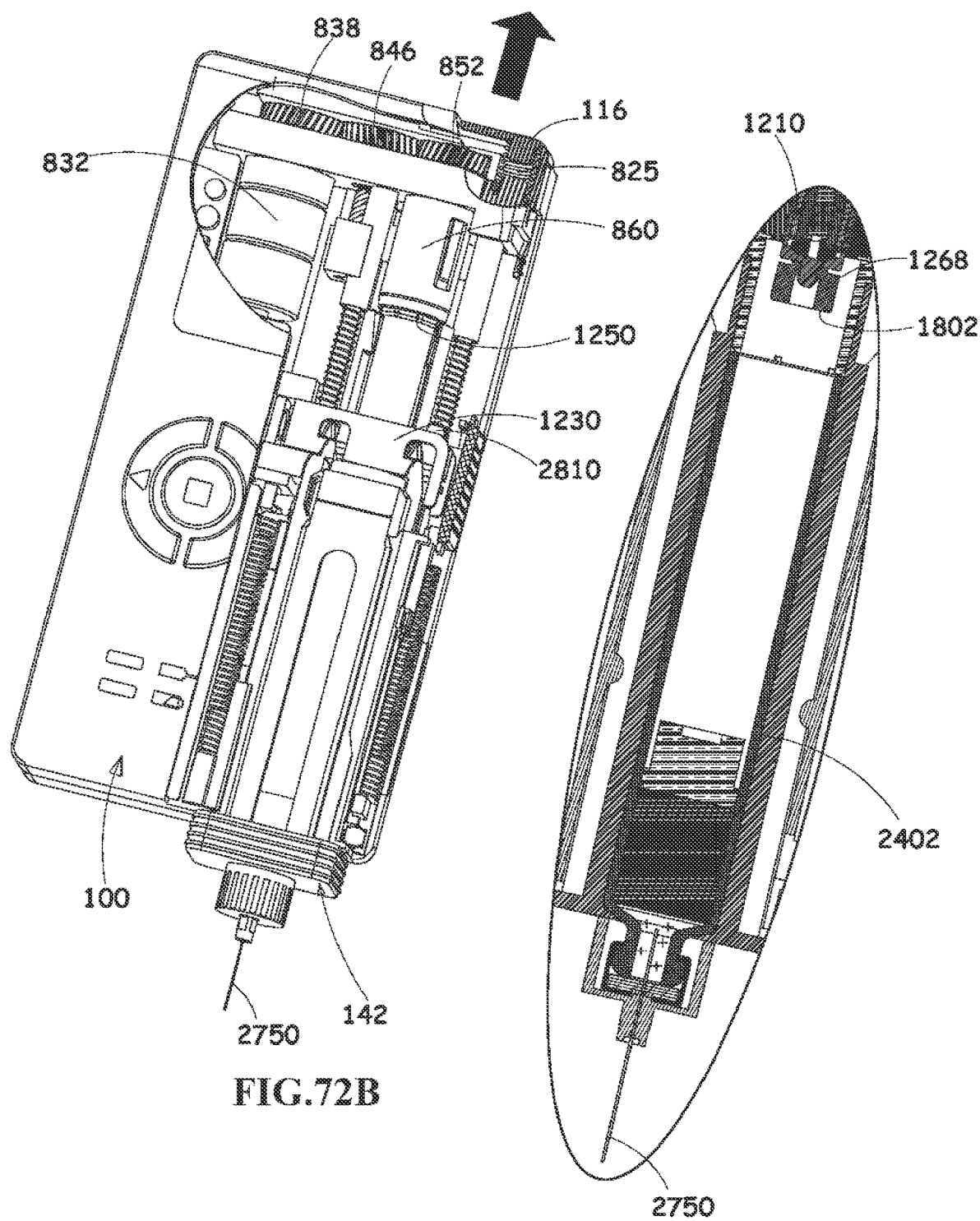
Figure 72C:
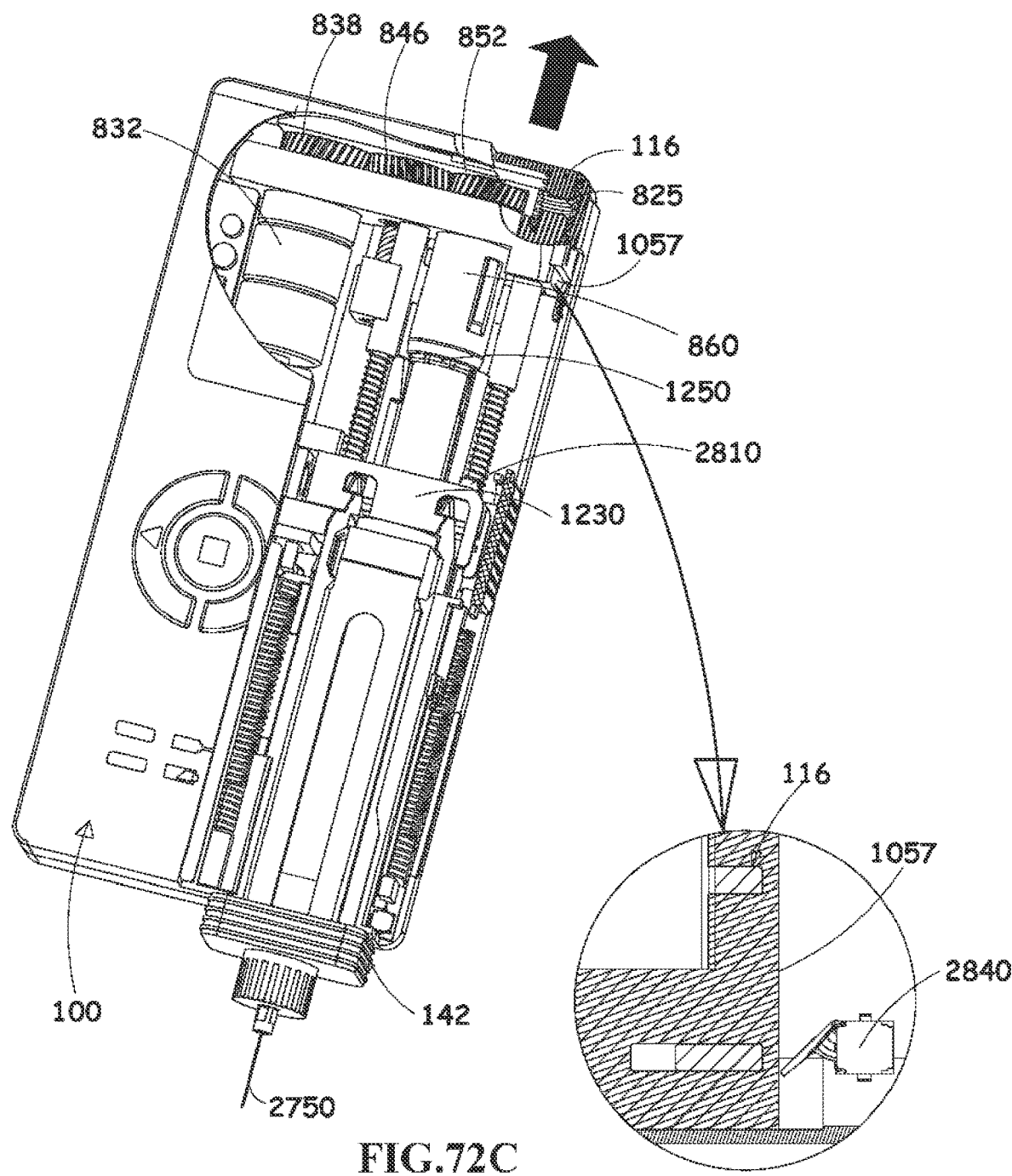
Figure 73A:
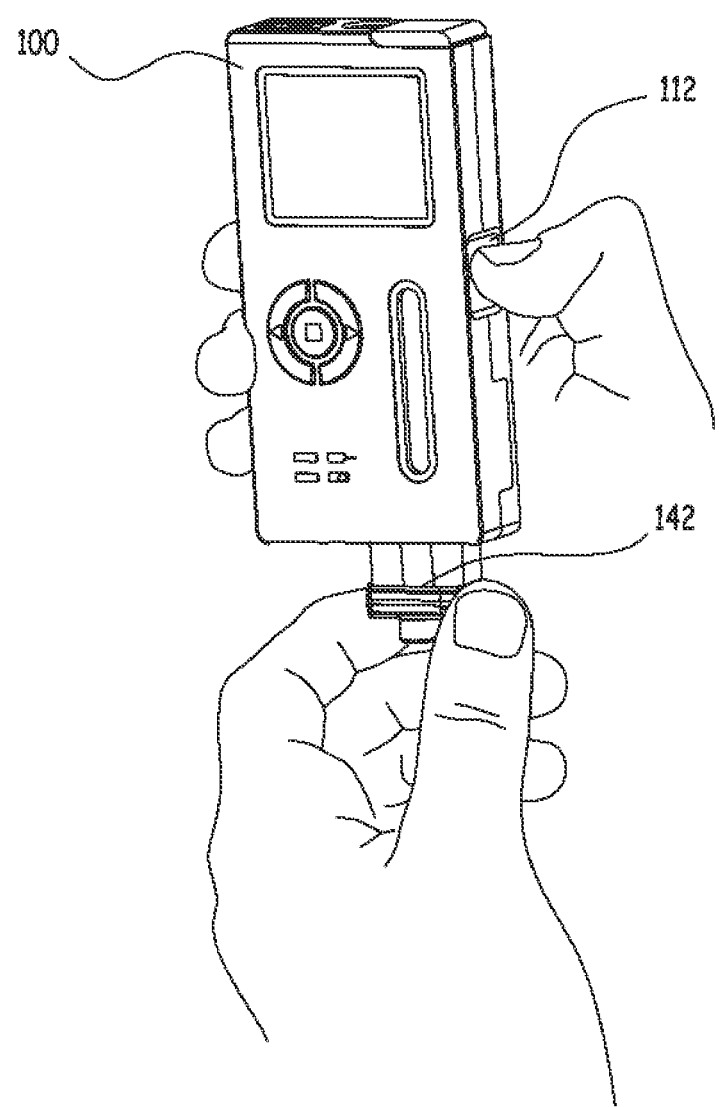
Figure 73B:
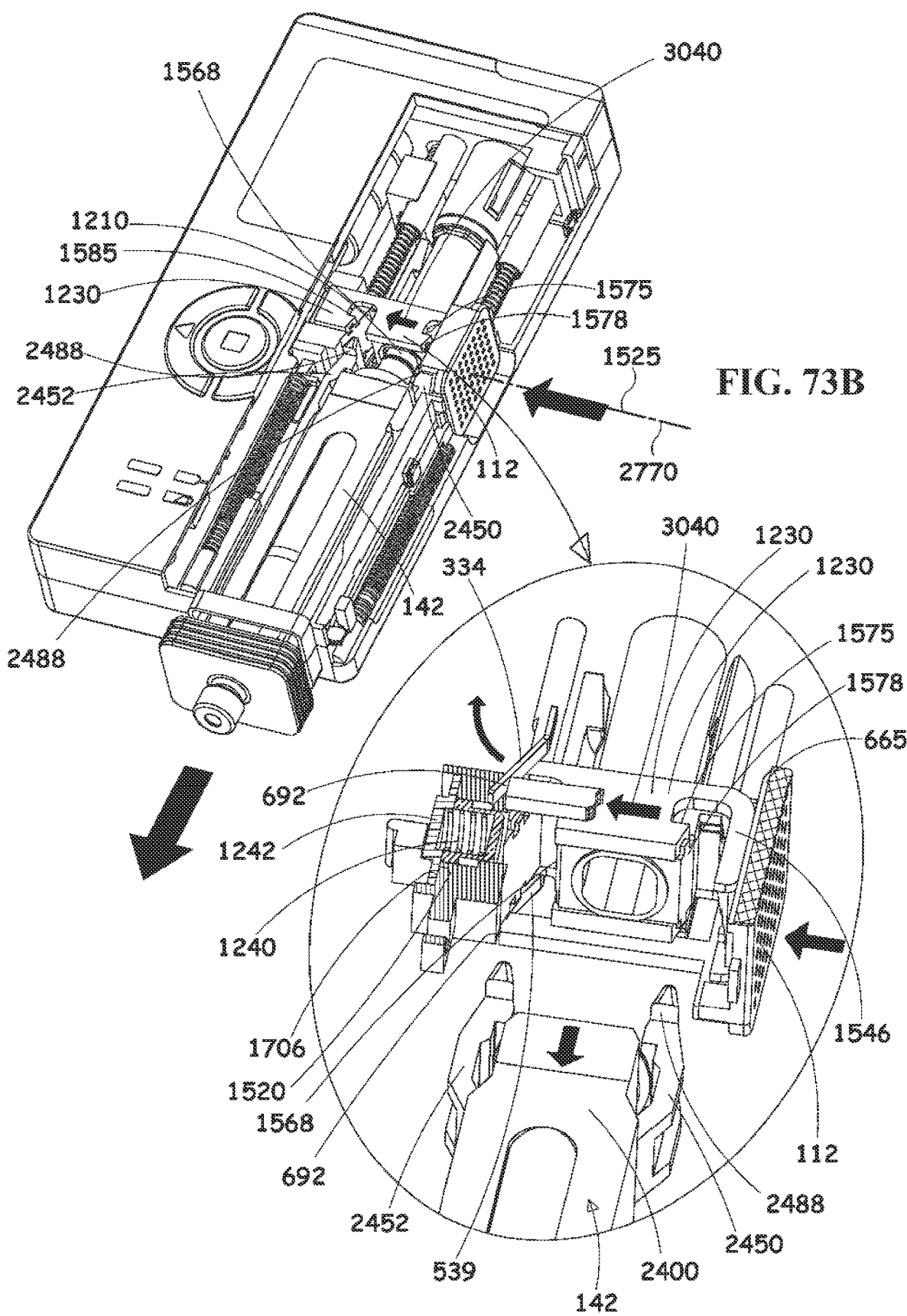
Figure 73C:
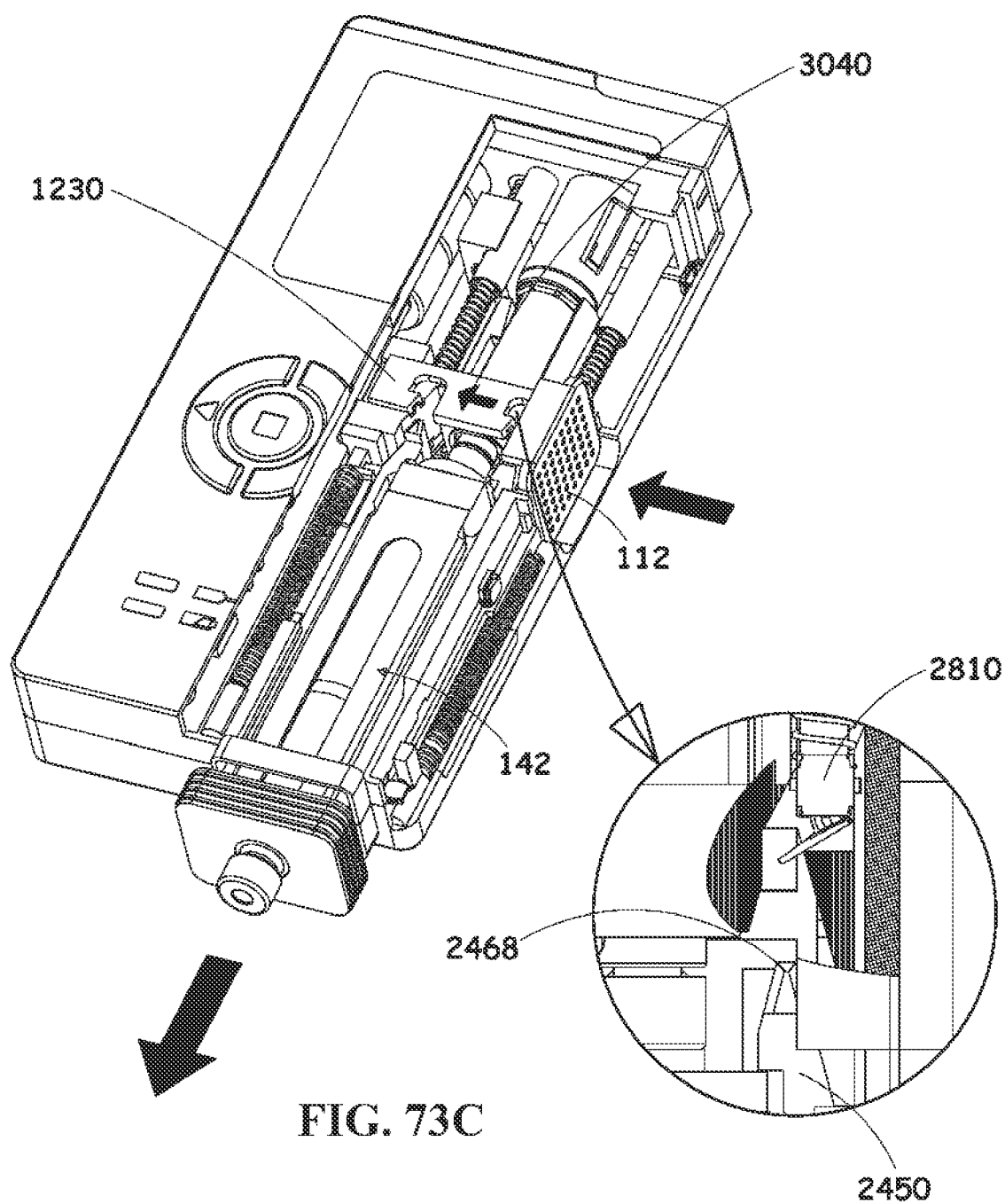
Figure 74A:
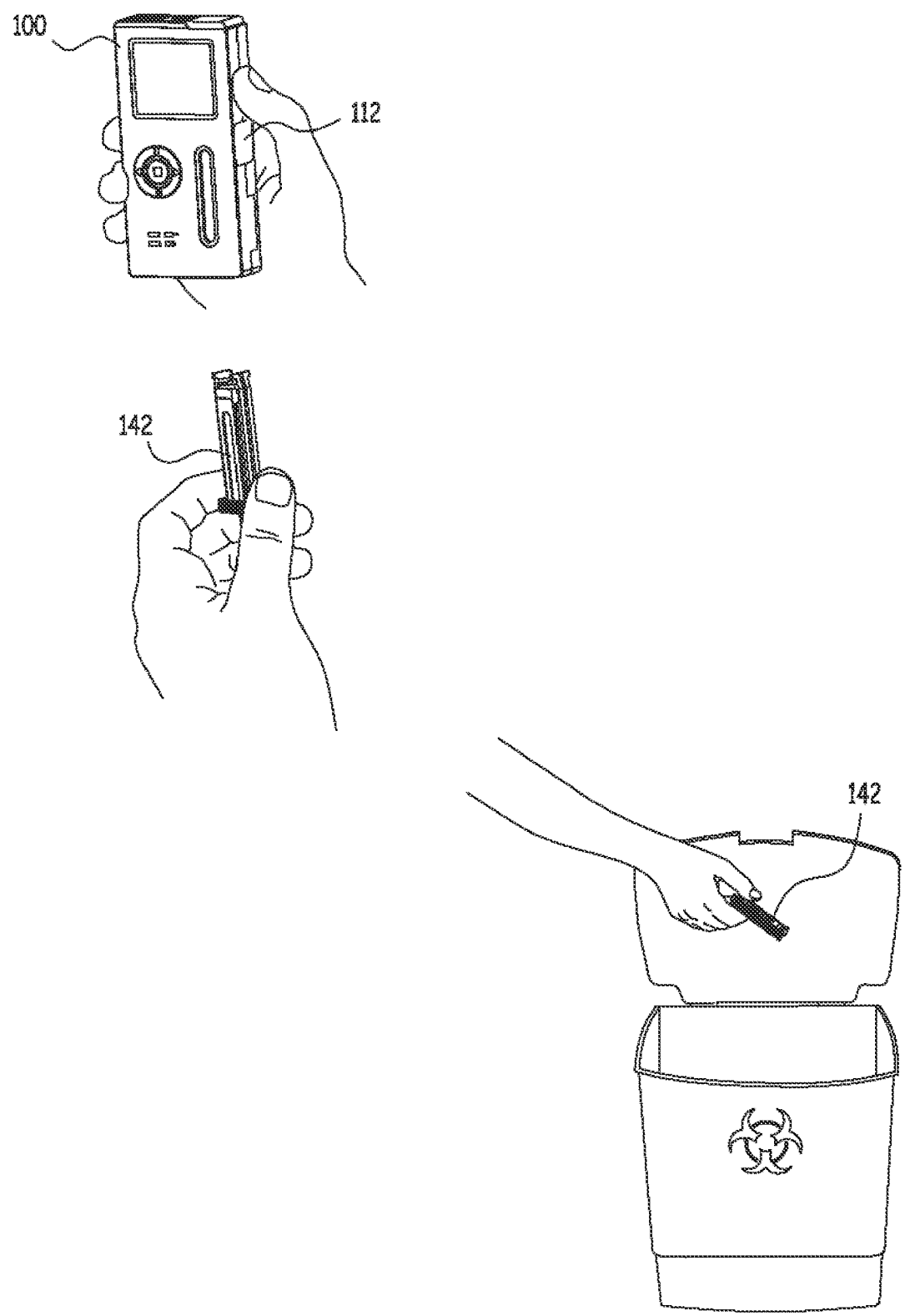
Figure 74B:
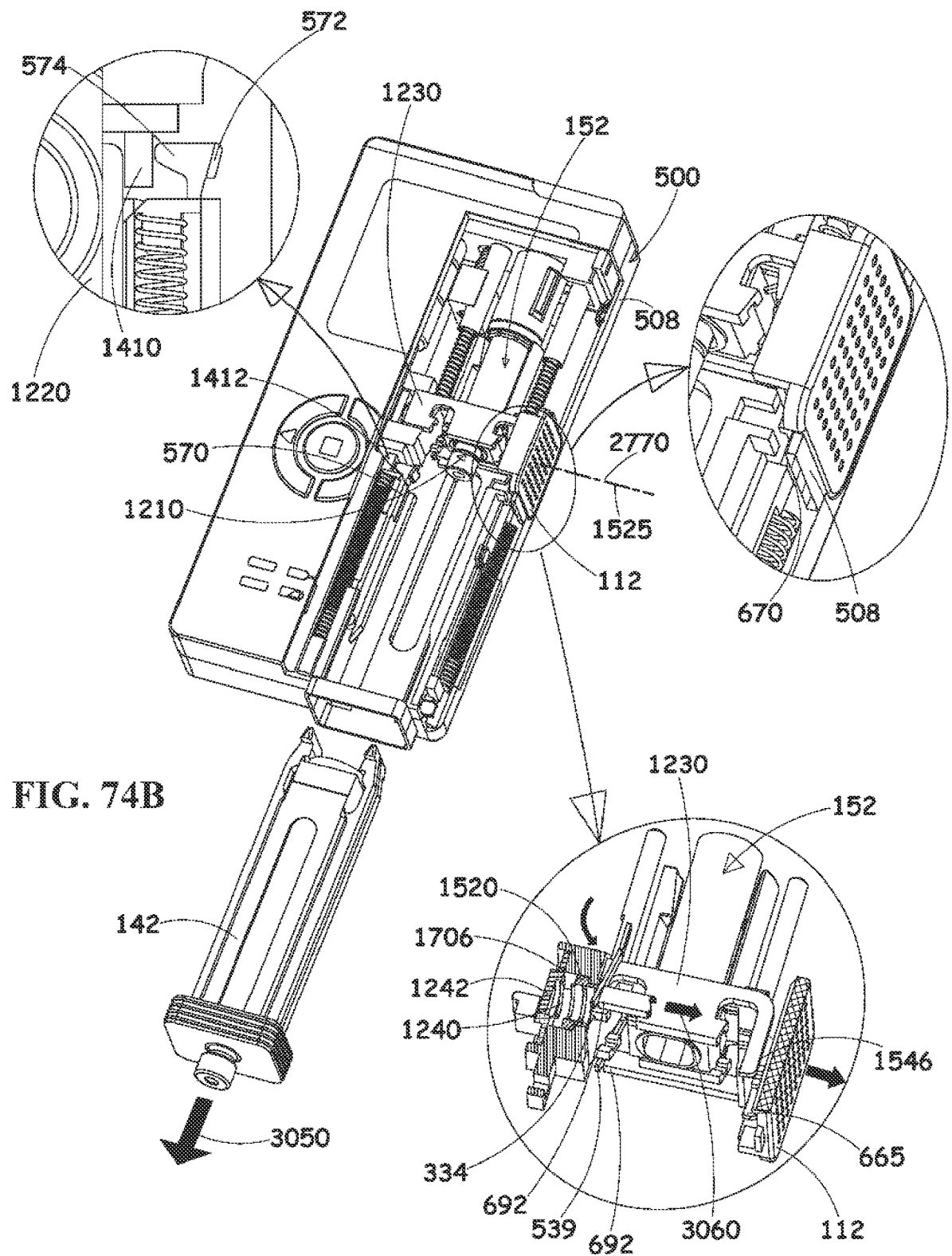
Figure 75:
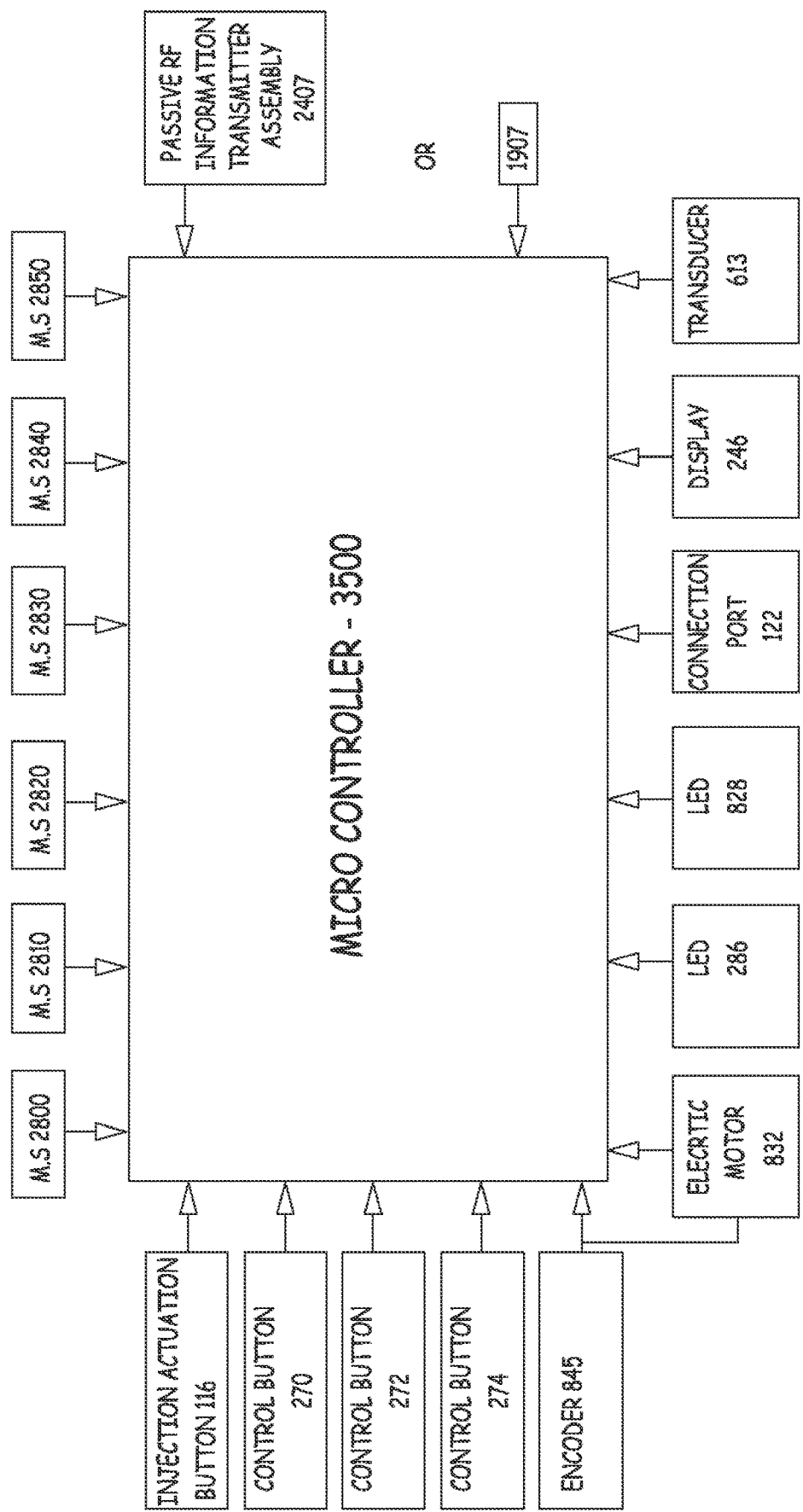
Figure 76A:
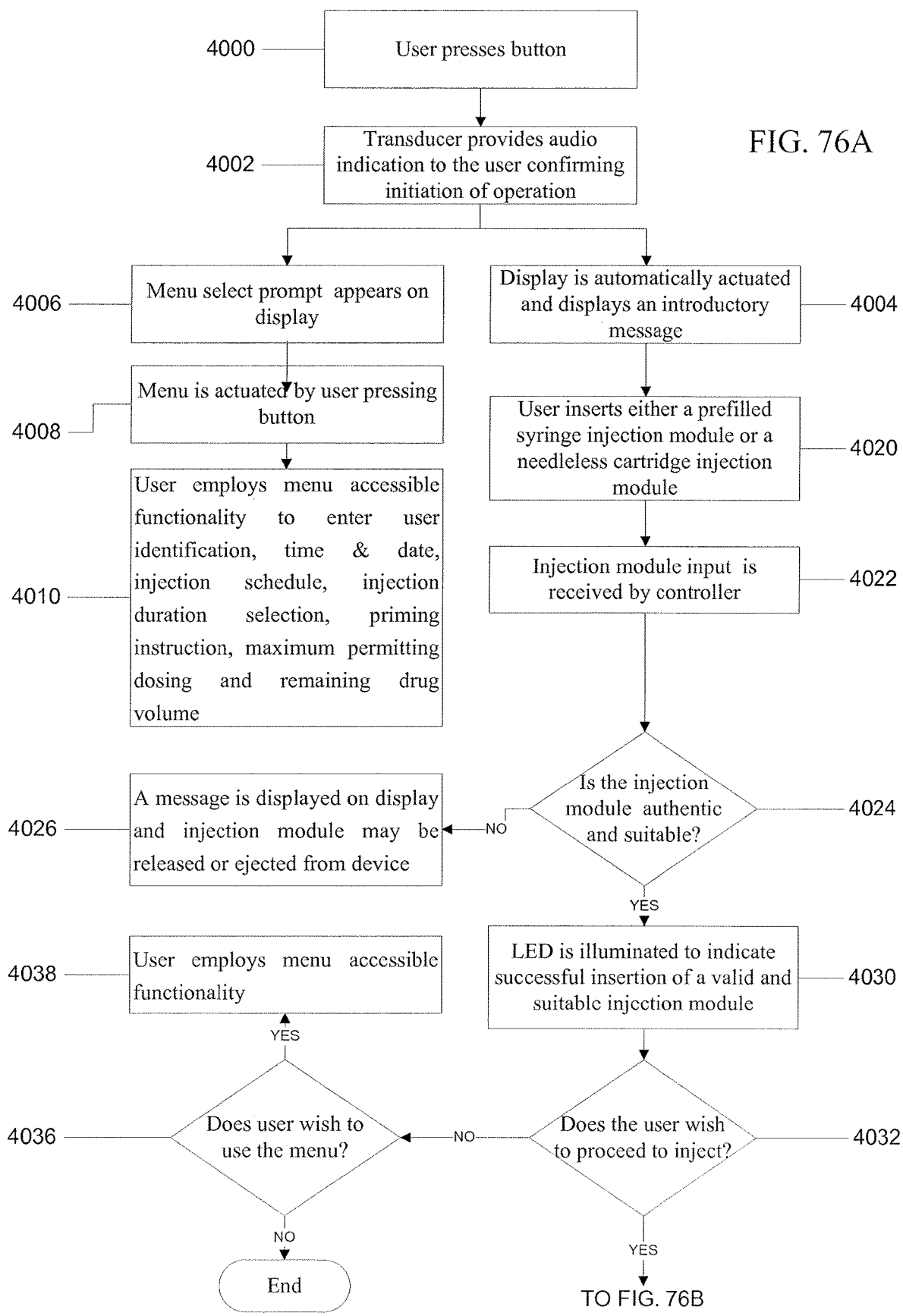
Figure 76B:
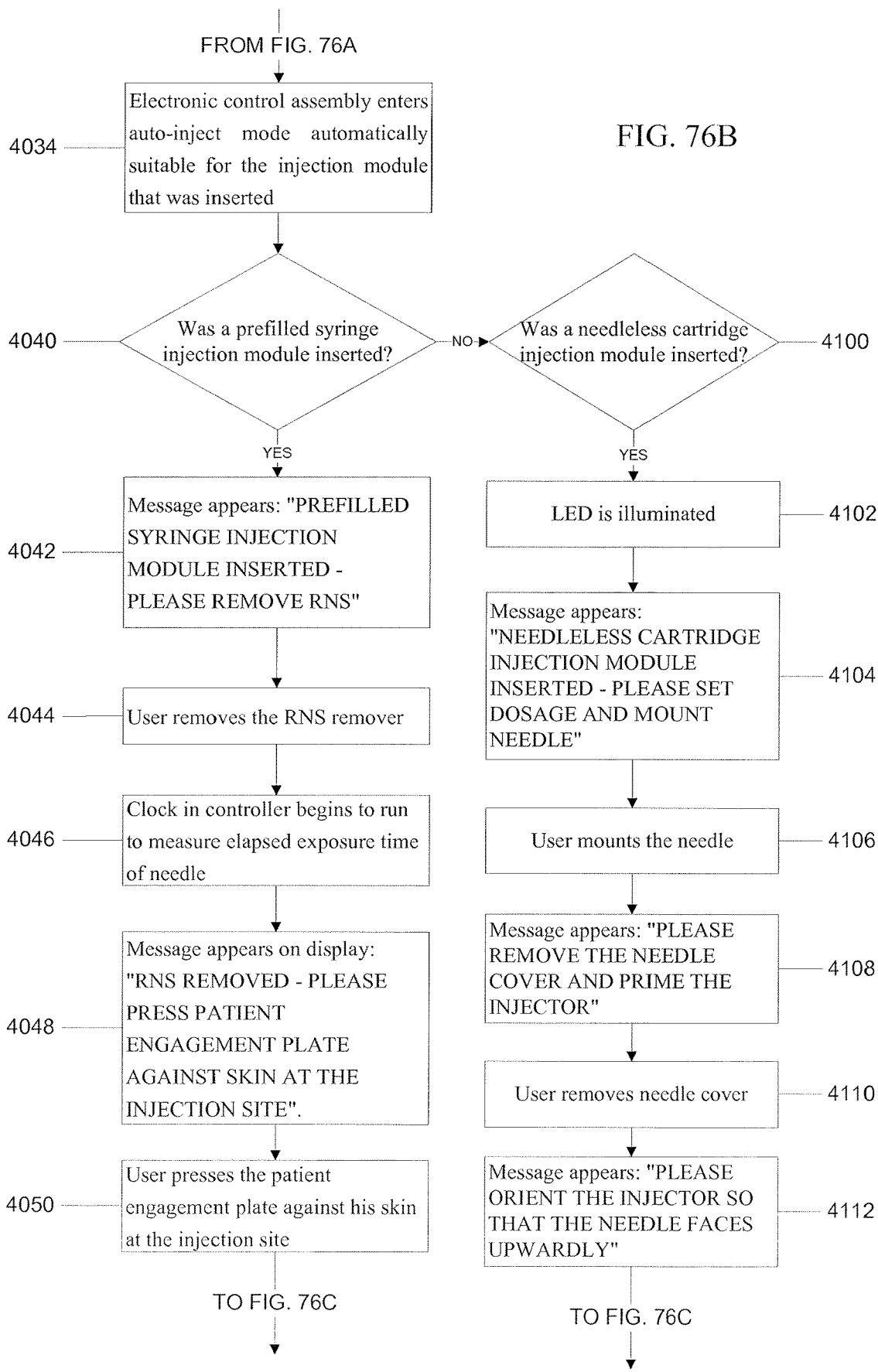
Figure 76C:
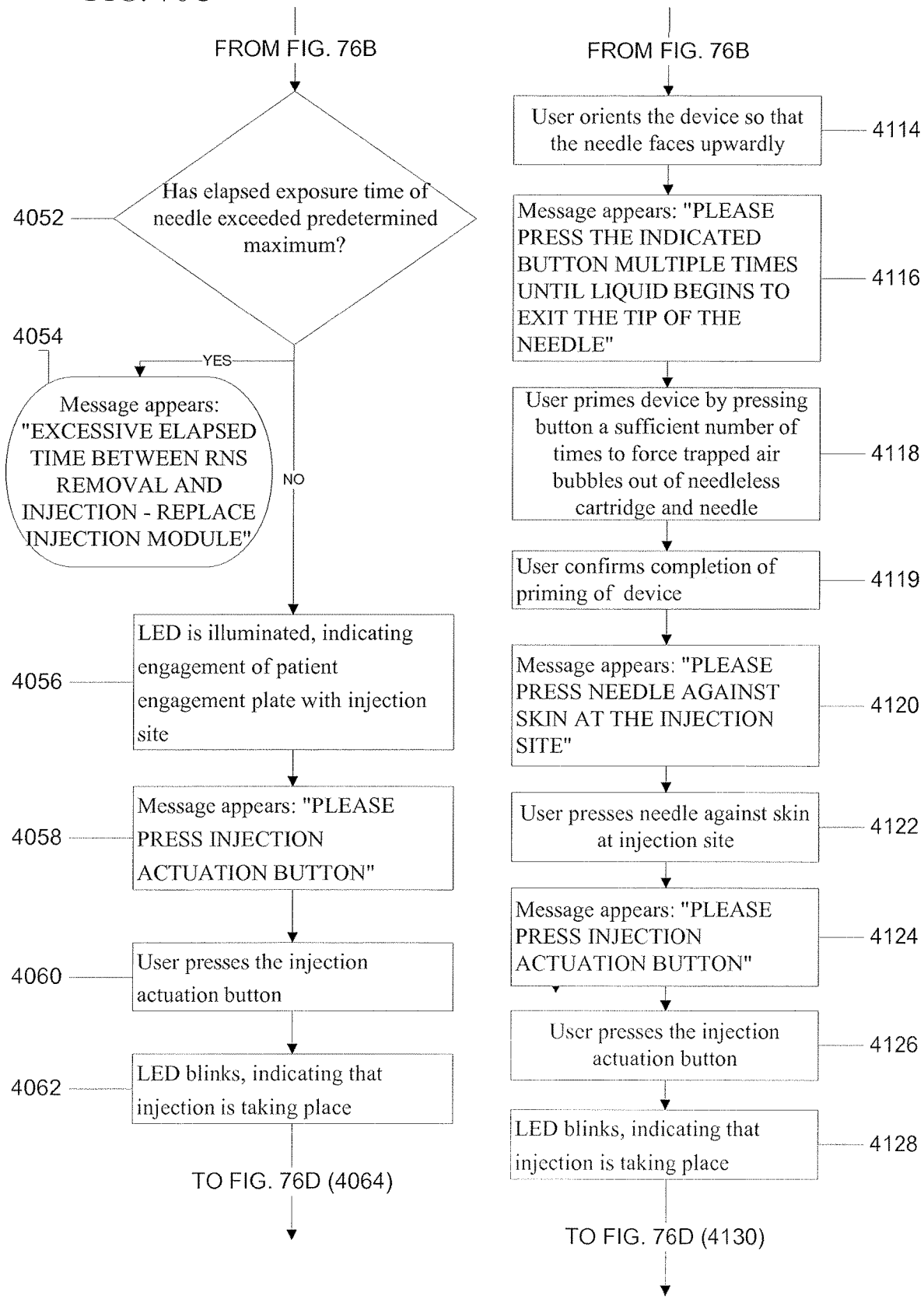
Figure 76D:
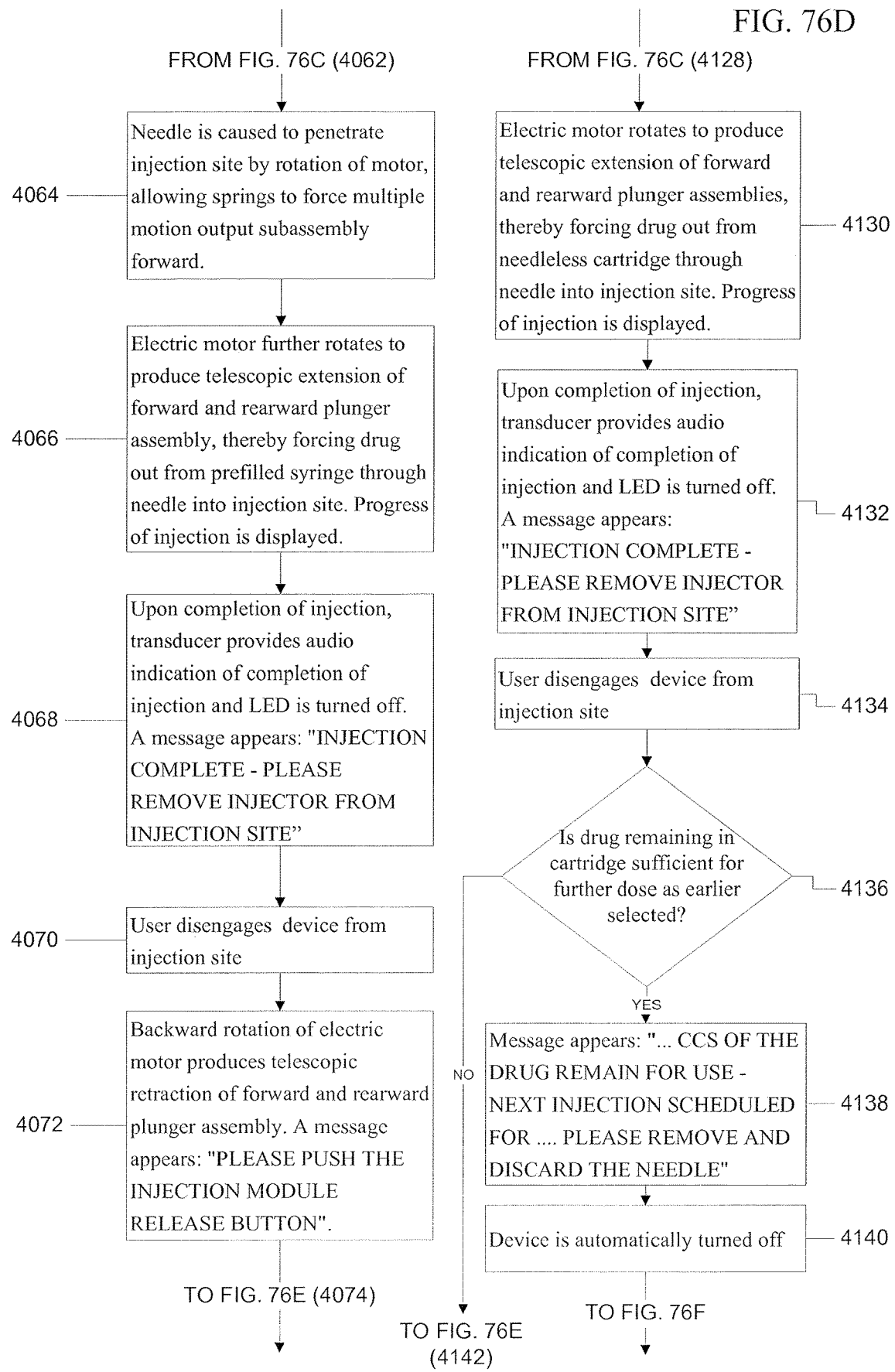
Figure 76E:
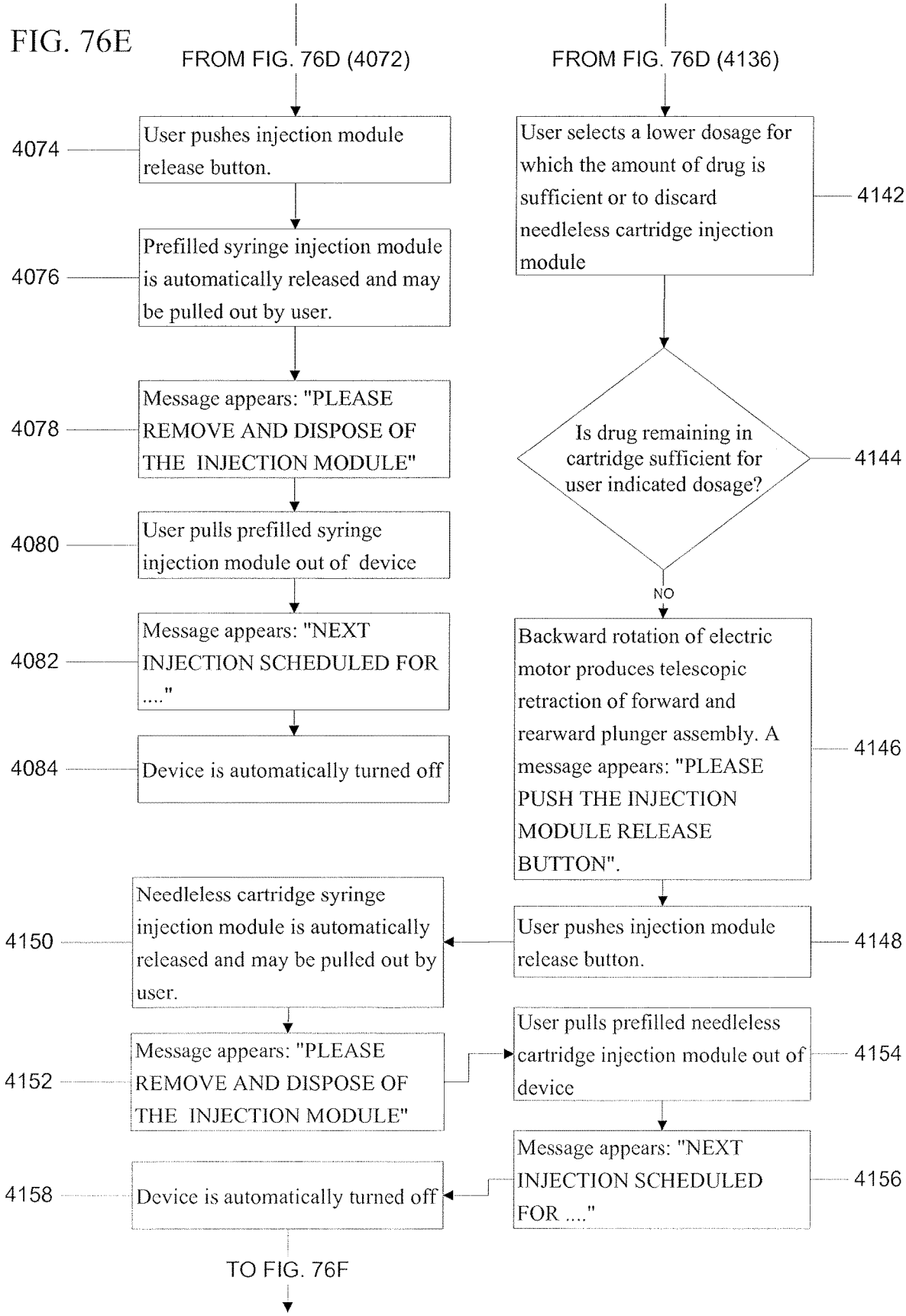

FIGS. 71A, 71B and 71C are simplified illustrations of the electronic automatic injection device employing a needleless cartridge injection module of FIGS. 1A-51B in a fifth illustrative operative state, which is a typical injection site engagement, needle penetration and injection state, which generally corresponds to the sixth and seventh states described above with reference to FIGS. 61A-62E of the electronic automatic injection device employing a prefilled syringe injection module;

FIGS. 72A, 72B and 72C are simplified illustrations of the electronic automatic injection device employing a needleless cartridge injection module of FIGS. 1A-51B in a sixth illustrative operative state, which is repeated typical dosage selection, needle replacement, injection site engagement, needle penetration and injection state, which generally corresponds to the third to fifth states described above with reference to FIGS. 68A-71C of the electronic automatic injection device employing a needleless cartridge injection module;

FIGS. 73A, 73B & 73C are simplified illustrations of the electronic automatic injection device employing a needleless cartridge injection module of FIGS. 1A-51B in a seventh illustrative operative state, which is a typical needleless cartridge injection module release state which corresponds to the ninth state of the electronic automatic injection device employing prefilled syringe injection module release state shown in FIGS. 64A-64D;

FIGS. 74A & 74B are simplified illustrations of the electronic automatic injection device employing a needleless cartridge injection module of FIGS. 1A-51B in an eighth illustrative operative state, which is a typical needleless cartridge injection module removal state which corresponds to the tenth state of the electronic automatic injection device employing prefilled syringe injection module release state shown in FIGS. 65A-65D;

FIG. 75 is a simplified functional block diagram illustration of the electronic control assembly forming part of the electronic automatic injection device of FIGS. 1A-74B; and FIGS. 76A-76F are together a simplified flowchart illustrating operation of the electronic control assembly of FIG. 75.

DETAILED DESCRIPTION OF A PREFERRED EMBODIMENT

Reference is now made to FIGS. 1A-1D and 2, which are illustrations of an electronic automatic injection device 100 constructed and operative in accordance with an embodiment of the present invention.

Figure 1D:
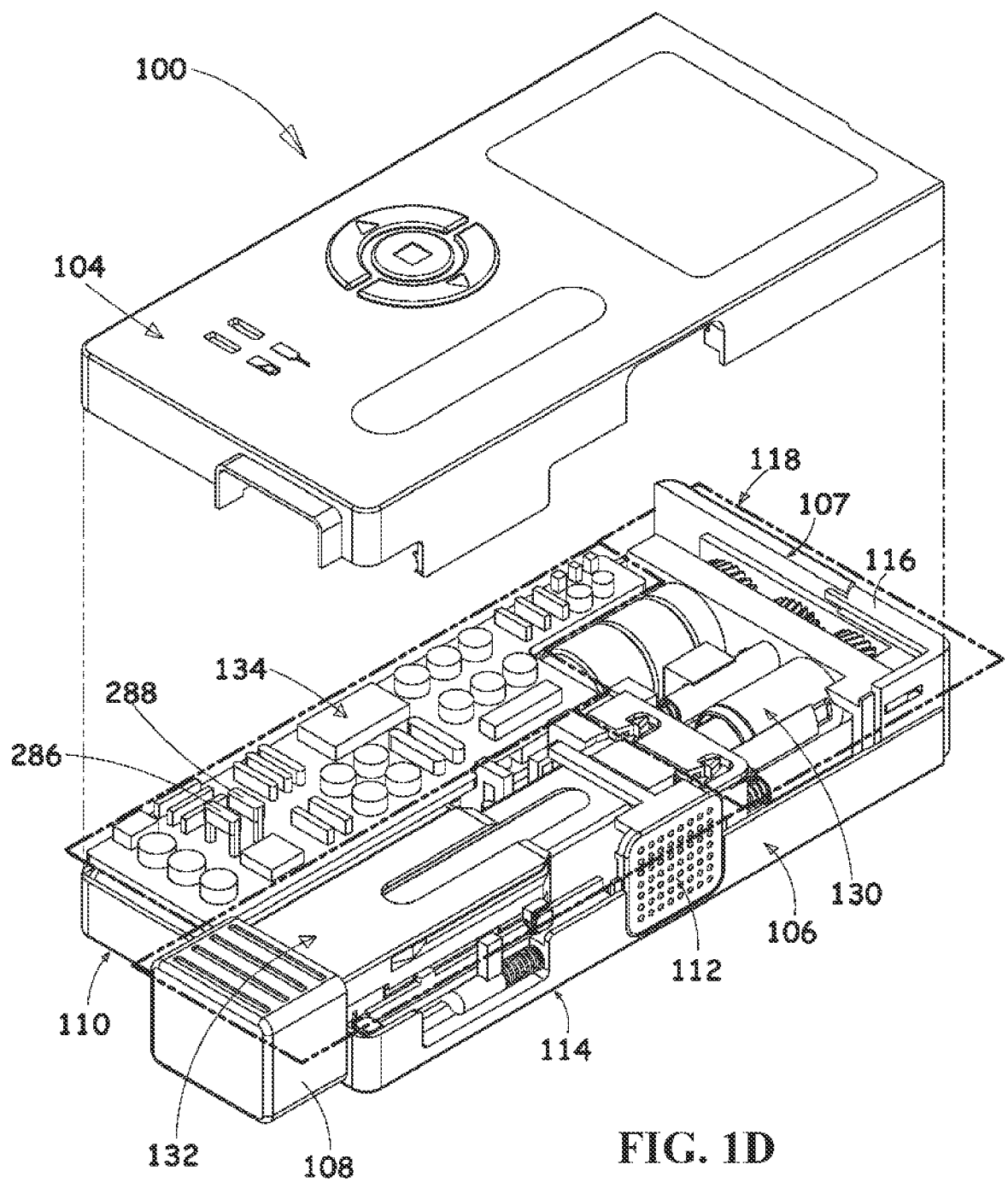
FIG. 1D is a simplified partially exploded view illustration of the assembled electronic automatic injection device of FIGS. 1A-1C.
Figure 2:
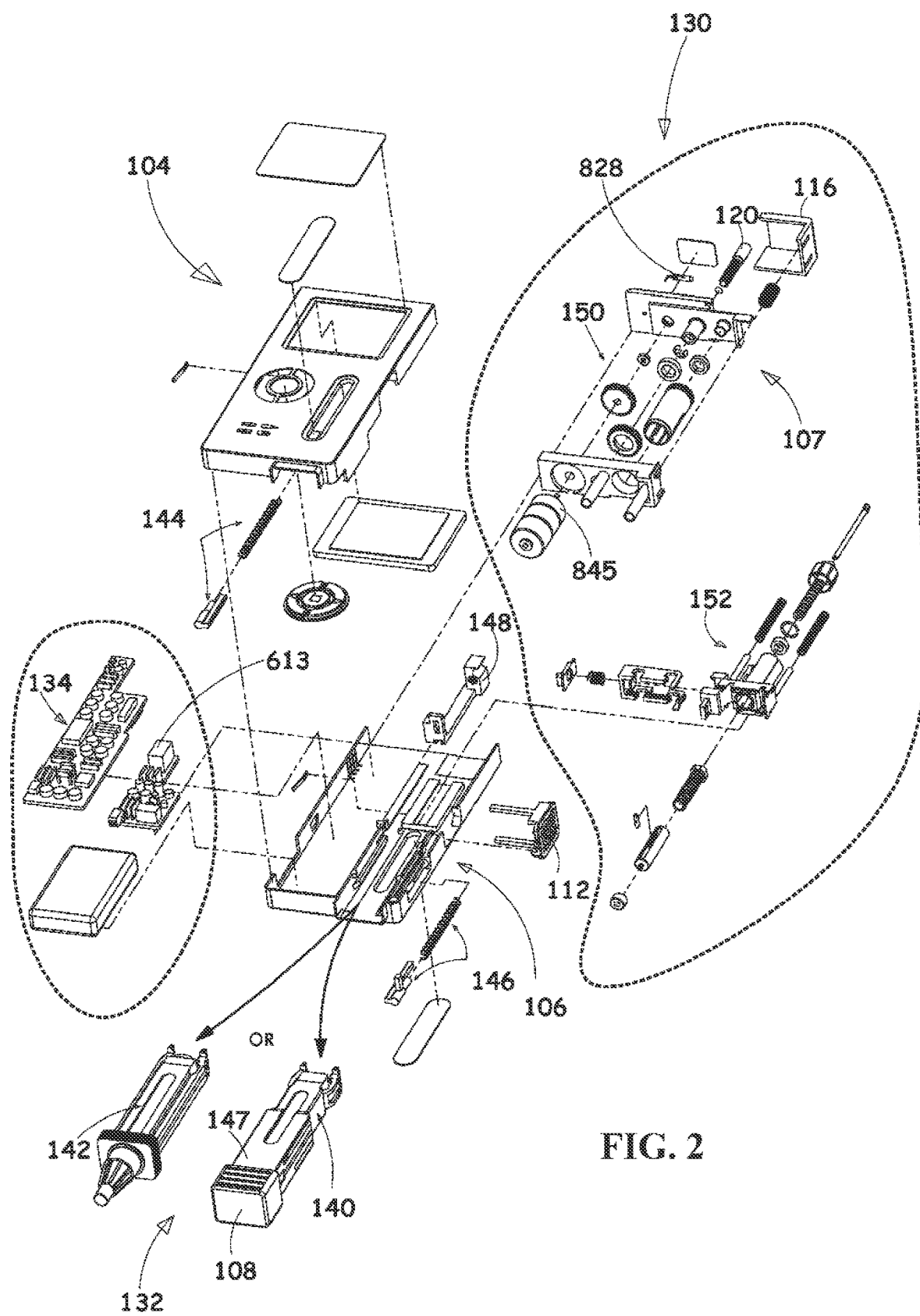
FIG. 2 is a simplified exploded view illustration of the electronic automatic injection device of FIGS. 1A-1D.

As seen in FIGS. 1A-2, the automatic injection device 100 comprises a housing 102 including an upper housing assembly 104, a lower housing assembly 106 and an end housing assembly 107. A removable needle shield (RNS) remover 108 protrudes from a forward end 110 of the housing 102. An injection module release button 112 is user accessible from a side 114 of the housing 102 and an injection actuation button 116 is user accessible from a rearward end 118 of the housing 102, opposite to end 110.

A physician accessible injection depth selector 120 is located at end 118 of the housing 102, adjacent injection actuation button 116. An electrical connection port 122 is located on a side 124 of the housing 102, which is opposite to the side 114 on which the injection module release button 112 is located. The connection port 122 may be, for example, a USB port which may provide a data and/or electrical power connection. Openings 126 are located on side 124 of the housing 102 adjacent the connection port 122 for allowing an audio output of a speaker (not shown) to be heard by a user.

A visual indicator assembly 128, typically including an LED light source and a cover, is located on the rearward end 118 of the housing 102.

As specifically seen in FIG. 1D, an injection module operating assembly 130 is mounted onto the lower housing assembly 106, extends into the upper housing assembly 104 and extends into the end housing assembly 107. An injection module 132 is slidably mounted onto both the lower housing assembly 106 and the upper housing assembly 104 and extends through an aperture (not shown) in the forward end 110. The injection module 132 is fixedly couplable to the injection module operating assembly 130. An electronic control assembly 134 is mounted to either or both the upper housing assembly 104 and the lower housing assembly 106.

It is appreciated that FIGS. 1A-1D illustrate the electronic automatic injection device 100 wherein the injection module 132 is a prefilled syringe. It is a particular feature of the present invention that as specifically seen in FIG. 2, injection module 132 may be provided in two alternative different configurations. The first configuration is a prefilled container with a needle attached thereto, here designated as prefilled syringe injection module (PFS) 140 and the second configuration is a needleless cartridge injection module (NC), here designated by reference numeral 142, having a replaceable needle. It is according a particular feature of the present invention that the automatic injection device 100 is configured to slidably receive either the PFS 140 or the NC 142.

Disposed within upper housing assembly 104 and lower housing assembly 106 are respective upper and lower needle shield biasing assemblies 144 and 146 which provide automatic displacement of a needle shield 147, onto which RNS remover 108 is mounted.

An injection depth selector travel track 148 is slidably mounted on the lower housing assembly 106 for operative engagement with the injection depth selector 120.

Injection module operating assembly 130 comprises a rotational motion output subassembly 150 and a multiple motion output subassembly 152, which is driven by subassembly 150.

Figure 3A:
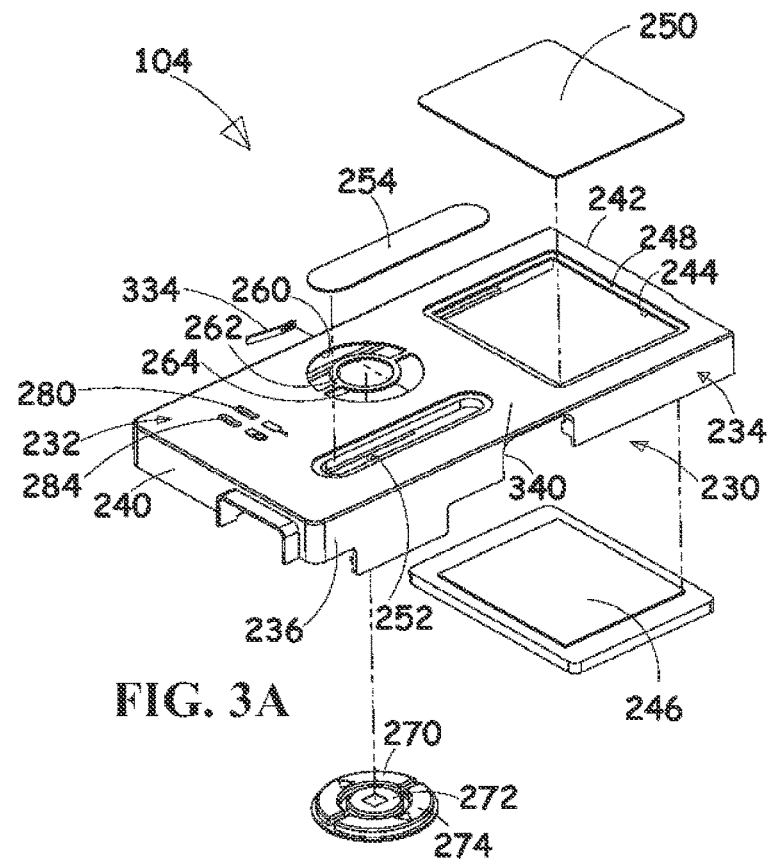
FIG. 3A is a simplified exploded illustration of the upper housing assembly of the electronic automatic injection device of FIGS. 1A-2 seen from a normally upward facing side thereof.
Figure 3B:
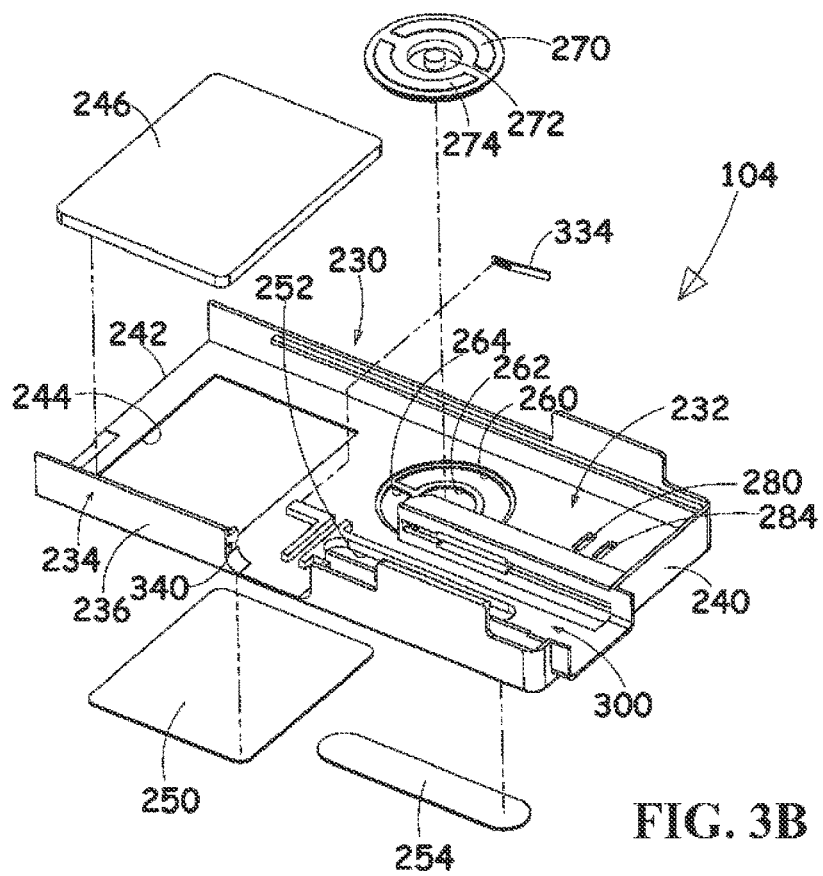
FIG. 3B is a simplified exploded illustration of the upper housing assembly of the electronic automatic injection device of FIGS. 1A-2 seen from a normally downward facing side thereof.
Figure 4A:
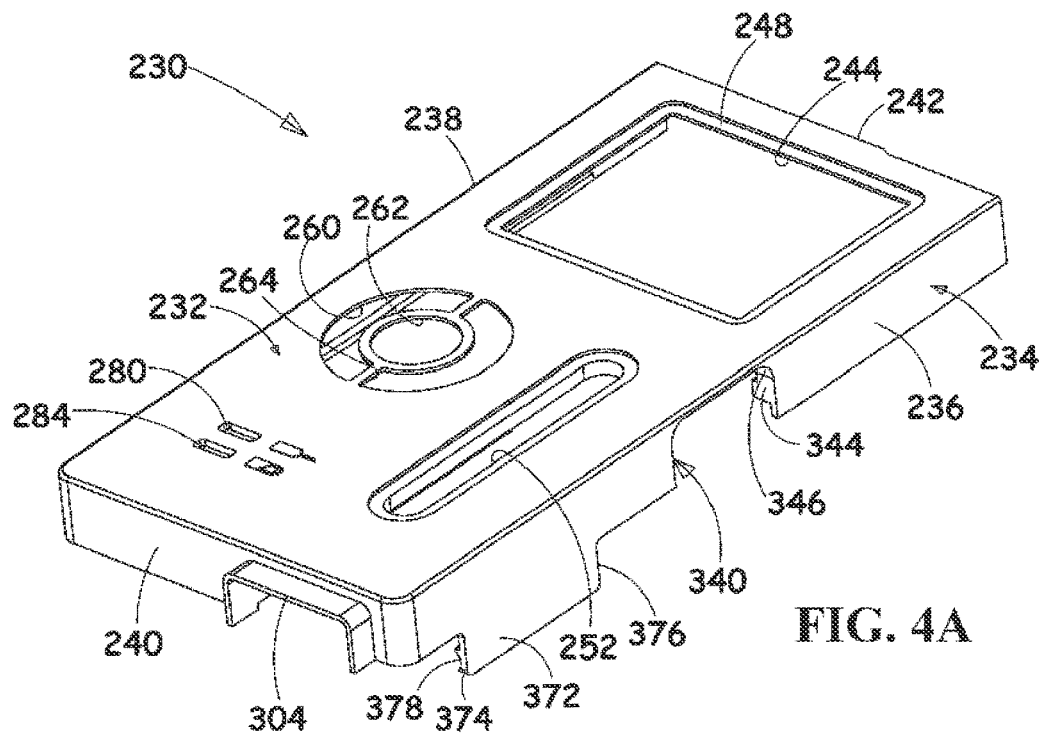
FIG. 4A is a simplified pictorial illustration of an upper housing portion of the upper housing assembly of the electronic automatic injection device of FIGS. 1A-2 seen from an upward facing side thereof.
Figure 4B:
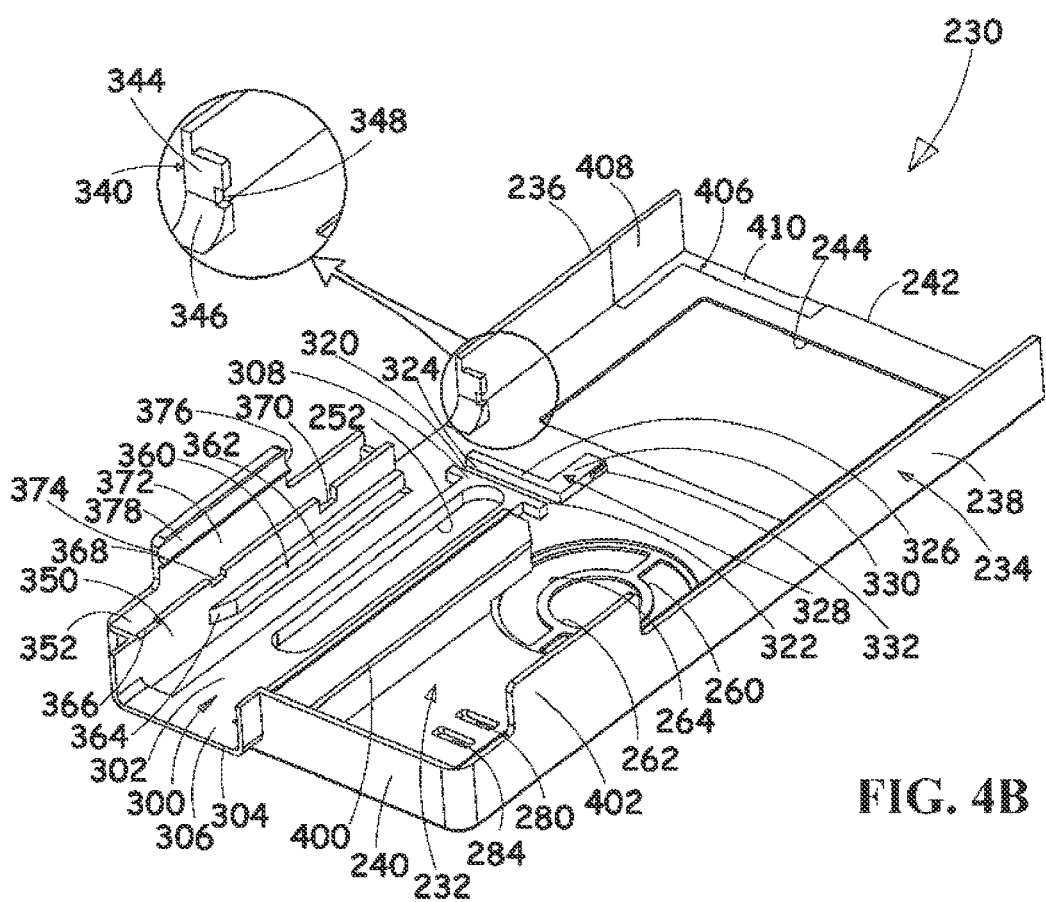
FIGS. 4B & 4C are simplified pictorial illustrations of two different views of the upper housing portion of the upper housing assembly of the electronic automatic injection device of FIGS. 1A-2 seen from a downward facing side thereof.
Figure 4C:
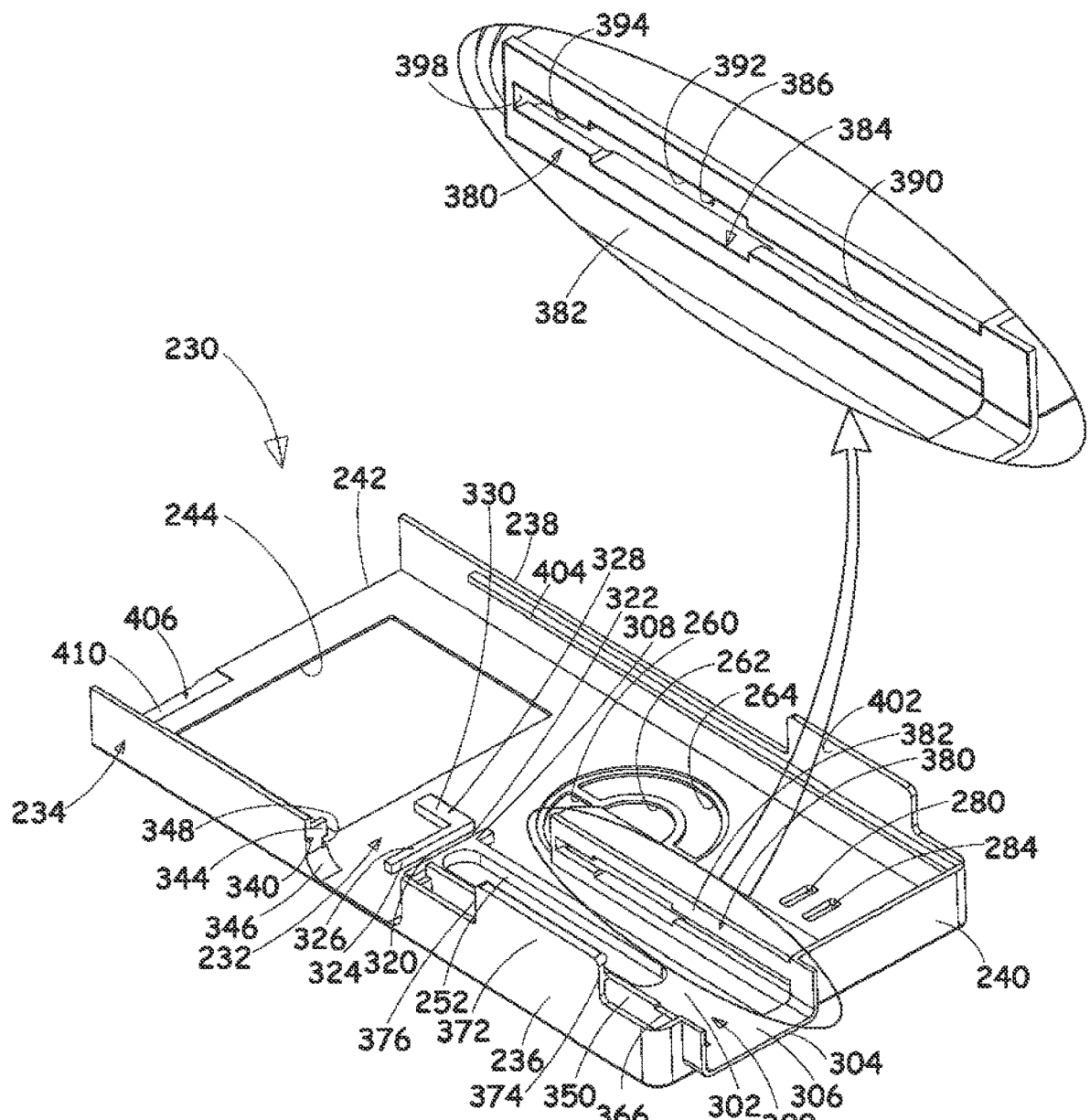
Figure 4D:
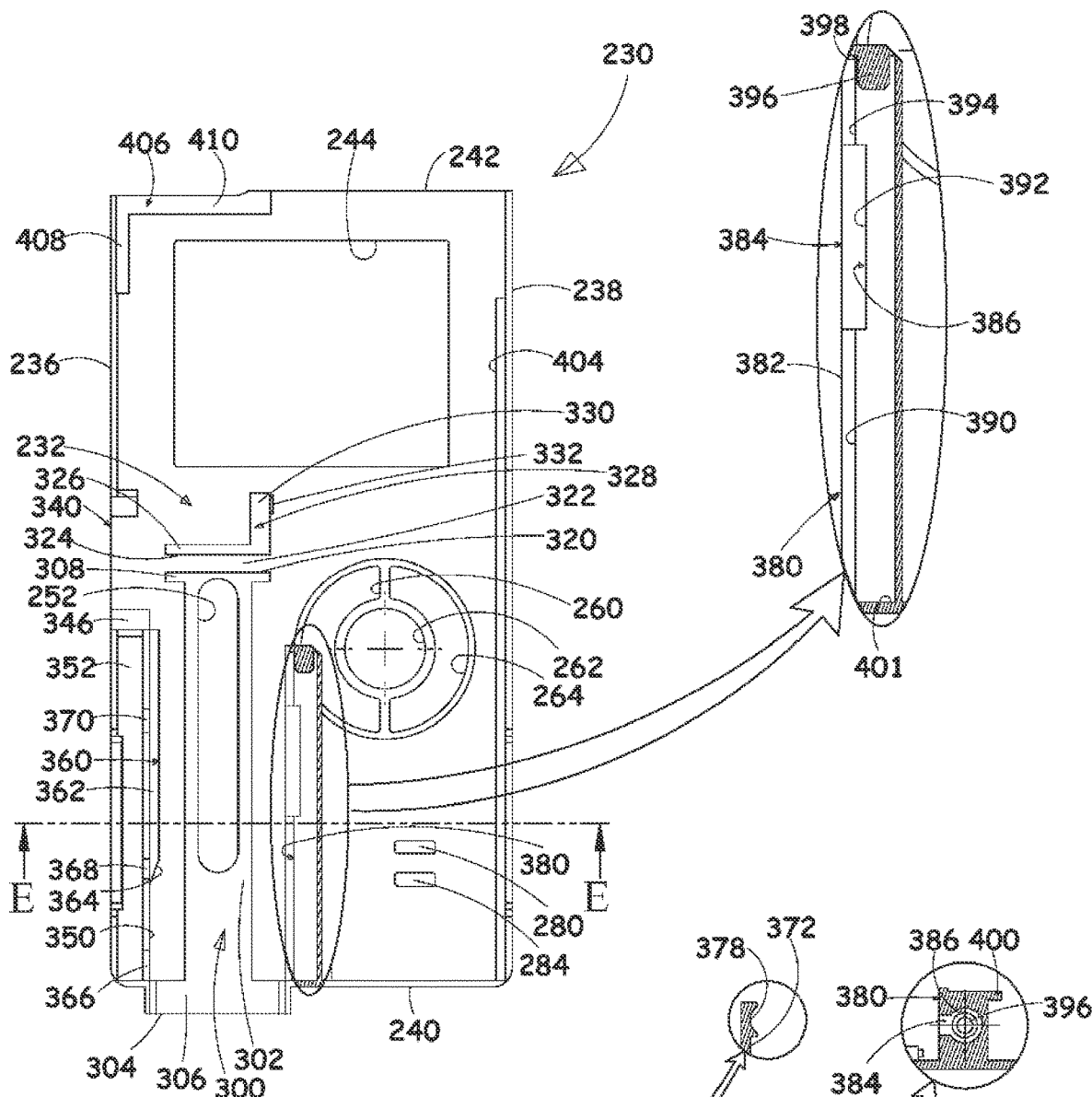
FIG. 4D is a simplified partially sectional illustration of the upper housing portion of the upper housing assembly of the electronic automatic injection device of FIGS. 1A-2 seen from a downward facing side thereof.
Figure 4E:
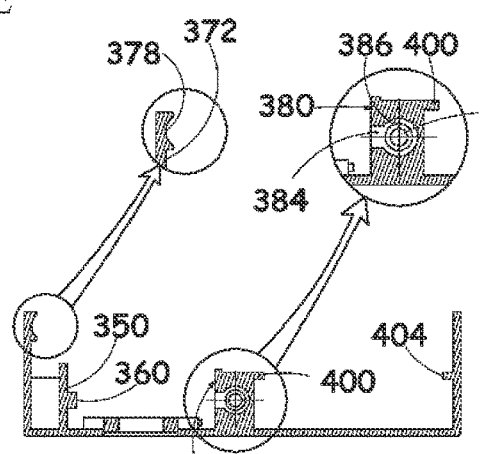
FIG. 4E is a simplified partially sectional illustration of the upper housing portion of FIG. 4D taken along the lines E-E of FIG. 4D.
Figure 5A:
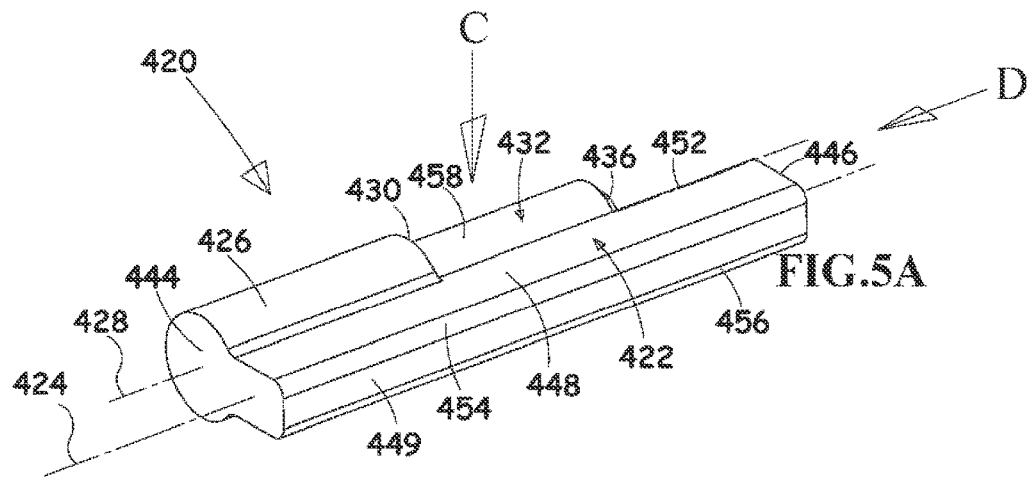
FIGS. 5A & 5B are simplified pictorial illustrations of a biasing element forming part of the upper housing assembly of the electronic automatic injection device of FIGS. 1A-2 seen from a forward end and a rearward end respectively.
Figure 5B:
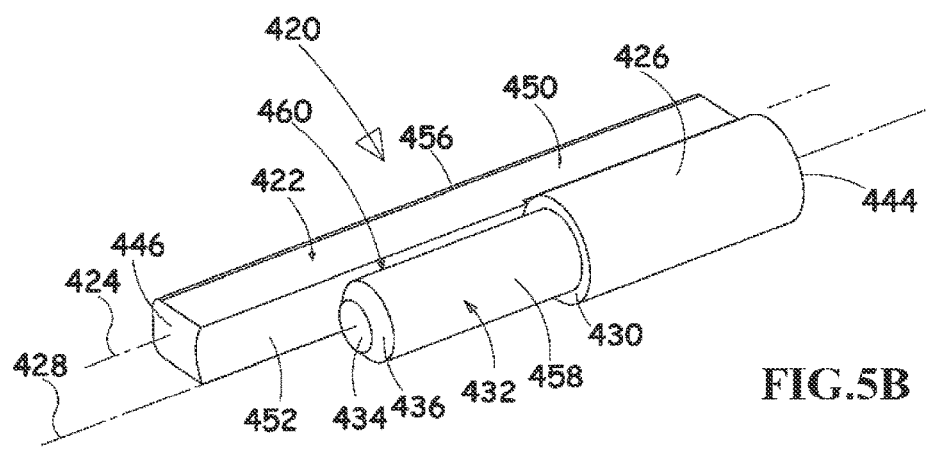
Figures 5C, 5D:
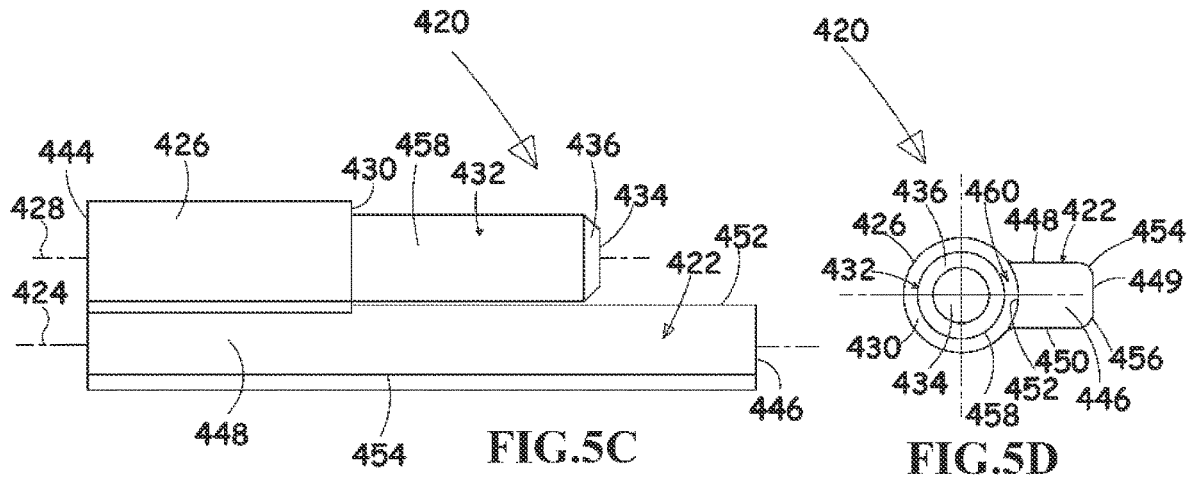
FIGS. 5C & 5D are simplified respective side view and end view illustrations of the biasing element of FIGS. 5A & 5B, taken in directions indicated by arrows C and D respectively in FIG. 5A.

Reference is now made to FIGS. 3A & 3B, which are simplified exploded view illustrations of the upper housing assembly 104 of the electronic automatic injection device 100 of FIGS. 1A-2. The upper housing assembly 104 includes an upper housing portion 230, preferably injection molded of plastic.

Referring additionally to FIGS. 4A-4D, it is seen that the upper housing portion 230 includes a planar portion 232 and a peripheral wall 234 including first and second side portions 236 and 238 and respective forward and rearward end portions 240 and 242. Forward end portion 240 forms part of forward housing end 110, while rearward end portion 242 forms part of rearward housing end 118.

Planar portion 232 of upper housing portion 230 includes a generally rectangular cut-out 244, which accommodates a display screen 246 such as Cat. Number DT022BTFT, commercially available from Displaytech Ltd., Carlsbad, CA, a circumferential recess 248 for accommodating a display cover 250, and an elongate cut-out 252 which accommodates a transparent window 254. Planar portion 232 also comprises an arrangement of apertures 260, 262 and 264 for accommodating respective control buttons 270, 272 and 274 commercially available from Abatek, Bassersdorf, Switzerland. Planar portion 232 additionally comprises an arrangement of apertures 280 and 284 for accommodating respective illuminated indicators, such as LEDs 286 and 288, commercially available from OSRAM, Regensburg, Germany.

Formed on an underside of upper housing portion 230 and extending inwardly from planar portion 232 towards lower housing assembly 106 is an upper injection module travel track protrusion 300. Injection module travel track protrusion 300 includes a generally elongate track portion 302, extending rearwardly towards end portion 242 from an edge location 304, which edge location 304 lies slightly forwardly of end portion 240. Elongate cut-out 252 is surrounded by protrusion 300. Protrusion 300 is also formed with an end strip 306 located at edge location 304 and an end strip 308 located slightly rearwardly of elongate cut-out 252 towards rearward end portion 242.

An edge surface 320 of end strip 308 defines one surface of a channel 322, the other surface 324 of which is defined by a parallel strip portion 326 of an L-shaped protrusion 328, also having a perpendicular strip portion 330 having a protrusion 332, which serves as a mounting for one end of a leaf spring 334.

A socket 340 is formed as a cut-out on side portion 236 and extends perpendicularly to channel 322. Socket 340 is preferably also defined by a pair of oppositely facing transverse wall portions 344 and a pair of generally oppositely facing curved wall portions 346. Wall portions 344 and 346 extend inwardly from side portion 236 towards side portion 238. A cut-out 348 is formed through wall portion 344.

Formed on an underside of upper housing portion 230 and extending rearwardly from end portion 240 adjacent edge location 304 is a wall 350, which is spaced from side portion 236 and defines therewith a recess 352. Extending rearwardly and inwardly from wall 350 towards side portion 238 is an upper outer side injection module travel track protrusion 360. Upper outer side injection module travel track protrusion 360 includes a generally elongate track portion 362 extending rearwardly from an angled portion 364 located rearwardly of edge location 304. Wall 350 has a forward upper cut-out 366 adjacent edge location 304 for engagement with a micro-switch (not shown). Typically two additional spaced apart upper cut-outs 368 and 370 are arranged on wall 350 rearwardly of cut-out 366.

Side portion 236 includes a protruding wall portion 372, which is located adjacent forward end portion 240 and extends downwardly from the remainder of side portion 236 partially along the length of injection module travel track protrusion 360. Protruding wall portion 372 has a forward edge 374 and a rearward edge 376 and includes an inner facing groove 378 having a concave cross section extending between forward edge 374 and rearward edge 376.

Formed on an underside of upper housing portion 230 and extending rearwardly from end portion 240 is an upper inner side injection module travel track protrusion 380. Upper inner side injection module travel track protrusion 380 includes a generally elongate flat track portion 382 extending rearwardly from edge location 304 and having formed therein an elongate slot 384. Slot 384 communicates with an elongate needle shield biasing spring enclosure 386 in which is located an elongate compression spring and is partially located a biasing element (FIGS. 5A-5D) which are parts of the upper biasing assembly 144 (FIG. 2). Slot 384 includes a relatively narrow forward portion 390 adjacent edge location 304, a relatively wide intermediate portion 392, which allows insertion of the upper biasing assembly 144, and a relatively narrow rearward portion 394.

The spring enclosure 386 includes a pin-shaped portion 396 at a rearward end 398 thereof which serves as a centering spring seat for the elongate compression spring which forms part of the upper biasing assembly 144 (FIG. 2). A PCB supporting rib 400 extends from injection module travel track protrusion 380 towards side portion 238. Spring enclosure also includes a rearward facing surface 401 at a forward end thereof.

Side portion 238 includes a protruding wall portion 402 located adjacent forward end portion 240 and extends downwardly from side portion 238 partially along the length thereof.

A PCB supporting rib 404 extends inwardly from side portion 238 rearwardly from end portion 240 toward end portion 242.

An injection actuation button accommodating recess 406, including a side portion 408 and an end portion 410 is located at a corner of the upper housing portion 230, defined by side portion 236 and end portion 242.

Reference now is specifically made to FIGS. 5A-5D, which illustrate a biasing element 420 which forms part of the upper biasing assembly 144 (FIG. 2).

The biasing element 420 is preferably an integrally formed element, typically formed of metal, and includes an elongate rod portion 422 extending along an axis 424. An elongate generally cylindrical portion 426 extends along an axis 428 parallel to axis 424. Portions 422 and 426 are joined to each other along the longitudinal extent of portion 426.

Generally cylindrical portion 426 extends only partially along the longitudinal exist of rod portion 422 and terminates in a ring surface 430. A further elongate generally cylindrical portion 432 extends rearwardly from ring surface 430 along axis 428 and terminates in a flat rearwardly facing surface 434, which is surrounded by a tapered ring surface 436. Longitudinal rod portion 422 and cylindrical element 426 together define a coplanar forward-facing surface 444. Longitudinal rod portion 422 defines a rearward-facing surface 446, which lies alongside and rearwardly of surface 434 of cylindrical element 432. The longitudinal rod portion 422 typically includes first, second and third generally planar elongate side surfaces 448, 449 and 450 and an elongate surface 452 having a concave cross section, which extends rearwardly from a location adjacent ring surface 430 to rearward-facing surface 446. Angled elongate surfaces 454 and 456 are disposed between surfaces 448 & 449 and surfaces 449 & 450 respectively.

It is noted that the radius of cylindrical portion 432 is less than that of cylindrical portion 426. The mutually closest parts of surface 452 and a side cylindrical surface 458 of cylindrical portion 432 are spaced from each other by a gap 460, which extends parallel to axes 424 and 428.

Reference is now made to FIGS. 6A & 6B, which are simplified respective partially exploded and assembled view illustrations of the upper biasing assembly 144 (FIG. 2) mounted in the elongate needle shield biasing spring enclosure 386.

As seen in FIGS. 6A & 6B, cylindrical portions 426 and 432 of biasing element 420 are inserted into a forward end of the enclosure 386 via relatively wide intermediate portion 392 of slot 384 such that elongate surfaces 448 and 450 of rod portion 422 extend along relatively narrow forward portion 390 of slot 384. A compression spring 462 is inserted into the enclosure 386 rearwardly of ring surface 430 and having a forward end thereof surrounding cylindrical portion 432 alongside elongate surface 452. An opposite end of spring 462 is seated on pin-shaped portion 396.

Reference is now made to FIGS. 7A & 7B, which are simplified exploded view illustrations of the lower housing assembly 106 of the electronic automatic injection device 100 of FIGS. 1A-2. The lower housing assembly 106 includes a lower housing portion 500, preferably injection molded of plastic.

Referring additionally to FIGS. 8A-8D, it is seen that the lower housing portion 500 includes a planar portion 502 and a peripheral wall 504 including first and second side portions 506 and 508 and respective forward and rearward end portions 510 and 512. Forward end portion 510 forms part of forward housing end 110 (FIGS. 1A-1D) while rearward end portion 512 forms part of rearward housing end 118 (FIGS. 1A-1D).

Planar portion 502 of lower housing portion 500 includes a generally elongate cut-out 514, which accommodates a transparent window 516.

Formed on an upper-facing side of lower housing portion 500 and extending inwardly from planar portion 502 towards upper housing assembly 104 is a lower injection module travel track protrusion 518. Injection module travel track protrusion 518 includes a generally elongate track portion 522, extending rearwardly towards end portion 512 from an edge location 524, which edge location 524 lies slightly forwardly of end portion 510. Elongate cut-out 514 is surrounded by protrusion 518. Protrusion 518 is also formed with an end strip 526 located at edge location 524 and an end strip 528 located slightly rearwardly of elongate cut-out 514 towards rearward end portion 512.

An edge surface 530 of end strip 528 defines one surface of a channel 532, the other surface 534 of which is defined by a parallel strip protrusion 536, a side surface 538 of which serves as a mounting for one end of a leaf spring 539.

A socket 540 is formed as a cut-out on side portion 508 and extends perpendicularly to channel 532. Socket 540 is preferably also defined by a pair of oppositely facing transverse wall portions 544 and a pair of generally oppositely facing curved wall portions 546. Wall portions 544 and 546 extend inwardly from side portion 508 towards side portion 506. A cut-out 558 is formed through wall portion 544.

Formed on an upper-facing side of lower housing portion 500 and extending rearwardly from end portion 510 adjacent edge location 524 is a wall 560, which is spaced from side portion 506. Extending rearwardly and inwardly from wall 560 towards side portion 508 is a lower inner side injection module travel track protrusion 562. Lower inner side injection module travel track protrusion 562 includes a generally elongate track portion 563 extending rearwardly from an angled portion 564 located rearwardly of edge location 524. Wall 560 has a forward upper cut-out 566 adjacent edge location 524 for engagement with the upper housing portion 230.

An injection module engagement protrusion 568 is preferably formed on wall 560. A flexible tab 570 extends rearwardly from wall 560 and is formed at a rearward end thereof with mutually oppositely facing protrusions 572 and 574 having respective protrusion surfaces 576 and 578.

Recess 580 extends through side portion 506 and is located adjacent forward end portion 510 for engagement with protruding wall portion 402 of the upper housing portion 230.

Formed on an upper-facing side of lower housing portion 500 and extending rearwardly from edge location 524 is a lower outer side injection module travel track protrusion 582, which is spaced from side portion 508. The protrusion 582 defines a rearward edge 586 and an upper edge 587 which is co-planar with an upper edge 588 of peripheral wall 504.

Lower outer side injection module travel track protrusion 582 includes a generally inwardly facing elongate flat track surface 590 and a generally outwardly facing surface 591. Both surfaces extend rearwardly from edge location 524 and have formed therein an elongate slot 592. Slot 592 communicates with an elongate needle shield biasing spring enclosure 594. An elongate compression spring is located within enclosure 594 as is part of a biasing element. The elongate compression spring and the biasing element are parts of the lower biasing assembly 146 (FIG. 2), which is described in detail hereinbelow with reference to FIGS. 12A & 12B. Slot 592 extends longitudinally rearwardly from forward end portion 510 to a location which is slightly forward of rearward edge 586.

An injection module engagement protrusion 596 is preferably formed on upper edge 588 of protrusion 582 and extends inwardly with respect to surface 590. An additional protrusion 598 extends above upper edge 588 of protrusion 582. Protrusion 598 defines an inwardly facing surface that is coplanar with surface 590 and defines an outwardly facing surface 600 which protrudes from surface 591 towards side portion 508. A micro-switch, such as Cat. Number D3SH, commercially available from OMRON, Kyoto, Japan, is preferably mounted on the outwardly facing surface 600. A surface 601 extends between protrusion 582 and side portion 508 and serves for mounting of a micro-switch, such as Cat. Number D3SH, commercially available from OMRON, Kyoto, Japan.

Side portion 508 is formed with a generally rectangular cut-out 602, which communicates with elongate needle shield biasing spring enclosure 594. Enclosure 594 extends from forward end 510 past cut-out 602 to rearward end 586 of protrusion 582. The cut-out 602 facilitates insertion of the lower biasing assembly 146 into the enclosure 594. Enclosure 594 includes a forward portion 605, a rearward portion 606 and an intermediate portion 607 alongside cut-out 602. Forward portion 605 defines a rearward-facing surface 608.

Cut-out 602 is formed in side portion 508 and located adjacent forward end portion 510 for engagement by protruding wall portion 372 of the upper housing portion 230.

An injection actuation button accommodating recess 610 is located at a corner of the lower housing portion 500, defined by side portion 508 and rearward end portion 512.

Apertures 612 defining sound passageways for an audio transducer 613 are formed at a corner of the lower housing portion 500, defined by side portion 506 and planar portion 502, and located adjacent the rearward end portion 512. An aperture 614 is formed on side portion 506 adjacent apertures 612 and forwardly thereof for accommodating connection port 122.

Parallel strip protrusion 536 is formed on a lower housing portion 500 of lower housing assembly 106 and extends upwardly from planar portion 502 towards upper housing assembly 104. Parallel strip protrusion 536 includes a generally elongate track portion 616 extending rearwardly towards end portion 512 from a location rearwardly from and adjacent to end strip 528. Parallel strip protrusion defines an elongate partially open recess 618, which extends along the elongate track portion 616, which recess 618 is slidably engaged by injection module operating assembly 130.

Formed on a lower housing portion 500 of lower housing assembly 106 and extending upwardly from planar portion 502 towards upper housing assembly 104 is a generally T-shaped needle penetration depth adjusting element travel track protrusion 620 for engaging an injection depth selector travel track 148.

Reference is now specifically made to FIGS. 9A & 9B, which illustrate the injection module release button 112 of the lower housing assembly 106.

Injection module release button 112 includes a generally planar portion 650 and a pair of generally T-shaped portions 652 and 654, extending in planes generally perpendicular to planar portion 650 at opposite side edges 656 and 658 of planar portion 650. Planar portion 650 includes a generally planar finger engagement surface 660 which typically includes an array 662 of recesses which create a relatively high-friction surface. Facing oppositely to surface 660 on an underside of planar portion 650 is a generally planar surface 664, having formed thereon a pair of elongate protrusions 665 which include engagement surfaces 666 having tapered ends 667. An additional protrusion 668 is located at an edge of one of elongate protrusions 665 and includes an engagement surface 669.

A pair of button travel stop protrusions 670 and 672 extend outwardly from respective edges 674 and 676 of planar portion 650 in the plane of generally planar surface 664.

Each of T-shaped protrusions 652 and 654 defines mutually opposite facing side surfaces 682 and 684 at a base 685 thereof, alongside and perpendicular to surface 664 and mutually opposite facing side surfaces 686 and 688 at an elongate portion 690 thereof. Each of protrusions 652 and 654 also defines a leaf spring engagement surface 692 at an end of elongate portion 690 thereof. Each of T-shaped protrusions 652 and 654 also defines a pair of coplanar surfaces 694 and 696 on base 685 thereof on opposite sides of elongate portion 690.

Reference is now made to FIGS. 10A-10D, which illustrate the injection depth selector travel track 148 of the lower housing assembly 106. The injection depth selector travel track 148 includes a forward portion 700 and a rearward portion 702, which are joined by a generally elongate track defining portion 704, defining together with underside surfaces of forward portion 700 and rearward portion 702 an elongate recess 706 having a generally T-shaped cross-section.

Forward portion 700 includes a generally rectangular plate-like upstanding portion 720 having a generally rectangular upstanding aperture 722 formed therein. Alongside portion 720 is a side upstanding portion 724 having a generally rectangular rearward-facing corner cut-out 726 formed therein.

Rearward portion 702 is a generally rectangular block having a throughgoing threaded aperture 730 and a partial circular cylindrical side cut-out 732 defining a partial circular cylindrical surface 734.

Forward portion 700 defines a forward facing surface 740 and a rearward facing surface 742. Forward portion 700 and track defining portion 704 together define a side facing surface 744. Track defining portion 704 also defines an upper-facing surface 746. Rearward portion 702 defines a rearward facing surface 748 and an upwardly-facing surface 750.

Reference now is specifically made to FIGS. 11A-11D, which illustrate a biasing element 768 which forms part of the lower biasing assembly 146 (FIG. 2).

The biasing element 768 is preferably an integrally formed element, typically formed of metal, and includes an elongate rod portion 770 extending along an axis 772. An elongate generally cylindrical portion 774 extends along an axis 776 parallel to axis 772. Portions 770 and 774 are joined to each other along the longitudinal extent of portion 774. A longitudinal protrusion 780 extends laterally outwardly from the cylindrical portion 774 and defines a rearwardly facing surface 782 and a forwardly facing surface 784.

Generally cylindrical portion 774 extends only partially along the longitudinal extent of rod portion 770 and terminates in a ring surface 786, which is coplanar with rearwardly facing surface 782. A further elongate generally cylindrical portion 787 extends rearwardly from ring surface 786 along axis 776 and terminates in a flat rearwardly facing surface 788, which is surrounded by a tapered ring surface 790.

Longitudinal rod portion 770 and cylindrical element 774 together define a coplanar forward-facing surface 792. Longitudinal rod portion 770 defines a rearward-facing surface 794, which lies alongside and rearwardly of surface 788 of cylindrical portion 787. The longitudinal rod portion 770 typically includes first, second and third generally planar elongate side surfaces 796, 798 and 800 and an elongate surface 802 having a concave cross section, which extends rearwardly from a location adjacent ring surface 786 to rearward-facing surface 794. Angled elongate surfaces 804 and 806 are disposed between surfaces 796 & 798 and surfaces 798 & 800 respectively.

It is noted that the radius of cylindrical portion 787 is less than that of cylindrical portion 774. The mutually closest parts of surface 802 and a side cylindrical surface 808 of cylindrical portion 787 are spaced from each other by a gap 810, which extends parallel to axes 772 and 776.

Figure 12A:
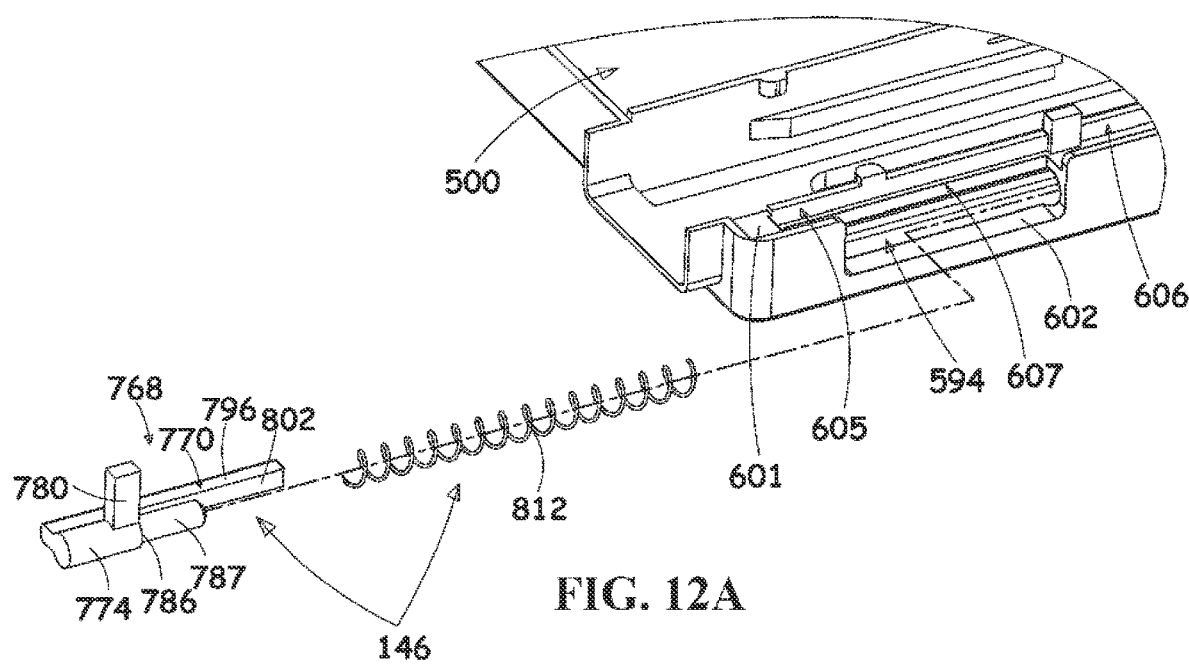
FIG. 12A is a simplified exploded view illustration of the lower housing assembly of FIGS. 7A & 7B together with the biasing element of FIGS. 11A-11D.

Reference is now made to FIGS. 12A-12C, which are simplified respective partially exploded and assembled view illustrations of the lower biasing assembly 146 (FIG. 2) mounted in the elongate needle shield biasing spring enclosure 594.

Figure 8A:
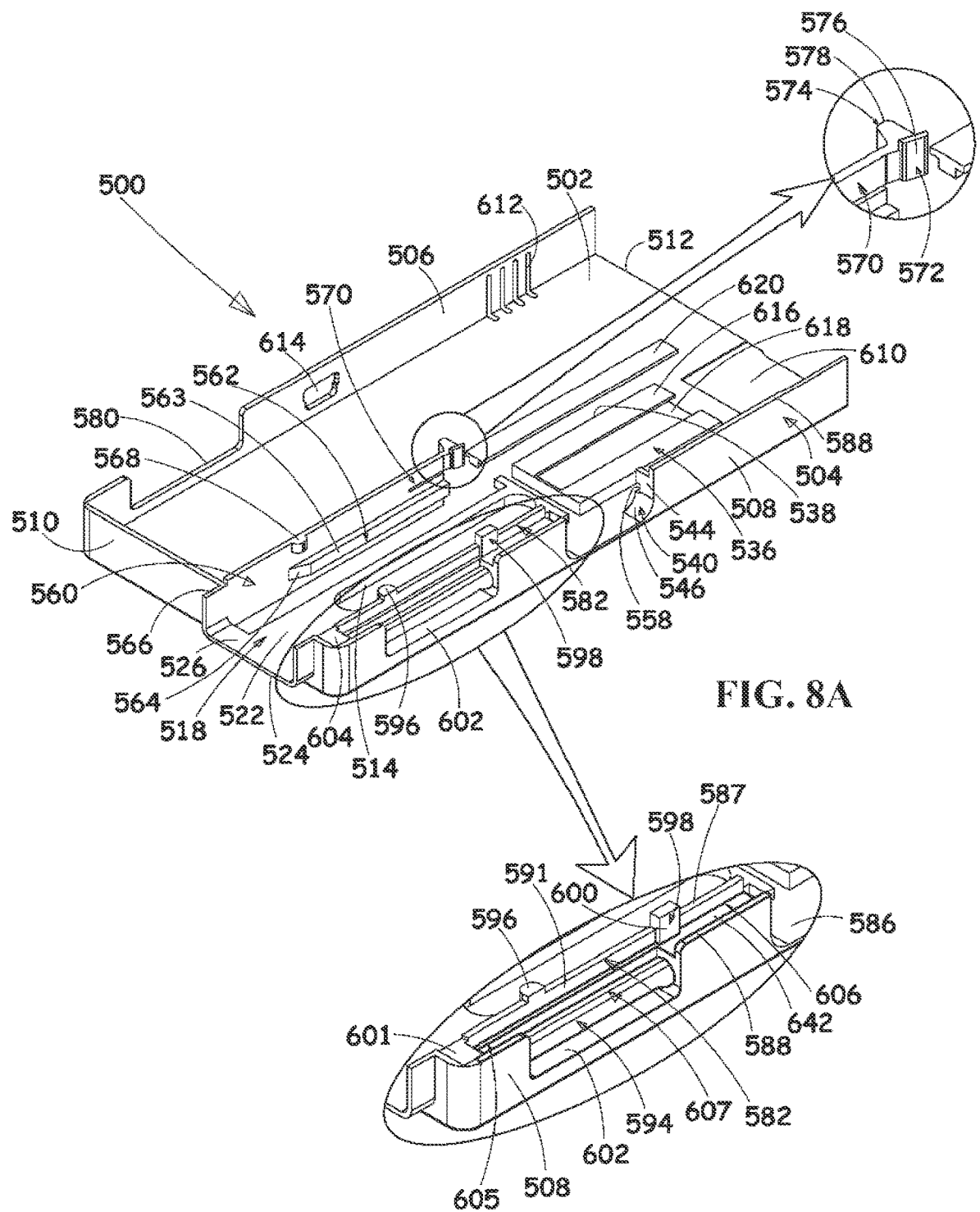
FIG. 8A is a simplified pictorial illustration of a lower housing portion of the lower housing assembly of the electronic automatic injection device of FIGS. 1A-2 seen from an upward facing side thereof.
Figure 8B:
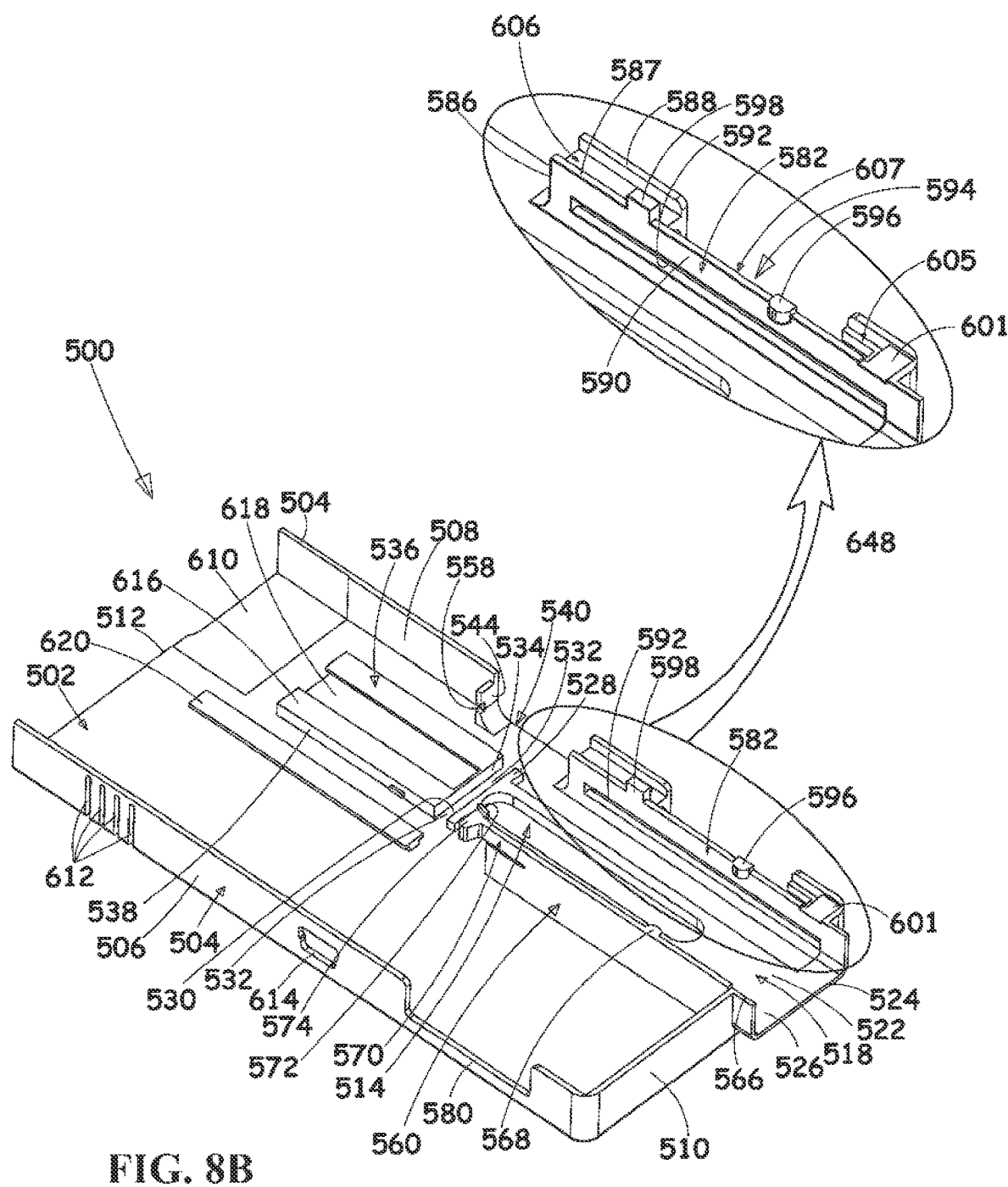

As seen in FIGS. 12A-12C, cylindrical portions 774 and 787 of biasing element 768 are inserted into the forward portion 605 of the enclosure 594 via cut-out 602 such that elongate surfaces 796 and 800 of rod portion 770 extend along slot 592 (FIG. 8B). A compression spring 812 is inserted into the enclosure 594 rearwardly of ring surface 786 and having a forward end thereof surrounding cylindrical portion 787 alongside elongate surface 802. Protrusion 780 of biasing element 768 lies alongside surface 601 of the lower housing portion 500 and protrudes upwardly through cut-out 602.

Figure 10A:
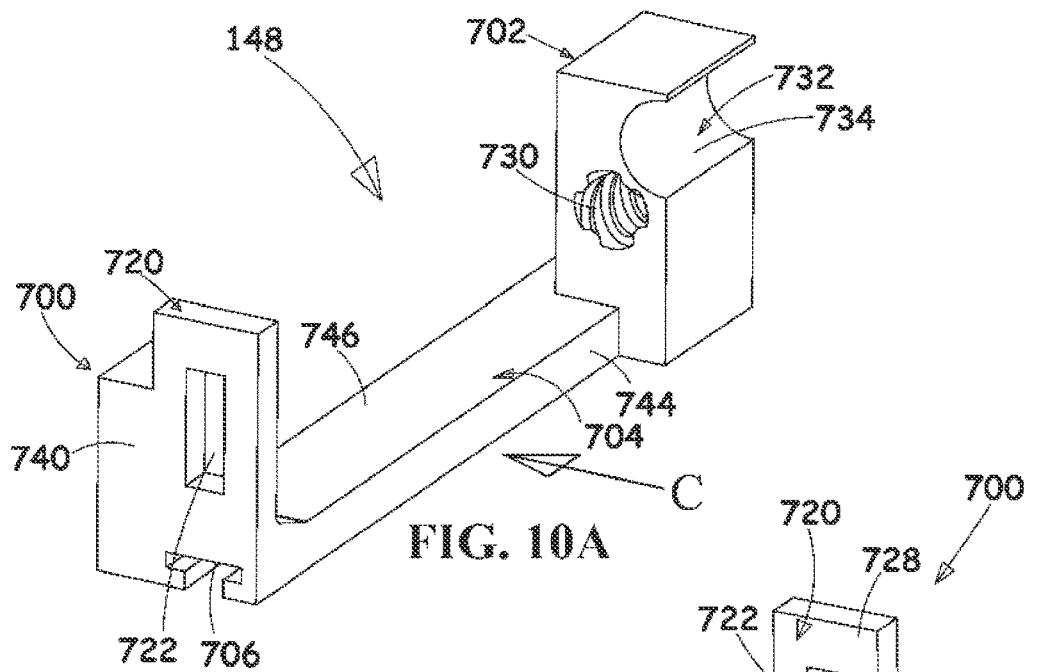
FIGS. 10A & 10B are pictorial illustrations of an injection depth selector travel track forming part of the electronic automatic injection device of FIGS. 1A-2 as seen from mutually opposite directions.
Figure 10B:
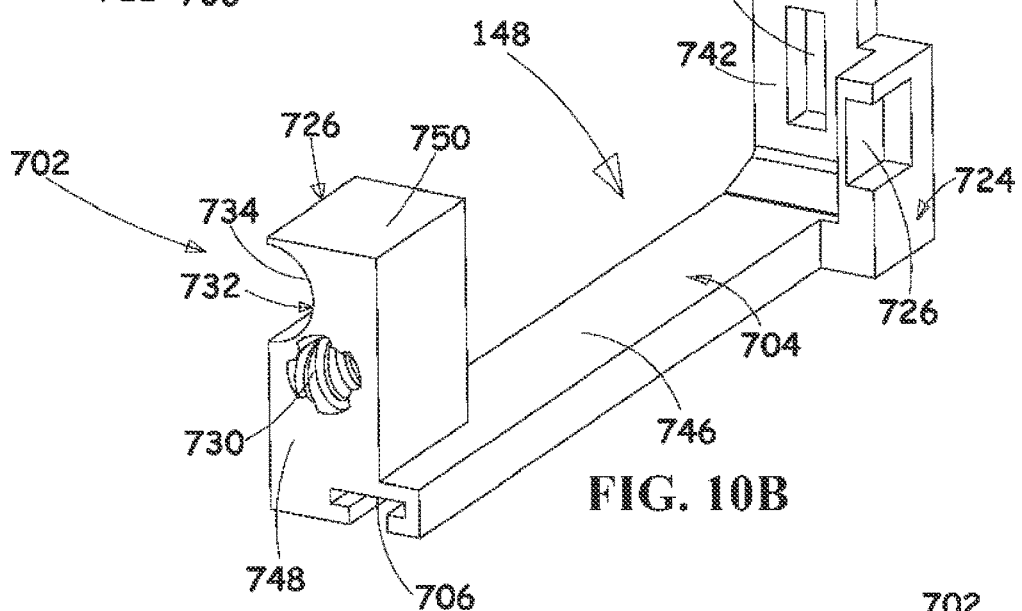
Figure 10C:
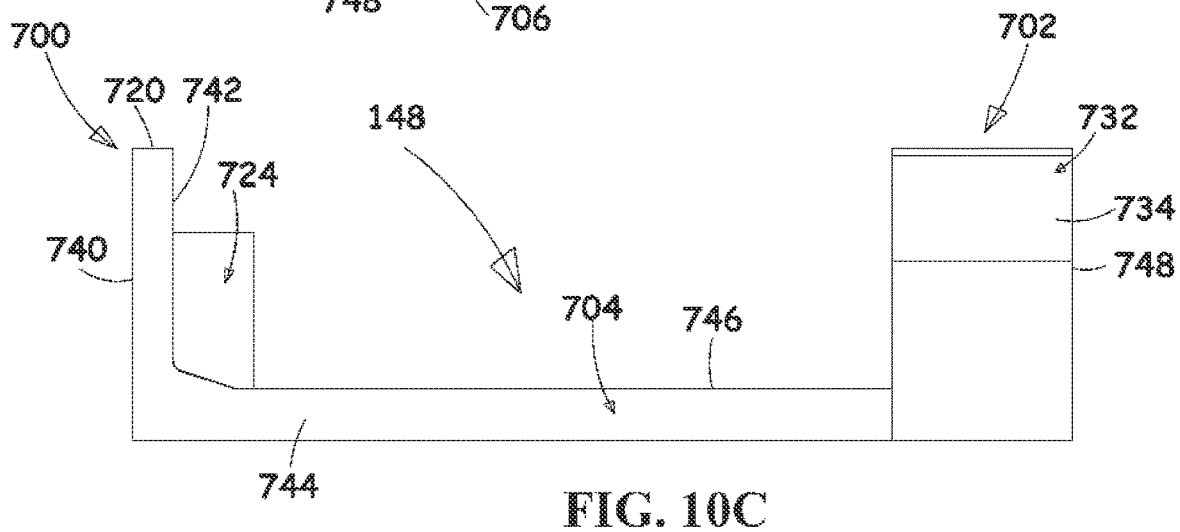
FIG. 10C is a side view illustration of the injection depth selector travel track of FIGS. 10A & 10B, taken along a direction indicated by an arrow C in FIG. 10A.
Figure 12D:
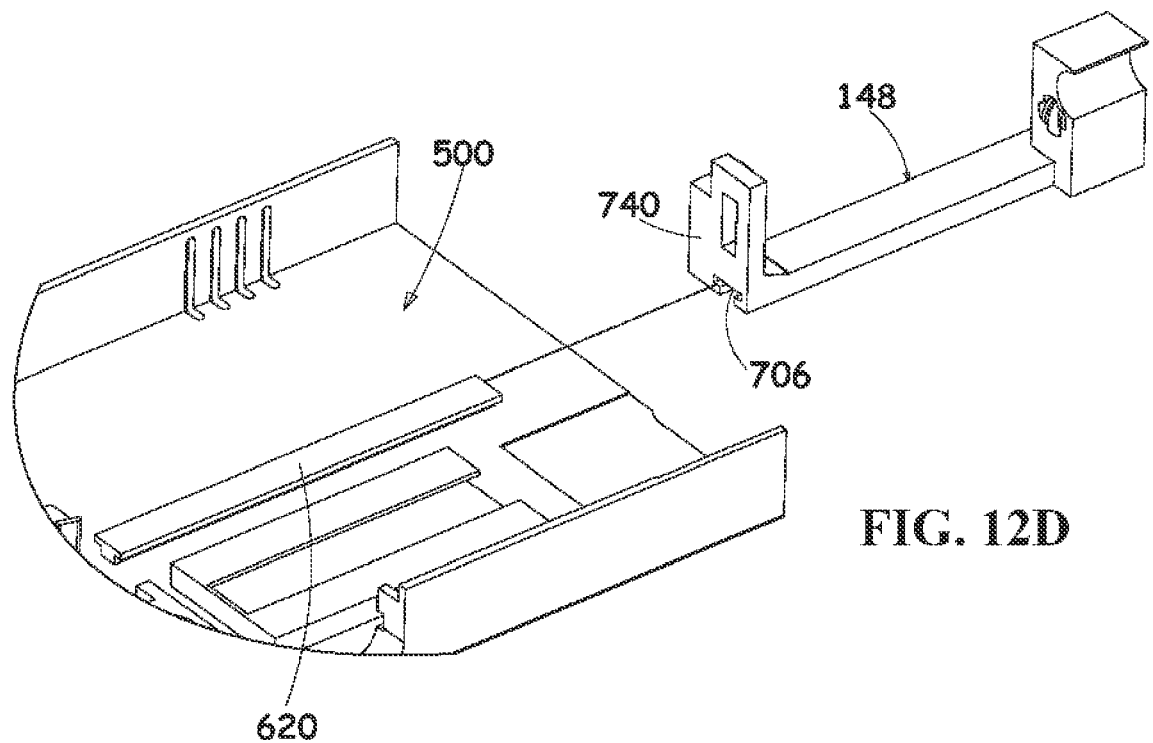
FIG. 12D is a simplified exploded view illustration of the lower housing assembly of FIGS. 7A & 7B together with the injection depth selector travel track of FIGS. 10A & 10B.
Figure 12E:
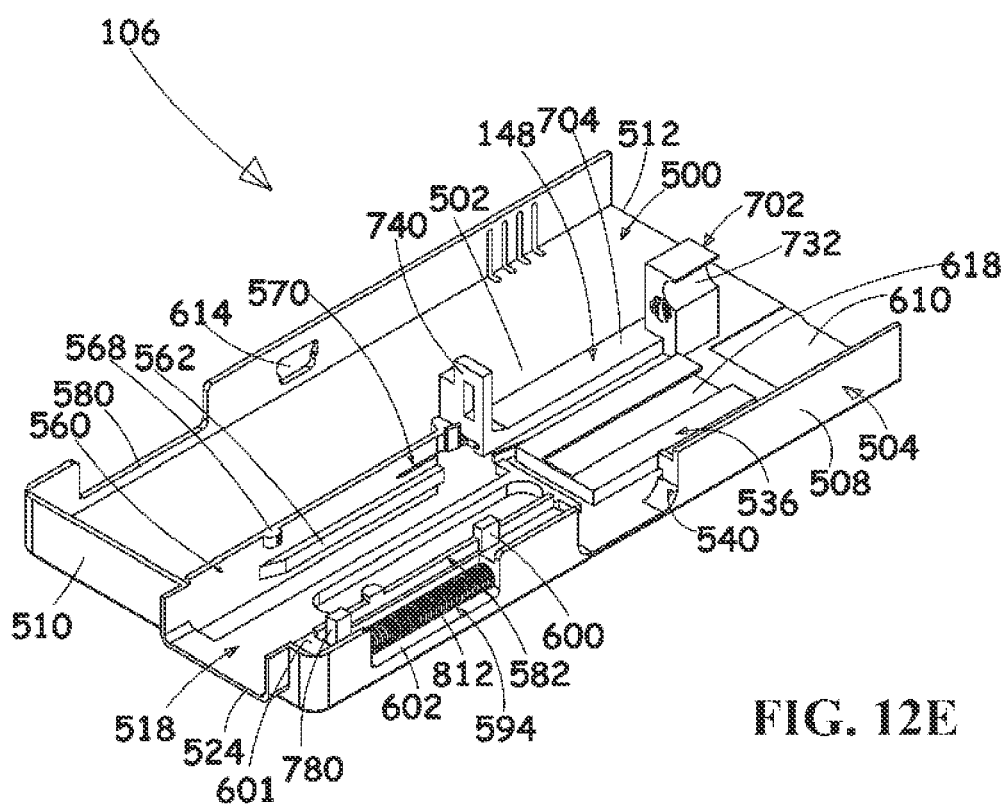
FIG. 12E is a simplified assembled view illustration corresponding to FIG. 12D and particularly showing the injection depth selector travel track of FIGS. 10A & 10B mounted in the lower housing assembly of the electronic automatic injection device of FIGS. 7A-8D.

Reference is now made to FIGS. 12D & 12E, which are simplified respective partially exploded and assembled view illustrations of the injection depth selector travel track of FIGS. 10A & 10B mounted in lower housing assembly 106.

Injection depth selector travel track 148 is slidably engaged with needle penetration depth adjusting element travel track 620, such that the T-shaped recess 706 slidably engages T-shaped travel track 620.

Figures 13A, 13B:
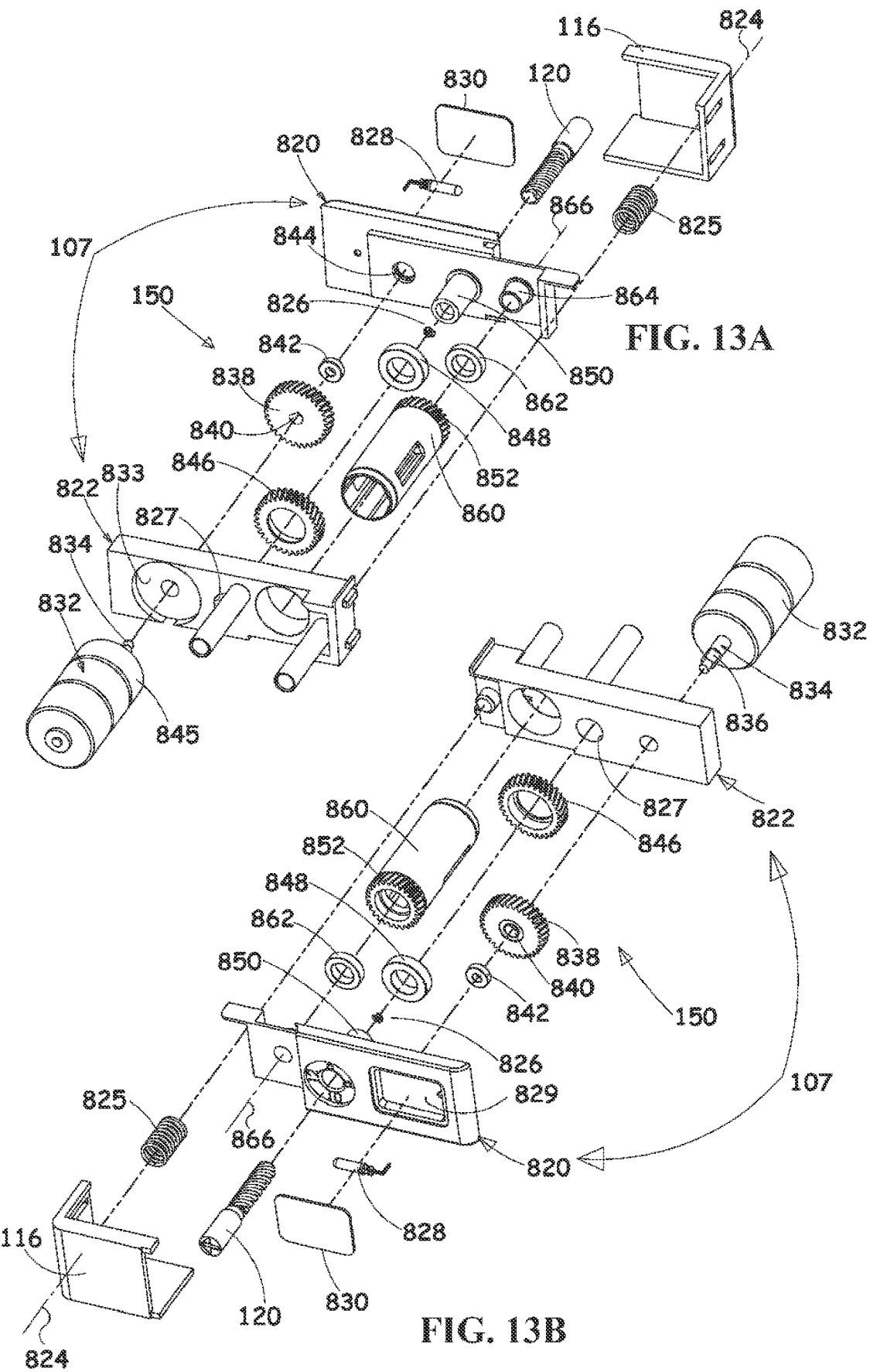
FIG. 13A is a simplified exploded view illustration of the end housing assembly of the electronic automatic injection device of FIGS. 1A-2, seen from a forward end thereof.
FIG. 13B is a simplified exploded view illustration of the end housing assembly of the electronic automatic injection device of FIGS. 1A-2, seen from a rearward end thereof.
Figure 14A:
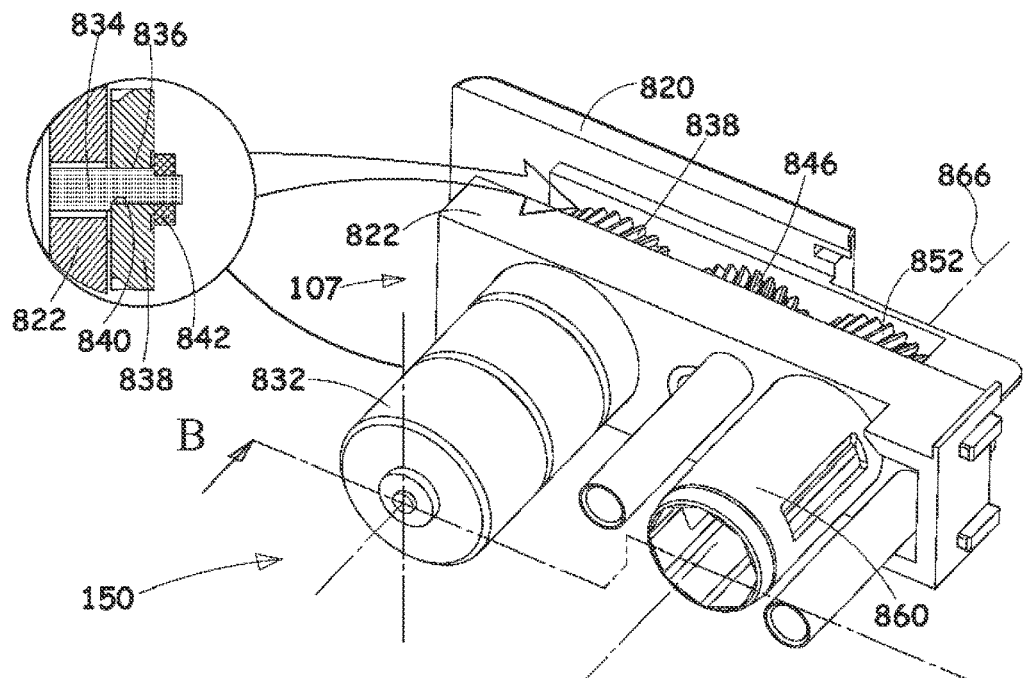
FIG. 14A is a simplified pictorial assembled view illustration of part of the end housing assembly of FIGS. 13A & 13B, taken in the same direction as FIG. 13A.
Figure 14B:
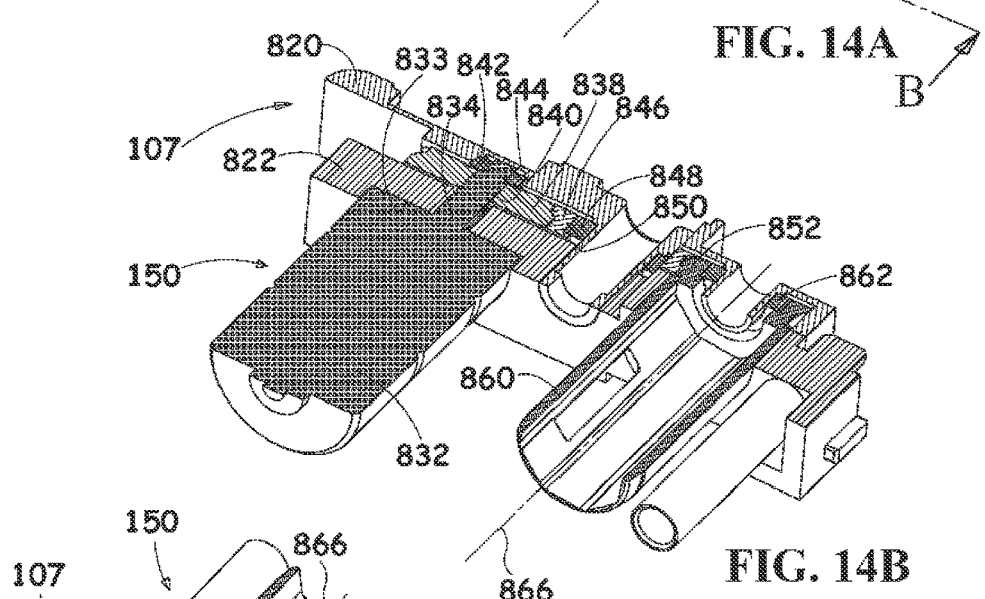
FIG. 14B is a simplified partially sectional, partially pictorial assembled view illustration taken along the lines B-B in FIG. 14A, taken in the same direction as FIG. 13A.
Figure 14C:
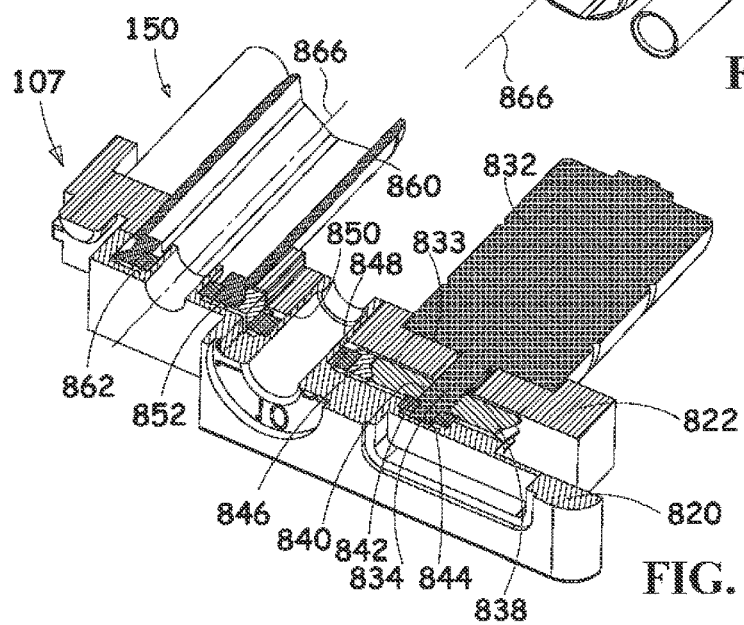
FIG. 14C is a simplified partially sectional, partially pictorial assembled view illustration taken along the lines B-B in FIG. 14A, taken in the same direction as FIG. 13B.

Reference is now made to FIGS. 13A & 13B, which are exploded views of the end housing assembly 107 of the electronic automatic injection device 100 of FIGS. 1A-2 taken from generally opposite directions and to FIGS. 14A-14C, which are partially corresponding assembled views.

The end housing assembly 107 includes a rearward housing portion 820 and a forward support portion 822, both of which are preferably injection molded of plastic.

Injection actuation button 116 (FIGS. 1A-2), is preferably injection molded of plastic and is slidably mounted on the rearward housing portion 820 and on the forward support portion 822 for displacement along an axis 824. An injection actuation button biasing spring 825 is disposed between the forward support portion 822 and the injection actuation button 116.

Injection depth selector 120 (FIG. 2) is mounted, as by a lock-washer 826, to the rearward housing portion 820 in a manner which permits rotation thereof but does not permit displacement thereof and extends forwardly through an aperture 827 formed in the forward support portion 822.

A visual indicator 828, such as a LED, commercially available from OSRAM, Regensburg, Germany, is located in a recess 829 formed in rearward housing portion 820 and covered by a transparent cover 830.

End housing assembly 107 further includes rotational motion output subassembly 150, which is described hereinbelow.

An electric motor 832, commercially available from BUHLER, Switzerland, is fixedly mounted onto forward support portion 822 at a recess 833 formed in forward support portion 822. An output shaft 834 of motor 830 includes a flat side surface 836 which is fixedly engaged by a gear 838 having a correspondingly shaped aperture 840.

The rearward end of output shaft 834 engages a bearing 842 which is fixedly seated in a bearing seat 844 formed in a forward surface of rearward housing portion 820.

An encoder is mounted onto output shaft 834 of electric motor 832 and provides an output indicating the rotational status of the output shaft 834 of electric motor 832.

Gear 838 drivingly engages a gear 846, which is fixedly mounted to a bearing 848, which is, in turn fixed onto a static sleeve 850, fixedly mounted to rearward housing portion 820. Gear 846 drivingly engages a toothed portion 852 of a multiple drive element 860. Multiple drive element 860 is rotatably mounted via a bearing 862 and a bearing seat 864 onto rearward housing portion 820 for rotation about an axis 866 which extends parallel to axis 824.

Reference is now made specifically to FIGS. 15A-15E, which illustrate the rearward housing portion 820 of the rearward housing assembly 107.

The rearward housing portion 820 includes a rearward portion 880, and a forward portion 882. The rearward portion 880 includes a first planar surface 884 and a second planar surface 886 disposed slightly forwardly with respect to the first planar surface 884. The rearward portion 880 includes side edge surfaces 888 and 890 respectively and top and bottom edge surfaces 896 and 898 respectively.

Rearward portion 880 includes generally rectangular recess 829, which accommodates the visual indicator assembly 128 (FIG. 1C). Recess 900 includes a peripheral wall surface 902 which is preferable sized to accommodate cover 830, which, together with visual indicator 828 constitutes visual indicator assembly 128 shown in FIG. 1C. The recess 829 defines a generally planar wall surface 904 that is located forwardly with respect to planar surface 884. An aperture 906 is formed in wall surface 904 for accommodating an electrical conductor connected to the visual indicator 828.

Rearward portion 880 additionally includes a generally circular recess 908 defining a wall surface 910, located forwardly with respect to planar surface 884 for providing a visual indication relating to needle penetration depth. An aperture 912 is formed in wall surface 910 and extends through the forward portion 882 for passage of needle penetration depth adjusting screw 120 therethrough. An aperture 914 extends through forward portion 882.

Forward portion 882 includes a transversely extending edge wall portion 916, which extends slightly forwardly from second planar surface 886 and also includes a flat portion 918, which extends perpendicularly to edge wall portion 916.

Forward portion 882 includes a rearwardly-facing first planar surface 920 and a forwardly-facing second planar surface 922. Forward portion 882 extends from edge wall portion 916 to a side edge surface 924.

Bearing seat 864 extends forwardly from second planar surface 922 and defines a longitudinal bore 932 therethrough, which communicates with aperture 914. The bearing seat 864 has an outer circumferential surface 934 and a forwardly facing circumferential protrusion 936 disposed around the circumferential surface 934 and extending slightly forwardly of second planar surface 922.

Static sleeve 850 extends forwardly from second planar surface 922 and defines a longitudinal bore 942 therethrough, which communicates with aperture 912. Static sleeve 850 has an outer circumferential surface 944 and a forwardly facing circumferential protrusion 946 disposed around the circumferential surface 944 and extending slightly forwardly from second planar surface 922. Static sleeve 850 is formed with an inwardly directly circumferential thickened portion 948, which is disposed at a forward end of sleeve 850 and defines a rearwardly facing shoulder 950.

The forward end of static sleeve 850 is disposed substantially forwardly of the forward end of bearing seat 864.

A recess 960 is formed on the second planar surface 922 and includes a rearward portion 962 having a first diameter and a forward portion 964 having a second diameter, which is substantially larger than the first diameter, the first and second portions 962 and 964 defining a forwardly facing shoulder 966 therebetween.

Recesses 970 and 972 are formed on adjacent top and bottom edge surfaces 896 and 898 of rearward portion 880 for limiting travel of injection actuation button 116.

Reference is specifically made to FIGS. 16A-16E, which illustrate the forward support portion 822.

The forward support portion 822 includes a rearward-facing surface 1000 and a forward-facing surface 1002. The forward support portion 822 defines side edge surfaces 1004 and 1006 and upper and lower edge surfaces 1008 and 1010. Lower edge surface 1010 includes first and second edge surface regions 1011 and 1012 defining a step 1013 therebetween.

Rearward surface 1000 includes a generally rectangular recess 1014. The recess 1014 is located at a corner between edge surface region 1012 and side edge surface 1006. A spring seating pin 1016 extends rearwardly from recess 1014 for seating spring 825 (FIGS. 13A & 13B).

A pair of mutually spaced guide ribs 1018 are formed on side edge surface 1006.

Forward support portion 822 includes a generally circular aperture 1020 positioned adjacent recess 1014. Forward support portion 822 also includes generally circular aperture 827, positioned adjacent bore 1020. Forward support portion 822 additionally includes a generally circular aperture 1024, positioned adjacent bore 827.

Formed on forward surface 1002 of forward support portion 822 is generally circular recess 833, which is concentric with aperture 1024. Extending forwardly from forward surface 1002 are hollow cylindrical protrusions 1028, arranged along an axis 1029, parallel to axis 866, and protrusion 1030, arranged along an axis 1031, parallel to axes 866 and 1029. Protrusion 1028 is positioned adjacent a corner formed by side edge surface 1006 and lower edge surface 1010. Protrusion 1030 is positioned between bores 827 and 1020 and is located slightly lower than the upper edge surface 1008. Protrusion 1028 includes a blind bore 1032 terminating at a rearward end surface 1034 and protrusion 1030 has a blind longitudinal bore 1036 terminating at a rearward end surface 1038.

Figure 17A:
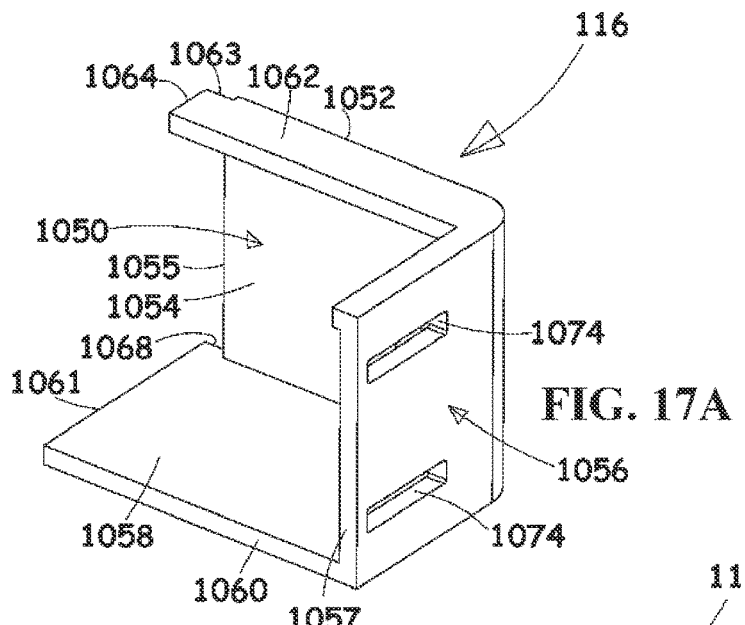
FIGS. 17A & 17B are simplified pictorial illustrations of an injection actuation button forming part of the end housing assembly of the electronic automatic injection device of FIGS. 1A-2.
Figure 17B:
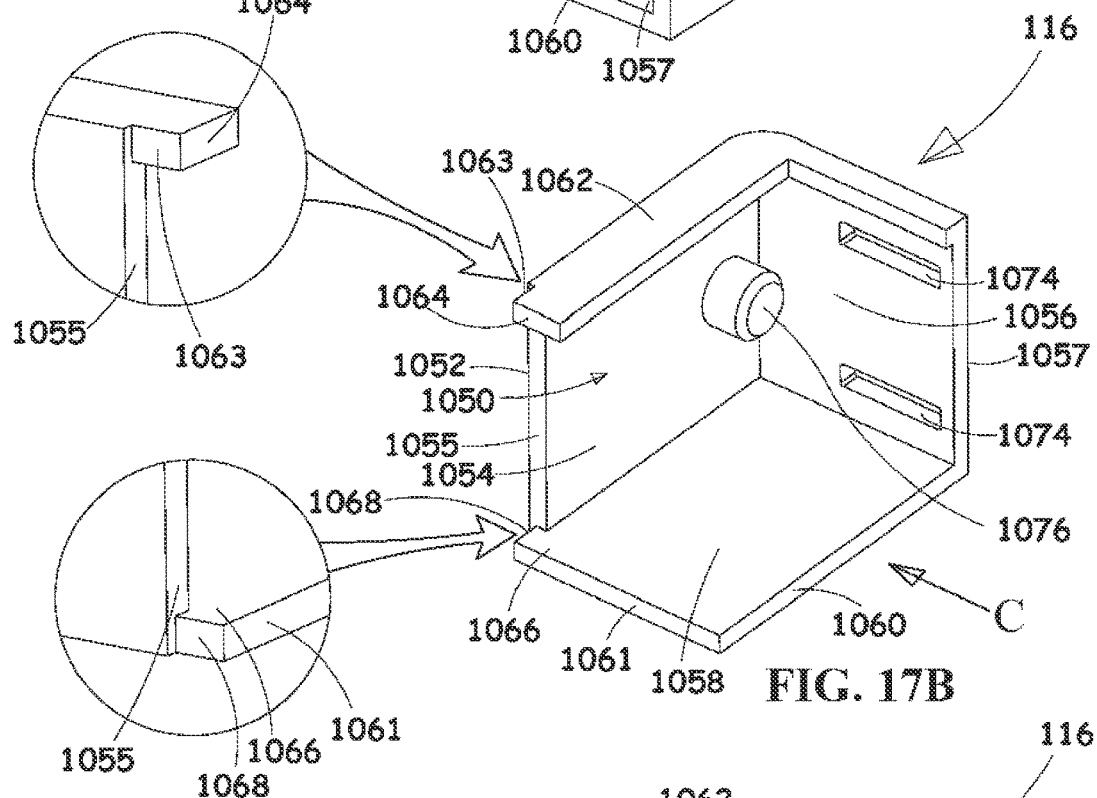
Figure 17C:
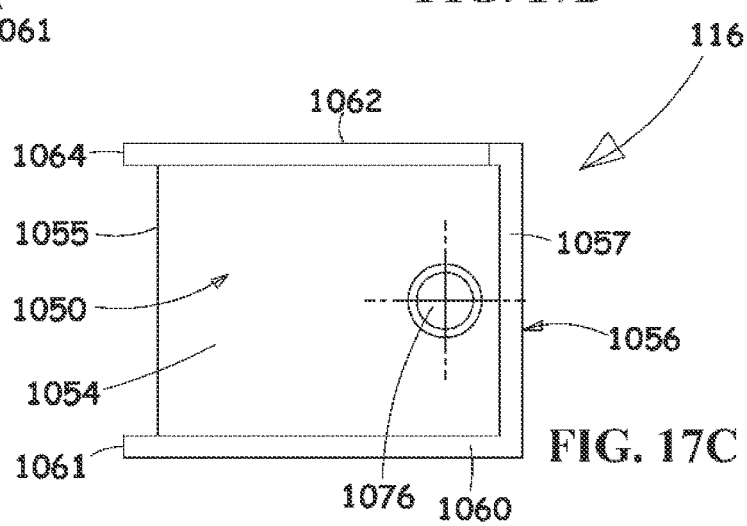
FIG. 17C is an elevation view illustration of the injection actuation button of FIGS. 17A-17B taken in a direction indicated by an arrow C in FIG. 17A.
Figure 19A:
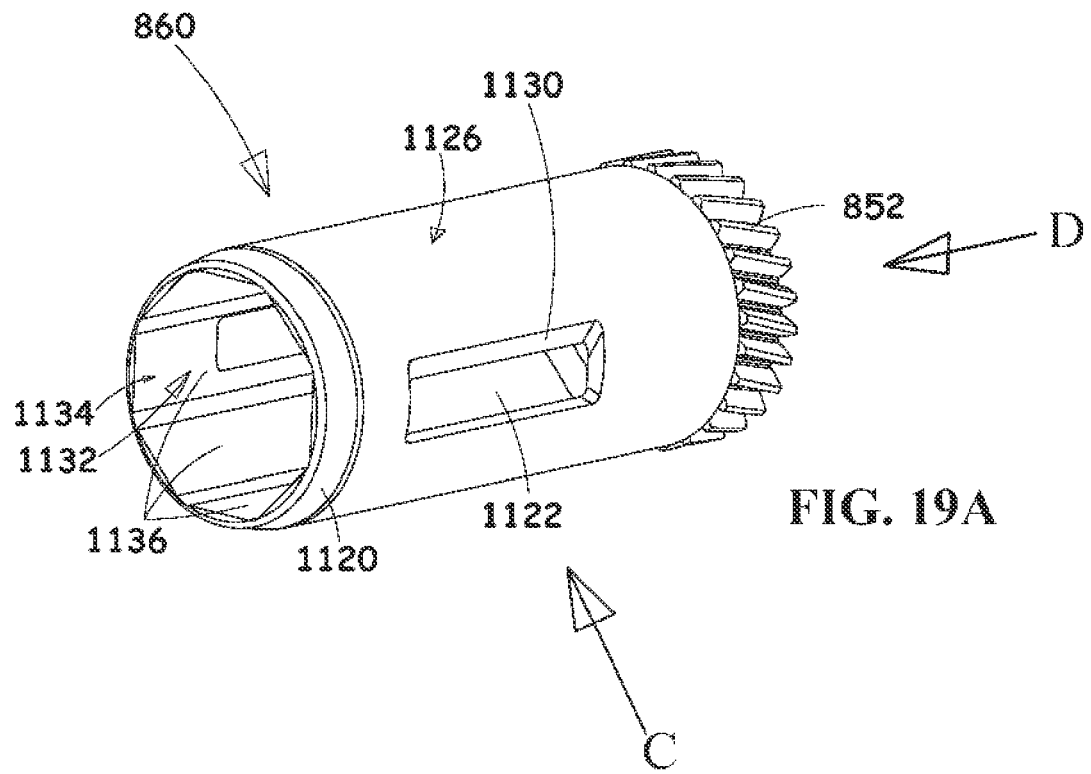
FIGS. 19A & 19B are simplified pictorial illustrations of a multiple drive element forming part of the end housing assembly of the electronic automatic injection device of FIGS. 1A-2 seen from respective forward and rearward ends thereof.
Figure 19B:
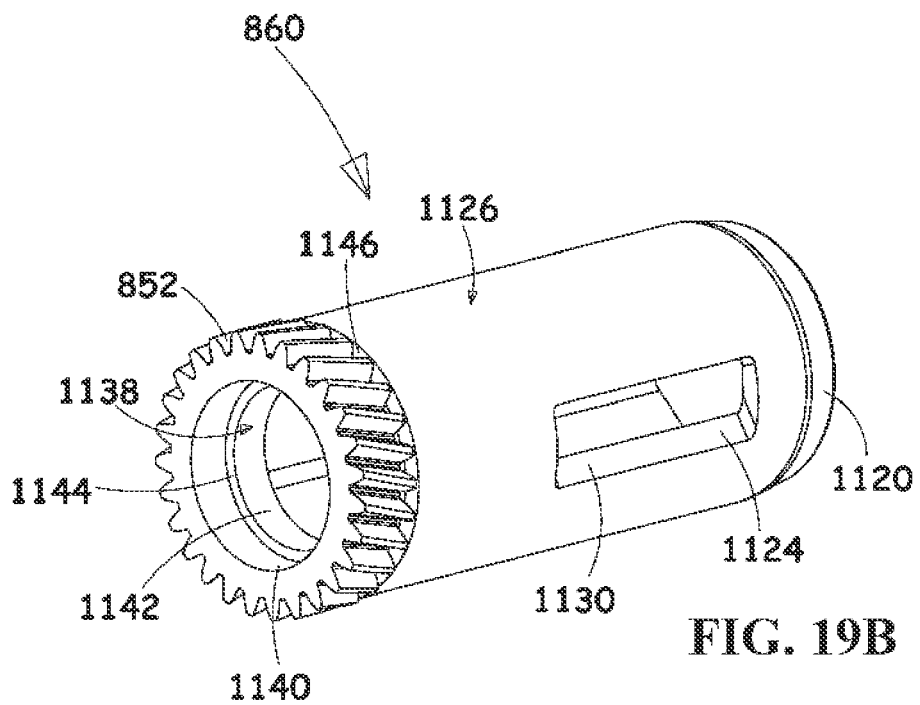

Reference is now made to FIGS. 17A-17C, which illustrate injection actuation button 116.

Injection actuation button 116 includes a planar wall 1050 having a rearward-facing surface 1052, a forward-facing surface 1054 and a side edge 1055. A side wall 1056 extends forwardly from planar wall 1050 and perpendicularly thereto defining a forward edge surface 1057. A lower wall 1058 extends forwardly and transversely from planar wall 1050 and defines a forward edge surface 1060 and a side edge surface 1061. An L-shaped upper wall 1062 lies at the top of walls 1050 and 1056. A cut-out 1063 is formed at an end 1064 of wall 1062 adjacent edge 1055 of wall 1050. It is noted that lower wall 1058 includes a portion 1066 which extends beyond edge 1055. It is noted that portion 1066 does not extend all of the way to rearward facing surface 1052 and thus defines with wall 1050 a cut-out 1068, which is similarly configured and oriented and spaced from cut-out 1063.

A pair of mutually spaced slots 1074 are formed in side wall 1056 and extend rearwardly from a location slightly rearwardly of forward edge surface 1057.

A spring seating pin 1076 extends forwardly from forward surface 1054 of planar wall 1050 for seating an end of spring 825. Spring seating pin 1076 is positioned adjacent a corner formed by forward-facing surface 1054 of wall 1050 and side wall 1056.

Reference is now made to FIGS. 18A-18D, which illustrate the injection depth selector 120 (FIGS. 13A & 13B).

Injection depth selector 120 is preferably integrally formed to have a rearward-facing first circular cylindrical portion 1100, extending along an axis 1101 and having a first diameter, an intermediate second circular cylindrical portion 1102 having a second diameter, less than the first diameter, a forwardmost third circular cylindrical portion 1104 having a third diameter, less than the second diameter and a forward-facing threaded portion 1106. A first shoulder surface 1108 is defined between portions 1100 and 1102 and a second shoulder surface 1110 is defined between portions 1102 and 1104.

Cylindrical portion 1100 is formed with a rearward-facing end surface 1112 in which is formed a recessed indicator arrow 1114, which includes a further recessed elongate portion 1116 for receiving a screwdriver, for producing desired rotation of the injection depth selector 120.

Reference is now made to FIGS. 19A-19F, which illustrate the multiple drive element 860.

The multiple drive element 860 is an integrally formed, generally hollow, generally cylindrical element, having toothed portion 852 at a rearward end thereof and an inwardly tapered outer surface 1120 at a forward end thereof.

First and second windows 1122 and 1124 are located in mutually oppositely located regions of a cylindrical wall 1126 of multiple drive element 860 and are each formed with at least one inwardly narrowing tapered longitudinal edge 1130.

The multiple drive element 860 is preferably formed with throughgoing bore 1132. A major portion 1134 of bore 1132 is preferably formed with a generally octagonal cross-section, thereby defining eight elongate wall panel portions 1136, two of which have windows 1122 and 1124 formed therein.

Adjacent a rearward end of the multiple drive element 860 and underlying toothed portion 852 there is defined a relatively thickened portion 1138 including a first inwardly facing cylindrical surface 1140 having a first diameter and a second inwardly facing cylindrical surface 1142, having a second diameter, smaller than the first diameter. A shoulder surface 1144 is defined between cylindrical surfaces 1140 and 1142. A circumferential slot 1146 is defined outwardly of cylindrical surface 1142, separating the toothed portion 852 from cylindrical wall 1126.

Figure 20A:
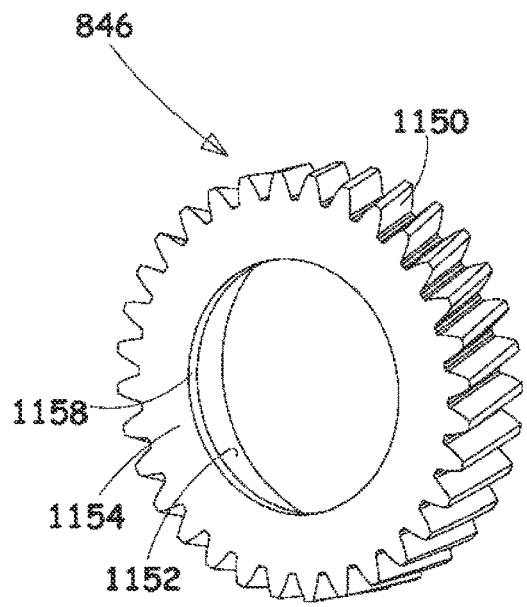
FIGS. 20A and 20B are simplified pictorial illustrations of one gear forming part of the end housing assembly of the electronic automatic injection device of FIGS. 1A-2 seen from respective forward and rearward ends thereof.
Figure 20B:
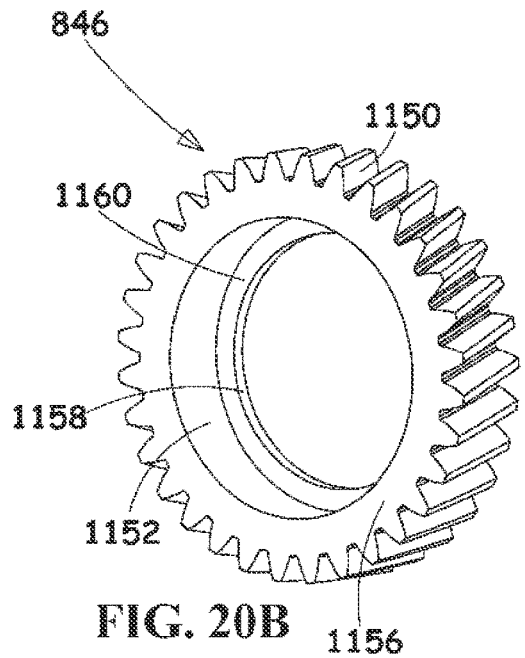

Reference is now made to FIGS. 20A & 20B, which illustrate gear 846. Gear 846 has an outer toothed surface 1150 and an inner-facing generally circular surface 1152. The toothed surface 1150 extends between a forward-facing surface 1154 and a rearward-facing surface 1156. A generally circular inwardly directed flange 1158 extends inwardly from the inner surface 1152 adjacent forward-facing surface 1154 and includes a rearward facing surface 1160. Bearing 848 (FIGS. 13A & 13B) is seated on rearward facing surface 1160 and on inner-facing generally circular surface 1152.

Figure 21A:
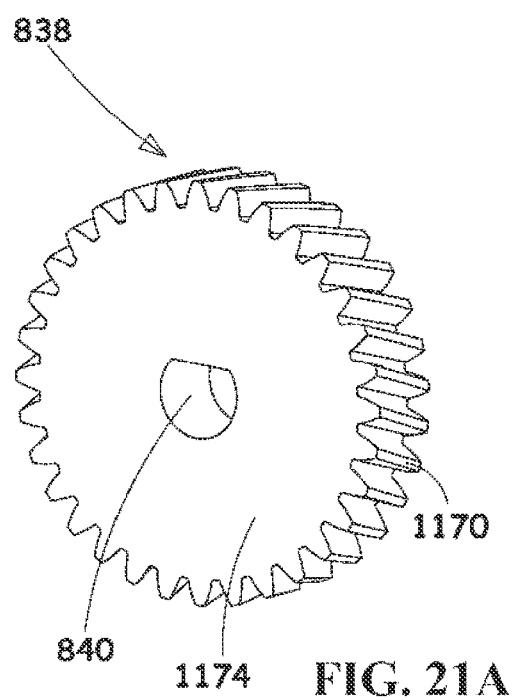
FIGS. 21A and 21B are simplified pictorial illustrations of another gear forming part of the end housing assembly of the electronic automatic injection device of FIGS. 1A-2 seen from respective forward and rearward ends thereof.
Figure 21B:
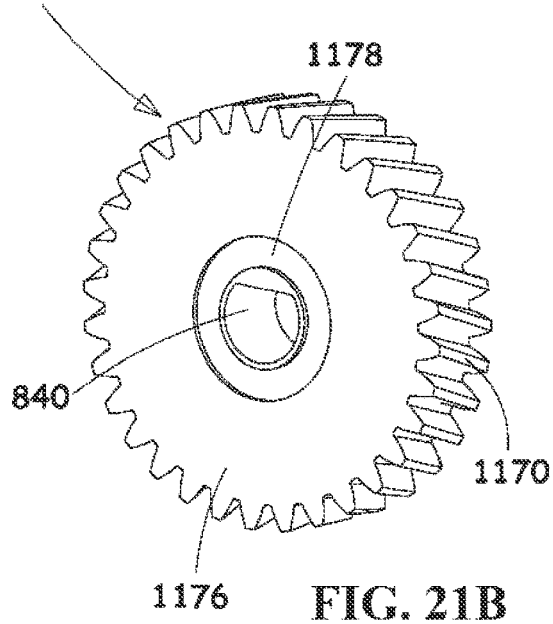

Reference is now made to FIGS. 21A & 21B, which illustrate gear 838. Gear 838 has outer toothed surface 1170 and, as noted above with reference to FIGS. 13A & 13B, an aperture 840. The toothed surface 1170 extends between a forward-facing surface 1174 and a rearward-facing surface 1176. A generally annular recess 1178 is formed on rearward-facing surface 1176 generally surrounding aperture 840 and serves as a seat for bearing 842.

Figure 22A:
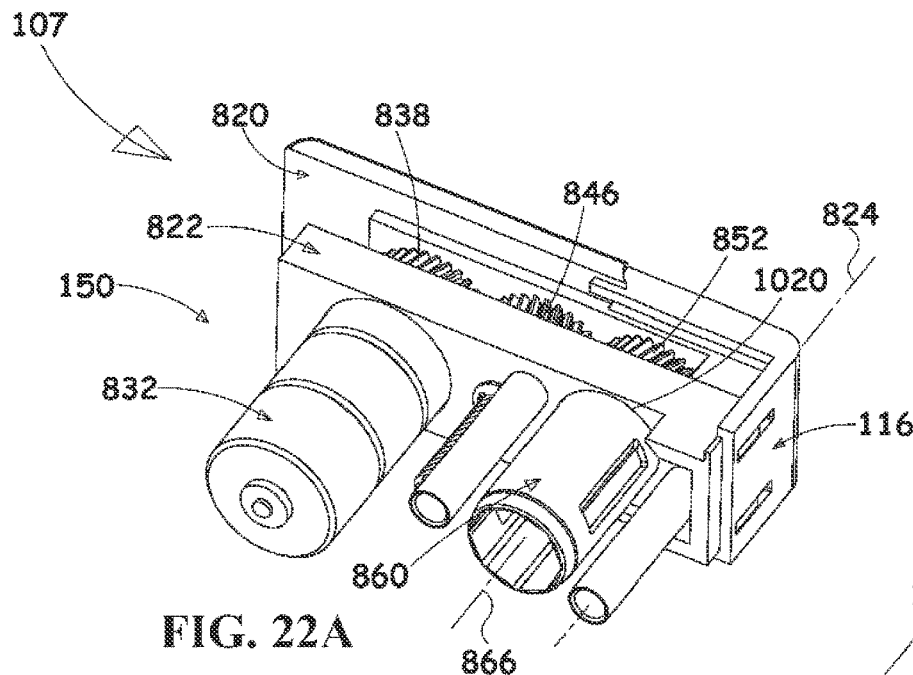
FIGS. 22A, 22B & 22C are simplified pictorial illustrations of the end housing assembly of the electronic automatic injection device of FIGS. 1A-2, seen from three different directions.
Figure 22B:
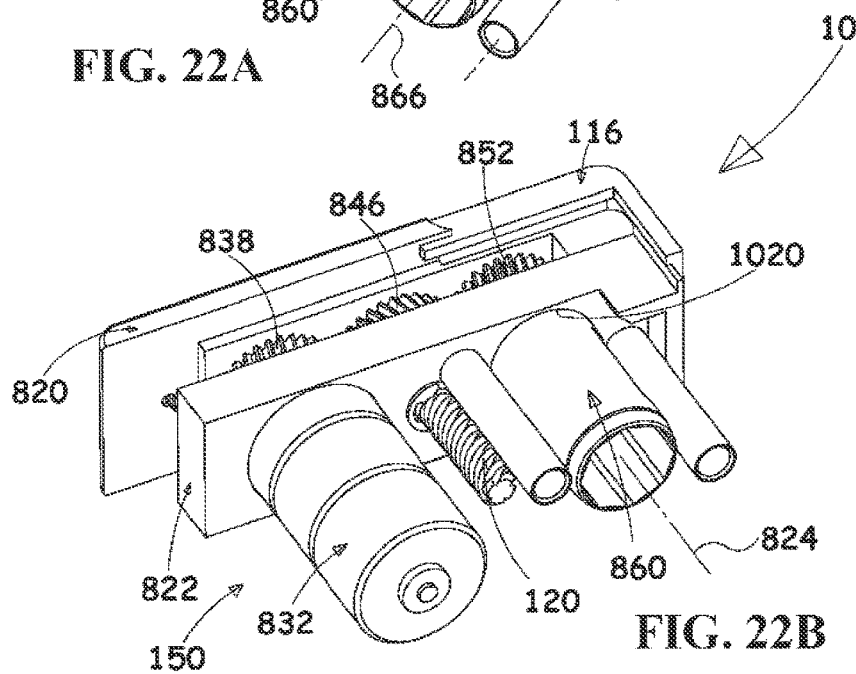
Figure 22C:
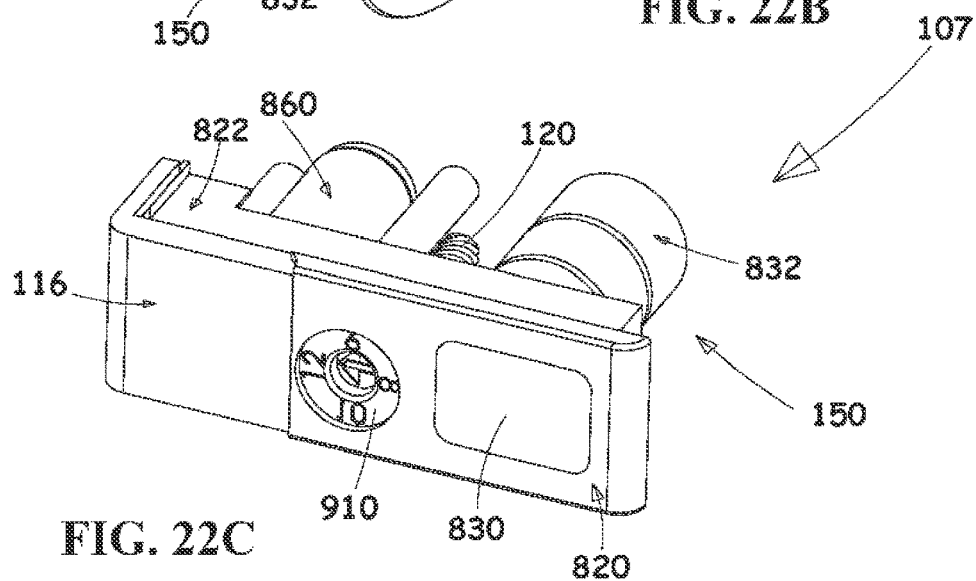
Figure 22D:
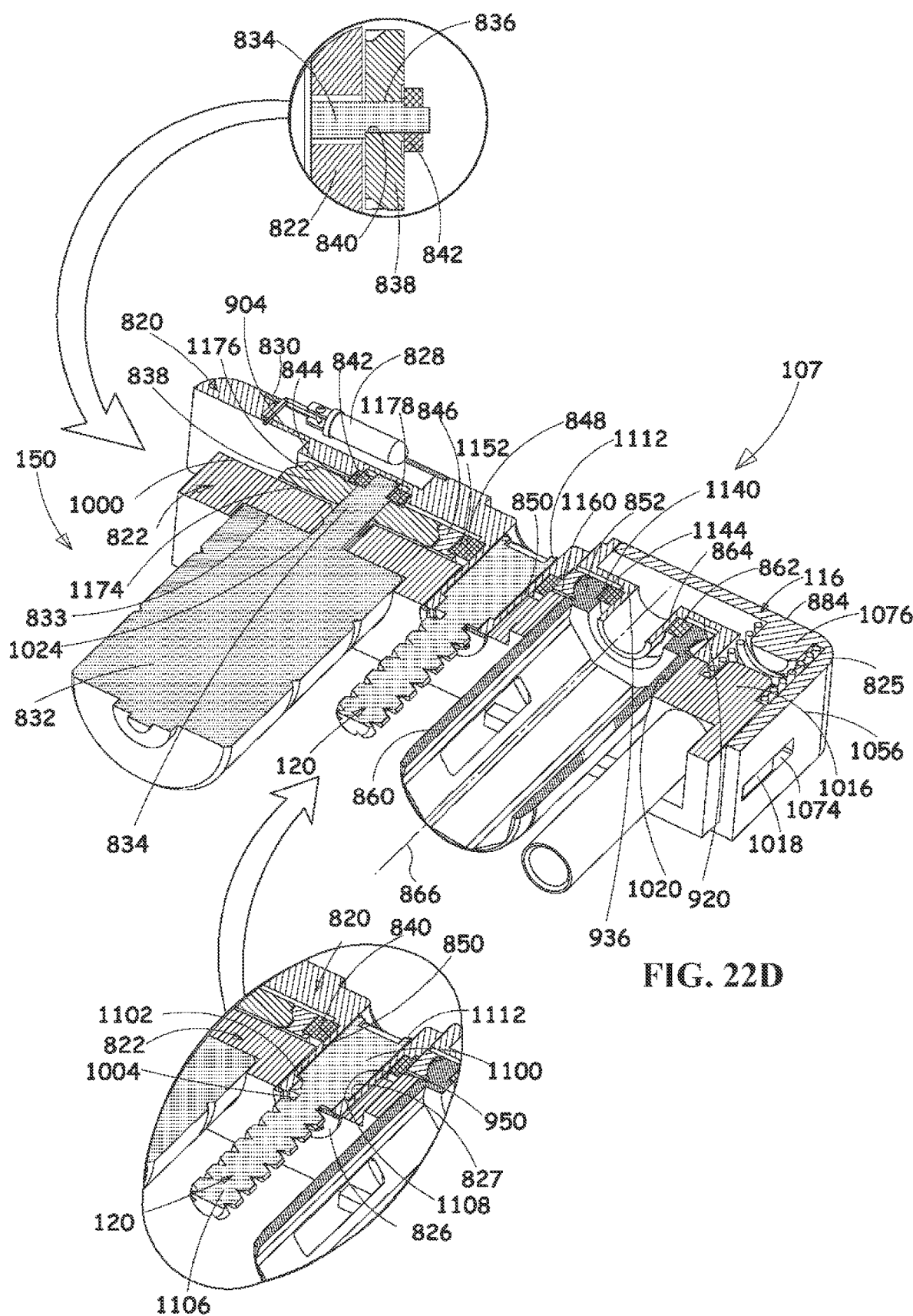
FIGS. 22D & 22E are sectional illustrations of the end housing assembly of the electronic automatic injection device of FIGS. 1A-2, taken respectively along lines D-D in FIG. 22A and along lines E-E in FIG. 22C.
Figure 22E:
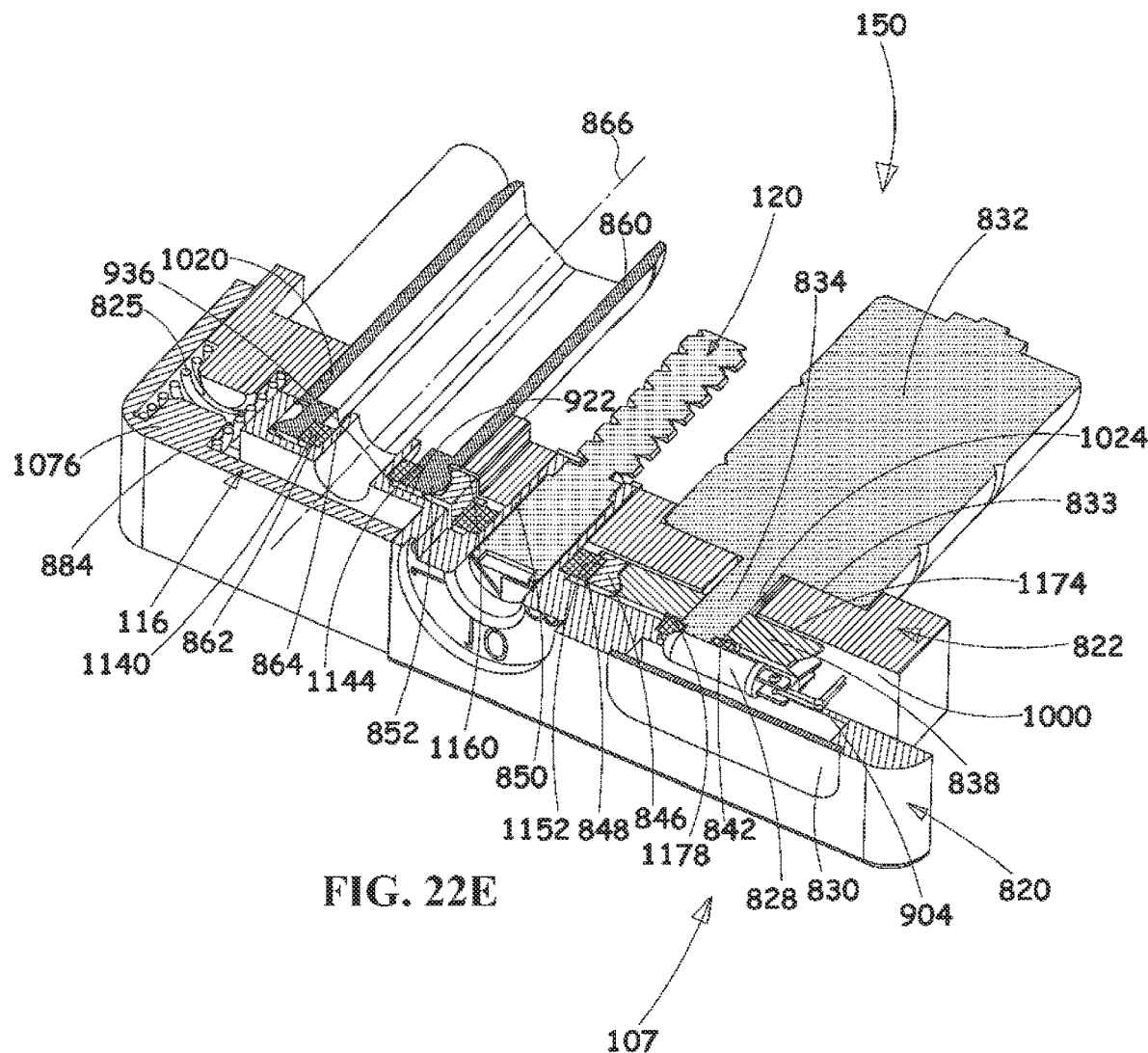
Figure 22F:
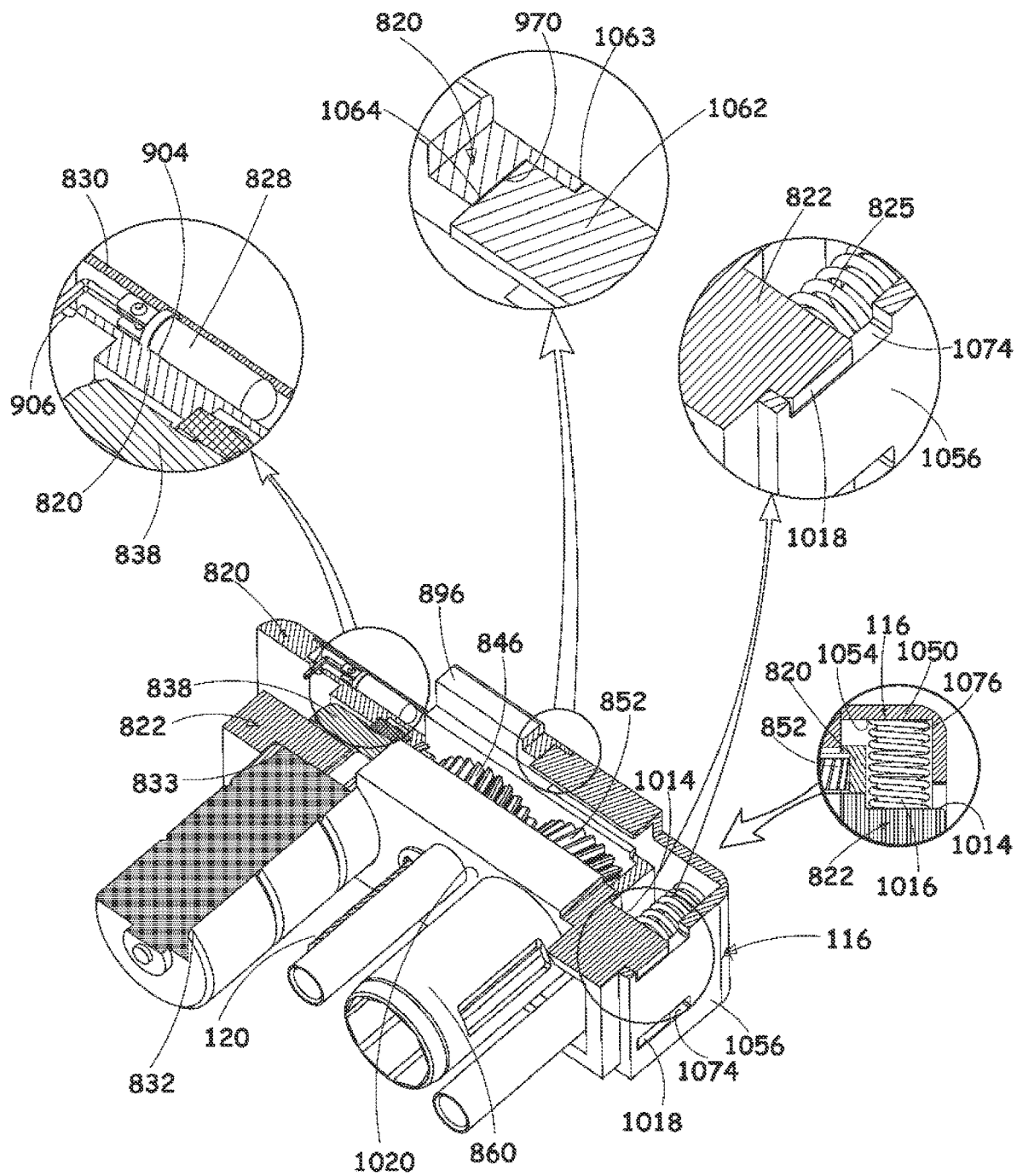
FIG. 22F is a simplified partially cut away illustration corresponding generally to FIG. 22A and illustrating details of the structure and assembly of the end housing assembly of the electronic automatic injection device of FIGS. 1A-2.

Reference is now made to FIGS. 22A, 22B & 22C, which are simplified pictorial illustrations of the end housing assembly of the electronic automatic injection device of FIGS. 1A-2, seen from three different directions, FIGS. 22D & 22E, which are sectional illustrations of the end housing assembly of the electronic automatic injection device of FIGS. 1A-2, taken respectively along lines D-D in FIG. 22A and along lines E-E in FIG. 22C and FIG. 22F, which is a simplified partially cut away illustration corresponding generally to FIG. 22A and illustrating details of the structure and assembly of the end housing assembly of the electronic automatic injection device of FIGS. 1A-2.

As seen in FIGS. 22A-22F, the end housing assembly 107 includes rearward housing portion 820 and forward support portion 822 and injection actuation button 116 which is slidably mounted on the rearward housing portion 820 and on the forward support portion 822 for displacement along an axis 824. Injection actuation button biasing spring 825 is disposed between the forward support portion 822 and the injection actuation button 116.

Figure 16A:
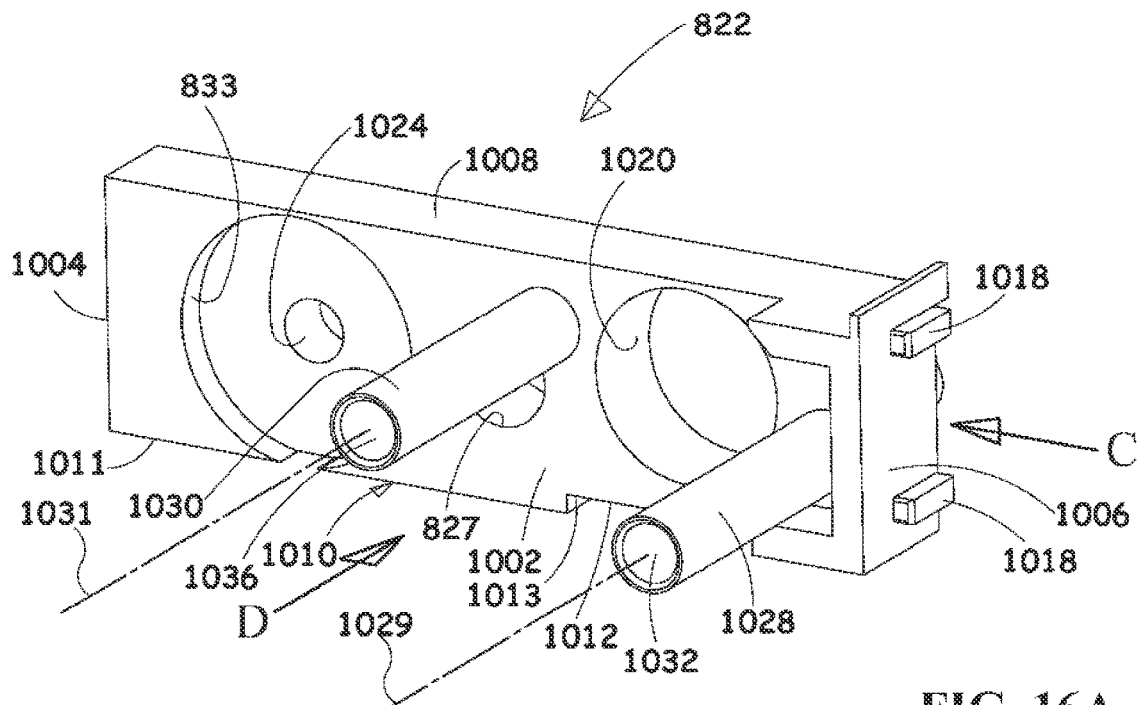
FIGS. 16A and 16B are simplified pictorial illustrations of a forward portion of the end housing assembly of the electronic automatic injection device of FIGS. 1A-2 seen from respective forward and rearward ends thereof
Figure 16B:
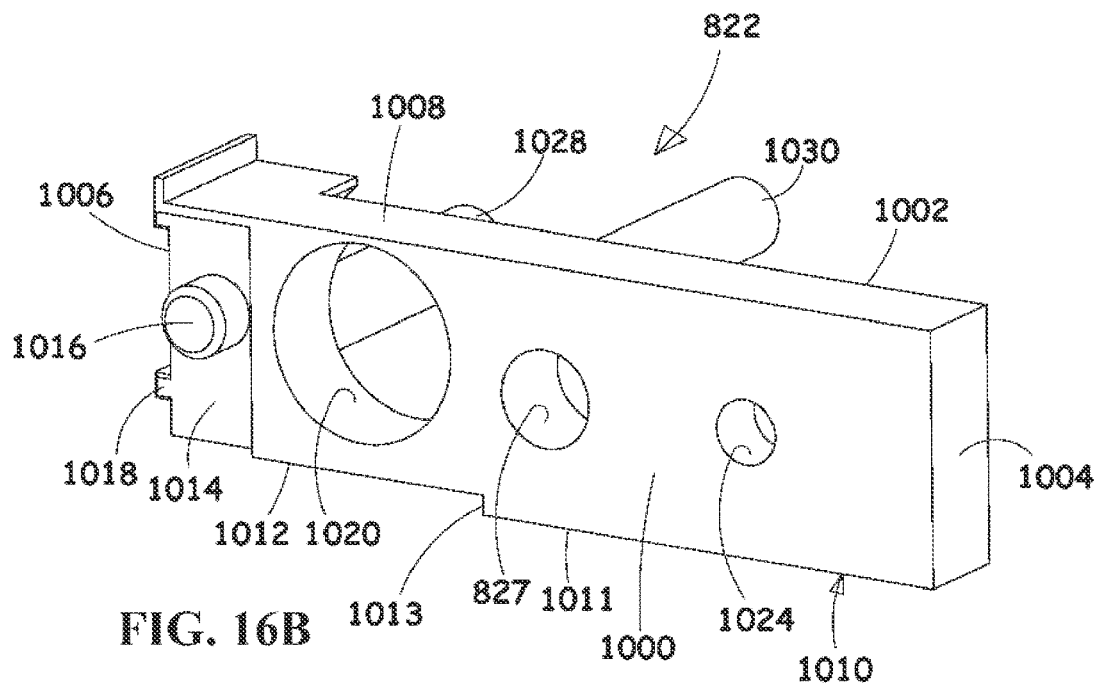
Figure 16C:
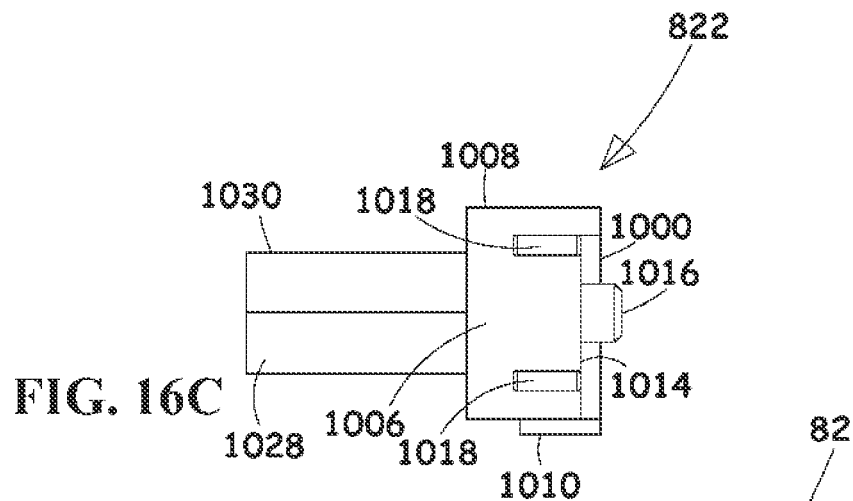
FIGS. 16C & 16D are elevation view illustrations of the forward portion of the end housing assembly of FIGS. 16A-16B, taken along respective directions indicated by arrows C and D in FIG. 16A.
Figure 16D:
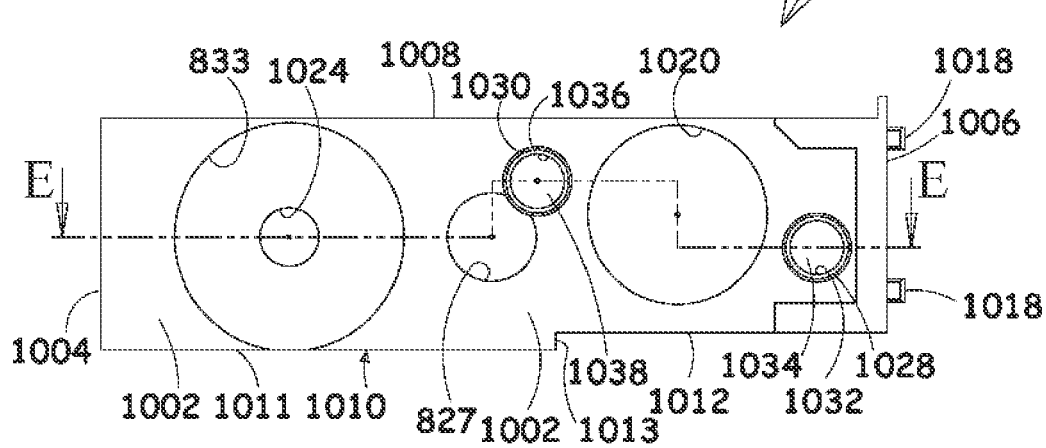
Figure 16E:
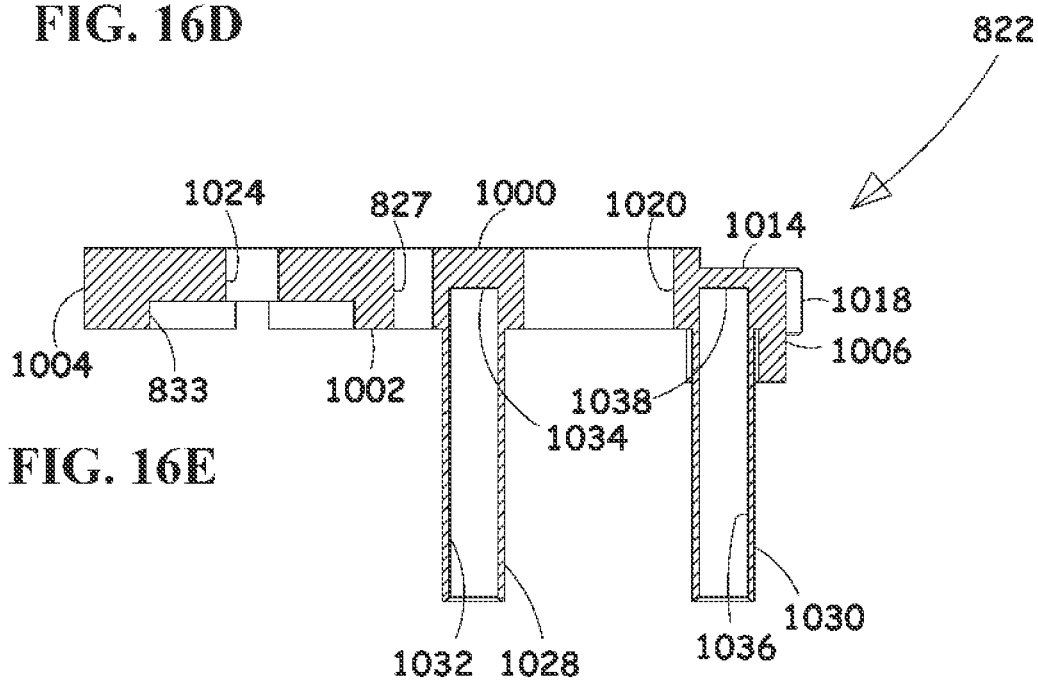
FIG. 16E is a sectional illustration of the forward portion of the end housing assembly, taken along lines E-E in FIG. 16.

Referring particularly to FIG. 22F, it is seen that spring 825 is seated at a forward end thereof on a spring seat defined by a spring seating pin 1016 which protrudes from recess 1014 formed in forward support portion 822 (FIGS. 16A & 16B). Spring 825 is also seated at a rearward end thereof on a spring seat defined by spring seating pin 1076 protruding from forward surface 1054 of planar wall 1050 of injection actuation button 116.

It is further seen that guide ribs 1018 of forward support portion 822 engage slots 1074 formed in side wall 1056 of injection actuation button 116. The elongate extent of slots 1074 determines the allowed travel of injection actuation button 116 relative to the rearward housing portion 820 and forward support portion 822 along axis 824.

It is additionally seen that cut-out 1063 formed in end 1064 of wall 1062 of injection actuation button 116 engages recess 970, formed in edge surface 896 of rearward housing portion 820. Additionally cut-out 1068 formed in portion 1066 of rearward-facing surface 1052 of wall 1050 of injection actuation button 116 engages recess 972, formed in edge surface 898 of rearward portion 820, although this engagement is not shown.

It is appreciated that the foregoing engagements guide and restrict the movement of injection actuation button 116 under manual actuation.

It is additionally seen that visual indicator 828 is disposed between rearward-facing wall surface 904 of rearward housing portion 820 and transparent cover 830.

Referring particularly to FIGS. 22D & 22E, it is seen that injection depth selector 120 (FIG. 2) is retained by lockwasher 826 in rotatable engagement with the rearward housing portion 820 and the forward support portion 822 in a manner which permits rotation thereof but does not permit displacement thereof.

More specifically, it is seen that cylindrical portion 1100 of injection depth selector 120 is rotatably retained in static sleeve 850 by engagement of thickened portion 948 of sleeve 850 with intermediate second circular cylindrical portion 1102 of injection depth selector 120, such that first shoulder surface 1108 abuts rearward facing shoulder surface 950. Lock washer 826 engages forwardmost third circular cylindrical portion 1104, such that injection depth selector 120 is thus retained against both forward and rearward axial motion parallel to axis 824.

It is noted additionally that rearward-facing end surface 1112 of injection depth selector 120 is recessed forwardly of planar surface 884 of rearward portion 880 of forward support portion 822, thereby to reduce the possibilities of inadvertent rotation thereof. It is seen that injection depth selector 120 extends forwardly through aperture 827 formed in the forward support portion 822 such that threaded portion 1106 extends forwardly thereof.

As noted above with reference to FIGS. 13A-14B, electric motor 832 is fixedly mounted onto forward support portion 822 at a recess 833 formed in forward support portion 822. Output shaft 834 of motor 832 extends through circular aperture 1024 formed in forward support portion 822 and fixedly engaged by gear whose forward surface 1174 is spaced slightly from rearward-facing surface 1000 of forward support portion 822 by engagement of forward surface 1174 with a shoulder defined between flat side surface 836 and a forward portion of output shaft 834. The rearward end of output shaft 834 fixedly engages an internal bearing ring of bearing 842, an external bearing ring of which is fixedly mounted in bearing seat 844 to a forward surface of rearward housing portion 820. The external bearing ring of bearing 842 is spaced from gear 838 by generally annular recess 1178, which is formed on rearward-facing surface 1176 of gear 838.

As noted above, gear 838 drivingly engages a gear 846, which is fixedly mounted to an external bearing ring of bearing 848 at inner-facing generally circular surface 1152 and rearward facing surface 1160 of gear 838. An internal bearing ring of bearing 848 is fixed to static sleeve 850, which is fixedly mounted to rearward housing portion 820.

As noted above, gear 846 drivingly engages a toothed portion 852 of a multiple drive element 860. Multiple drive element 860 extends forwardly through generally circular aperture 1020 of forward support portion 822 and is rotatably mounted onto forward support portion 822 via bearing 862 and a bearing seat 864 onto rearward housing portion 820 for rotation about an axis 866 which extends parallel to axis 824. It is noted that forwardly-facing circumferential protrusion 936 serves to physically separate an outer bearing ring of bearing 862 from planar surface 922 of rearward housing portion 820 to permit relative rotation therebetween. It is further noted that an outer bearing ring of bearing 862 is seated on shoulder surface 1144 and cylindrical surface 1140 of circumferential slot 1146 of multiple drive element 860.

Figure 23:
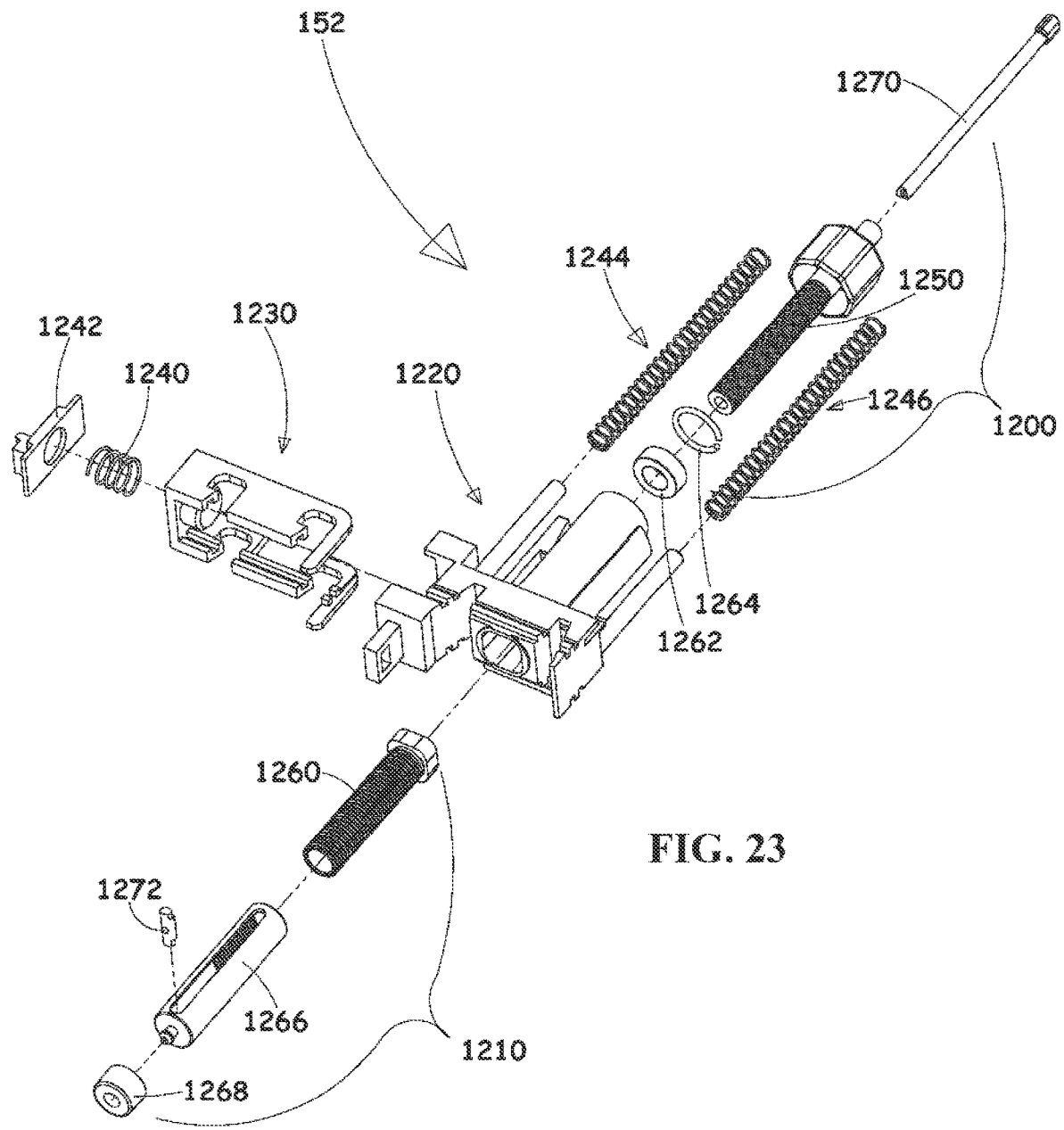
FIG. 23 is a simplified exploded illustration of a multiple motion output subassembly of the electronic automatic injection device of FIGS. 1A-2, shown from a forward end.

Reference is now made to FIG. 23, which illustrates a simplified exploded view of the multiple motion output subassembly 152 (FIG. 2) of the electronic automatic injection device 100. As seen in FIG. 23, a rearward plunger assembly 1200 and a forward plunger assembly 1210 are each partially inserted into a base element 1220 (FIGS. 24A-24I). A locking element 1230 (FIGS. 25A-25C) is slidably mounted onto base element 1220 by means of a compression spring 1240 and a spring seat 1242 (FIGS. 26A & 26B). First and second compression springs 1244 and 1246 are provided for mounting the base element 1220 on the end housing assembly 107 (FIG. 2).

The rearward plunger assembly 1200 comprises a rearward driving screw 1250 (FIG. 27A-27C), an intermediate screw 1260 (FIG. 28A-28C), which is slidably at least partially inserted into base element 1220. The rearward driving screw 1250 is threadably inserted into the intermediate screw 1260 and is rotatably mounted onto base element 1220 via a bearing 1262 and a lock washer 1264.

A forward driven element 1266 (FIGS. 29A-29C) is rotatably mounted onto the intermediate screw 1260. A piston engaging element 1268 (FIGS. 30A-30C) is rotatably mounted to a forward end of forward driven element 1266. A driving rod 1270 (FIGS. 31A-31C) is axially slidably inserted through the rearward driving screw 1250, the intermediate screw 1260 and at least partially through the forward driven element 1266, such that axial movement of the driving rod 1270 relative to elements 1250, 1260 and 1266 is permitted and rotational movement of driving pin 1270 relative to rearward driving element 1250 is prevented. Furthermore, rotational movement of driving rod 1270 relative to forward driven element 1266 is prevented by means of engagement between driving rod 1270, forward driven element 1266 and an engaging element 1272.

Reference is now made to FIGS. 24A-24H, which illustrate the base element 1220 of the multiple motion output subassembly 152 of the electronic automatic injection device 100. As seen in FIGS. 24A-24H, the base element 1220 includes a central wall portion 1300, defining a rearward-facing surface 1304, first and second side portions, respectively designated by reference numerals 1306 and 1308 and a bottom track following portion 1310 having a bottom facing track following surface 1312.

Extending rearwardly from rearward-facing surface 1304 are first and second spring seating pins 1314 and 1316, onto which are mounted springs 1244 and 1246 (FIG. 23) respectively. Also extending rearwardly from rearward-facing surface 1304 are first and second flexible engagement fingers 1324 and 1326, which are removably engageable with respective slots 1122 and 1124 of multiple drive element 860. Further extending rearwardly from rearward-facing surface 1304 is a plunger assembly receiving cylinder 1330.

Figure 24A:
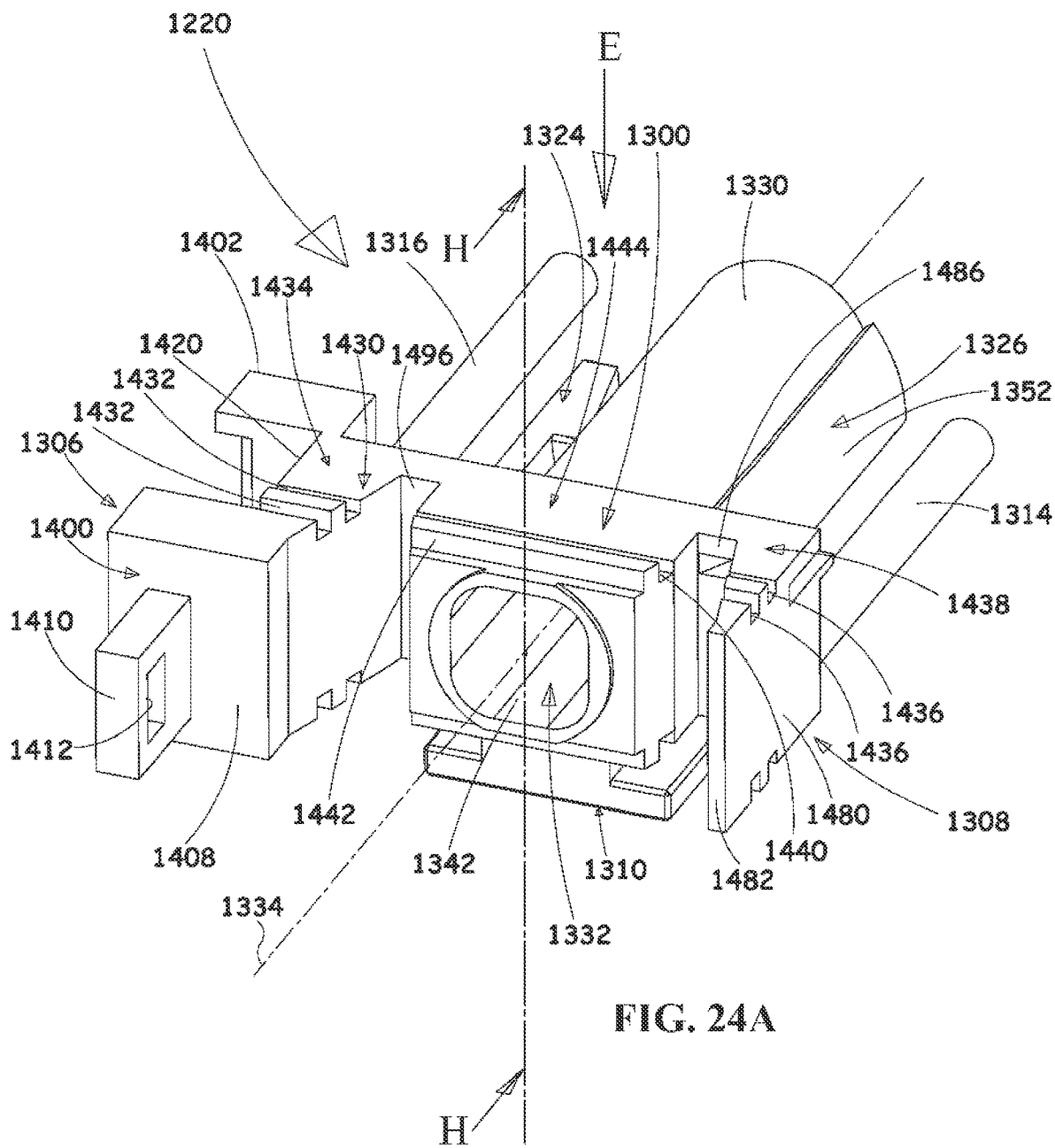
FIGS. 24A & 24B are simplified pictorial illustrations of a base element of the multiple motion output subassembly seen in a downward-facing view from a forward-facing end and a rearward-facing end respectively.
Figure 24B:
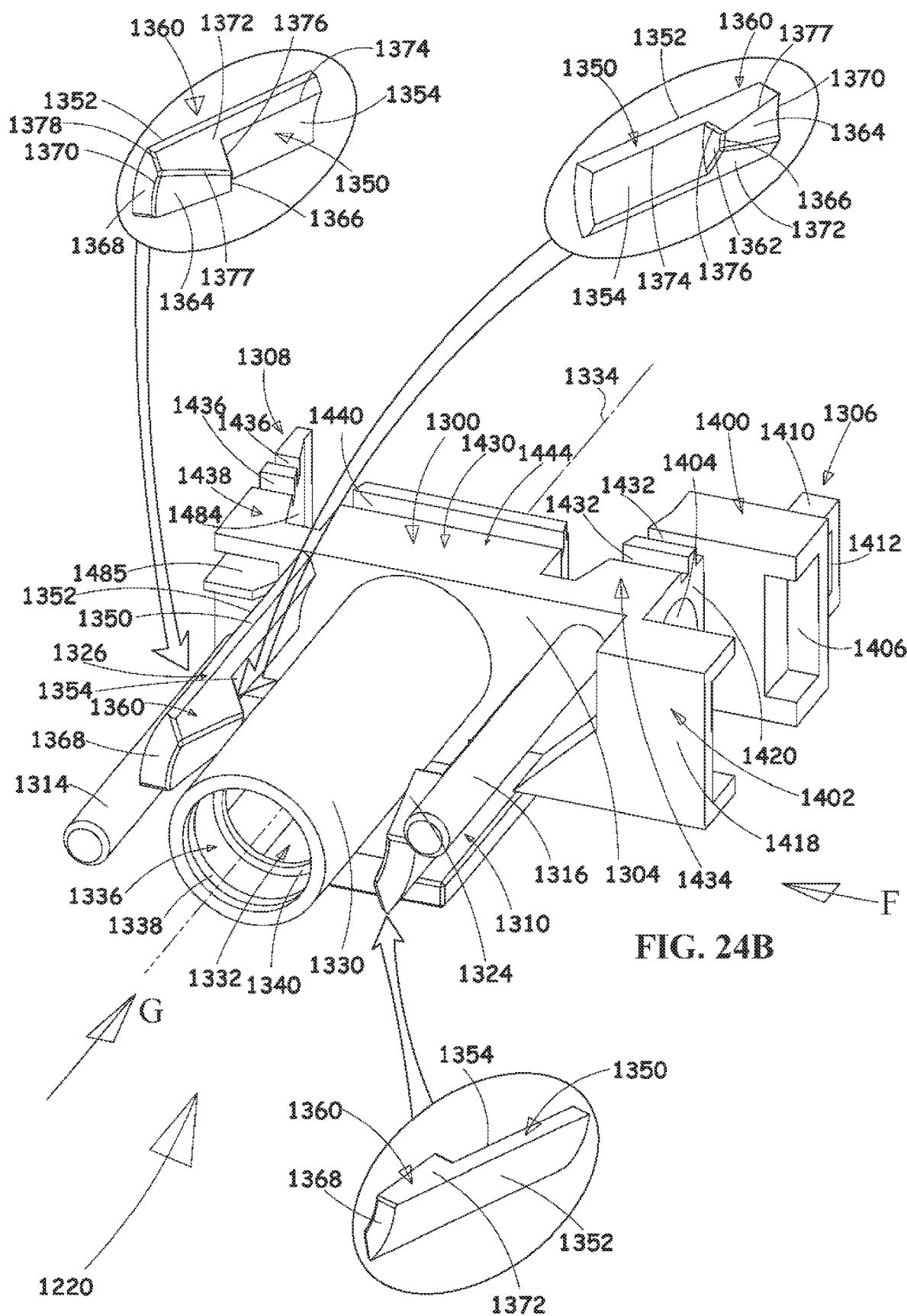
Figure 24C:
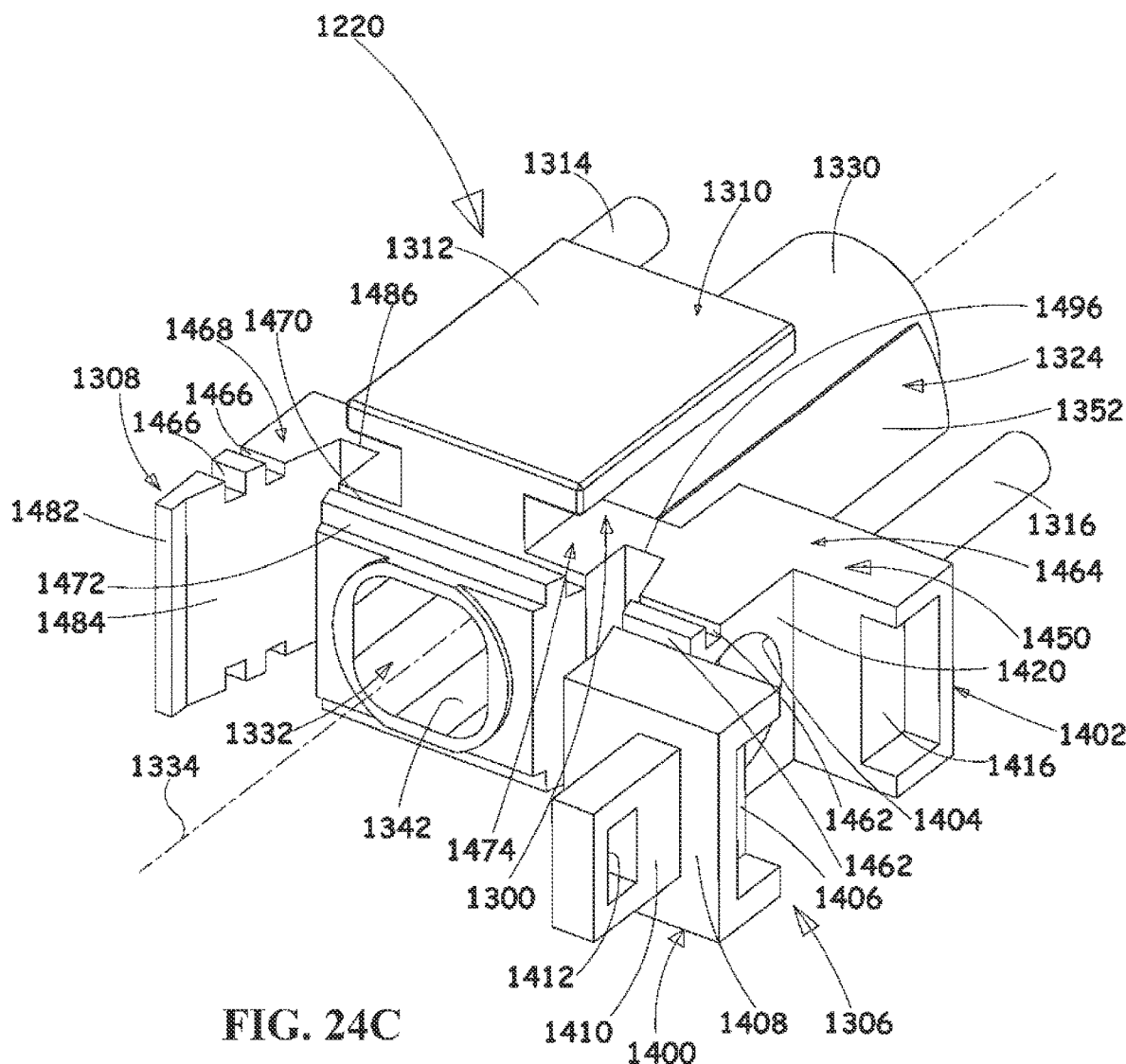
FIGS. 24C and 24D are simplified pictorial illustrations of the base element of FIGS. 24A & 24B seen in an upward-facing view from a forward-facing end and a rearward-facing end respectively.
Figure 24D:
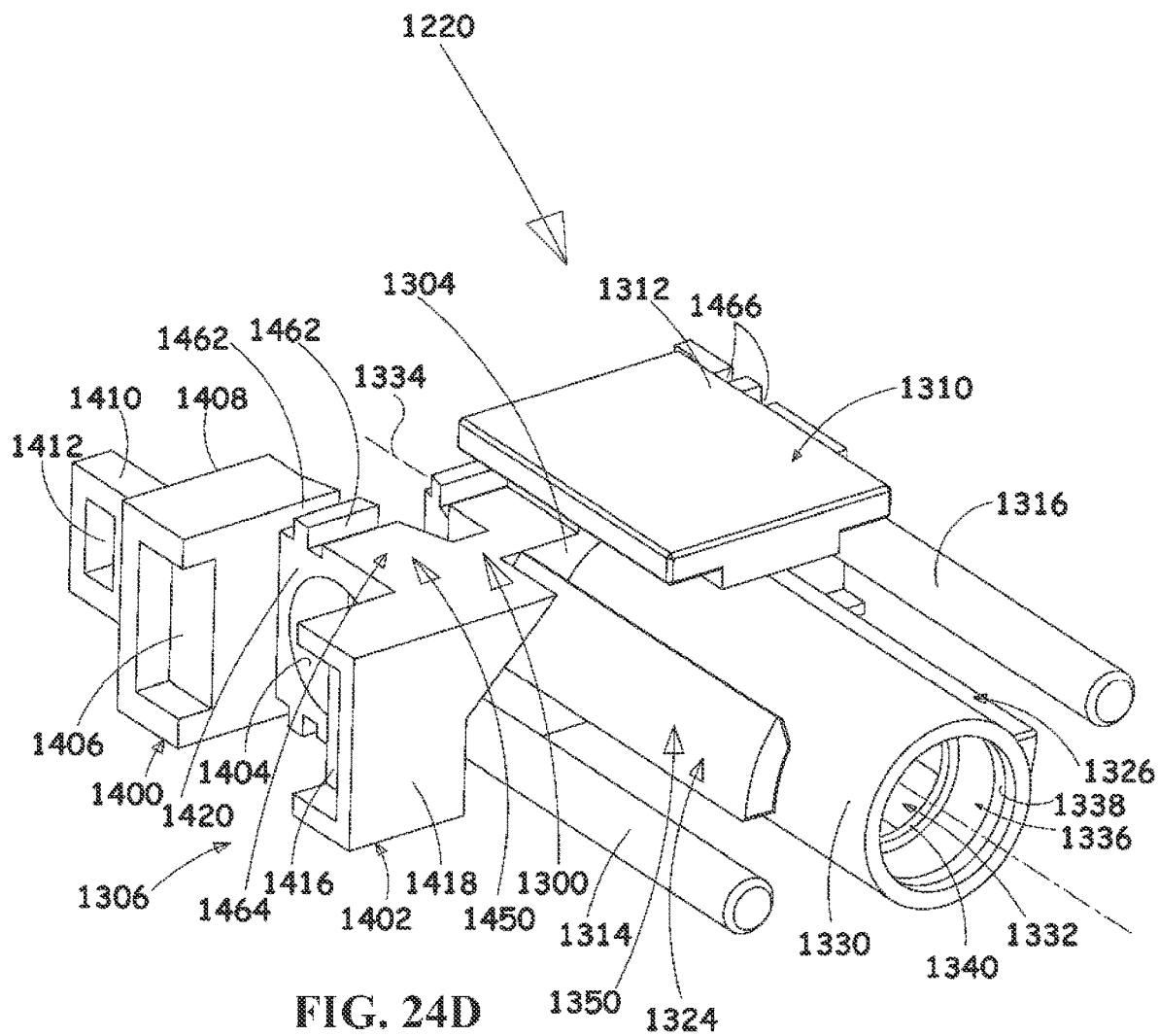
Figure 24G:
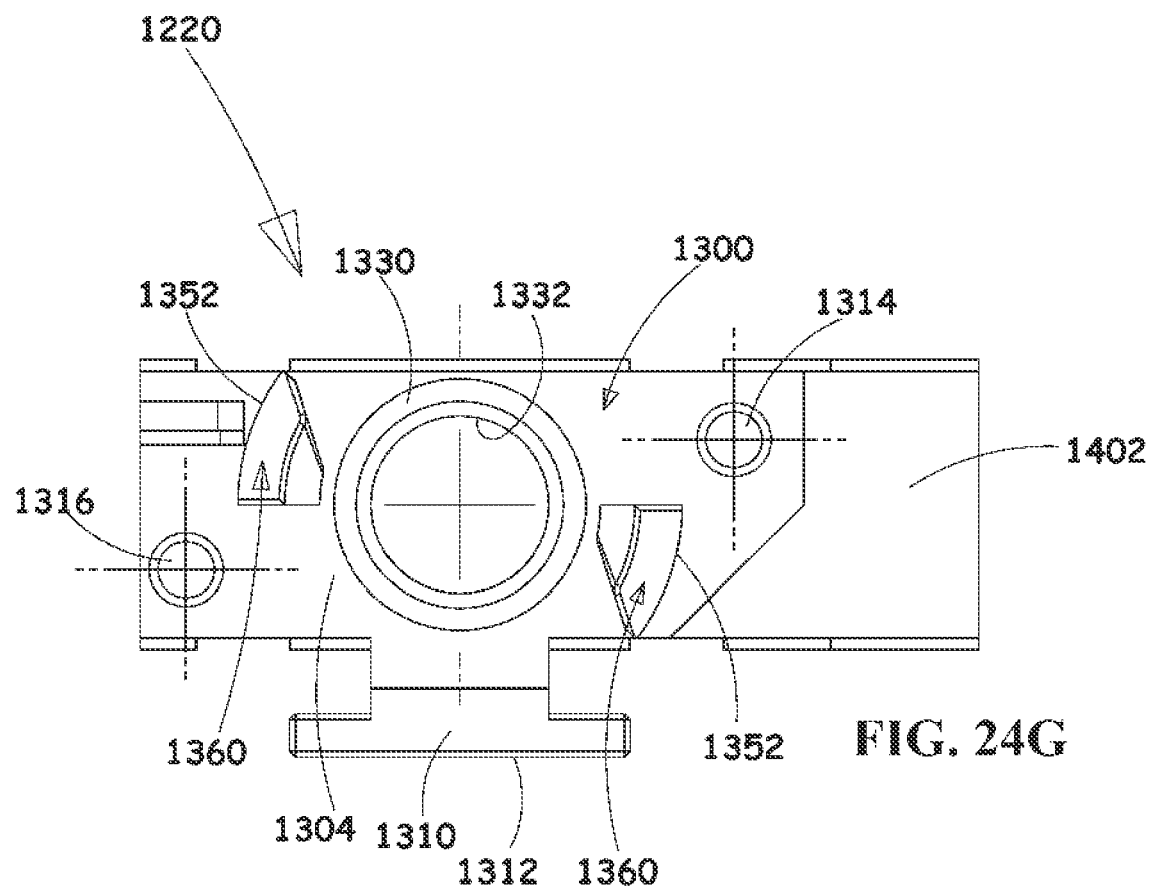
Figure 24H:
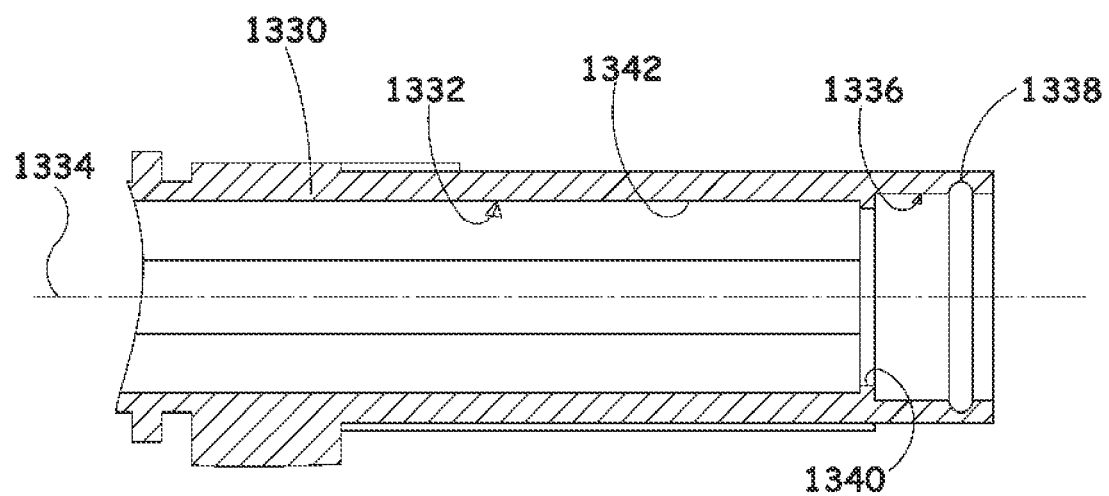

As seen particularly in FIG. 24H, plunger assembly receiving cylinder 1330 has a throughgoing axial bore 1332, extending along an axis 1334. Bore 1332 has a generally circular cross section at a rearward portion 1336 thereof and is formed with a circumferential recess 1338. An internally directed flange 1340 separates rearward portion 1336 from a forward portion 1342 of bore 1332. Forward portion 1342 has a generally square cross section, having rounded corners.

The configuration of each of flexible engagement fingers 1324 and 1326 is seen clearly in enlargements A and B in FIG. 24B. As seen there, each of flexible engagement fingers 1324 and 1326 includes a shaft portion 1350 having a generally convex radially outward facing surface 1352 and a generally concave radially inward facing surface 1354. Rearwardly of shaft portion 1350 is an engagement tooth portion 1360 which includes a forwardly and radially inwardly facing inclined surface 1362, which intersects a rearwardly and radially inwardly facing surface 1364 at an edge 1366. Tooth portion 1360 also includes a radially inwardly tapered, forwardly inclined, rearwardly facing edge surface 1368, which engages surface 1364 at an edge 1370. Each engagement finger also includes a pair of rearwardly inwardly tapered side surfaces 1372, which intersect respective surfaces 1354, 1362, 1364 and 1368 at respective edges 1374, 1376, 1377 and 1378.

First side portion 1306 includes forward and rearward bulkhead portions 1400 and 1402 respectively which are located in mutually spaced facing relationship on respective forward and rearward sides of a circular spring seat recess 1404, which accommodates spring 1240 (FIG. 23).

Forward bulkhead portion 1400 includes a side and rearward facing, generally rectangular corner recess 1406 and defines a forward facing wall 1408 from which extends forwardly a generally rectangular protrusion 1410 having a rectangular aperture 1412.

Rearward bulkhead portion 1402 includes a side and forward facing, generally rectangular corner recess 1416, which faces corner recess 1406, and defines a rearward facing wall 1418.

A side facing surface 1420 surrounds an opening of recess 1404 and extends between forward and rearward bulkhead portions 1400 and 1402.

A double-grooved top transverse track is defined on a top surface 1430 of the base element 1220 and includes the following mutually axial portions: a pair of parallel grooves 1432 formed in a top surface portion 1434 which intersects side facing surface 1420, a pair of parallel grooves 1436 formed in a top surface portion 1438 of second side portion 1308, and a groove 1440 and an elongate forward facing recess 1442, spaced from and parallel to groove 1440, formed in a top surface portion 1444 of central wall portion 1300.

A double-grooved bottom transverse track is defined on a bottom surface 1450 of the base element 1220 and includes the following mutually axial portions: a pair of parallel grooves 1462 formed in a bottom surface portion 1464 which intersects side facing surface 1420, a pair of parallel grooves 1466 formed in a bottom surface portion 1468 of second side portion 1308, and a groove 1470 and an elongate forward facing recess 1472, spaced from and parallel to groove 1470, formed in a bottom surface portion 1474 of central wall portion 1300.

Second side portion 1308 defines a side facing surface 1480, which intersects respective top and bottom surfaces 1438 and 1468, a forward facing edge surface 1482, an inclined inwardly facing surface 1484, and a microswitch support surface 1485.

Inclined inwardly facing surface 1484 is defined by an angled forwardly facing cut out 1486 which partially separates central wall portion 1300 from second side portion 1308 and also defines a forwardly facing surface 1488 as well as a side facing central wall portion surface 1490 which includes an axial portion 1492 and a more forwardly angled portion 1494.

An angled forwardly facing cut out 1496 partially separates central wall portion 1300 from first side portion 1306 and also defines a forwardly facing surface 1498 as well as a side facing central wall portion surface 1500, which includes an axial portion 1502 and a more forwardly axial portion 1504.

Figures 25A, 25B:
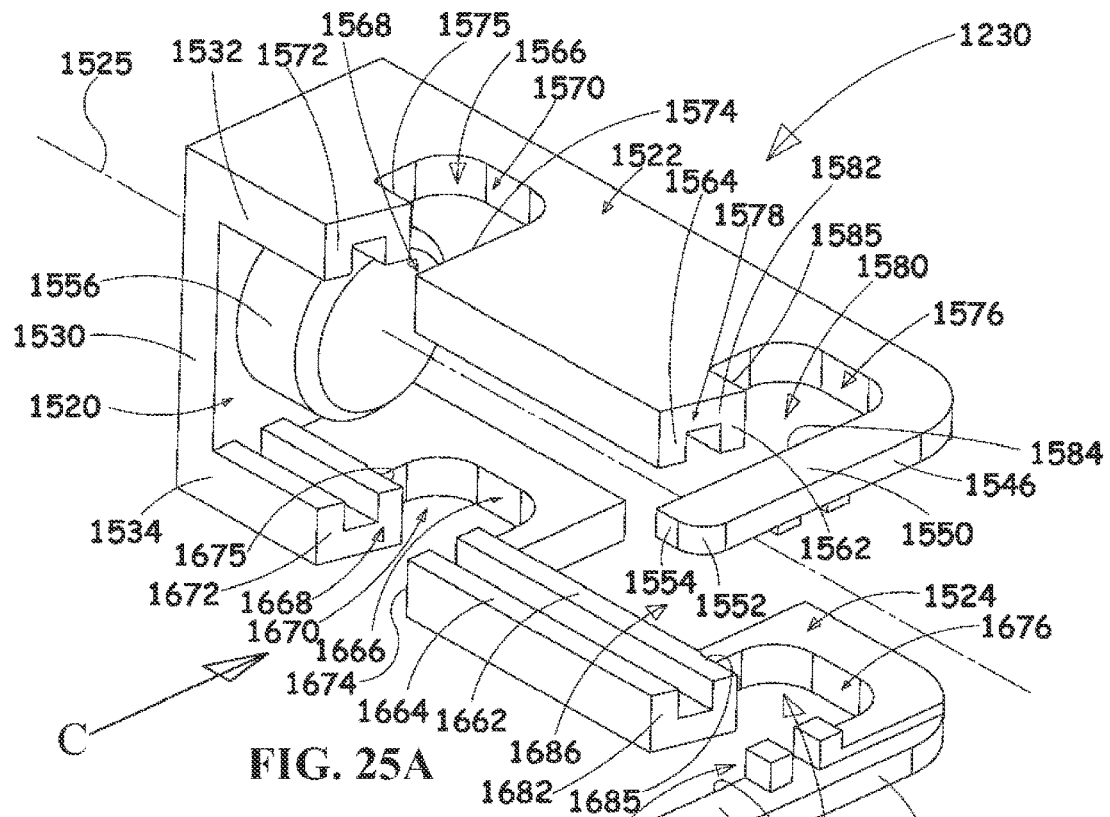
FIGS. 25A & 25B are simplified pictorial illustrations of a locking element forming part of the multiple motion output subassembly of FIG. 23, seen from respective forward and rearward ends thereof.
Figure 25C:
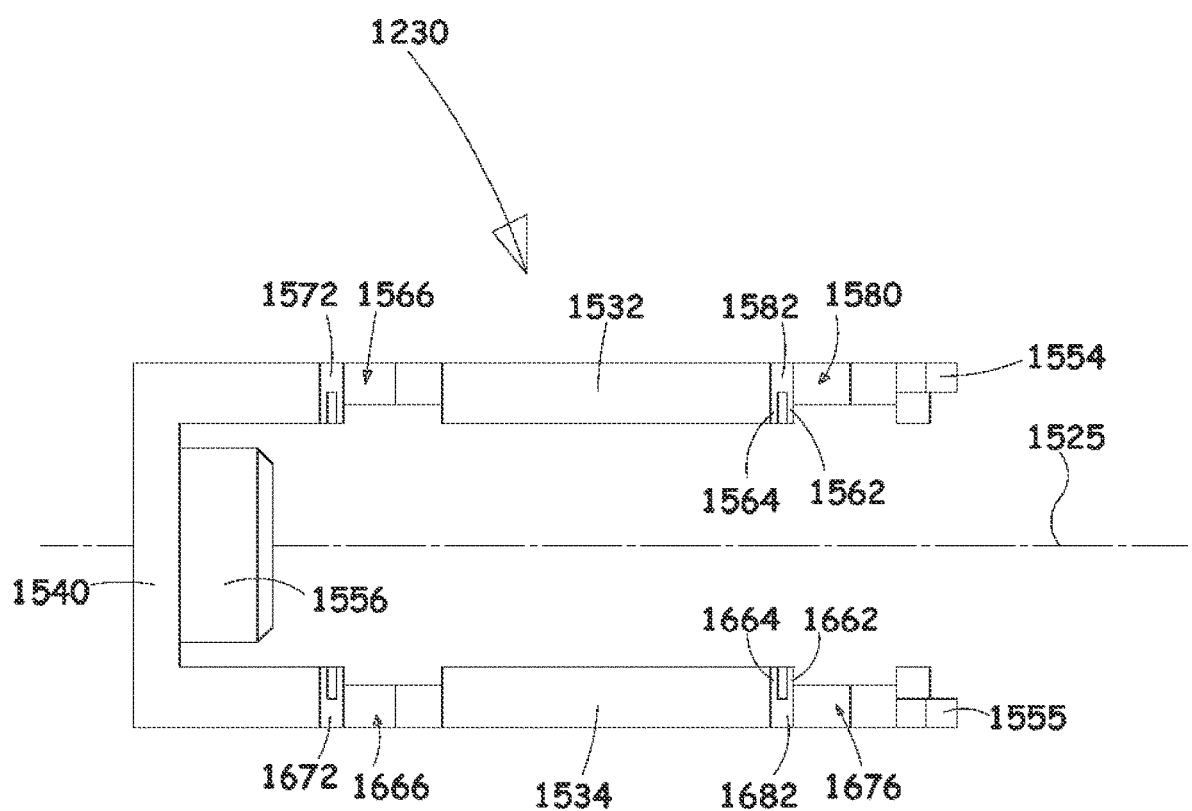
FIG. 25C is a simplified elevation view illustration of the locking element of FIGS. 25A & 25B, taken along the line C in FIG. 25A.
Figure 26A:
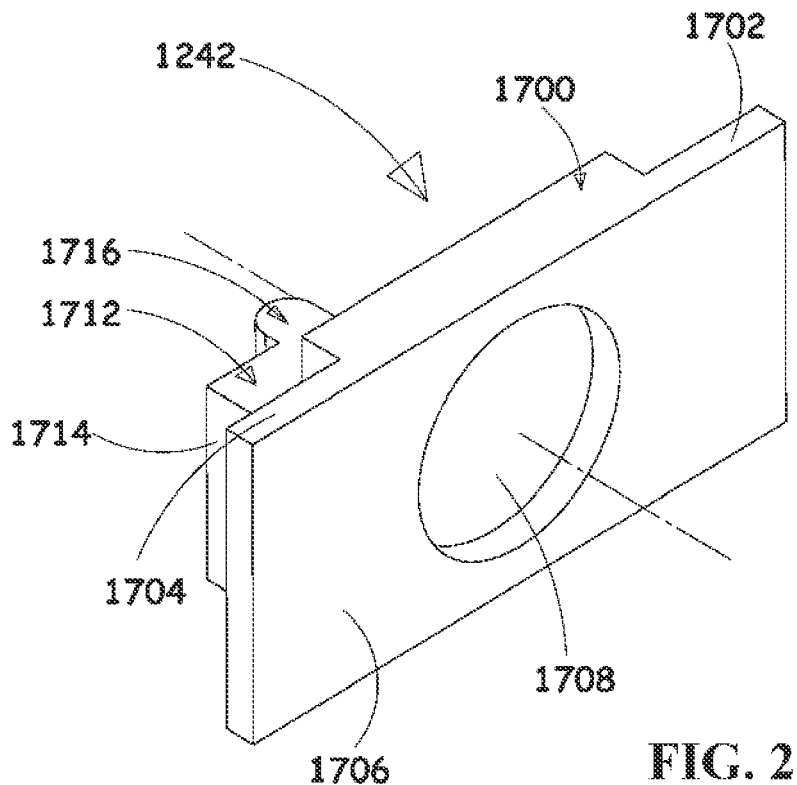
FIGS. 26A & 26B are simplified pictorial illustrations of a spring seat forming part of the multiple motion output subassembly of FIG. 23, seen from respective forward and rearward ends thereof.
Figure 26B:
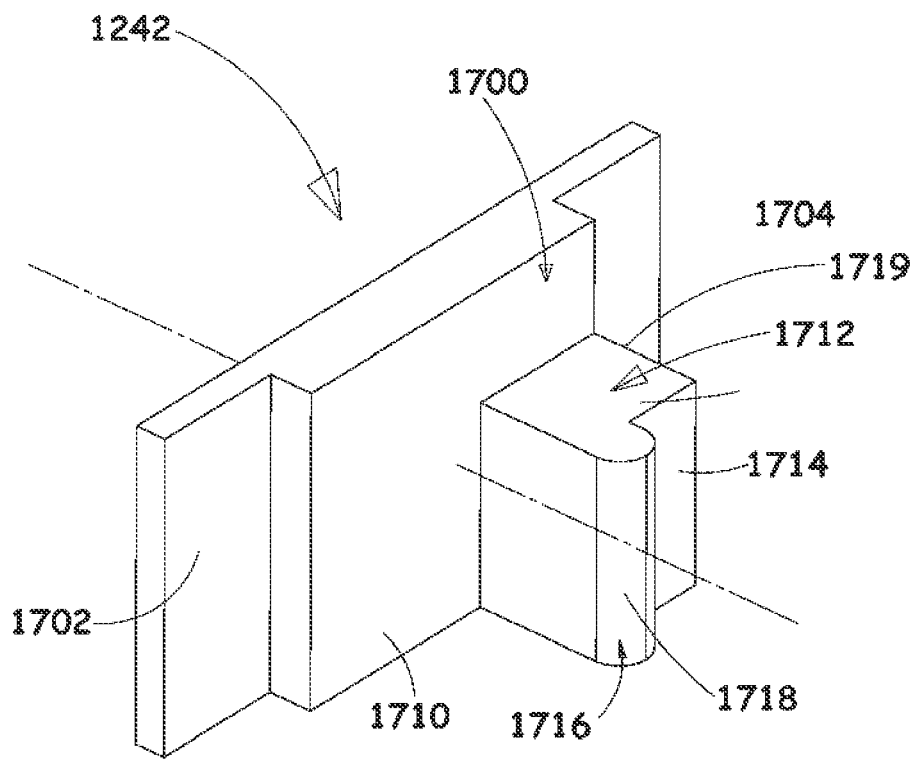

Reference is now made to FIGS. 25A & 25B, which are simplified pictorial illustrations of locking element 1230 forming part of the multiple motion output subassembly 152 of FIG. 23, seen from respective forward and rearward ends thereof and to FIG. 25C, which is a simplified elevation view illustration of the locking element of FIGS. 25A & 25B, taken along the line C in FIG. 25A.

As seen in FIGS. 25A-25C, locking element 1230 is a generally U-shaped element, which is integrally formed to have a base wall portion 1520 and a pair of side wall portions 1522 and 1524, which extend in spaced generally parallel relationship, perpendicularly to base wall portion 1520, parallel to an axis 1525. Base wall portion 1520 and side wall portions 1522 and 1524 define respective first edge surfaces 1530, 1532 and 1534, which extend parallel to axis 1525; respective second edge surfaces 1540, 1542 and 1544, facing in a direction opposite to edge surfaces 1530, 1532 and 1534 and also extending parallel to axis 1525; and end edge surfaces 1546 and 1548, which extend perpendicularly to axis 1525. It is noted that edge surfaces 1546 and 1548 extends beyond respective edge surfaces 1532 and 1534 and thus define respective protruding finger portions 1550 and 1551 having respective curved corner edge surfaces 1552 and 1553 and edge surfaces 1554 and 1555.

Base wall portion 1520 defines a generally hollow circular cylindrical spring seat protrusion 1556, which extends a short distance between side wall portions 1522 and 1524 along axis 1525. A circular cylindrical recess 1558 is formed in protrusion 1556.

Side wall portion 1522 is formed with a pair of inwardly protruding elongate tracks 1562 and 1564 which extend parallel to axis 1525 all along the side wall portion 1522. Side wall portion 1522 is also formed with a first cut out 1566, adjacent base wall portion 1520. First cut out 1566 includes a tapered relatively narrow portion 1568 which extends from edge surface 1532 and cuts through tracks 1562 and 1564, and a relatively wide portion 1570. The tapered relatively narrow portion 1568 includes an inclined edge surface 1572 and an oppositely facing edge surface 1574, an extension of which defines an edge of relatively wide portion 1570. Inclined edge surface 1572 joins a shoulder edge surface 1575, which separates the relatively narrow portion 1568 from the relatively wide portion 1570.

Side wall portion 1522 is additionally formed with a second cut out 1576, adjacent end edge surface 1546. Second cut out 1576 includes a tapered relatively narrow portion 1578 which extends from edge surface 1532 and cuts through tracks 1562 and 1564, and a relatively wide portion 1580. The tapered relatively narrow portion 1578 includes an inclined edge surface 1582 and an oppositely facing edge surface 1584, an extension of which defines an edge of relatively wide portion 1580. Inclined edge surface 1582 joins a shoulder edge surface 1585, which separates the relatively narrow portion 1578 from the relatively wide portion 1580.

Side wall portion 1524 is formed with a pair of inwardly protruding elongate tracks 1662 and 1664 which extend parallel to axis 1525 all along the side wall portion 1524. Side wall portion 1524 is also formed with a first cut out 1666, adjacent base wall portion 1520. First cut out 1666 includes a tapered relatively narrow portion 1668 which extends from edge surface 1632 and cuts through tracks 1662 and 1664, and a relatively wide portion 1670. The tapered relatively narrow portion 1668 includes an inclined edge surface 1672 and an oppositely facing edge surface 1674, an extension of which defines an edge of relatively wide portion 1670. Inclined edge surface 1672 joins a shoulder edge surface 1675, which separates the relatively narrow portion 1668 from the relatively wide portion 1670.

Side wall portion 1524 is additionally formed with a second cut out 1676, adjacent end edge surface 1646. Second cut out 1676 includes a tapered relatively narrow portion 1678 which extends from edge surface 1632 and cuts through tracks 1662 and 1664 and a relatively wide portion 1680. The tapered relatively narrow portion 1678 includes an inclined edge surface 1682 and an oppositely facing edge surface 1684, an extension of which defines an edge of relatively wide portion 1680. Inclined edge surface 1682 joins a shoulder edge surface 1685, which separates the relatively narrow portion 1678 from the relatively wide portion 1680.

Side wall portion 1524 is further provided with a generally rectangular cut out 1686 which extends from edge surface 1544 up to track 1662.

Reference is now made to FIGS. 26A & 26B, which are simplified pictorial illustrations of spring seat 1242 forming part of the multiple motion output subassembly 152 of FIG. 23, seen from respective forward and rearward ends thereof. As seen in FIGS. 26A & 26B, the spring seat 1242 in an integrally formed element which comprises a central, generally rectangular planar portion 1700 and a pair of generally rectangular side planar portions 1702 and 1704, extending outwardly therefrom. Side planar portions 1702 and 1704 typically have a thickness which is less than half of the thickness of central planar portion 1700.

Central planar portion 1700 and side planar portions 1702 and 1704 together define a planar surface 1706 having formed therewithin a generally cylindrical recess 1708, whose depth is typically similar to the thickness of side planar portions 1702.

Central planar portion 1700 also defines a planar surface 1710, which faces in a direction opposite to that of planar surface 1706. A protrusion 1712 extends outwardly from planar surface 1710 adjacent side planar portion 1702 and includes a generally rectangular block shaped portion 1714 and an elongate protruding portion 1716 which defines a generally circular semi-cylindrical microswitch engagement surface 1718. A side of protrusion 1712 defines a further microswitch engagement surface 1719.

Reference is now made to FIGS. 27A & 27B, which are simplified pictorial illustrations of rearward driving screw 1250, forming part of the multiple motion output subassembly 152 of FIG. 23, seen from respective forward and rearward ends thereof and to FIG. 27C, which is a simplified sectional illustration of the rearward driving screw of FIGS. 27A & 27B, taken along the line C in FIG. 27A.

As seen in FIGS. 27A-27C, the rearward driving screw 1250 is preferably an integrally formed element including a shaft portion 1720 extending along an axis 1721. A flange 1722 extends radially outwardly from shaft portion 1720 to a generally octagonal cylindrical portion 1724, having a generally octagonal cylindrical outer surface 1726 which includes eight flat portions 1728 separated by respective curved portions 1730. Shaft portion 1720 defines a forward edge 1732 and a rearward edge 1734.

Shaft portion 1720 defines a threaded forward outward facing surface portion 1736, rearwardly of which is a generally circular cylindrical outward facing surface portion 1738, rearwardly of which is a generally circular cylindrical collar portion 1740 from which flange 1722 extends radially. Rearward of collar portion 1740 there is provided a further generally circular cylindrical outward facing surface portion 1742, which extends axially rearwardly of octagonal cylindrical portion 1734. A forward facing shoulder 1744 is defined between generally circular cylindrical outward facing surface portion 1738 and generally circular cylindrical collar portion 1740.

Shaft portion 1720 is formed with a throughgoing bore extending along axis 1721. The throughgoing bore includes a generally circular cylindrical portion 1746 at a forward end of the shaft portion 1720 and a generally obround cylindrical portion 1748 at a rearward end of the shaft portion 1720. A forwardly facing shoulder 1749 is defined between the cylindrical portions 1746 and 1748.

Figure 28A:
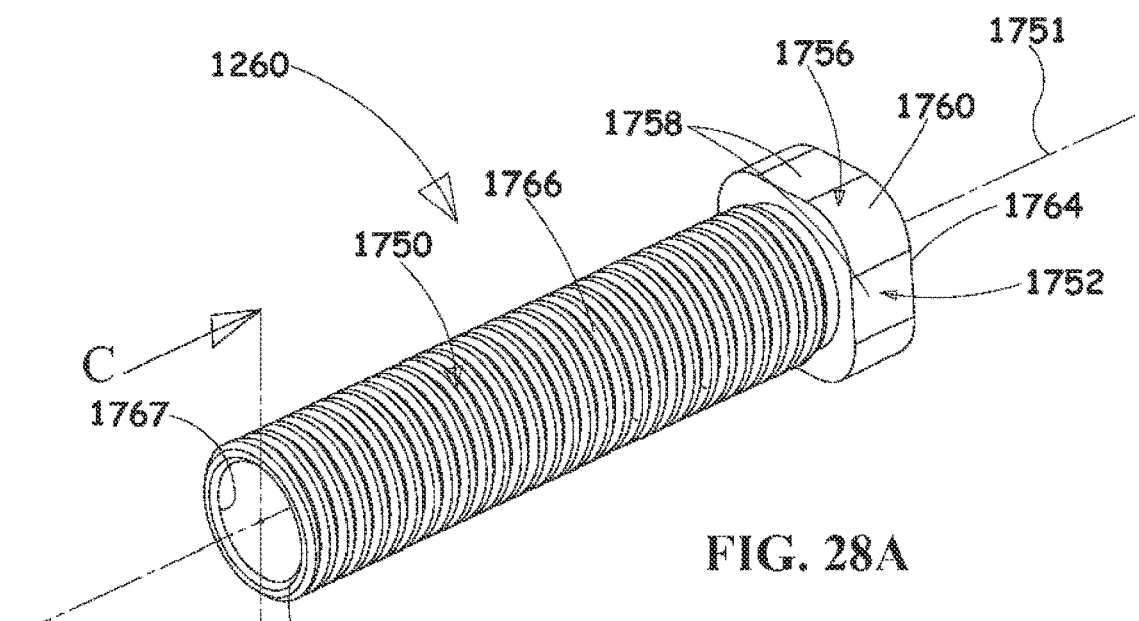
FIGS. 28A & 28B are simplified pictorial illustrations of an intermediate screw, forming part of the multiple motion output subassembly of FIG. 23, seen from respective forward and rearward ends thereof.
Figure 28B:
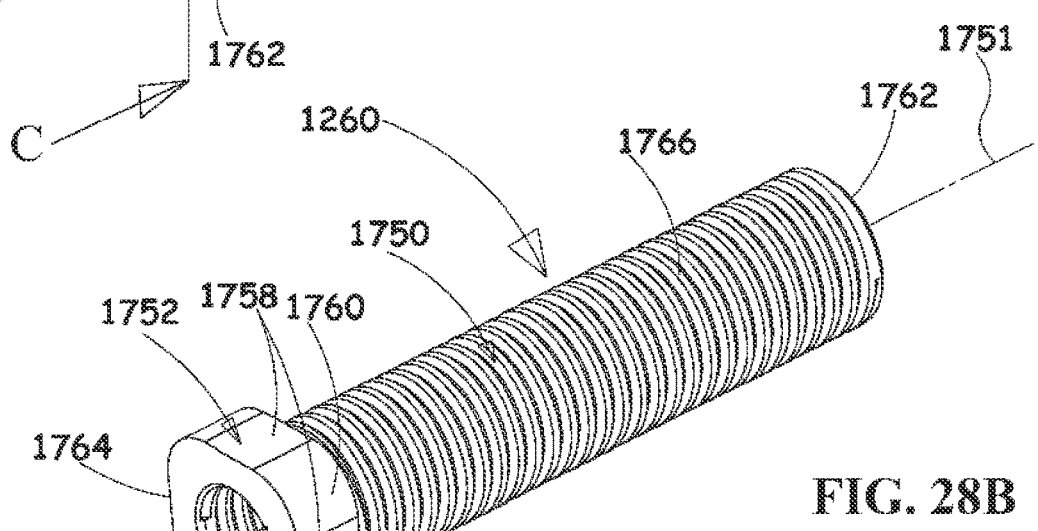
Figure 28C:
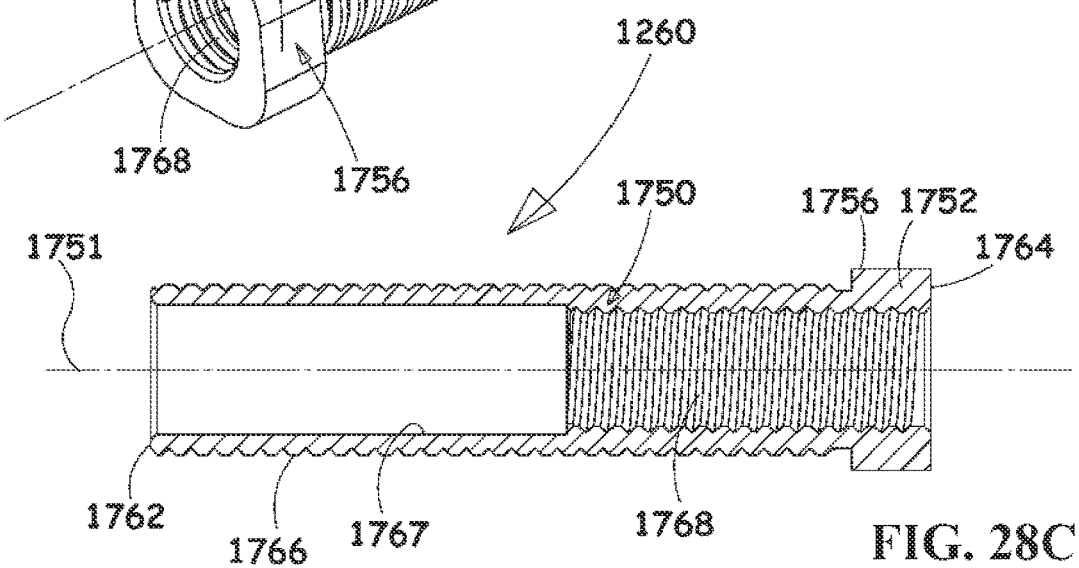
FIG. 28C is a simplified sectional illustration of the intermediate screw of FIGS. 28A & 28B, taken along the line C in FIG. 28A.

Reference is now made to FIGS. 28A & 28B, which are simplified pictorial illustrations of intermediate screw 1260, forming part of the multiple motion output subassembly 152 of FIG. 23, seen from respective forward and rearward ends thereof and to FIG. 28C, which is a simplified sectional illustration of the intermediate screw of FIGS. 28A & 28B, taken along the line C in FIG. 28A.

As seen in FIGS. 28A-28C, the intermediate screw 1260 is preferably an integrally formed element including a shaft portion 1750 extending along an axis 1751 and a nut portion 1752 at a rearward end thereof. Nut portion 1752 has a generally rounded square cylindrical outer surface 1756 which includes four flat portions 1758 separated by respective curved portions 1760. Shaft portion 1750 defines a forward edge 1762 and nut portion 1752 defines a rearward edge 1764.

Shaft portion 1750 defines a counterclockwise threaded outward facing surface portion 1766 and is formed with a throughgoing bore extending along axis 1751. The throughgoing bore includes a generally circular cylindrical portion 1767 at a forward end of the shaft portion 1750 and a generally clockwise threaded cylindrical portion 1768 at a rearward end of the shaft portion 1750 which also underlies nut portion 1752.

Figure 29A:
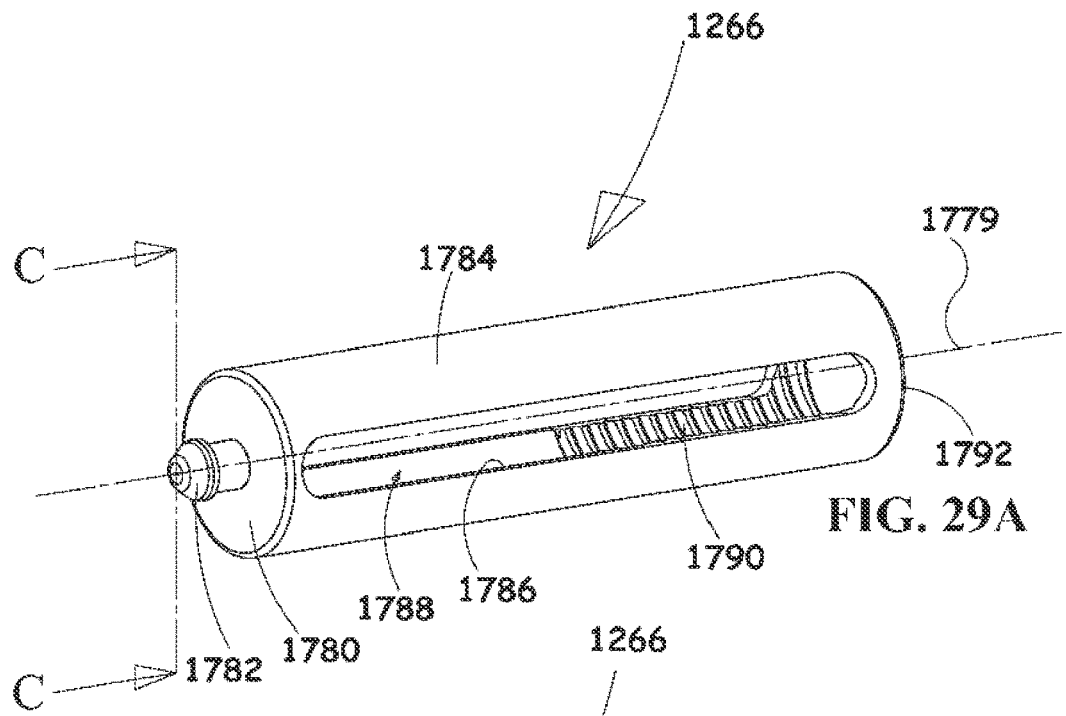
FIGS. 29A & 29B are simplified pictorial illustrations of a forward driven element, forming part of the multiple motion output subassembly of FIG. 23, seen from respective forward and rearward ends thereof.
Figure 29B:
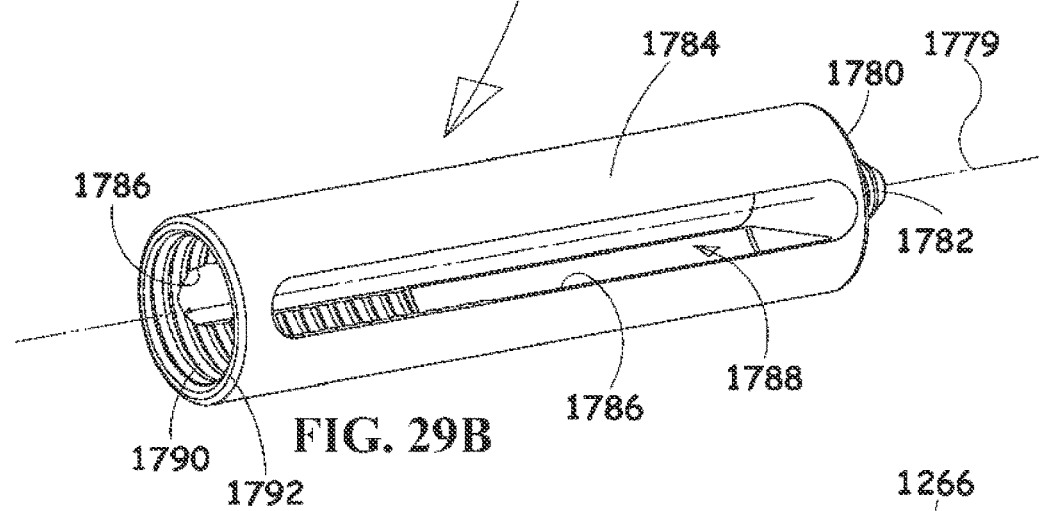
Figure 29C:
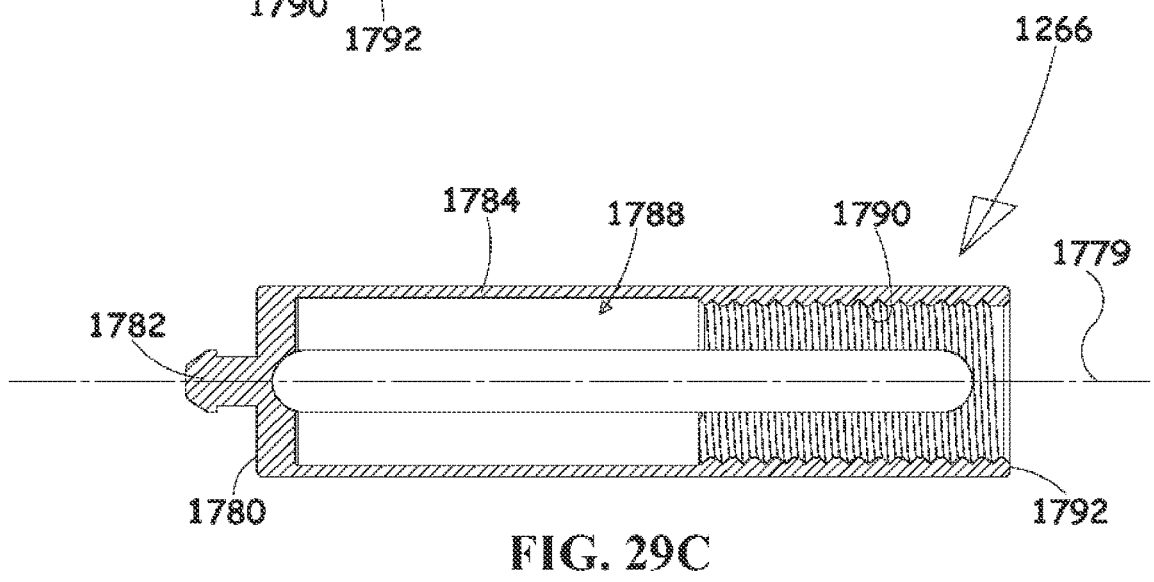
FIG. 29C is a simplified sectional illustration of the forward driven element of FIGS. 29A & 29B, taken along the line C in FIG. 29A.

Reference is now made to FIGS. 29A & 29B, which are simplified pictorial illustrations of forward driven element 1266, forming part of the multiple motion output subassembly 152 of FIG. 23, seen from respective forward and rearward ends thereof and to FIG. 29C, which is a simplified sectional illustration of the forward driven element of FIGS. 29A & 29B, taken along the line C in FIG. 29A.

As seen in FIGS. 29A-29C, the forward driven element 1266 is preferably an integrally formed generally cylindrical element extending along an axis 1779 and including at a forward end 1780 thereof a sealed nipple portion 1782. Rearward of sealed nipple portion 1782 there is provided a cylindrical portion 1784, having formed therein a pair of mutually facing elongate slots 1786.

Cylindrical portion 1784 is formed with a non-throughgoing bore extending along axis 1779. The non-throughgoing bore includes a generally circular cylindrical bore portion 1788 at a forward end of cylindrical portion 1784 and a counterclockwise threaded bore portion 1790 at a rearward end 1792 of cylindrical portion 1784.

Figure 30A:
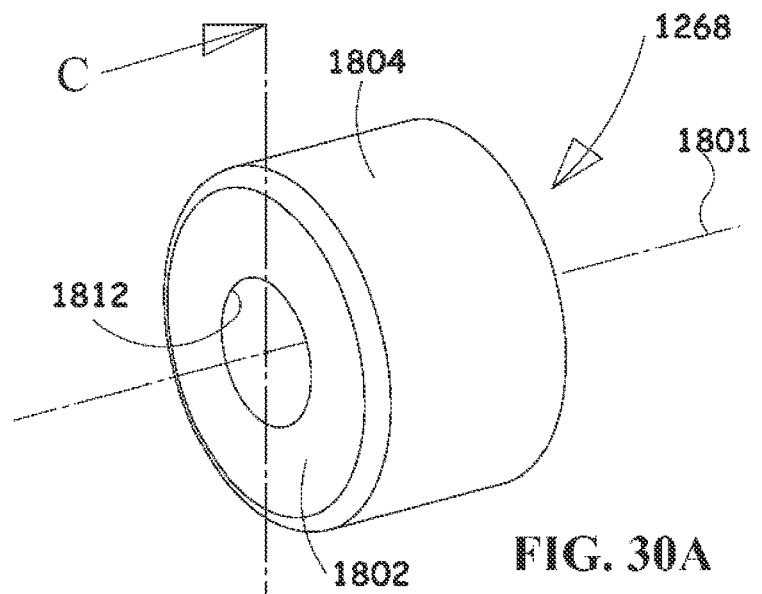
FIGS. 30A & 30B are simplified pictorial illustrations of a piston engaging element, forming part of the multiple motion output subassembly of FIG. 23, seen from respective forward and rearward ends thereof.
Figure 30B:
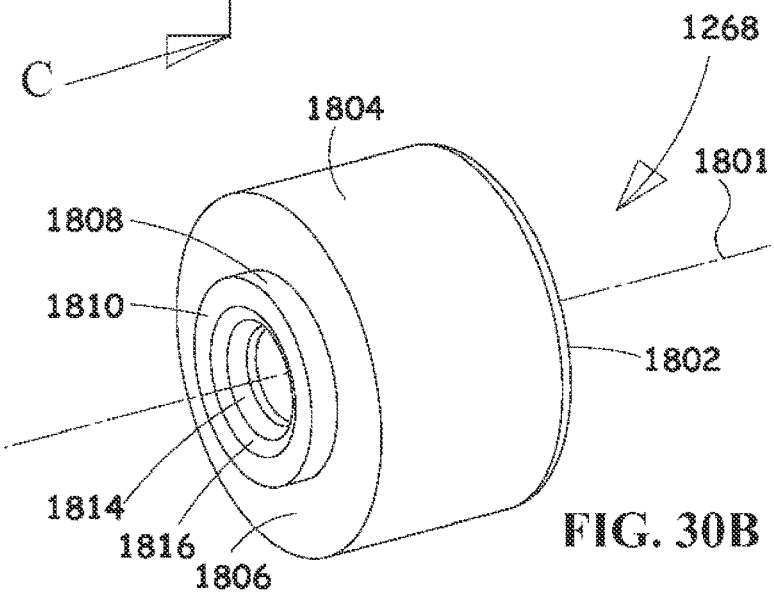
Figure 30C:
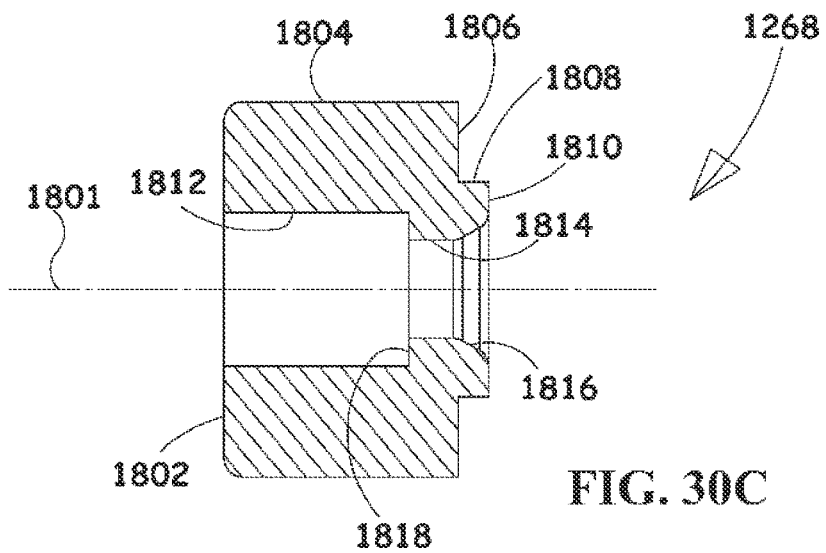
FIG. 30C is a simplified sectional illustration of the piston engaging element of FIGS. 30A & 30B, taken along the line C in FIG. 30A.

Reference is now made to FIGS. 30A & 30B, which are simplified pictorial illustrations of piston engaging element 1268, forming part of the multiple motion output subassembly 152 of FIG. 23, seen from respective forward and rearward ends thereof and to FIG. 30C, which is a simplified sectional illustration of the piston engaging element of FIGS. 30A & 30B, taken along the line C in FIG. 30A.

As seen in FIGS. 30A-30C, the piston engaging element 1268 is preferably an integrally formed generally cylindrical element extending along an axis 1801 and including at a forward end a forward-facing surface 1802, rearwardly of which is a circular cylindrical surface 1804. Rearward of circular cylindrical surface a rearward facing ring surface 1806, rearwardly of which extends a cylindrical surface 1808, whose outer diameter is less than that of cylindrical surface 1804 and which terminates in a rearward-facing surface 1810.

Piston engagement element 1268 is formed with a throughgoing bore extending along axis 1801. The throughgoing bore includes a generally circular cylindrical bore portion 1812 at a forward end thereof, rearwardly of which is a generally circular cylindrical bore portion 1814, whose inner diameter is less than that of cylindrical bore portion 1812. Rearwardly of cylindrical bore portion 1814 is an outwardly tapered bore portion 1816 which terminates a rearward-facing surface 1810. A ring shaped, forward facing shoulder surface 1818 is defined between generally circular cylindrical bore portion 1812 and generally circular cylindrical bore portion 1814.

Figure 31A:
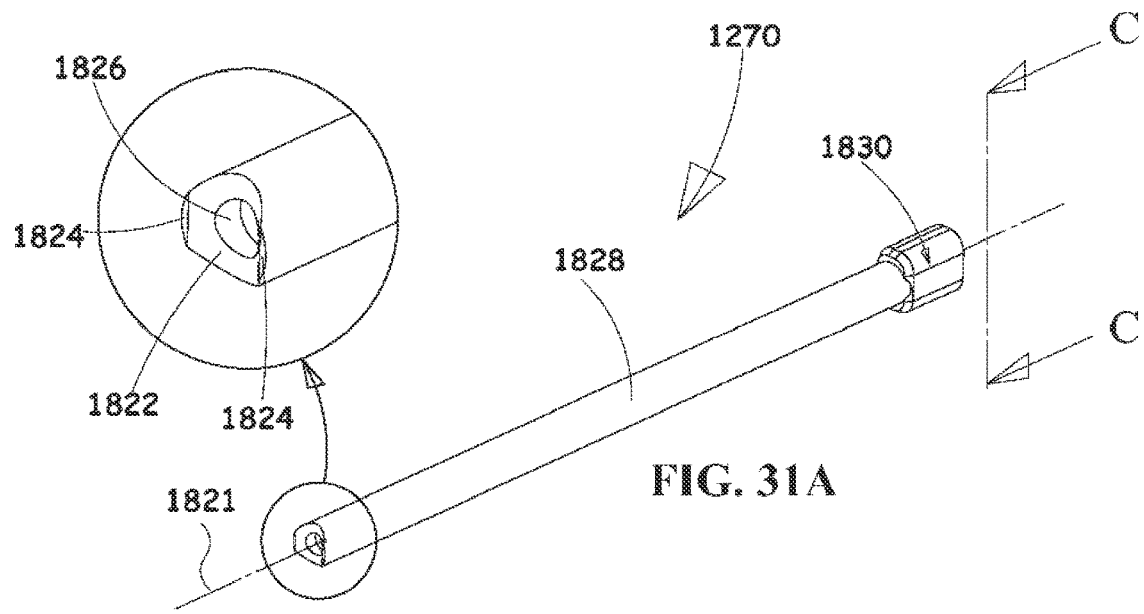
FIGS. 31A & 31B are simplified pictorial illustrations of a driving rod, forming part of the multiple motion output subassembly of FIG. 23, seen from respective forward and rearward ends thereof.
Figure 31B:
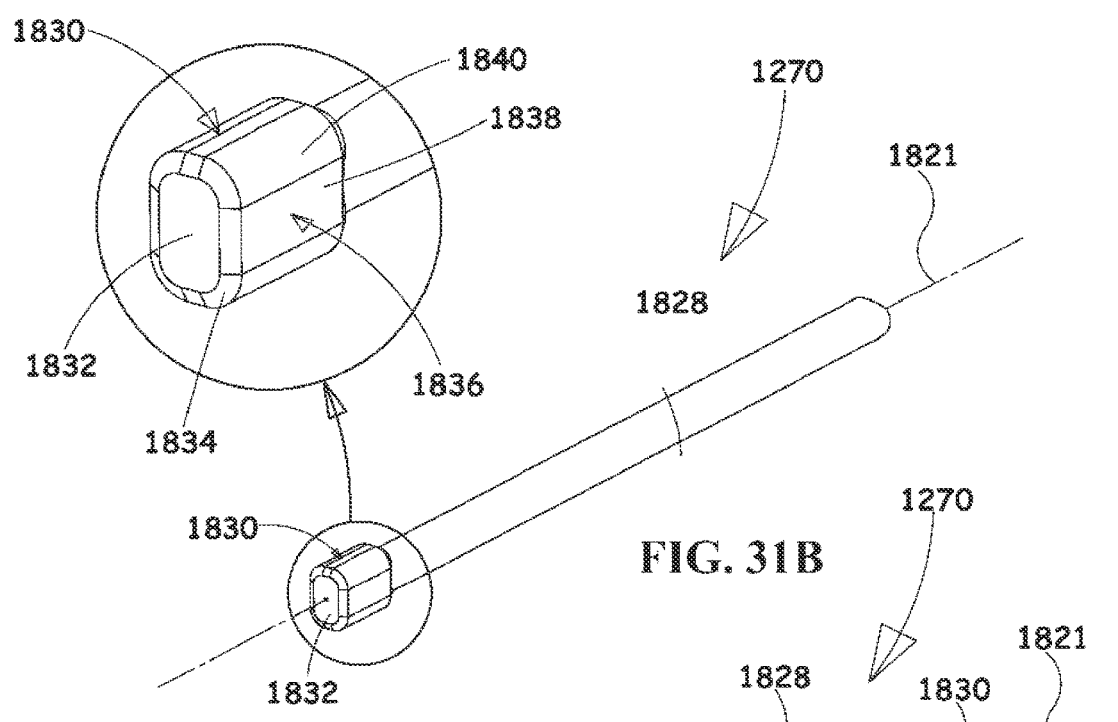
Figure 31C:
FIG. 31C is a simplified sectional illustration of the driving rod of FIGS. 31A & 31B, taken along the line C in FIG. 31A.

Reference is now made to FIGS. 31A & 31B, which are simplified pictorial illustrations of driving rod 1270, forming part of the multiple motion output subassembly 152 of FIG. 23, seen from respective forward and rearward ends thereof and to FIG. 31C, which is a simplified sectional illustration of the driving rod of FIGS. 31A & 31B, taken along the line C in FIG. 31A.

As seen in FIGS. 31A-31C, the driving rod 1270 is preferably an integrally formed generally solid circular cylindrical element extending along an axis 1821 and including at a forward end a generally concave forward-facing surface 1822 having on opposite side edges thereof a pair of forward-facing edge surface 1824 and at a center thereof having a circular cylindrical recess 1826. Driving rod 1270 includes a solid elongate circular cylindrical body portion 1828 which extends along axis 1821, rearwardly of which is an enlarged, generally obround end portion 1830 defining a generally obround flat rearward-facing surface 1832, forwardly of which is a generally obround tapered circumferential surface 1834. Forwardly of surface 1834 is a generally obround cylindrical surface 1836 which typically includes four flat portions 1838 separated by respective curved portions 1840.

Figure 32A:
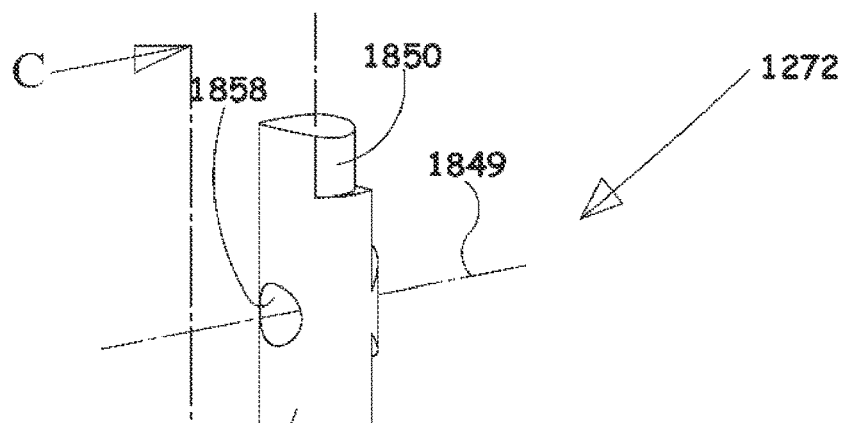
FIGS. 32A & 32B are simplified pictorial illustrations of an engaging element, forming part of the multiple motion output subassembly of FIG. 23, seen from respective forward and rearward ends thereof.
Figure 32B:
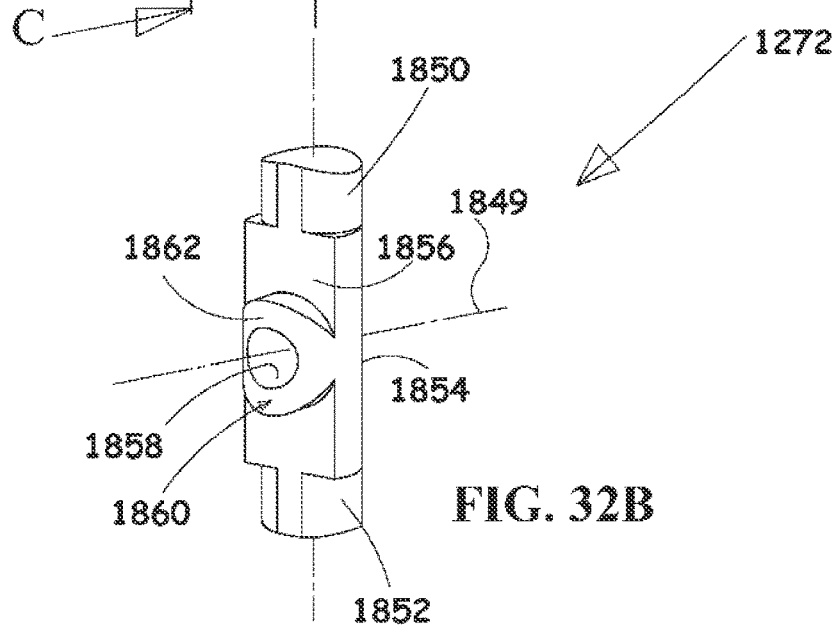
Figure 32C:
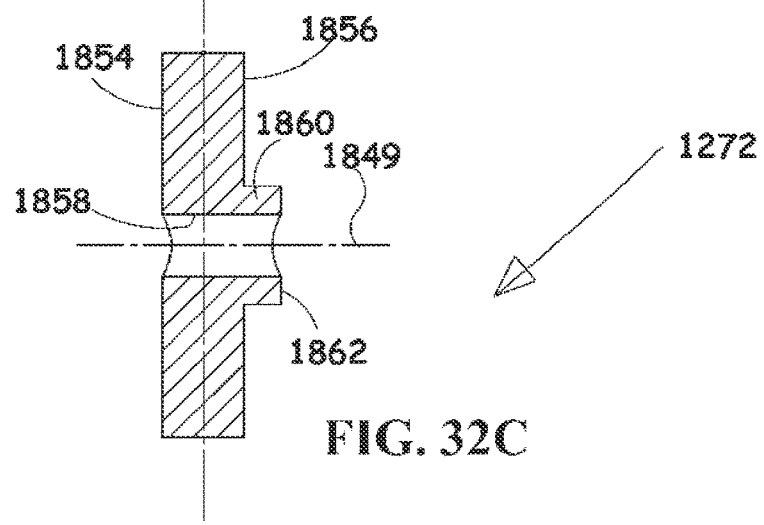
FIG. 32C is a simplified sectional illustration of the engaging element of FIGS. 32A & 32B, taken along the line C in FIG. 32A.

Reference is now made to FIGS. 32A & 32B, which are simplified pictorial illustrations of engaging element 1272, forming part of the multiple motion output subassembly 152 of FIG. 23, seen from respective forward and rearward ends thereof and to FIG. 32C, which is a simplified sectional illustration of the engaging element of FIGS. 32A & 32B, taken along the line C in FIG. 32A.

As seen in FIGS. 32A-32C, engaging element 1272 is a generally elongate solid element arranged along an axis 1849 and having first and second generally convex end surfaces 1850 and 1852, a generally convex forward-facing surface 1854 and a generally flat rearward-facing surface 1856. A throughgoing transverse bore 1858 extends through element 1272 from forward-facing surface 1854 to rearward-facing surface 1856 and is surrounded at rearward facing surface by a rearward-facing ring portion 1860, having a convex rearward-facing surface 1862.

Figure 33A:
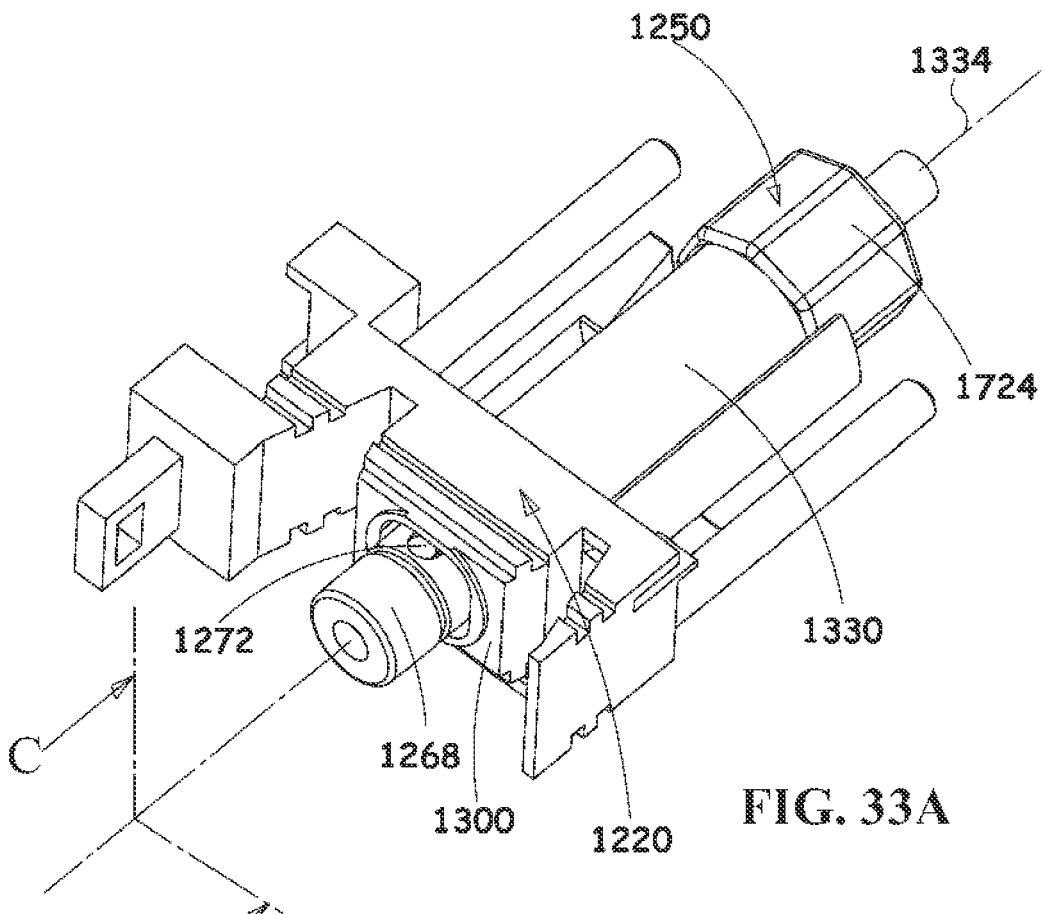
FIGS. 33A & 33B are simplified pictorial illustrations of a partial assembly of the multiple motion output subassembly of FIG. 23 in a retracted position, seen from respective forward and rearward ends thereof.
Figure 33B:
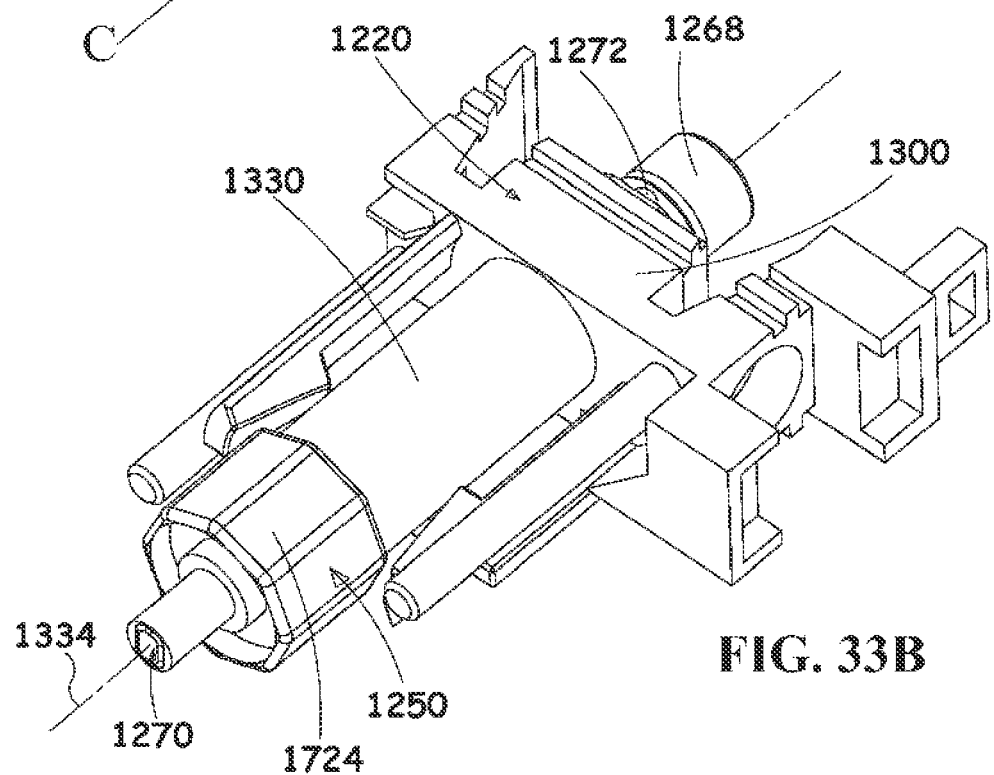
Figure 34:
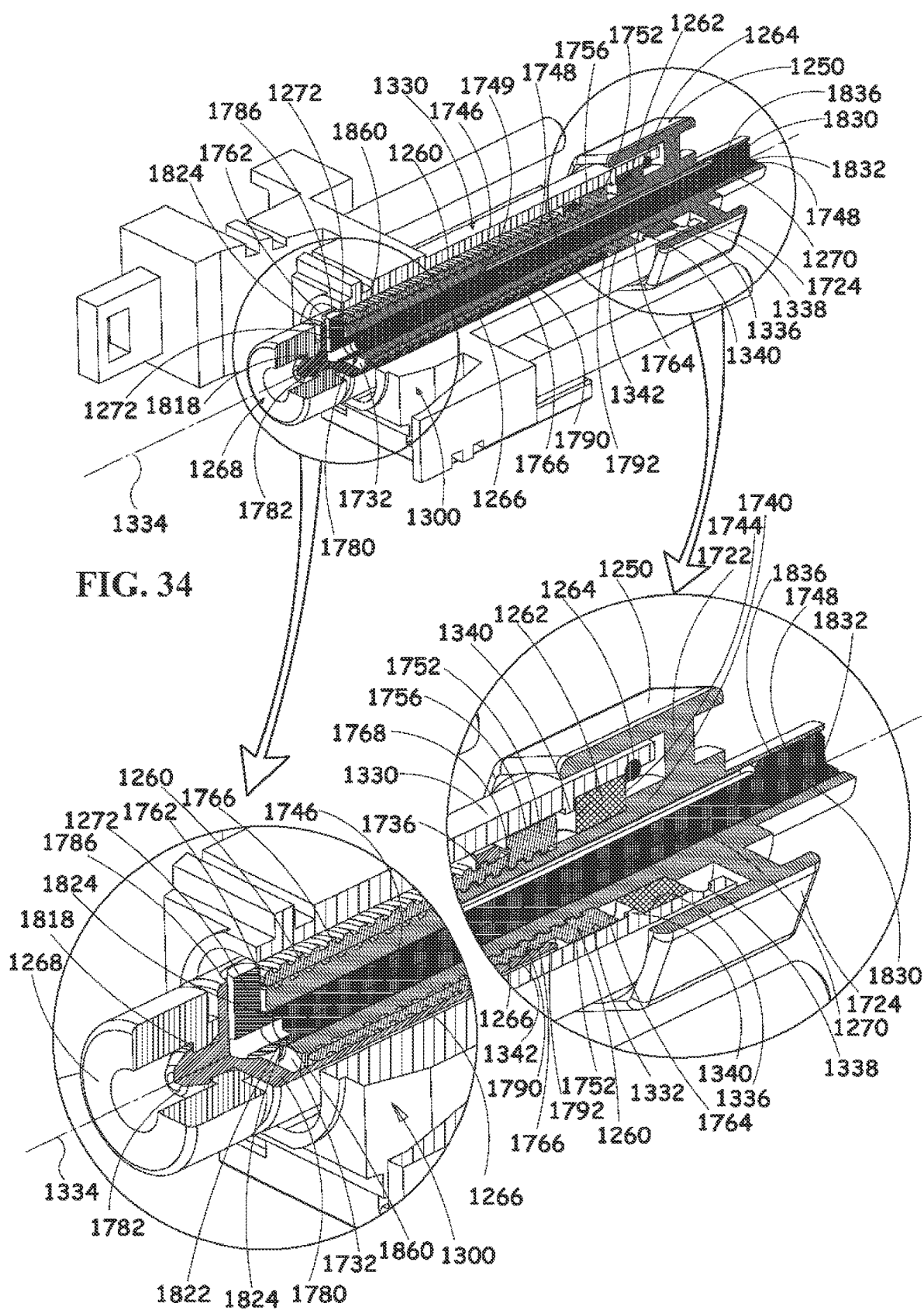
FIG. 34 is a simplified partially sectional illustration of the partial assembly of the multiple motion output subassembly of FIG. 23 taken along lines C-C in FIG. 33A and showing a retracted operative orientation thereof.

Reference is now made to FIGS. 33A & 33B, which are simplified pictorial illustrations of a partial assembly of the multiple motion output subassembly 152 of FIG. 23 in a retracted position, seen from respective forward and rearward ends thereof; and to FIG. 34, which is a simplified partially sectional illustration taken along lines C-C of FIG. 33A showing the partial assembly of the multiple motion output subassembly 152 of FIG. 23 in a retracted operative orientation.

It is seen in FIGS. 33A-34 that rearward driving screw 1250 is partially inserted into plunger assembly receiving cylinder 1330 of base element 1220, such that flange 1722 of rearward driving screw 1250 is positioned adjacent to and outwardly spaced from the rearward end of the plunger assembly receiving cylinder 1330 and forward edge 1732 of the rearward driving screw 1250 is substantially coplanar with the forward end of central portion of the central wall 1300.

Bearing 1262 is seated within rearward portion 1336 of bore 1332 of plunger assembly receiving cylinder 1330 and abuts at a forward-facing axial side of bearing 1262 internally directed flange 1340 and abuts at a rearward-facing axial side of bearing 1262 forwardly facing shoulder 1744 of rearward driving screw 1250. The bearing 1262 is seated in a radially tight fit manner between rearward portion 1336 of bore 1332 of the plunger assembly receiving cylinder 1330 and collar portion 1740 of rearward driving screw 1250.

Lock washer 1264 is seated within recess 1338 of bore 1332 of the base element 1220 and supports the bearing 1262 at fixed axial position relative the base element 1220.

Octagonal cylindrical portion 1724 of rearward driving screw 1250 is rotatably mounted in partially overlapping relationship over the rearward end of the plunger assembly receiving cylinder 1330. Axial relative movement between the base element 1220 and the rearward driving screw 1250 is prevented by fixed axial mounting of the bearing 1262.

Obround cylindrical surface 1836 of the obround end portion 1830 of the driving pin 1270 corresponds in shape to the corresponding surface of obround cylindrical portion 1748 of the rearward driving screw 1250, which surface touchingly surrounds surface 1836, such that relative rotational movement between the driving pin 1270 and the rearward driving screw 1250 is prevented and common rotational movement of the driving pin 1270 and the rearward driving screw 1250 is permitted.

Square cylindrical outer surface 1756 of nut portion 1752 of intermediate screw 1260 engages a generally square socket defined by forward portion 1342 of bore 1332 of plunger assembly receiving cylinder 1330, such that relative rotational movement between intermediate screw 1260 and plunger assembly receiving cylinder 1330 of base element 1220 is prevented. Relative axial movement between the intermediate screw 1260 and the base element 1220 takes place when rearward driving screw 1250 is rotated.

Rearward-facing ring portion 1860 of engaging element 1272 engages concave forward-facing surface 1822 of the driving pin 1270. The engaging element 1272 is fixedly connected to the driving pin 1270, such as by heat welding.

Rotational movement of the rearward driving screw 1250 relative to the base element 1220 produces rotational movement of the driving pin 1270 and of the engaging element 1272 together about axis 1334, due to the above-described non-mutually rotatable relationship between the rearward screw 1250, the driving pin 1270 and the engaging element 1272. Rotational movement of the rearward driving screw 1250 additionally produces axial movement along axis 1334 of the intermediate screw 1260 relative to the base element 1220 due to the threaded interconnection between the rearward driving screw 1250 and the intermediate screw 1260. Simultaneously, rotational movement of the engaging element 1272 produces rotational movement of the forward element 1266 relative to the base element 1220, which rotational movement produces simultaneous axial movement between forward element 1266 and intermediate screw 1260 along axis 1334 due to the threaded interconnection therebetween.

Piston engaging element 1268 is mounted onto nipple portion 1782 of the forward driven element 1266, such that the nipple 1782 is locked behind forward facing shoulder surface 1818 of piston engaging element 1268. This connection between the forward driven element 1266 and piston engaging element 1268 permits rotational movement thereof relative to forward driven element 1266 about axis 1334.

In the retracted operative orientation partial assembly of the multiple motion output subassembly 152, driving pin 1270 is slidably located in obround cylindrical portion 1748 and circular cylindrical portion 1746 of the rearward driving screw 1250, such that forward-facing edge surfaces 1824 of the driving pin 1270 are substantially coplanar with forward edge 1732 of the rearward driving screw 1250 and such that rearward-facing surface 1832 of obround end portion 1830 of the driving pin 1270 is rearwardly spaced from rearwardly facing shoulder 1749 of rearward driving screw 1250.

It is further seen in FIGS. 33A-34 that the intermediate screw 1260 is fully inserted into forward portion 1342 of bore 1332 of plunger assembly receiving cylinder 1330 such that the rearward edge 1764 of the intermediate screw 1260 is positioned adjacent to but forwardly spaced from internally directed flange 1340 of the plunger assembly receiving cylinder 1330.

Threaded cylindrical portion 1768 of the intermediate screw 1260 is fully rearwardly threaded onto threaded forward outward facing surface portion 1736 of the rearward driving screw 1250, such that forward edge 1762 of intermediate screw 1260 is substantially coplanar with forward edge 1732 of rearward driving screw 1250.

It is additionally seen in FIGS. 33A-34 that forward driven element 1266 is fully rearwardly positioned within forward portion 1342 of bore 1332 of plunger assembly receiving cylinder 1330 and is fully rearwardly threaded onto the intermediate screw 1260, such that rearward end 1792 of element 1266 is positioned adjacent the nut portion 1752 of the intermediate screw 1260.

Threaded bore portion 1790 of forward driven element 1266 is fully rearwardly threaded onto threaded outward facing surface portion 1766 of intermediate screw 1260.

Engaging element 1272 engages the forward ends of elongate slots 1786 of forward driven element 1266, such that the engaging element 1272 is positioned adjacent forward end 1780 of forward driven element 1266.

Figure 35:
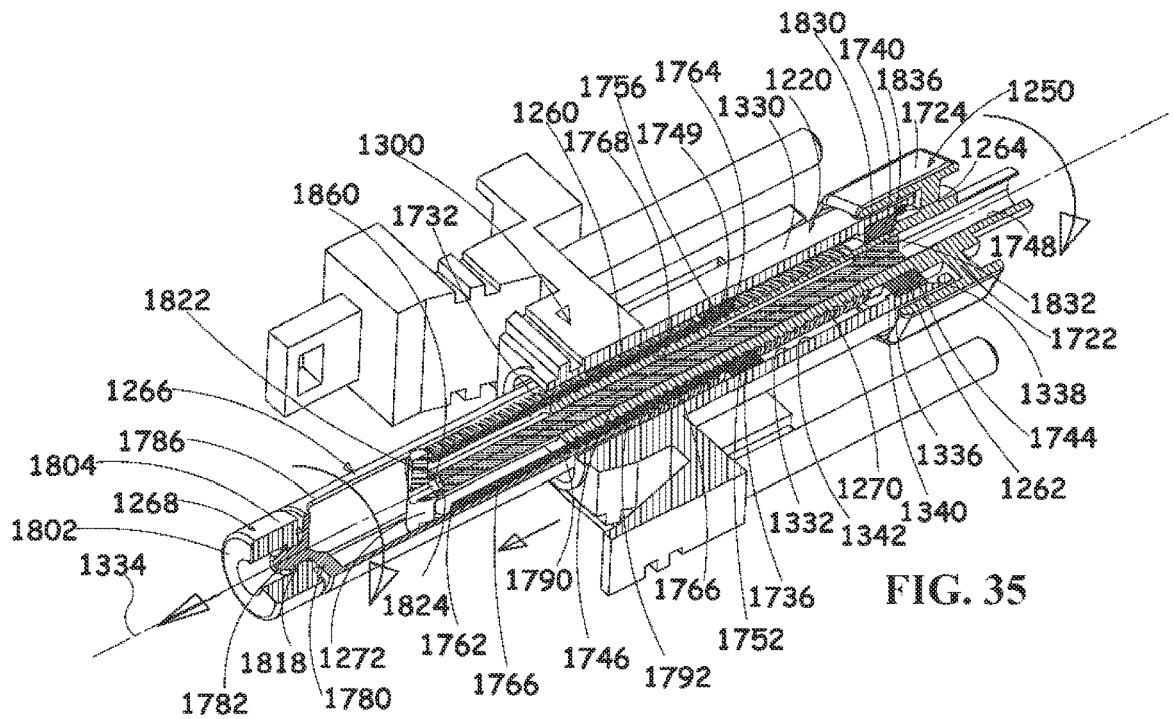
FIG. 35 is a simplified partially sectional illustration of the partial assembly of the multiple motion output subassembly of FIG. 23 corresponding to FIG. 34 but in a partially extended operative orientation.

Reference is now made to FIG. 35, which is a simplified partially sectional illustration of the partial assembly of the multiple motion output subassembly 152 of FIG. 23, seen in a partially-extended operative orientation.

In the partially-extended operative orientation of the partial assembly of the multiple motion output subassembly 152, driving pin 1270 is forwardly displaced along axis 1334 from its position in the retracted operative orientation of the partial assembly, such that forward-facing edge surfaces 1824 of the driving pin 1270 are disposed forwardly of forward edge 1732 of the rearward driving screw 1250 and such that rearward-facing surface 1832 of obround end portion 1830 of the driving pin 1270 is rearwardly spaced from rearwardly facing shoulder 1749 of rearward driving screw 1250 by a lesser amount as compared with its position in the retracted operative orientation of the partial assembly.

It is further seen in FIG. 35 that the intermediate screw 1260 is less than fully inserted into forward portion 1342 of bore 1332 of plunger assembly receiving cylinder 1330 such that the rearward edge 1764 of the intermediate screw 1260 is more forwardly spaced from internally directed flange 1340 of the plunger assembly receiving cylinder 1330 as compared with its position in the retracted operative orientation of the partial assembly.

Additionally, threaded cylindrical portion 1768 of the intermediate screw 1260 is less than fully rearwardly threaded onto threaded forward outward facing surface portion 1736 of the rearward driving screw 1250, such that forward edge 1762 of intermediate screw 1260 is forwardly spaced with respect to forward edge 1732 of rearward driving screw 1250.

It is further seen in FIG. 35 that forward driven element 1266 is less than fully rearwardly positioned within forward portion 1342 of bore 1332 of plunger assembly receiving cylinder 1330 and is less than fully rearwardly threaded onto the intermediate screw 1260, such that rearward end 1792 of element 1266 is forwardly spaced with respect to the nut portion 1752 of the intermediate screw 1260.

It is additionally seen that threaded bore portion 1790 of forward driven element 1266 is less than fully threaded onto threaded outward facing surface portion 1766 of intermediate screw 1260.

Engaging element 1272 engages the intermediate locations along elongate slots 1786 of forward driven element 1266, such that the engaging element 1272 is rearwardly spaced with respect to forward end 1780 of forward driven element 1266.

Figure 36:
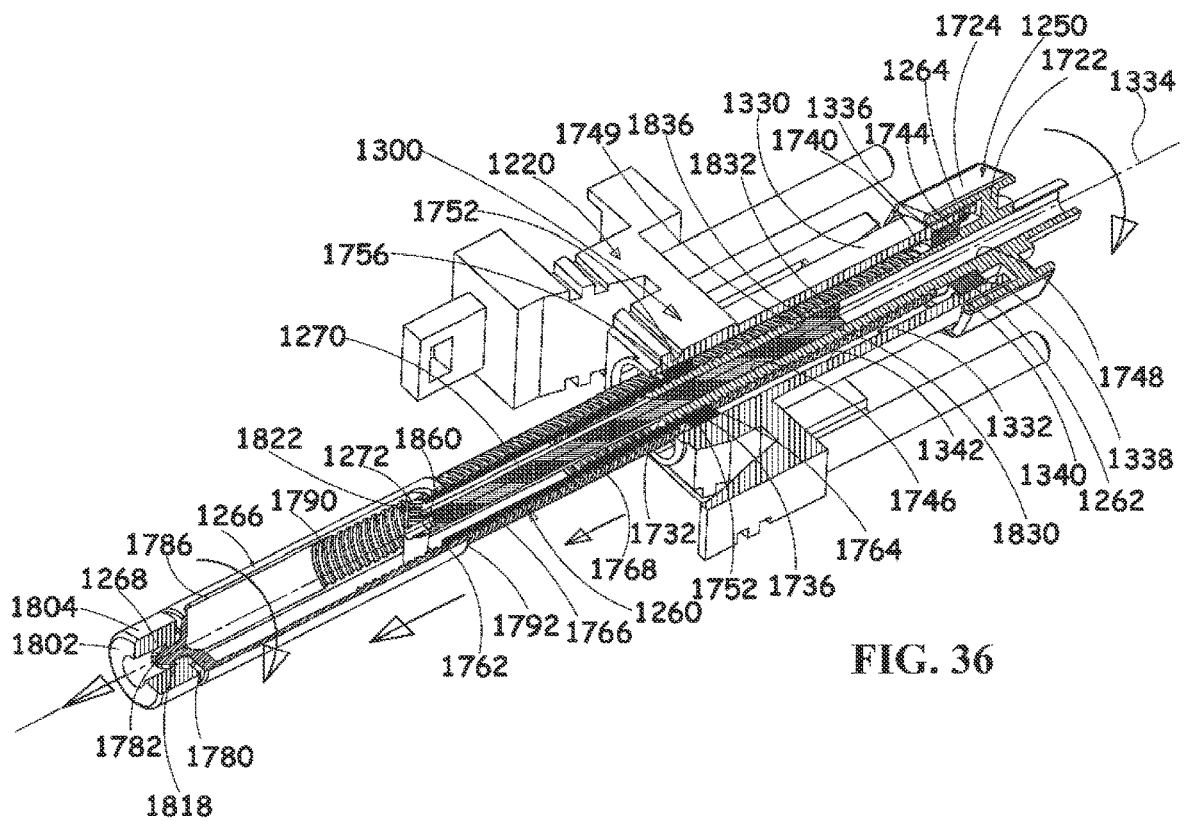
FIG. 36 is a simplified partially sectional illustration of the partial assembly of the multiple motion output subassembly of FIG. 23 corresponding to FIG. 35 but in a fully extended operative orientation.
Figure 37:
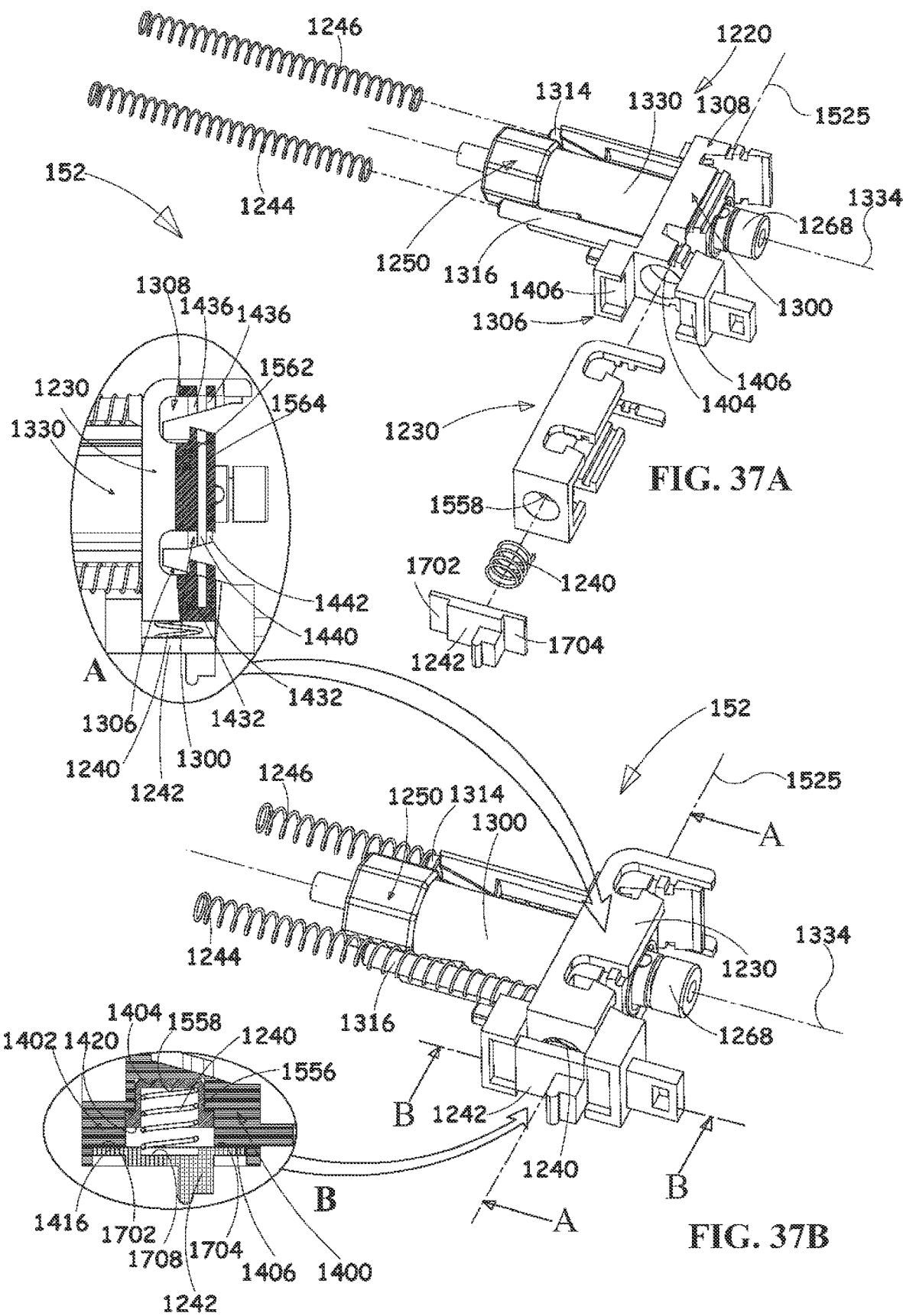
FIGS. 37A and 37B are simplified partially sectional respective partially exploded and assembled view illustrations of the multiple motion output subassembly of FIG. 23.

Reference is now made to FIG. 36, which is a simplified partially sectional illustration of the partial assembly of the multiple motion output subassembly 152 of FIG. 23, seen in a fully-extended operative orientation.

In the fully-extended operative orientation of the partial assembly of the multiple motion output subassembly 152, driving pin 1270 is further forwardly displaced along axis 1334 from its position in the retracted operative orientation of the partial assembly, such that forward-facing edge surfaces 1824 of the driving pin 1270 are disposed fully forwardly of forward edge 1732 of the rearward driving screw 1250 and such that rearward-facing surface 1832 of obround end portion 1830 of the driving pin 1270 abuts rearwardly facing shoulder 1749 of rearward driving screw 1250.

It is further seen in FIG. 36 that the intermediate screw 1260 is nearly fully removed from forward portion 1342 of bore 1332 of plunger assembly receiving cylinder 1330 such that the rearward edge 1764 of the intermediate screw 1260 is fully forwardly spaced from internally directed flange 1340 of the plunger assembly receiving cylinder 1330.

Additionally, threaded cylindrical portion 1768 of the intermediate screw 1260 is even less rearwardly threaded onto threaded forward outward facing surface portion 1736 of the rearward driving screw 1250, such that forward edge 1762 of intermediate screw 1260 is more forwardly spaced with respect to forward edge 1732 of rearward driving screw 1250.

It is further seen in FIG. 36 that forward driven element 1266 is entirely outside of forward portion 1342 of bore 1332 of plunger assembly receiving cylinder 1330 and is in its fully forward threaded position relative to intermediate screw 1260, such that rearward end 1792 of element 1266 is more forwardly spaced with respect to the nut portion 1752 of the intermediate screw 1260.

It is additionally seen that threaded bore portion 1790 of forward driven element 1266 is even less threaded onto threaded outward facing surface portion 1766 of intermediate screw 1260.

Engaging element 1272 engages the rearward ends of elongate slots 1786 of forward driven element 1266, such that the engaging element 1272 is more rearwardly spaced with respect to forward end 1780 of forward driven element 1266.

Reference is now made to FIGS. 37A and 37B, which are simplified partially sectional respective partially exploded and assembled view illustrations of the multiple motion output subassembly of FIG. 23, which includes, inter alia base element 1220 and locking element 1230. Referring specifically to FIG. 37B, it is seen that an enlargement A is taken along lines A-A in the non-enlarged portion of FIG. 37B. Likewise, an enlargement B is taken along lines B-B in the non-enlarged portion of FIG. 37B.

FIGS. 37A & 37B show the operative engagement of the locking element 1230 and the base element 1220. It is seen that locking element is biased by spring 1240 along axis 1525, which intersects axis 1334, so as to normally assume a locking orientation for locking engagement with an injection module 132 (FIG. 2). As will be described hereinbelow, insertion of injection module 132 into operative engagement with the multiple motion output subassembly 152 causes locking element 1230 to be displaced along axis 1525 against the urging of spring 1240 so as to permit insertion of injection module 132 into operative engagement with multiple motion output subassembly 152. Once injection module 132 has been fully inserted, spring 1240 urges locking element 1230 back into its locking orientation, thereby locking the injection module 132 to the multiple motion output subassembly 152.

Displacement of locking element 1230 along axis 1525 takes place along mutually engaging elongate tracks defined by grooves 1432, 1436 & 1440 and forward facing recess 1442 on the base element 1220 and elongate tracks 1562 and 1564 on the locking element 1230.

Spring 1240 is seen to be seated at one end thereof in recess 1708 formed in spring seat 1242 and at an opposite end thereof in recess 1558 formed in locking element 1230.

Reference is now made to FIGS. 38-43D, which illustrate a prefilled syringe injection module 140 (FIG. 2) constructed and operative in accordance with a preferred embodiment of the present invention. As seen in FIGS. 38-43D, the prefilled syringe injection module 140 preferably includes a mounting element 1900 in which is partially disposed a conventional prefilled syringe 1902 arranged along a longitudinal axis 1903, such as, for example, a commercially available syringe sold under the catalog designation BD-Hypak™ or may be any other suitable syringe, having a needle 1904 and a removable needle shield (RNS) 1905 having a rearward facing edge 1906. The prefilled syringe 1902 extends forwardly of mounting element 1900 into needle shield element 147 (FIG. 2) which preferably has associated therewith a wireless communicator providing wireless communication functionality, such as a passive RF information transmitter assembly 1907, such as Cat. Number NT2H1311G0DUD, commercially available from NXP Semiconductors, San Jose, CA, USA. An RNS remover 108 (FIGS. 1A-2) is operatively associated with needle shield element 147.

Figure 38:
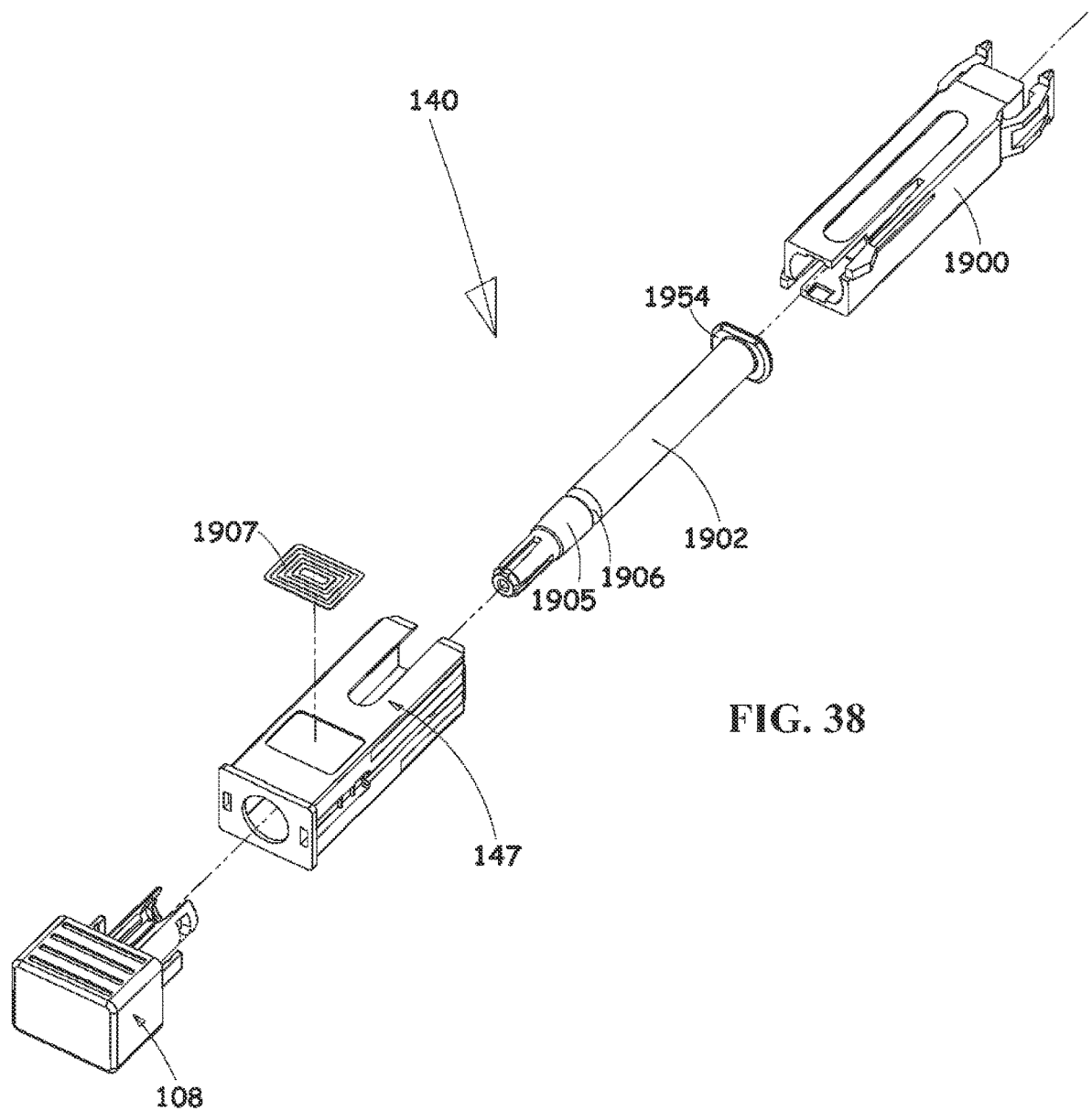
FIG. 38 is a simplified exploded view illustration of a prefilled syringe injection module constructed and operative in accordance with a preferred embodiment of the present invention.
Figure 39D:
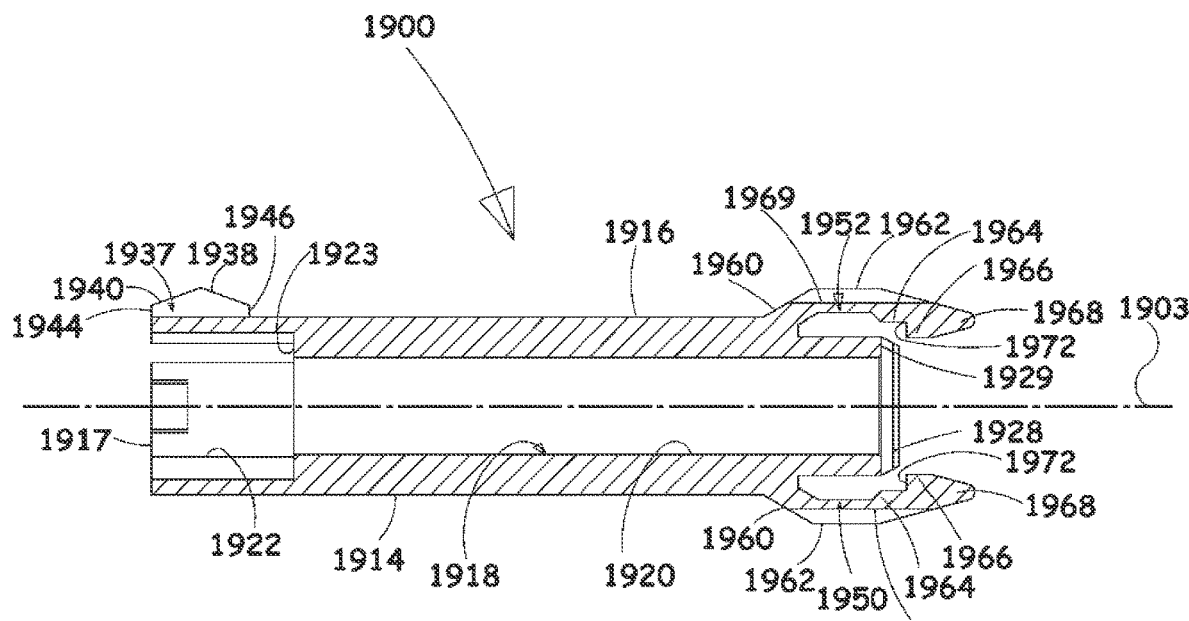
Figure 39E:
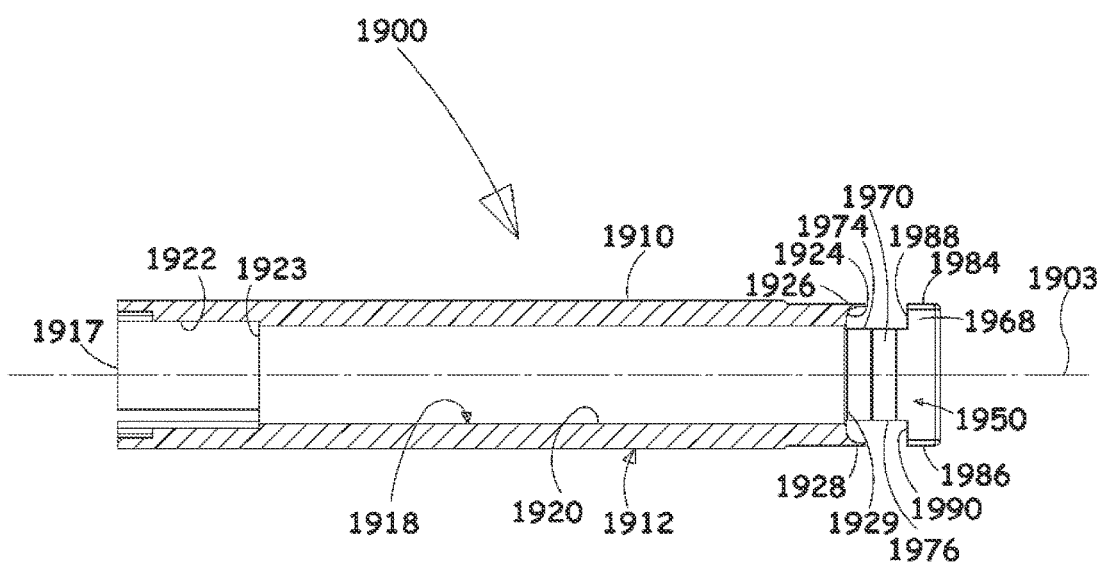

Reference is now specifically made to FIGS. 39A and 39B, which are simplified pictorial illustrations of mounting element 1900 forming part of the prefilled syringe injection module of FIG. 38, seen from a forward end and a rearward end respectively and to FIGS. 39C, 39D and 39E, which are respective simplified sectional illustrations of the mounting element of FIGS. 39A & 39B, taken along respective lines C-C, D-D and E-E.

As seen in FIGS. 39A-39E, mounting element 1900 is a generally elongate element extending along an axis 1903 and having a generally square cross section including elongate top and bottom walls 1910 and 1912, which are identical, and elongate side walls 1914 and 1916. Walls 1910, 1912, 1914 and 1916 together define a planar forward-facing circumferential edge surface 1917. Mounting element has a throughgoing bore 1918 including a main portion 1920, which has a circular cross section and a forward portion 1922 having an obround cross section. A forward facing shoulder surface 1923 is defined between the main portion 1920 and the forward portion 1922. A rearward end of bore 1918 communicates with a recess 1924 having top and bottom rearwardly directed walls 1926 and 1928, which extend rearwardly from a rearward-facing surface 1929.

Top and bottom walls 1910 and 1912, each preferably have an outer facing elongate window recess 1930 including an internal wall having a curved cross section, as seen particularly in FIG. 39C. Rearward of recess 1930, top and bottom walls 1910 and 1912 include stepped down rearward portions 1932 and 1933 which terminate in respective rearwardly directed walls 1926 and 1928.

A pair of flexible diagonally opposed needle shield engaging fingers 1934 are provided at two forward-facing corners of the mounting element 1900 and each include an elongate arm portion 1936 and a forward portion 1937 including mutually oppositely inclined rearward and forward facing edge surfaces 1938 and 1940 and forward and rearward facing surfaces 1944 and 1946. It is noted that the part of forward portion 1937 defined by surfaces 1938, 1940, 1944 and 1946 extends sideways beyond side walls 1914 and 1916.

A pair of somewhat flexible arms 1950 and 1952 extend sideways from respective side walls 1914 and 1916 respectively and preferably serve two functions:

retention of the prefilled syringe element 1902 in bore 1918, such that an obround flange 1954 of the prefilled syringe element 1902 lies in recess 1924 between top and bottom rearwardly directed walls 1926 and 1928 and against rearward-facing surface 1929; and engagement with multiple motion output subassembly 152.

Each of arms 1950 and 1952 includes an outwardly and rearwardly directed portion 1960, an intermediate portion 1962, a forward thickened portion 1964, a rearward thickened portion 1966 and a rearwardly facing end tapered portion 1968. A recess 1969 is formed along outward facing surfaces of portions 1960, 1962 and 1964. Forward thickened portion 1964 defines an inwardly facing surface 1970 and rearward thickened portion 1966 defines a forward facing shoulder surface 1972, which extends perpendicularly with respect to and intersects surface 1970.

Portions 1960, 1962, 1964 and 1966 define coplanar top and bottom edge surfaces 1974 and 1976. Rearwardly facing end tapered portion 1968 define upwardly and downwardly extending edges, which extend beyond surfaces 1974 and 1976 and define respective edge surfaces 1984 and 1986. Forward facing shoulder surfaces 1988 and 1990 are defined between respective edge surfaces 1974 & 1984 and 1976 & 1986 respectively.

Figure 40A:
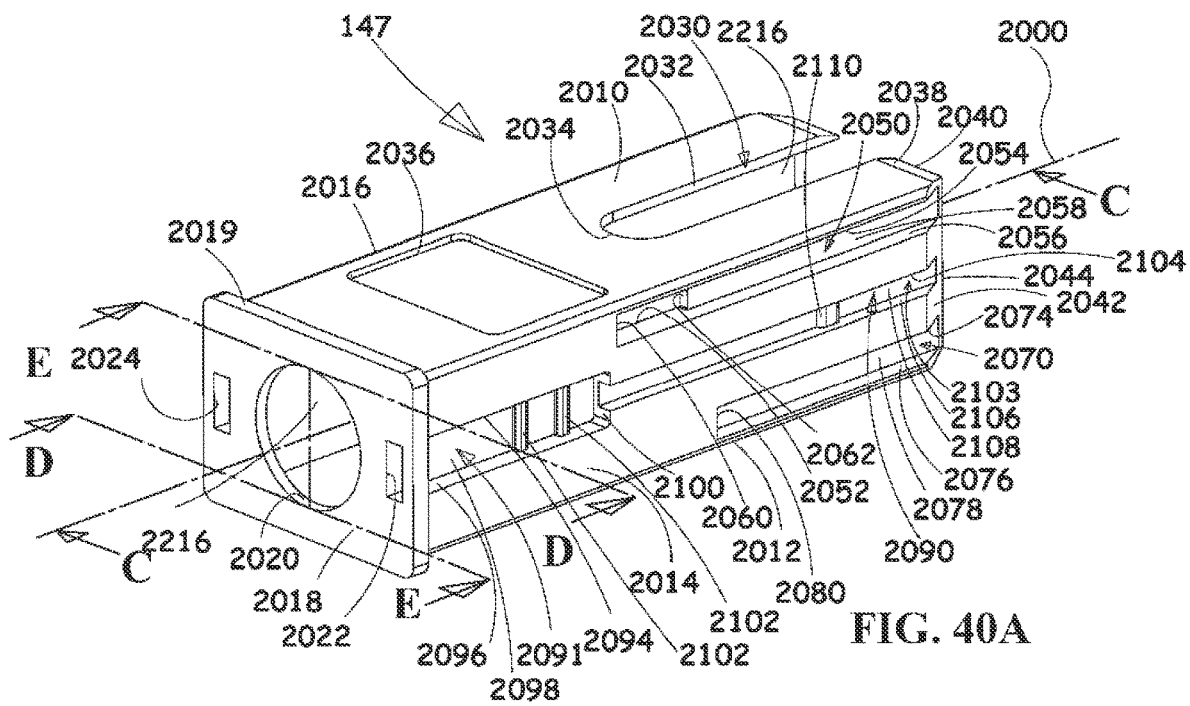
FIGS. 40A and 40B are simplified pictorial illustrations of a needle shield element forming part of the prefilled syringe injection module of FIG. 38, seen from a forward end and a rearward end respectively.
Figure 40B:
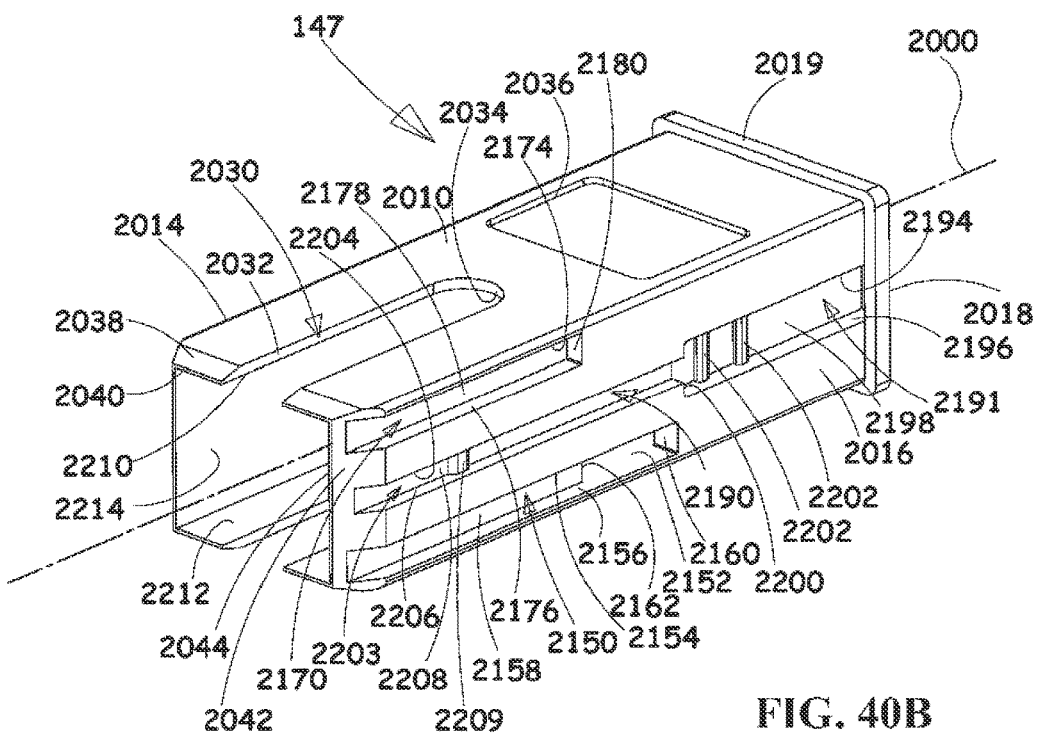
Figure 40C:
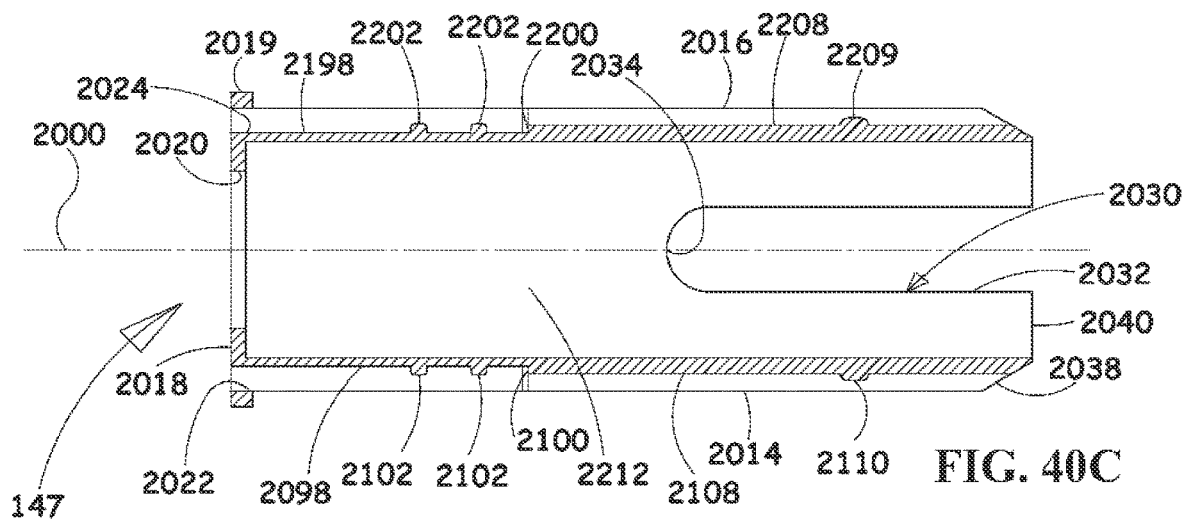
FIGS. 40C, 40D and 40E are respective simplified sectional illustrations of the needle shield element of FIGS. 40A & 40B, taken along respective lines C-C, D-D & E-E.
Figure 40D:
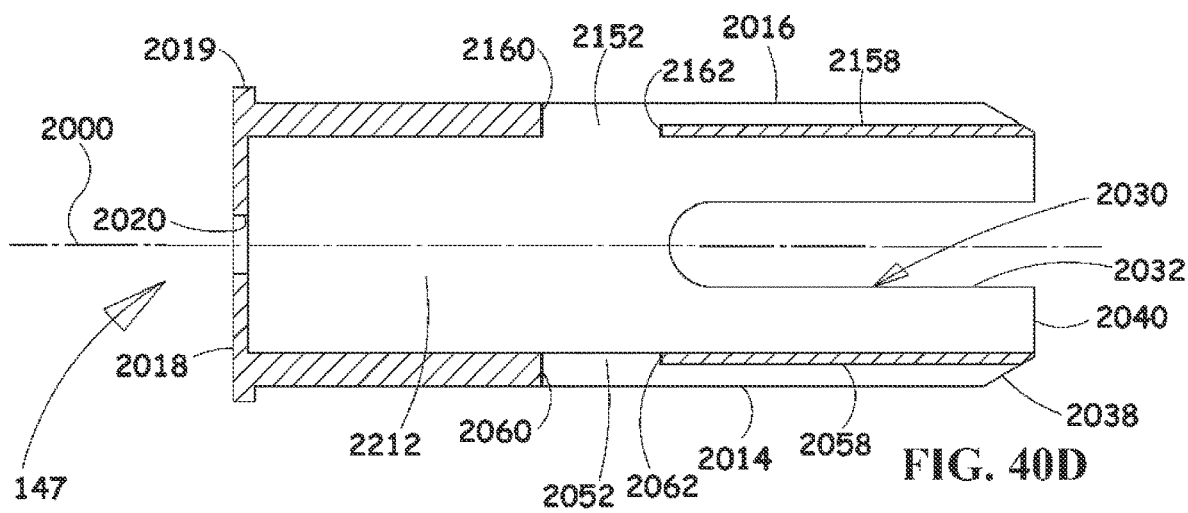
Figure 40E:
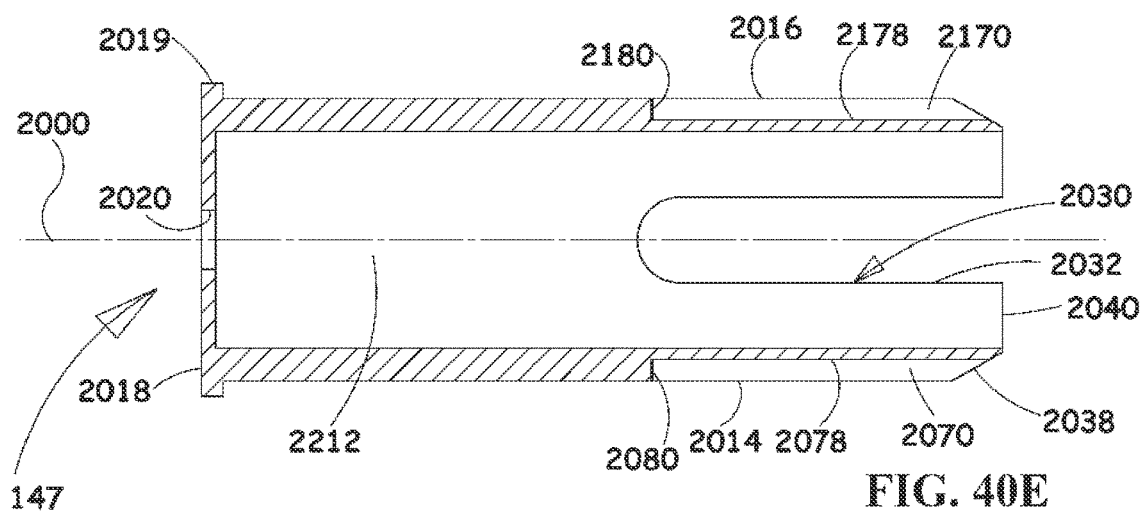

Reference is now made to FIGS. 40A and 40B, which are simplified pictorial illustrations of needle shield element 147 (FIG. 2) of the prefilled syringe injection module 140 of FIG. 38, seen from a forward end and a rearward end respectively and to FIGS. 40C, 40D and 40E, which are respective simplified sectional illustrations of the needle shield element of FIGS. 40A & 40B, taken along respective lines C-C, D-D and E-E.

As seen in FIGS. 40A-40E, the needle shield element 147 is a generally elongate element arranged about a longitudinal axis 2000 and having a generally square cross section including elongate top and bottom walls 2010 and 2012, which are nearly identical, and elongate side walls 2014 and 2016. Walls 2010, 2012, 2014 and 2016 each join a planar forward-facing patient engagement plate 2018 having a circumferential edge surface 2019 which extends slightly beyond walls 2010, 2012, 2014 and 2016. Patient engagement plate 2018 is formed with a central aperture 2020 for accommodating injection needle 1904 (not shown) and a pair of side apertures 2022 and 2024.

Top and bottom walls 2010 and 2012 each define an axial slot 2030 having an inner edge surface 2032 which is rounded at a forward end 2034 thereof. Top wall 2010 is preferably formed with a rectangular recess 2036 for accommodating passive RF information transmitter assembly 1907 (FIG. 38).

Each of top and bottom walls 2010 and 2012 defines an inwardly tapered rearward end portion 2038 having a rearward facing edge 2040.

Each of elongate side walls 2014 and 2016 defines an inwardly tapered rearward end portion 2042 having a rearward facing edge 2044.

Elongate side wall 2014 includes a top rearward elongate recess 2050 having at a forward portion thereof an aperture 2052. Recess 2050 has respective top and bottom recess wall surfaces 2054 and 2056, a side wall surface 2058 and a rearward facing forward end wall surface 2060. Aperture 2052 defines a forward facing edge surface 2062 which intersects wall surface 2058.

Elongate side wall 2014 also includes a bottom rearward elongate recess 2070. Recess 2070 has respective top and bottom recess wall surfaces 2074 and 2076, a side wall surface 2078 and a rearward facing forward end wall surface 2080.

Elongate side wall 2014 further includes an intermediate elongate recess 2090. Recess 2090 includes a forward portion 2091 which has respective top and bottom forward recess wall surfaces 2094 and 2096, a side wall surface 2098 and a bifurcated forward facing rearward end wall surface 2100. Side wall surface 2098 is preferably formed with a pair of mutually spaced side facing rounded protrusions 2102. Recess 2090 also includes a rearward portion 2103 which has respective top and bottom rearward recess wall surfaces 2104 and 2106, a side wall surface 2108 and communicates with the forward portion 2091 at bifurcated surface 2100. Side wall surface 2108 is preferably formed with a side facing protrusion 2110.

Elongate side wall 2016 includes a bottom rearward elongate recess 2150 having at a forward portion thereof an aperture 2152. Recess 2150 has respective top and bottom recess wall surfaces 2154 and 2156, a side wall surface 2158 and a rearward facing forward end wall surface 2160. Aperture 2152 defines a forward facing edge surface 2162, which intersects wall surface 2158.

Elongate side wall 2016 also includes a top rearward elongate recess 2170. Recess 2170 has respective top and bottom recess wall surfaces 2174 and 2176, a side wall surface 2178 and a rearward facing forward end wall surface 2180.

Elongate side wall 2016 further includes an intermediate elongate recess 2190. Recess 2190 includes a forward portion 2191 which has respective top and bottom forward recess wall surfaces 2194 and 2196, a side wall surface 2198 and a bifurcated forward facing rearward end wall surface 2200. Side wall surface 2198 is preferably formed with a pair of mutually spaced side facing rounded protrusions 2202. Recess 2190 also includes a rearward portion 2203 which has respective top and bottom rearward recess wall surfaces 2204 and 2206, a side wall surface 2208 and communicates with the forward portion 2291 at bifurcated surface 2200. Side wall surface 2208 is preferably formed with a side facing protrusion 2209.

Walls 2010, 2012, 2014 and 2016 are formed with respective interior facing surfaces 2210, 2212, 2214 and 2216 and patient engagement plate 2018 is formed with a rearward facing internal surface 2218.

Figure 41A:
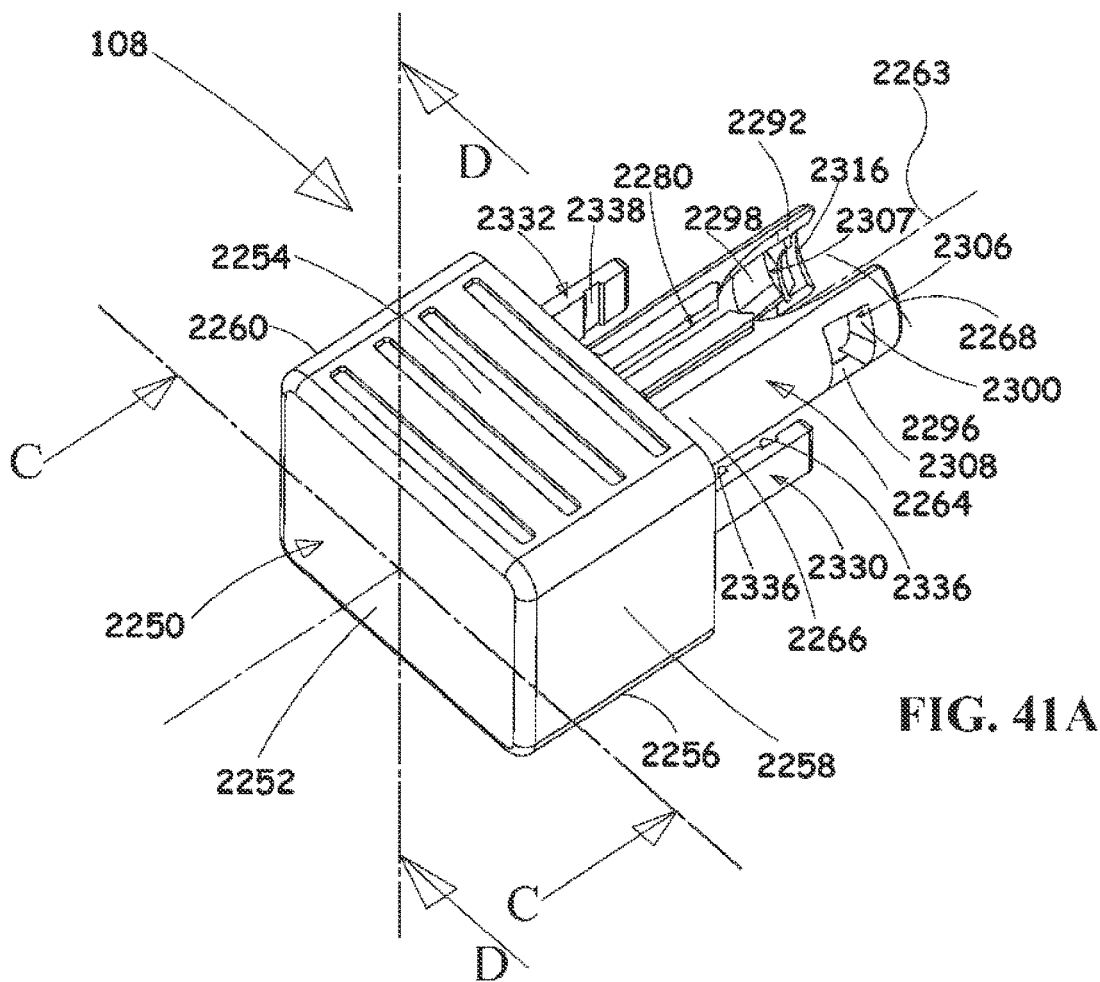
FIGS. 41A and 41B are simplified pictorial illustrations of an RNS remover element forming part of the prefilled syringe injection module of FIG. 38, seen from a forward end and a rearward end respectively.
Figure 41B:
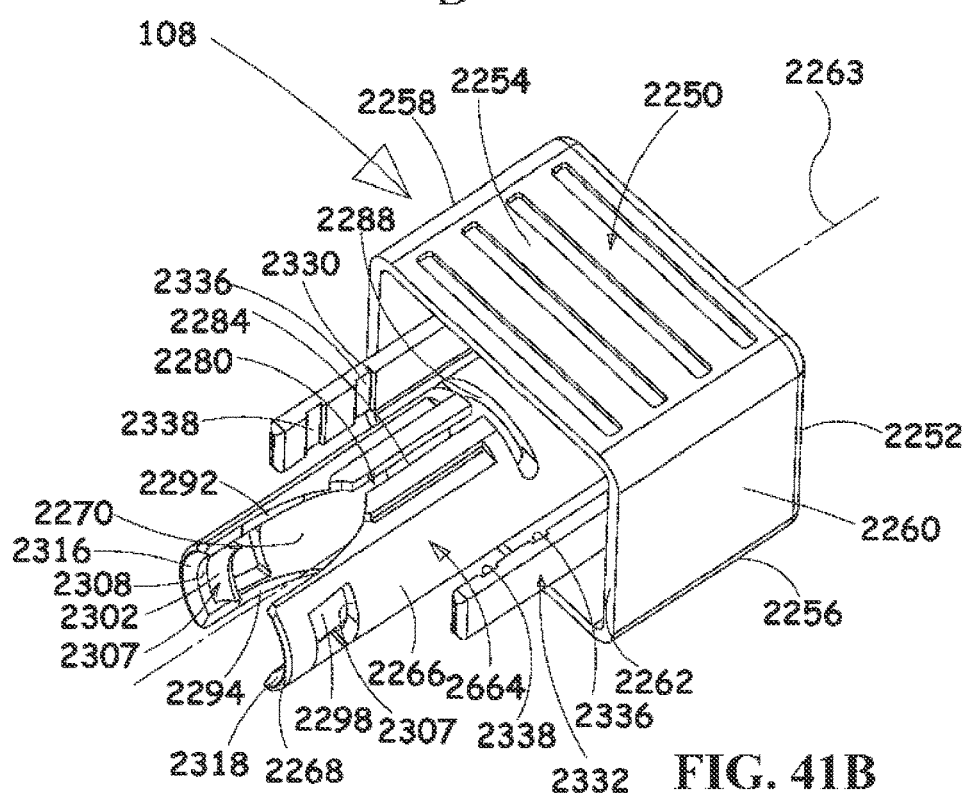
Figure 41C:
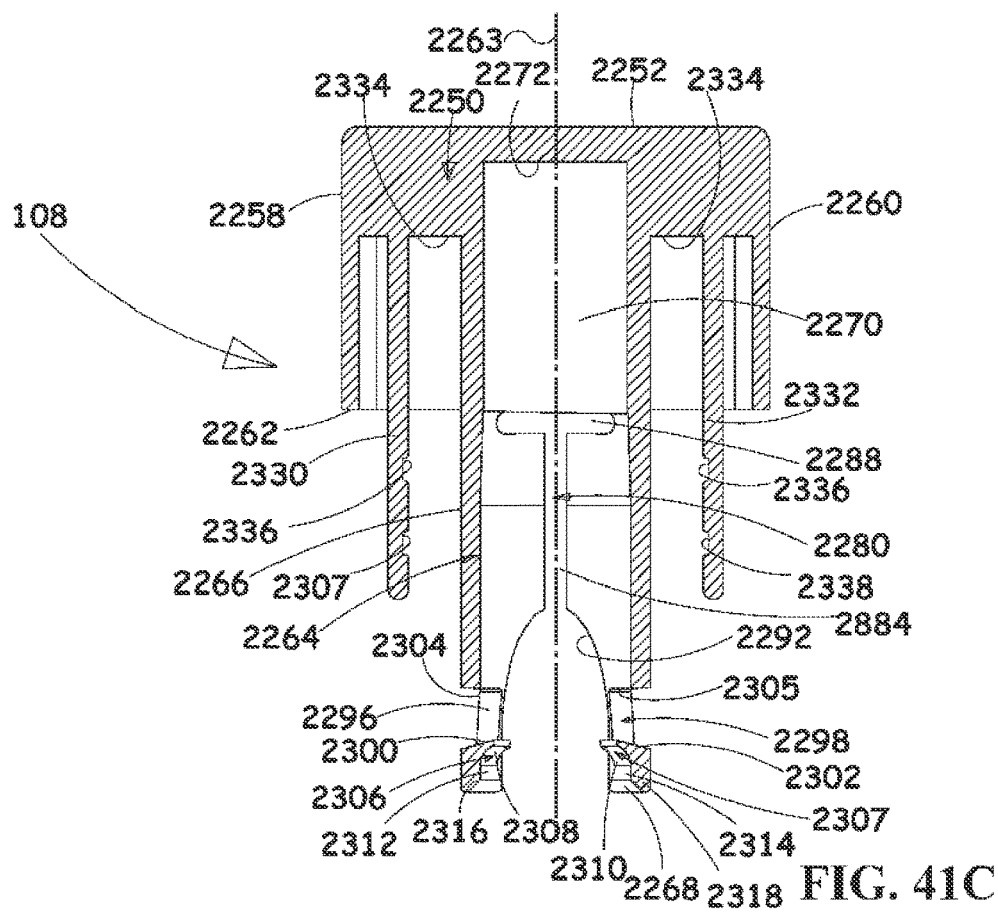
FIGS. 41C and 41D are respective simplified sectional illustrations of the RNS remover element of FIGS. 41A & 41B, taken along respective lines C-C & D-D.
Figure 41D:
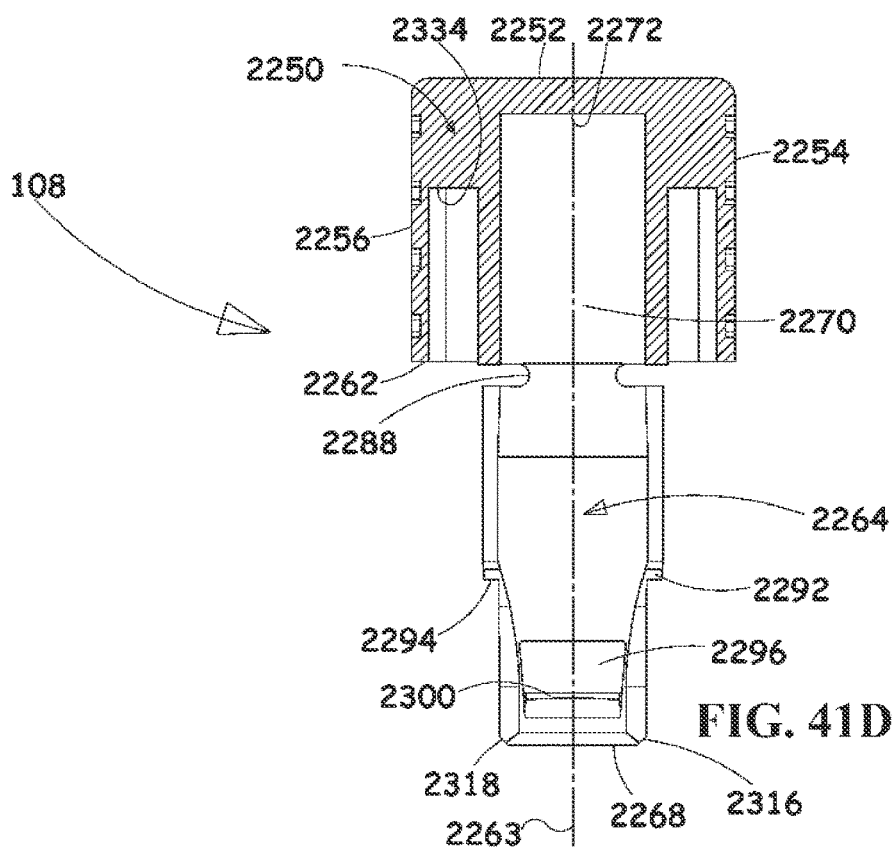

Reference is now made to FIGS. 41A and 41B, which are simplified pictorial illustrations of RNS remover element 108 (FIG. 2) forming part of the prefilled syringe injection module of FIG. 38, seen from a forward end and a rearward end respectively and to FIGS. 41C and 41D, which are respective simplified sectional illustrations of the RNS remover element of FIGS. 41A & 41B, taken along respective lines C-C & D-D.

As seen in FIGS. 41A-41D, the RNS remover 108 includes a cap portion 2250 including a forward-facing rectangular planar surface 2252, respective top and bottom rectangular planar surfaces 2254 and 2256 and respective first and second side rectangular planar surfaces 2258 and 2260. Planar surfaces 2254, 2256, 2258 and 2260 together have a circumferential rearwardly facing edge surface 2262. Extending rearwardly along an axis 2263 from a location rearward of forward-facing rectangular planar surface 2252 is a rearwardly-extending hollow pipe portion 2264, having an outer, generally circular cylindrical surface 2266 and a rearward edge surface 2268. Pipe portion 2264 is formed with a central bore 2270 extending forwardly from rearward edge surface 2268 to a rearward facing forward end surface 2272.

Pipe portion 2264 is formed with a pair of mutually circumferentially spaced transversely directed elongate cut outs 2280 and 2282. Communicating with transversely directed elongate cut outs 2280 and 2282 are a pair of mutually circumferentially spaced axially directed elongate cut outs 2284 and 2286 each having thickened elongate edge regions which are respectively designated by reference numerals 2288 and 2290. Each of axially directed elongate cut outs 2284 and 2286 terminates rearwardly in a rearwardly widening dome shaped cut out. These cut outs are respectively designated by reference numerals 2292 and 2294.

Mutually facing apertures 2296 and 2298 are formed in pipe portion 2264 at locations forwardly spaced from rearward edge surface 2268. Apertures 2296 and 2298 have forward facing edge surfaces 2300 and 2302 respectively and thickened rearward-facing edge surfaces 2304 and 2305 respectively, which forward facing edge surfaces 2300 and 2302 form part of respective inwardly facing protrusions 2306 and 2307. Rearwardly of apertures 2296 and 2298 there are formed mutually facing rearwardly outwardly tapering surfaces 2308 and 2310, which intersect respective thickened rearward-facing edge surfaces 2304 and 2306. Rearwardly of surfaces 2308 and 2310 are generally circular cylindrical surface segments 2312 and 2314. A pair of outwardly tapering generally circular surfaces 2316 and 2318 join surface segments 2312 and 2314 to rearward edge surface 2268.

A pair of mutually spaced generally axial shafts 2330 and 2332 extend rearwardly from a rearward facing surface 2334 and are reach preferably formed with a pair of mutually axially separated transverse recesses 2336 and 2338.

Figure 42A:
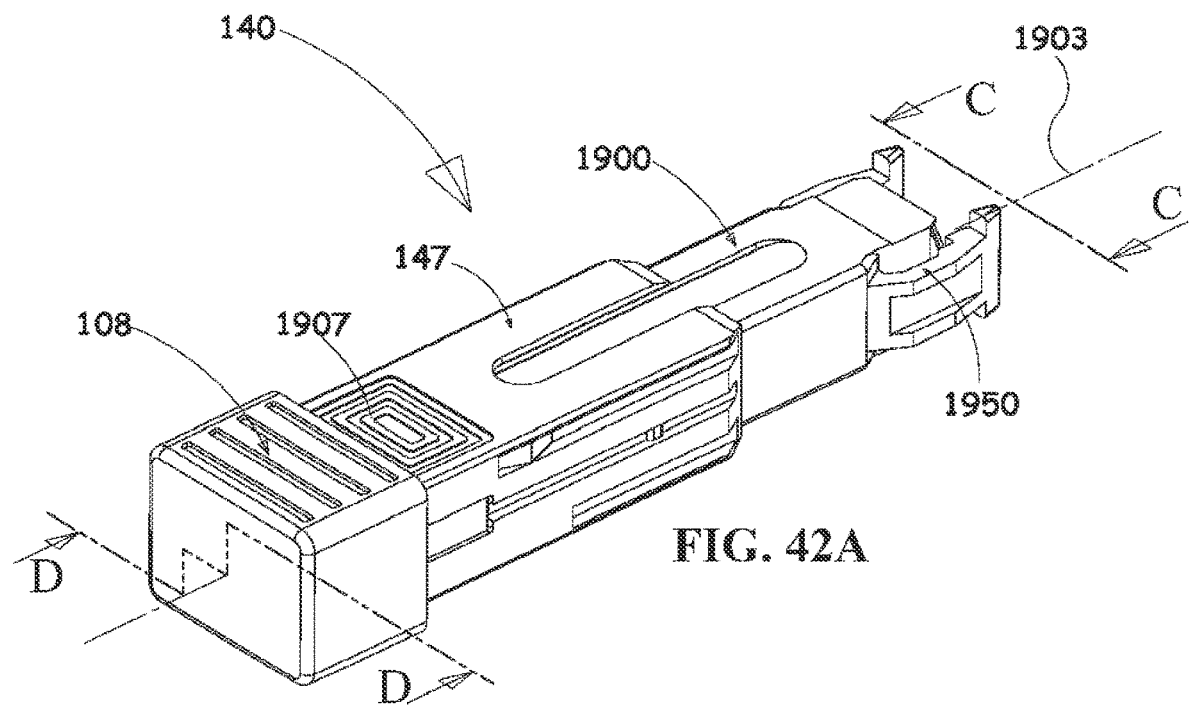
FIGS. 42A & 42B are simplified respective assembled view illustrations of the prefilled syringe injection module of FIGS. 38-41D in a first operative orientation, seen from a forward end and a rearward end respectively.
Figure 42B:
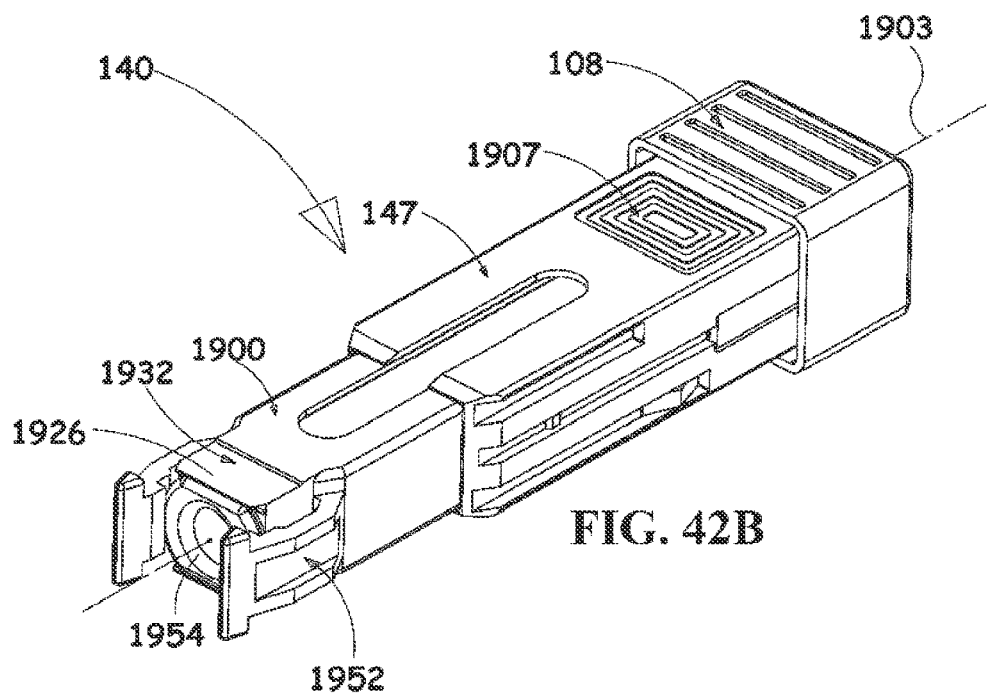
Figure 42C:
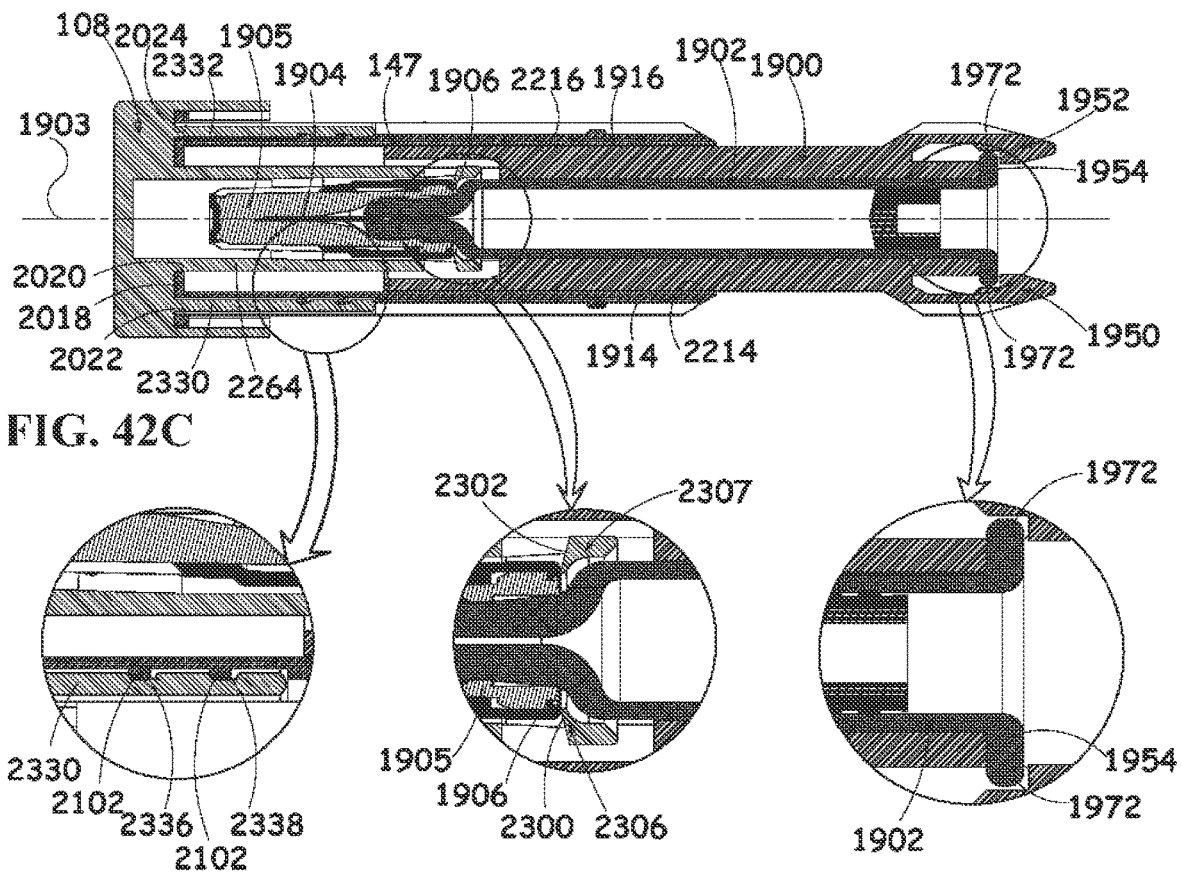
FIGS. 42C and 42D are respective simplified sectional illustrations of the prefilled syringe injection module of FIGS. 42A & 42B, taken along respective lines C-C & D-D.
Figure 42D:
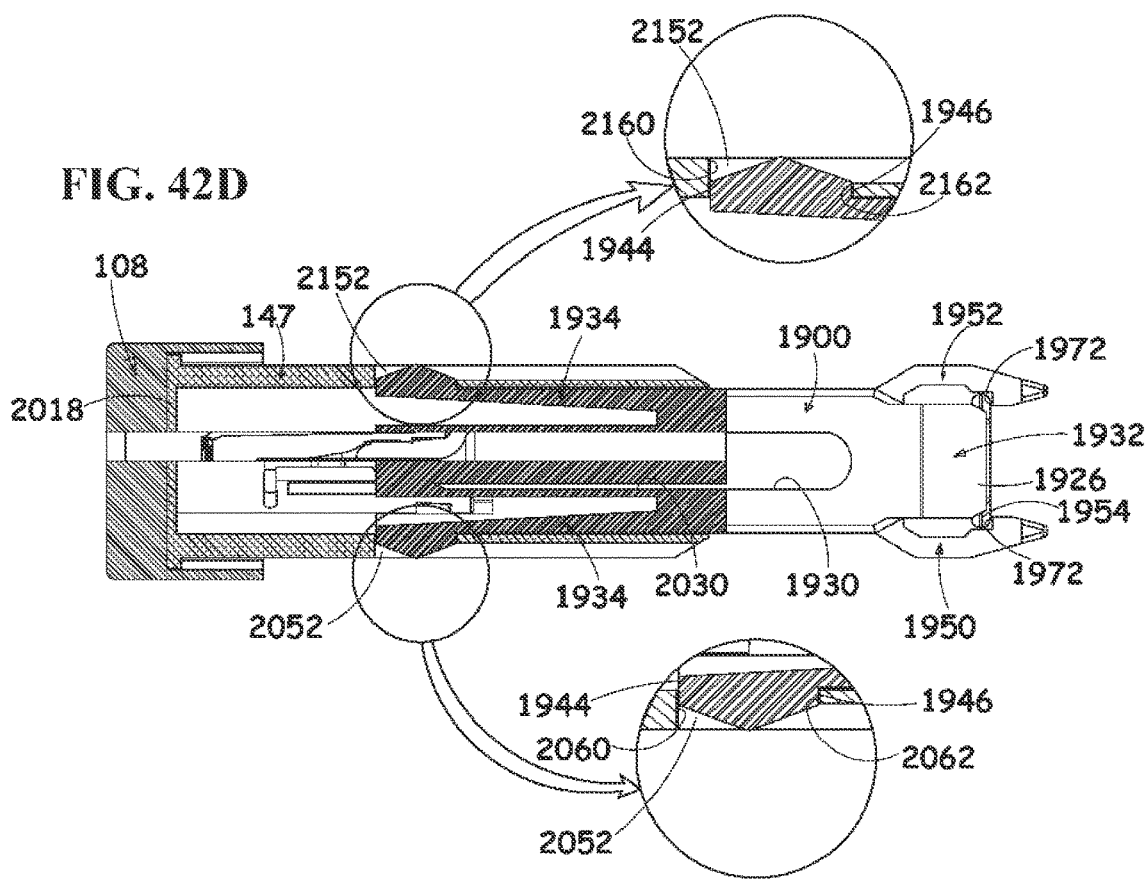

Reference is now made to FIGS. 42A & 42B, which are simplified respective assembled view illustrations of the prefilled syringe injection module of FIGS. 39A-41D in a first operative orientation, seen from a forward end and a rearward end respectively and to FIGS. 42C and 42D, which are respective simplified sectional illustrations of the prefilled syringe injection module of FIGS. 39A-42B, taken along respective lines C-C & D-D. FIGS. 42A-42D illustrate a typical "out of the box" operative orientation of the prefilled syringe injection module 140 as it is transported and stored prior to use.

As seen in FIGS. 42A-42D, the prefilled syringe 1902 is securely retained within the mounting element 1900 by snap-fit engagement of surfaces 1972 of arms 1950 and 1952 of mounting element 1900. A desired azimuthal orientation of the prefilled syringe 1902 about axis 1903 is ensured by engagement of edges of flange 1954 of prefilled syringe 1902 with side walls 1926 and 1928 of mounting element 1900.

It is further seen that the needle shield element 147 is mounted onto the mounting element 1900, such that outer elongate surfaces 1910, 1912, 1914 and 1916 of the mounting element 1900 engage respective inner elongate surfaces 2210, 2212, 2214 and 2216 of needle shield element 147. Needle shield element 147 is axially retained in position relative to mounting element 1900 by engagement of flexible diagonally opposed needle shield engaging fingers 1934 of the mounting element 1900 in apertures 2152 and 2052, such that respective surfaces 1944 and 1946 of one of fingers 1934 engage corresponding respective surfaces 2060 and 2062 of aperture 2052 and respective surfaces 1944 and 1946 of the other of fingers 1934 engage corresponding respective surfaces 2160 and 2162 of aperture 2152. In this position, window recesses 1930 in mounting element 1900 are aligned with respective slots 2030 formed in needle shield element 147.

It is additionally seen that RNS remover 108 is mounted onto needle shield element 147 by engagement of mutually spaced side facing rounded protrusions 2102 of the needle shield element 147 in recesses 2336 and 2338 of respective shafts 2330 and 2332 of the RNS remover 108, which extend through respective apertures 2022 and 2024, formed in the patient engagement plate 2018 of the needle shield element 147. The RNS remover 108 is also mounted onto the prefilled syringe 1902 by engagement of the inwardly facing protrusions 2306 and 2307 with opposite side surfaces of prefilled syringe 1902 just rearwardly of rearward edge 1906 of RNS 1905, such that forward facing edge surfaces 2300 and 2302 lie in touching or near touching relationship with rearward edge 1906. In this operative orientation, pipe portion 2264 extends through aperture 2020 in patient engagement plate 2018 of the needle shield element 147.

Figure 43A:
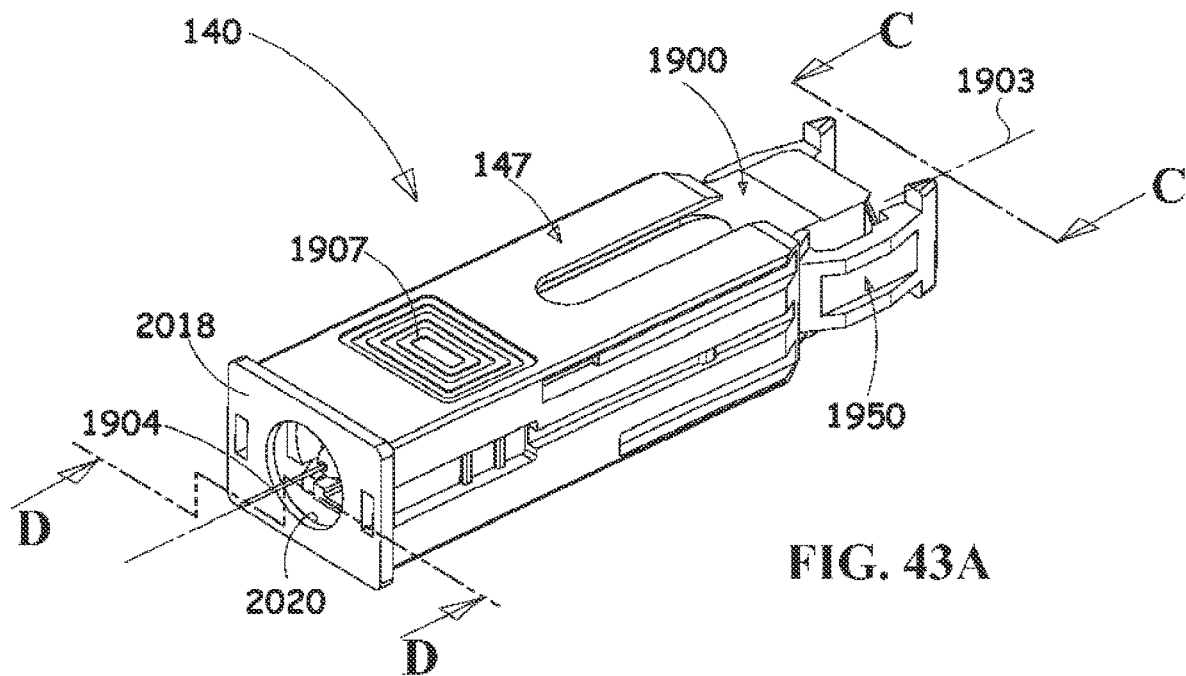
FIGS. 43A & 43B are simplified respective assembled view illustrations of the prefilled syringe injection module of FIGS. 38-42D in a second operative orientation, seen from a forward end and a rearward end respectively.
Figure 43B:
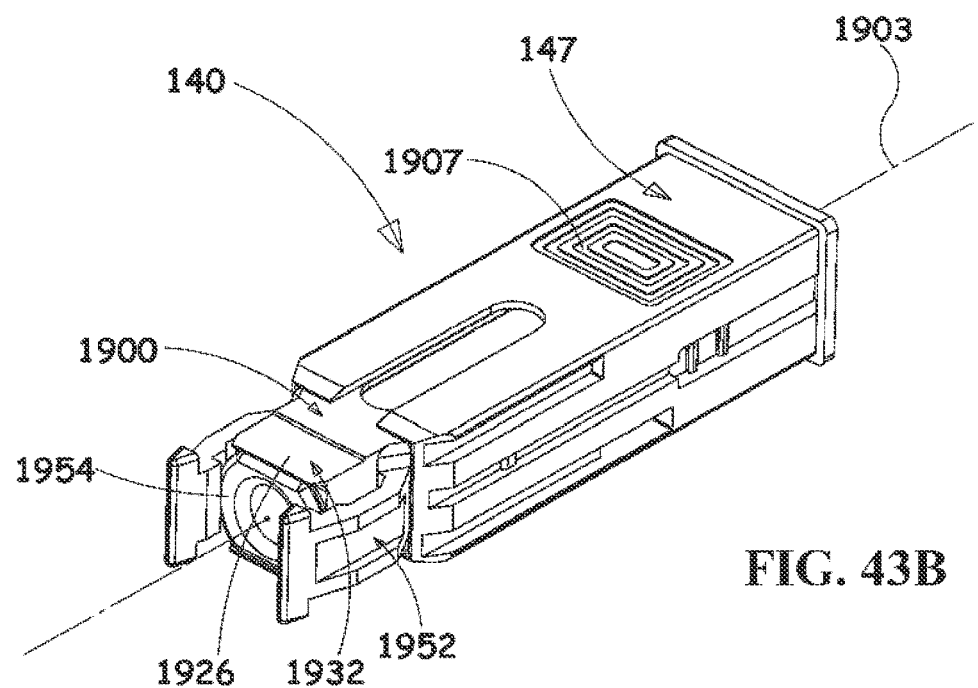
Figure 43C:
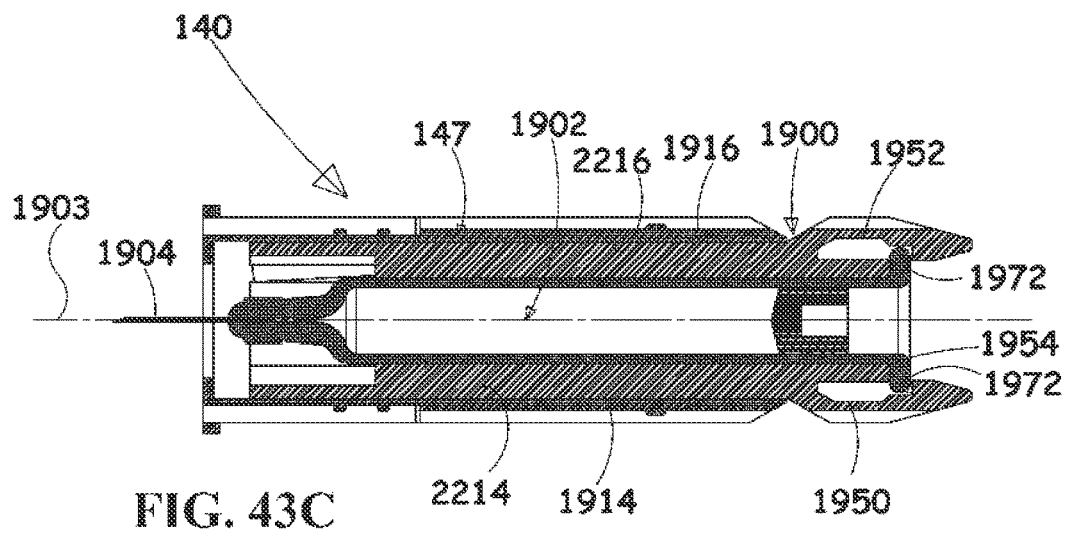
FIGS. 43C and 43D are respective simplified sectional illustrations of the prefilled syringe injection module of FIGS. 43A & 43B, taken along respective lines C-C & D-D.
Figure 43D:
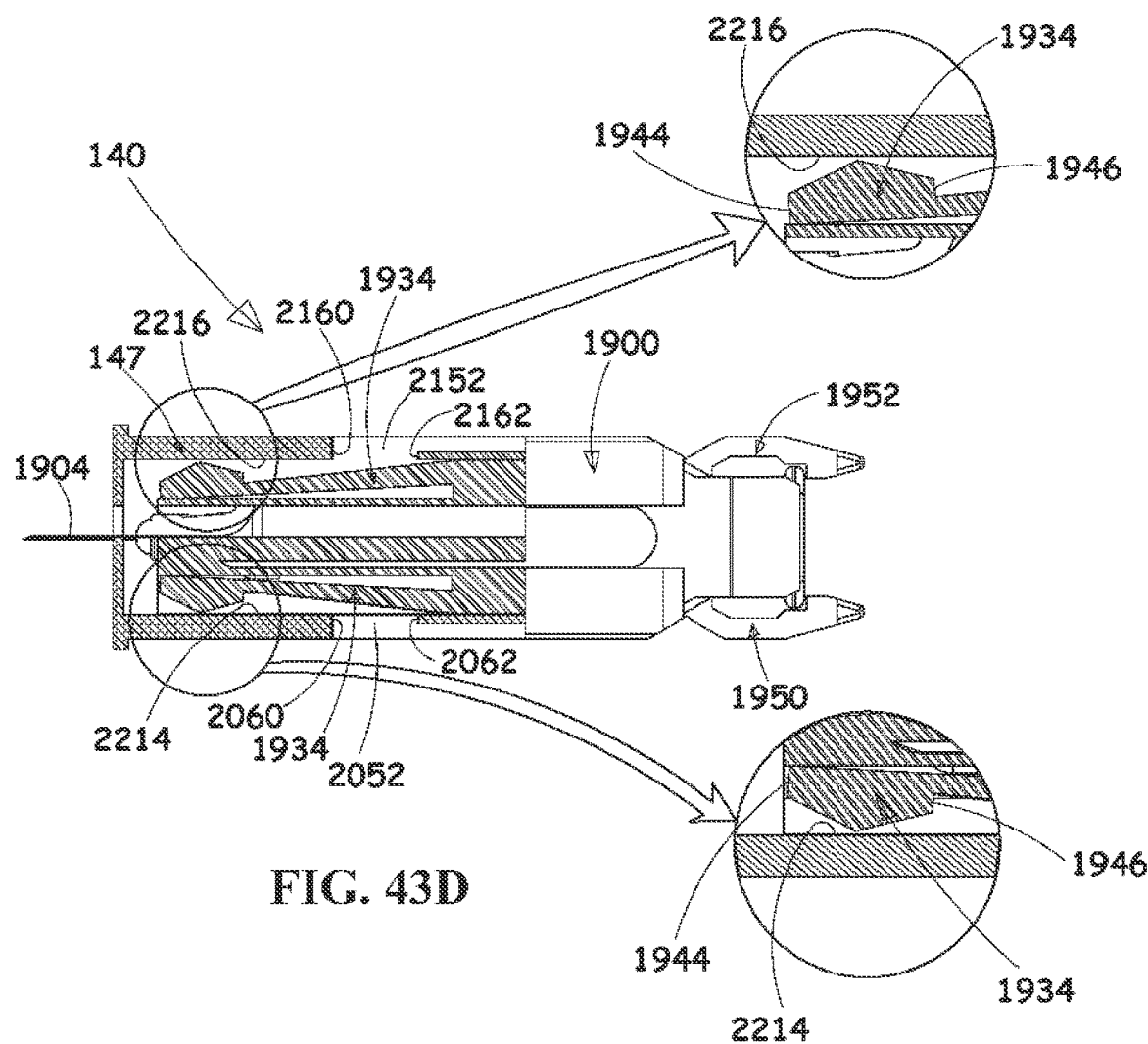

Reference is now made to FIGS. 43A & 43B, which are simplified respective assembled view illustrations of the prefilled syringe injection module of FIGS. 39A-42D in a second operative orientation, seen from a forward end and a rearward end respectively and to FIGS. 43C and 43D, which are respective simplified sectional illustrations of the prefilled syringe injection module of FIGS. 39A-42D, taken along respective lines C-C & D-D. FIGS. 43A-43D illustrate a typical "needle penetration-pre injection" operative orientation of the prefilled syringe injection module 140.

As seen in FIGS. 43A-43D, the prefilled syringe 1902 remains securely retained within the mounting element 1900 by snap-fit engagement of surfaces 1972 of arms 1950 and 1952 of mounting element 1900. The desired azimuthal orientation of the prefilled syringe 1902 about axis 1903 remains ensured by engagement of edges of flange 1954 of prefilled syringe 1902 with side walls 1926 and 1928 of mounting element 1900.

It is further seen that the needle shield element 147 remains mounted onto the mounting element 1900, such that outer elongate surfaces 1910, 1912, 1914 and 1916 of the mounting element 1900 engage respective inner elongate surfaces 2210, 2212, 2214 and 2216 of needle shield element 147.

In the second operative orientation as compared with the first operative orientation, mounting element 1900 has been displaced forwardly relative to the needle shield element 147, enabled by radially inward displacement of flexible diagonally opposed needle shield engaging fingers 1934 of the mounting element 1900 out of engagement with apertures 2152 and 2052, such that respective surfaces 1944 and 1946 of one of fingers 1934 no longer engage corresponding respective surfaces 2060 and 2062 of aperture 2052 and respective surfaces 1944 and 1946 of the other of fingers 1934 no longer engage corresponding respective surfaces 2160 and 2162 of aperture 2152. Fingers 1934 now engage inner elongate surfaces 2214 and 2216 of needle shield element 147. Needle 1904 thus extends forwardly of aperture 2020 in patient engagement plane 2018 of needle shield element 147.

It is appreciated that prior to arrangement of the prefilled syringe injection module 140 in the second operative orientation, RNS remover 108 is manually removed, as by the user, thus removing the RNS 1905 from its earlier position covering needle 1904. This removal is effected by virtue of the engagement of the inwardly facing protrusions 2306 and 2307 with opposite side surfaces of prefilled syringe 1902 just rearwardly of rearward edge 1906 of RNS 1905, such that forward facing edge surfaces 2300 and 2302 lie in touching or near touching relationship with rearward edge 1906. Removal of the RNS remover 108 forwardly along axis 1903 thus pulls the RNS 1905 axially along with it and away from and out of engagement with needle 1904.

Reference is now made to FIGS. 44-48C, which illustrate needleless cartridge injection module 142 (FIG. 2), constructed and operative in accordance with a preferred embodiment of the present invention. As seen in FIGS. 44-48C, the needleless cartridge injection module 142 preferably includes a mounting element 2400 in which is partially disposed a conventional needleless cartridge 2402, such as, for example, a Cat. Number 61007, commercially available from GERRESHEIMER, Dusseldorf, Germany, having a needle mount portion 2403 extending forwardly of a neck portion 2404, the needle mount portion including a septum 2405. The needleless cartridge 2402 includes a piston 2406. The mounting element 2400 preferably has associated therewith a wireless communicator providing wireless communication functionality, such as a passive RF information transmitter assembly 2407, such as Cat. Number NT2H1311G0DUD, commercially available from NXP Semiconductors, San Jose, CA, USA. A removable needle assembly 2408 is provided for selectable operative association with the needleless cartridge 2402. A piston extension element 2410 is provided for operative association with piston 2406.

Figure 44:
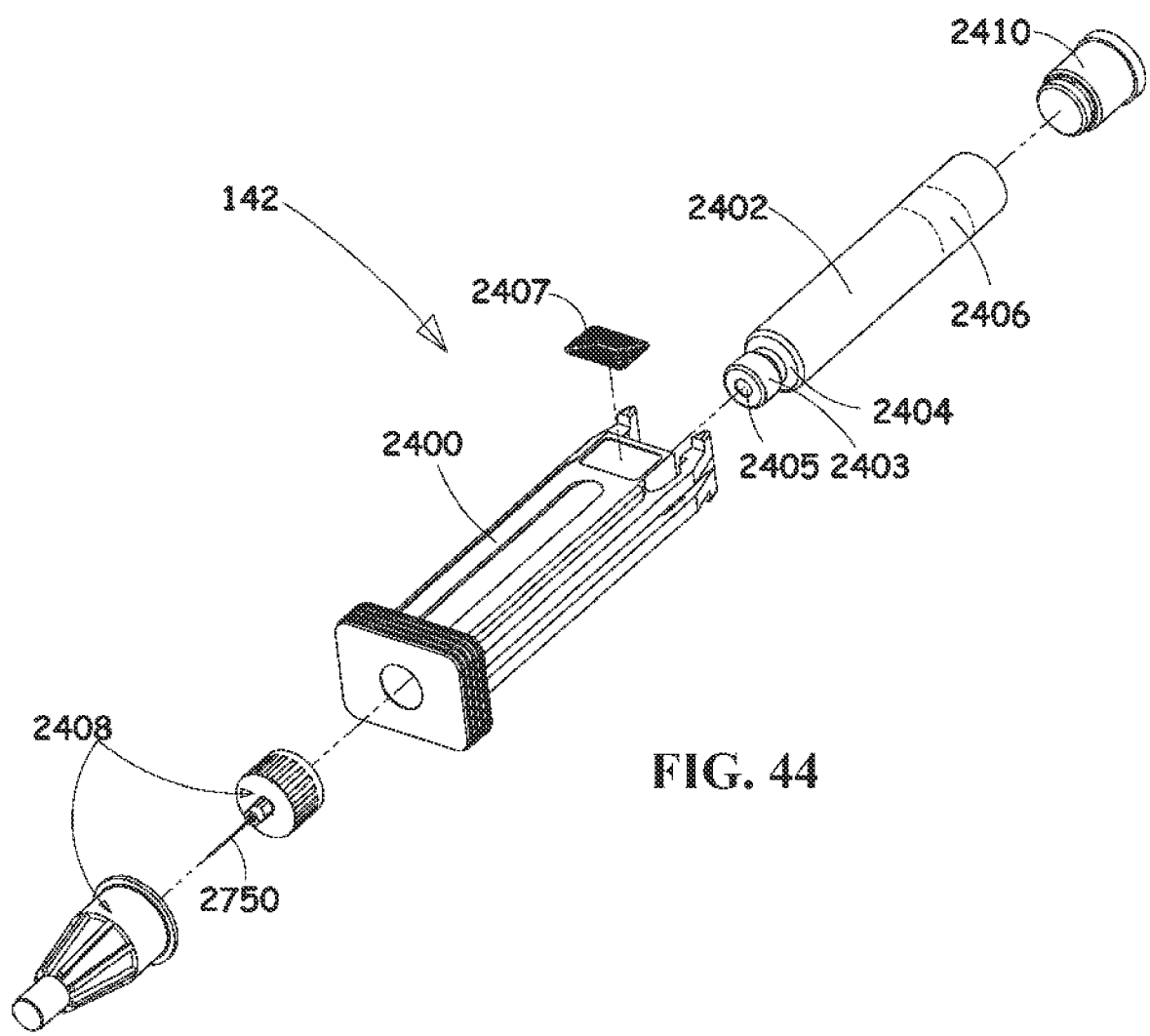
FIG. 44 is a simplified exploded view illustration of a needleless cartridge injection module constructed and operative in accordance with a preferred embodiment of the present invention.
Figure 45A:
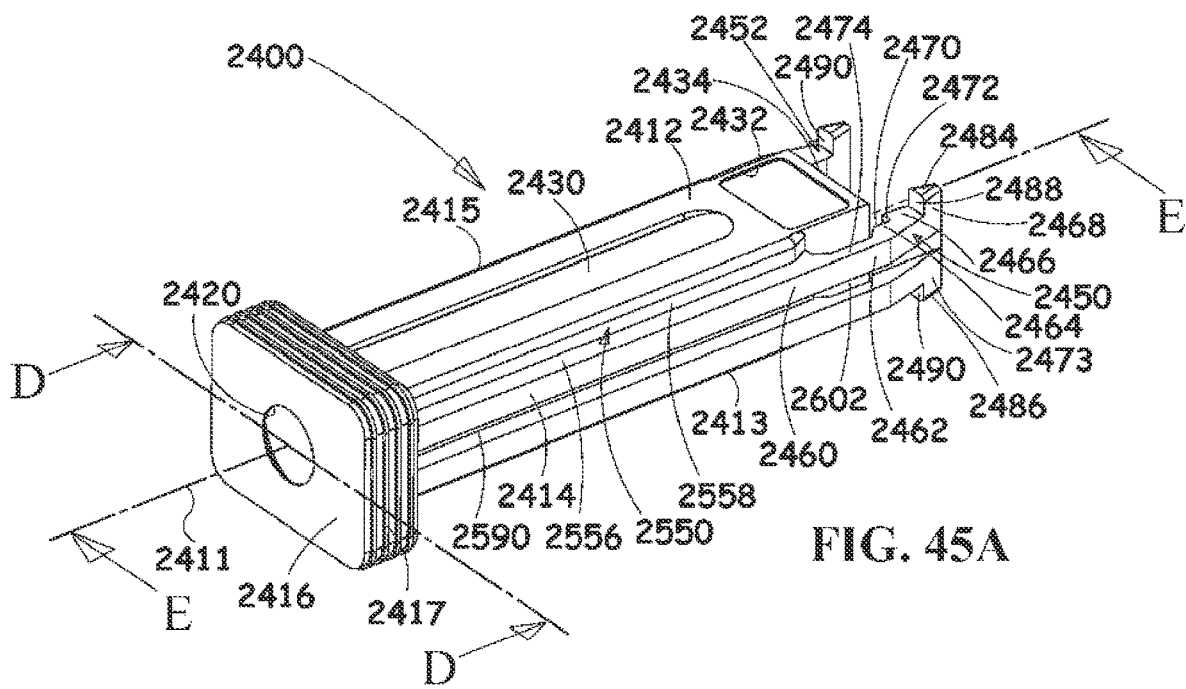
FIGS. 45A and 45B are simplified pictorial illustrations of a mounting element forming part of the needleless cartridge injection module of FIG. 44, seen from a forward end and a rearward end respectively.
Figure 45B:
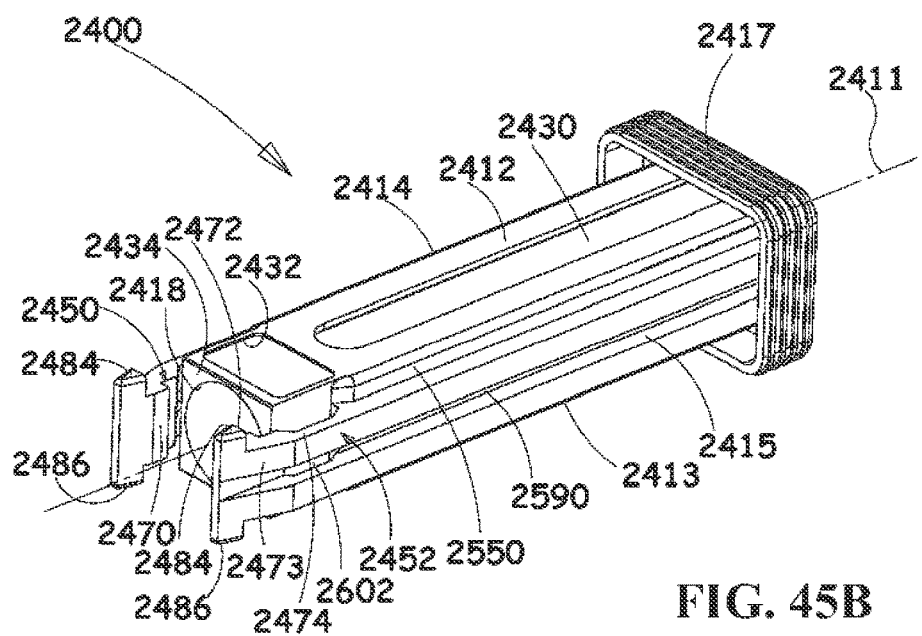
Figure 45C:
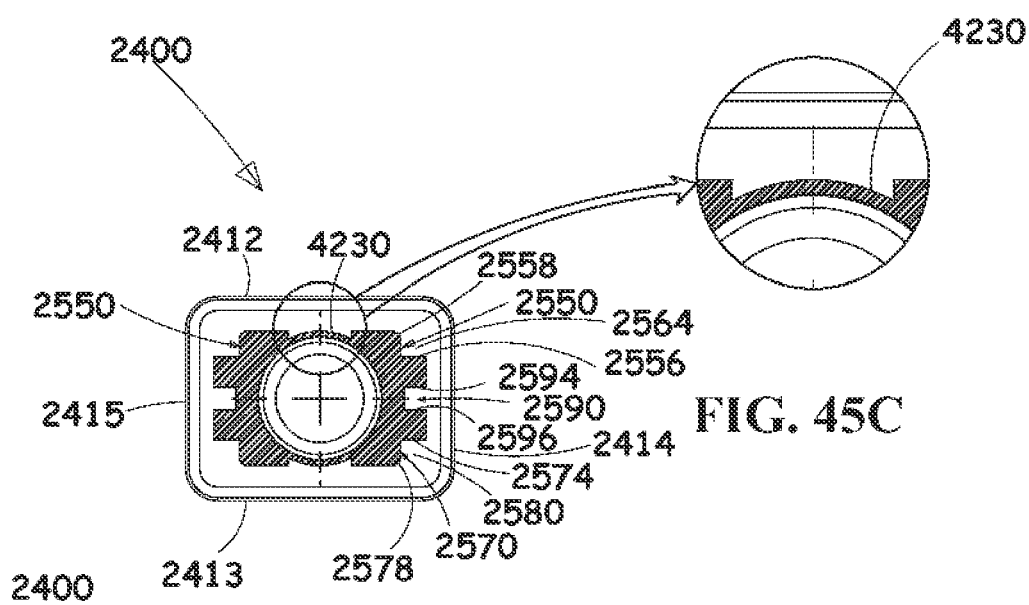
FIGS. 45C, 45D and 45E are respective simplified sectional illustrations of the mounting element of FIGS. 45A & 45B, taken along respective lines C-C, D-D and E-E.
Figure 45D:
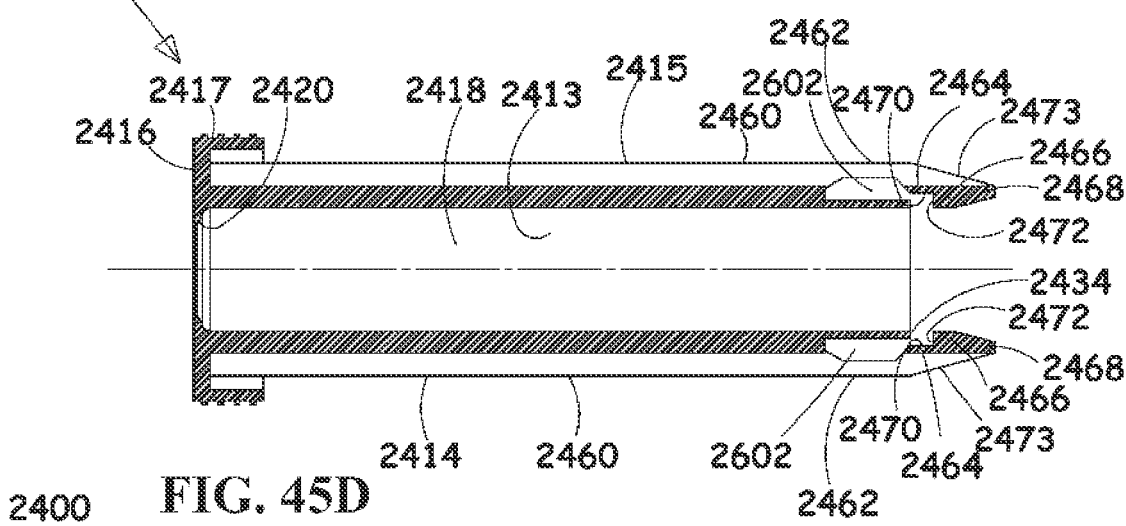
Figure 45E:
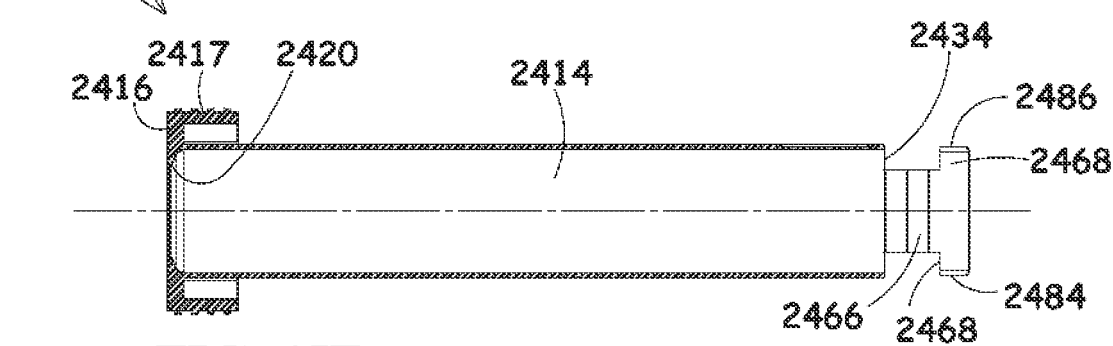

Reference is now specifically made to FIGS. 45A and 45B, which are simplified pictorial illustrations of mounting element 2400 forming part of the needleless cartridge injection module of FIG. 44, seen from a forward end and a rearward end respectively and to FIGS. 45C, 45D and 45E, which are respective simplified sectional illustrations of the mounting element of FIGS. 45A & 45B, taken along respective lines C-C, D-D and E-E.

As seen in FIGS. 45A-45E, mounting element 2400 is a generally elongate element extending along an axis 2411 and having a generally square cross section including elongate top and bottom walls 2412 and 2413, which are identical, and elongate side walls 2414 and 2415. Walls 2412, 2313, 2414 and 2415 together join a forward-facing wall 2416 having a circumferential edge 2417. Mounting element has a throughgoing bore 2418 having a circular cross section and a forward inwardly tapered portion 2420 both of which have a circular cross section.

Top and bottom walls 2412 and 2413, each preferably have an outer facing elongate window recess 2430 including an internal wall having a curved cross section, as seen particularly in FIG. 45C. Top wall 2412 preferably includes a recess 2432 for accommodating passive RF information transmitter assembly 2407 (FIG. 44).

A rearward end of bore 2418 terminates at a rearward-facing planar surface 2434.

A pair of somewhat flexible arms 2450 and 2452 extend sideways from respective side walls 2414 and 2415 respectively and preferably serve two functions:
retention of the piston extension element 2410 and the needleless cartridge 2402 in bore 2418; and
engagement with multiple motion output subassembly 152.

Each of arms 2450 and 2452 includes an outwardly directed portion 2460, an intermediate portion 2462, a forward thickened portion 2464, a rearward thickened portion 2466 and a rearwardly facing end tapered portion 2468. Forward thickened portion 2464 defines an inwardly facing surface 2470 and rearward thickened portion 2466 defines a forward facing shoulder surface 2472, which extends perpendicularly with respect to and intersects surface 2470. Portions 2460, 2462, 2464, 2466 and 2468 together define an inwardly tapered outer surface 2473.

Portions 2460, 2462, 2464 and 2466 define coplanar top and bottom edge surfaces 2474 and 2476. Rearwardly facing end tapered portions 2468 define upwardly and downwardly extending edges, which extend beyond surfaces 2474 and 2476 and define respective edge surfaces 2484 and 2486. Forward facing shoulder surfaces 2488 and 2490 are defined between respective edge surfaces 2474 & 2484 and 2476 & 2486 respectively.

Elongate side walls 2413 and 2415 each include a top elongate open-sided recess 2550. Recess 2550 has a bottom recess wall surface 2556, a side wall surface 2558 and a rearward facing forward end wall surface 2564.

Elongate side walls 2413 and 2415 also each include a bottom elongate open-sided recess 2570. Recess 2570 has a top recess wall surface 2574, a side wall surface 2578 and a rearward facing forward end wall surface 2580.

Elongate side walls 2413 and 2415 further each include an intermediate elongate recess 2590. Recess 2090 includes top and bottom recess wall surfaces 2594 and 2596, a side wall surface 2598 and a forward facing rearward end wall surface 2600. Side wall surface 2598 is preferably formed with an aperture 2602.

Figure 46A:
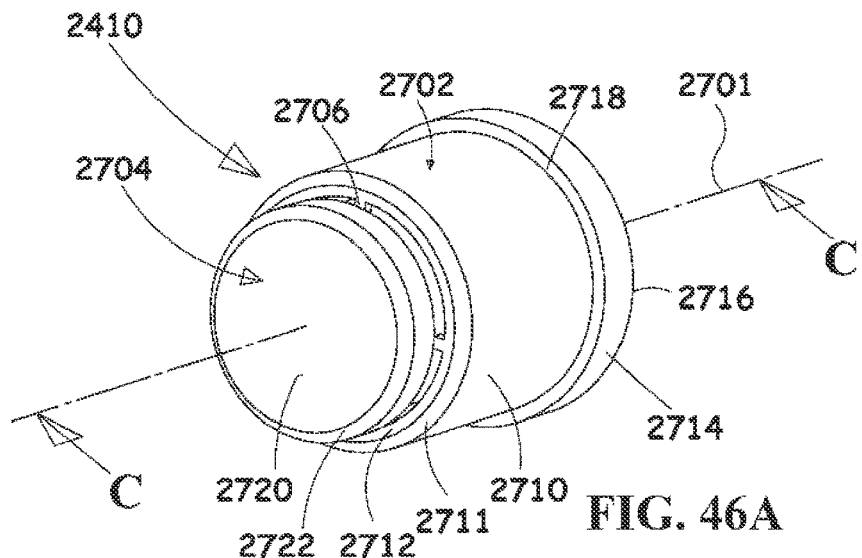
FIGS. 46A and 46B are simplified pictorial illustrations of a piston extension element forming part of the needleless cartridge injection module of FIG. 44, seen from a forward end and a rearward end respectively.
Figure 46B:
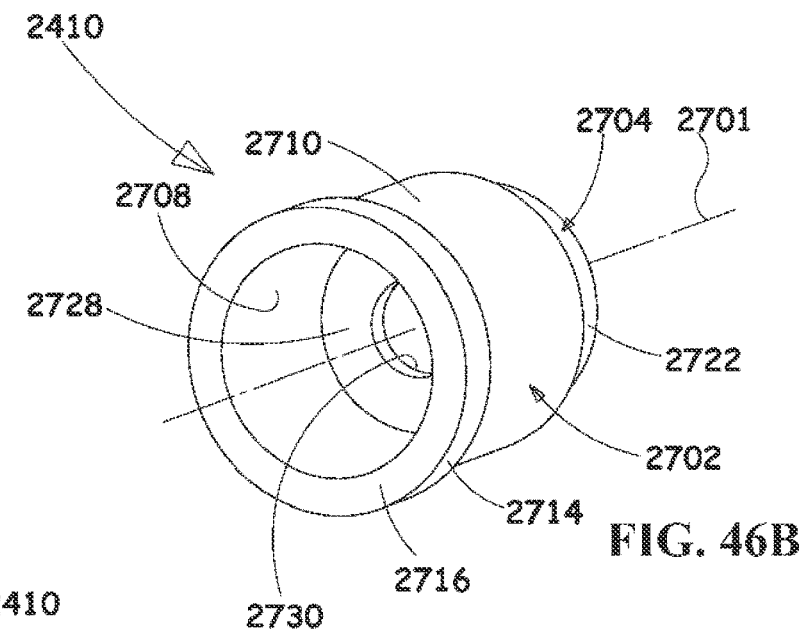
Figure 46C:
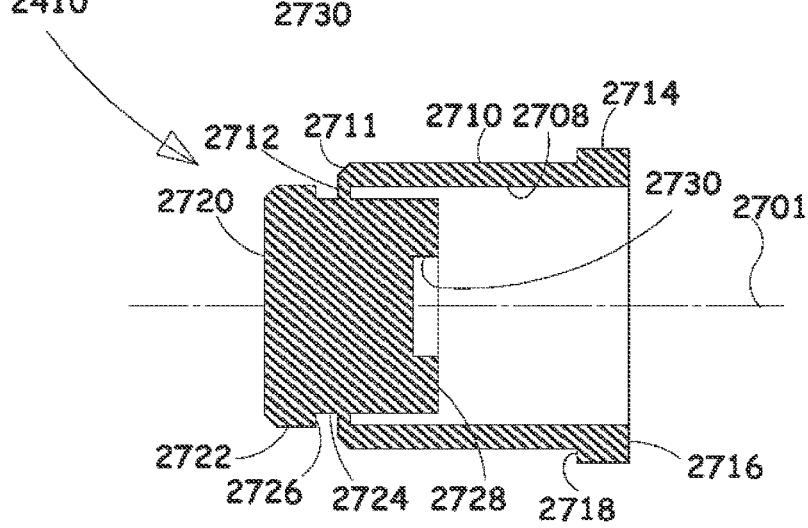
FIG. 46C is a simplified sectional illustration of the piston extension element of FIGS. 46A & 46B, taken along lines C-C.

Reference is now made to FIGS. 46A and 46B, which are simplified pictorial illustrations of piston extension element 2410, forming part of the needleless cartridge injection module 142 of FIG. 44, seen from a forward end and a rearward end respectively and to FIG. 46C, which is a simplified sectional illustration of the piston extension element 2410 of FIGS. 46A & 46B, taken along lines C-C.

As seen in FIGS. 46A-46C, the piston extension element 2410 is a generally circularly symmetrical element arranged about an axis 2701 and which includes a generally cylindrical retaining portion 2702 and a piston extending portion 2704, which are separatably joined by a plurality of frangible radially extending connection portions 2706. Retaining portion 2702 has a generally circularly cylindrical inner surface 2708 and a generally circularly cylindrical outer surface 2710 and includes an inclined forward and outward facing edge portion 2711 surrounding a forward facing edge portion 2712. At a rearward end thereof, retaining portion 2702 defines a thickened portion 2714 having a rearwardly facing edge surface 2716 and defining a forwardly facing shoulder surface 2718 which intersects surface 2710.

Piston extending portion 2704 is a generally circularly symmetric portion which defines a forward facing piston engaging surface 2720 and a circumferential edge surface 2722 extending rearwardly from surface 2720. Rearwardly of surface 2722 is a generally cylindrical outer surface 2724 which defines a rearward facing shoulder surface 2726 with surface 2722 and terminates in a rearward-facing surface 2728. A central circular recess 2730 is defined in rearward-facing surface 2728.

Figure 47A:
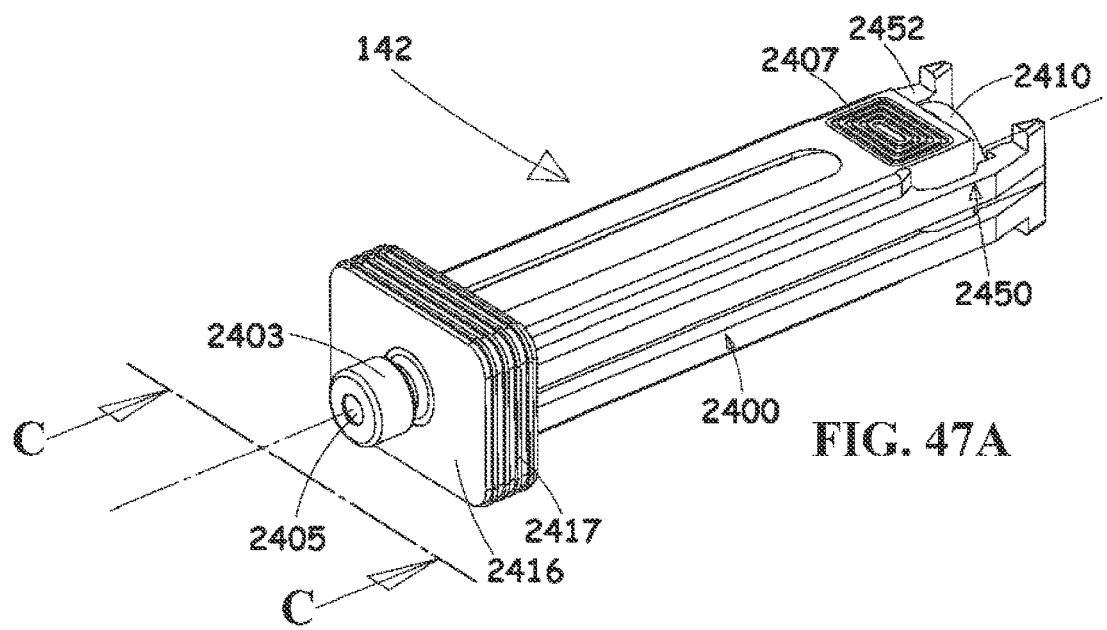
FIGS. 47A & 47B are simplified respective assembled view illustrations of the needleless cartridge injection module of FIGS. 44-46C in a first operative orientation, seen from a forward end and a rearward end respectively.
Figure 47B:
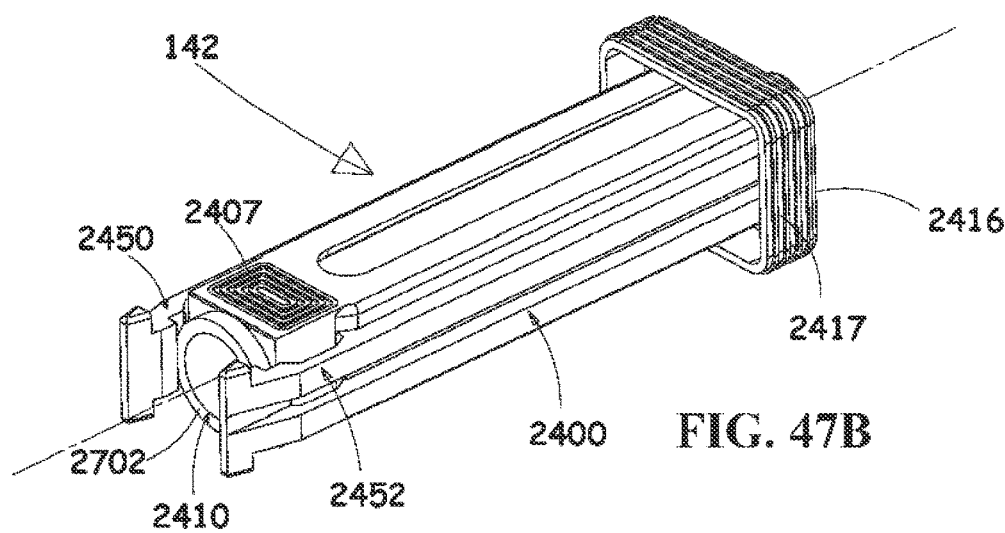
Figure 47C:
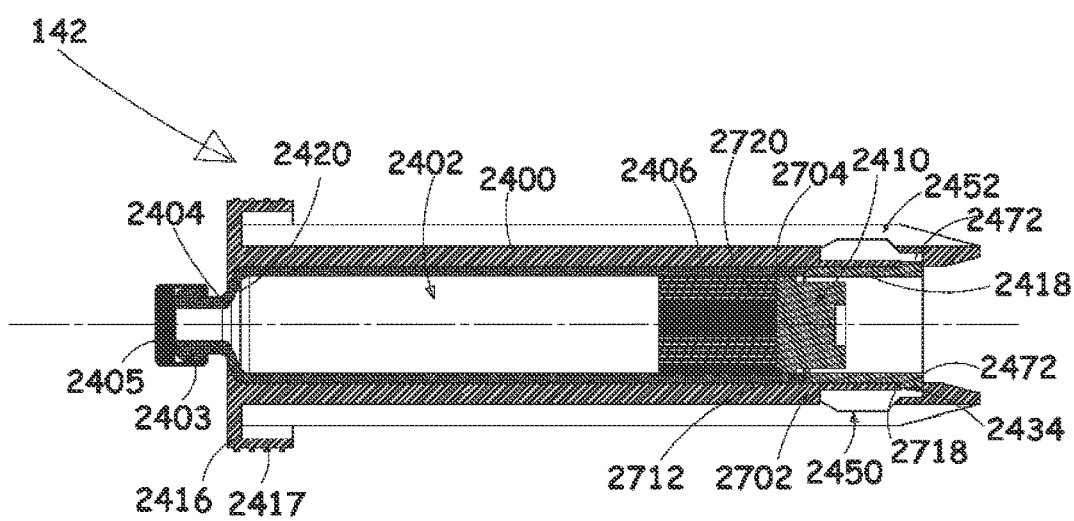
FIG. 47C is a simplified sectional illustration of the needleless cartridge injection module of FIGS. 47A & 47B, taken along lines C-C.

Reference is now made to FIGS. 47A & 47B, which are simplified respective assembled view illustrations of the needleless cartridge injection module 142 of FIGS. 44-46C in a first operative orientation, seen from a forward end and a rearward end respectively and to FIG. 47C, which is a simplified sectional illustration of the needleless cartridge injection module of FIGS. 47A & 47B, taken along lines C-C. FIGS. 47A-47C illustrate a typical "out of the box" operative orientation of the needleless cartridge injection module 142 as it is transported and stored prior to use.

As seen in FIGS. 47A-47C, the needleless cartridge 2402 and the piston extension element 2410 are securely retained within the mounting element 2400 by snap-fit engagement of surfaces 2472 of arms 2450 and 2452 of mounting element 2400. Retaining portion 2702 is seated rearwardly and inwardly of the rearward end of bore 2418 formed in mounting element 2400. Specifically, shoulder surface 2718 of retaining portion 2702 engages surface 2434 of the mounting element and the forward-facing edge surface 2712 of the retaining element 2702 engages a rearward edge of needleless cartridge 2402, thus retaining it in place relative to the mounting element 2400.

Piston engaging portion 2704 remains connected to retaining portion 2702 and its forward facing surface 2720 engages a rearward facing surface of piston 2406 of the needleless cartridge 2402.

Neck portion 2404 of the needleless cartridge 2402 lies in forward portion 2420 of bore 2418 of the mounting element 2400 such that the needle mount portion 2403 of needleless cartridge 2402 extends forwardly of bore 2418.

Figure 48A:
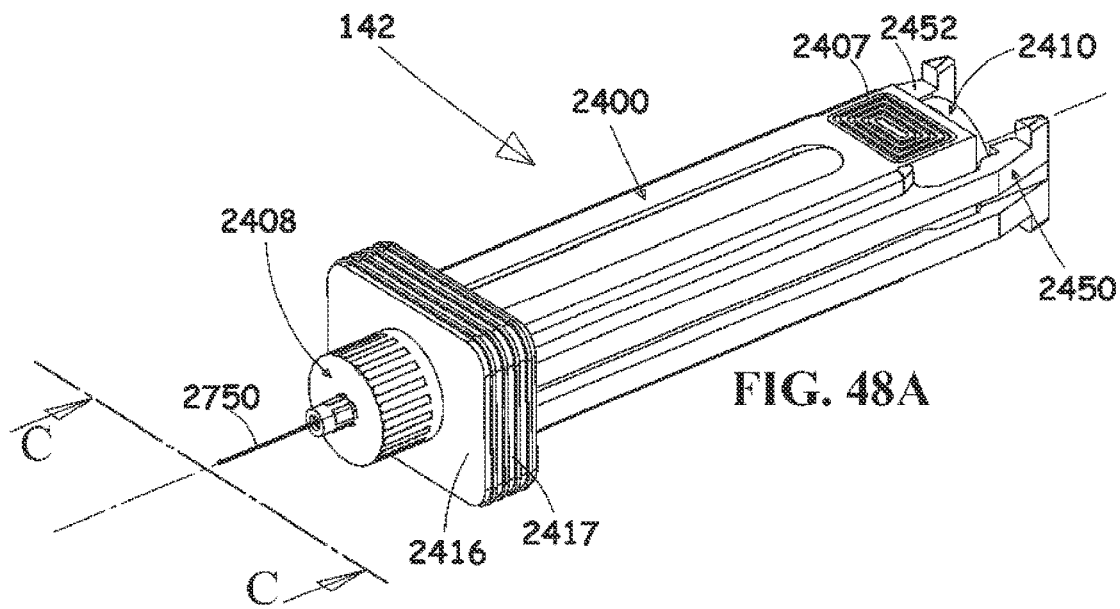
FIGS. 48A & 48B are simplified respective assembled view illustrations of the needleless cartridge injection module of FIGS. 44-47C in a second operative orientation, seen from a forward end and a rearward end respectively.
Figure 48B:
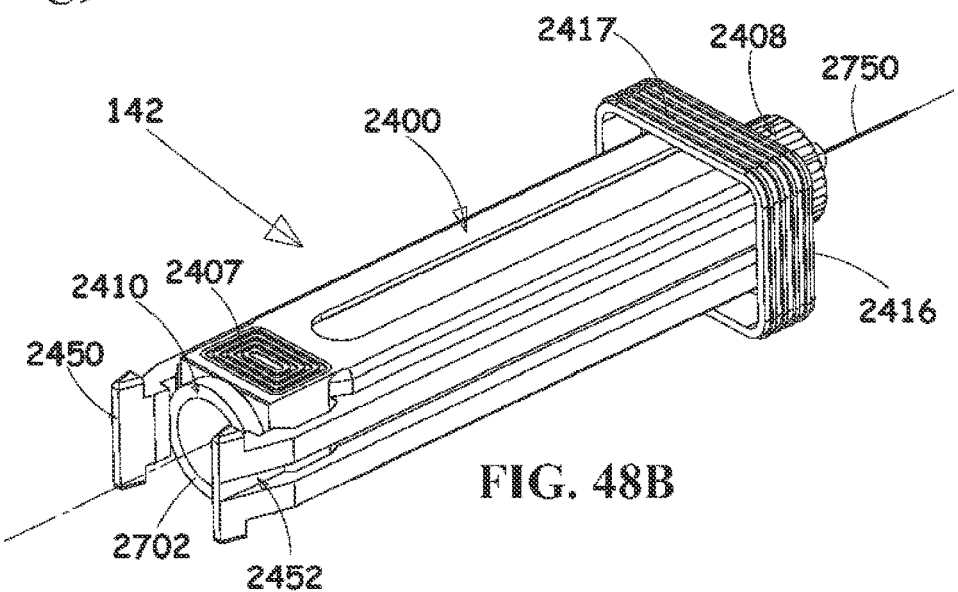
Figure 48C:
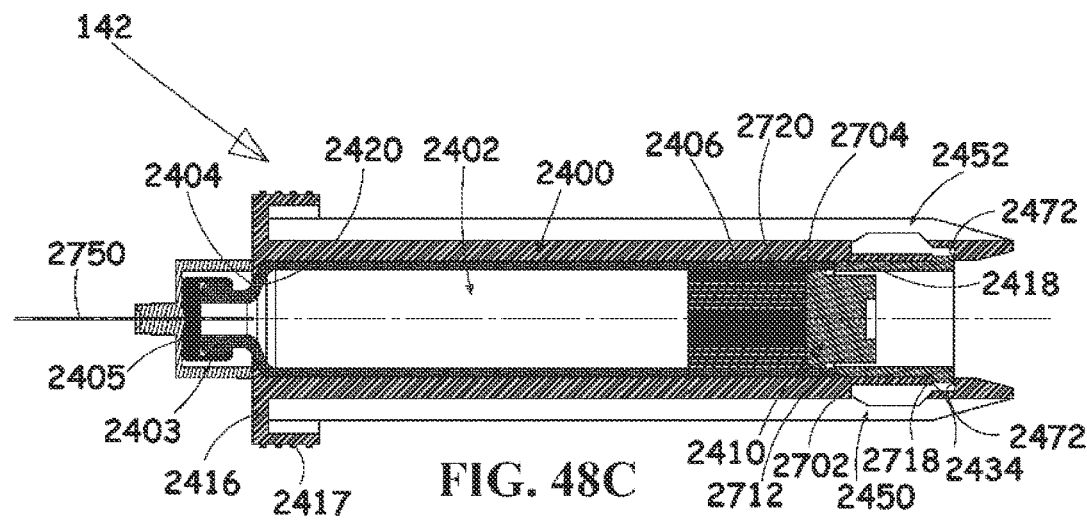
FIG. 48C is a simplified sectional illustration of the needleless cartridge injection module of FIGS. 48A & 47B, taken along lines C-C.

Reference is now made to FIGS. 48A & 48B, which are simplified respective assembled view illustrations of the needleless cartridge injection module of FIGS. 44-47C in a second operative orientation, seen from a forward end and a rearward end respectively and to FIG. 48C, which is a simplified sectional illustration of the needleless cartridge injection module of FIGS. 48A & 48B, taken along lines C-C. FIGS. 48A-48C illustrate a typical "ready to prime" operative orientation of the needleless cartridge injection module.

As seen in FIGS. 48A-48C, the needleless cartridge 2402 and the piston extension element 2410 remain securely retained within the mounting element 2400 by snap-fit engagement of surfaces 2472 of arms 2450 and 2452 of mounting element 2400. Retaining portion 2702 is seated rearwardly and inwardly of the rearward end of bore 2418 formed in mounting element 2400.

Piston engaging portion 2704 remains connected to retaining portion 2702 and its forward facing surface 2720 engages a rearward facing surface of piston 2406 of the needleless cartridge 2402.

Neck portion 2404 of the needleless cartridge 2402 remains in forward portion 2420 of bore 2418 of the mounting element 2400 such that the needle mount portion 2403 of needleless cartridge 2402 extends forwardly of bore 2418.

A needle 2750, forming part of needle assembly 2408, is seen to be mounted onto need mount portion 2403 of needleless cartridge 2402.

Figure 49A:
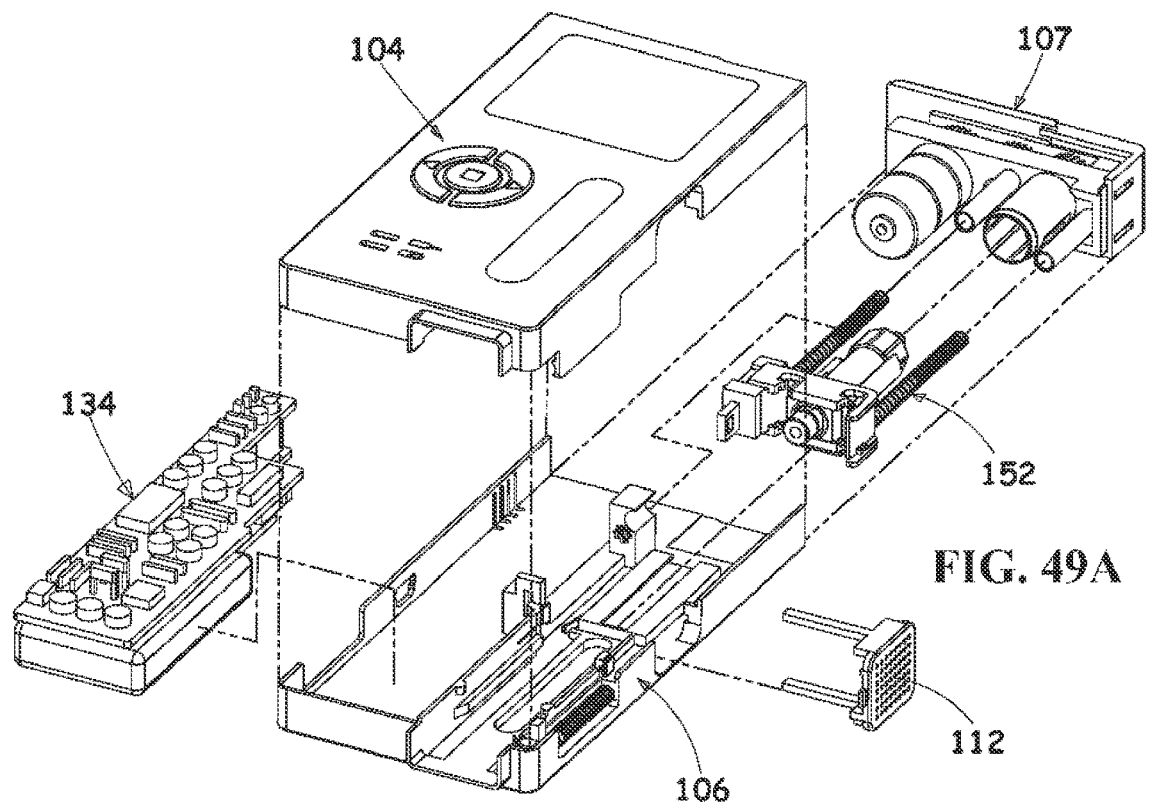
FIGS. 49A and 49B are simplified partially exploded view illustrations of the electronic automatic injection device of FIGS. 1A-2 taken from opposite sides.
Figure 49B:
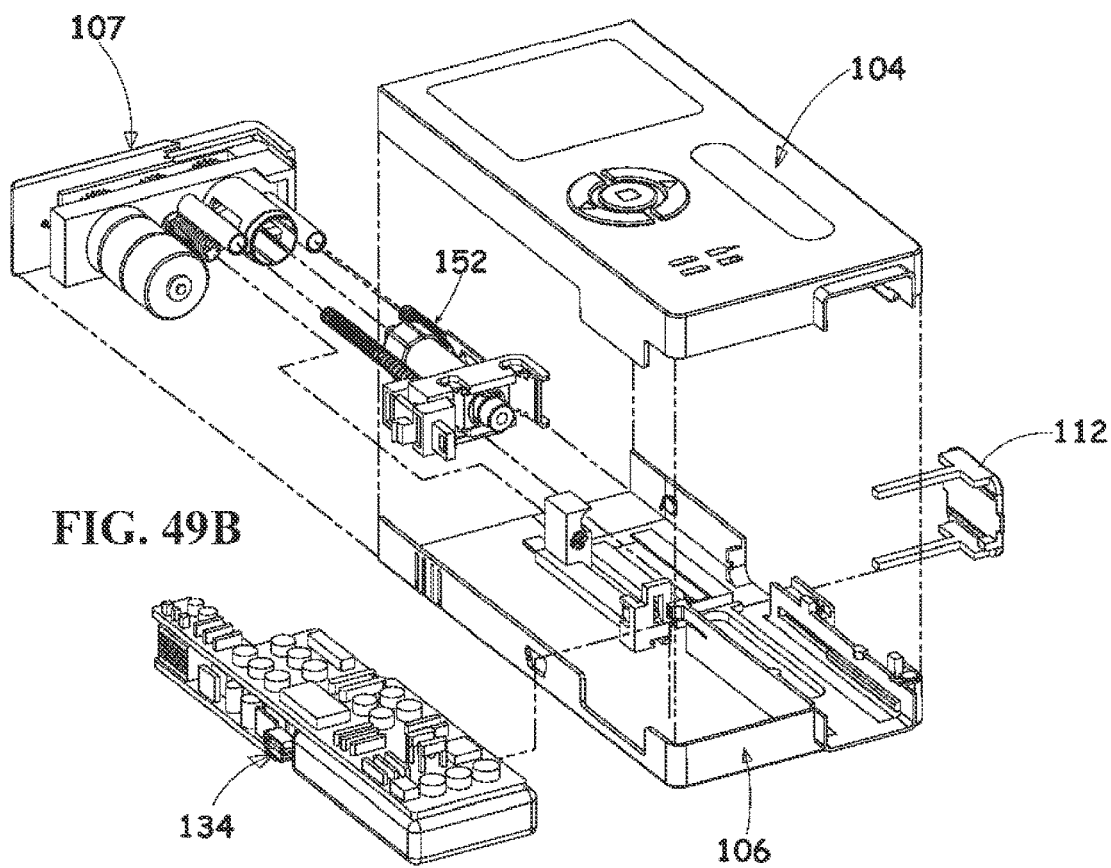

Reference is now made to FIGS. 49A and 49B, which are simplified partially exploded view illustrations of the electronic automatic injection device of FIGS. 1A-2 taken from opposite sides. FIGS. 49A & 49B show the mutual arrangement of upper housing assembly 104, the lower housing assembly 106 and the end housing assembly 107 as well as of multiple motion output subassembly 152, injection module release button 112 and the electronic control assembly 134.

Figure 50A:
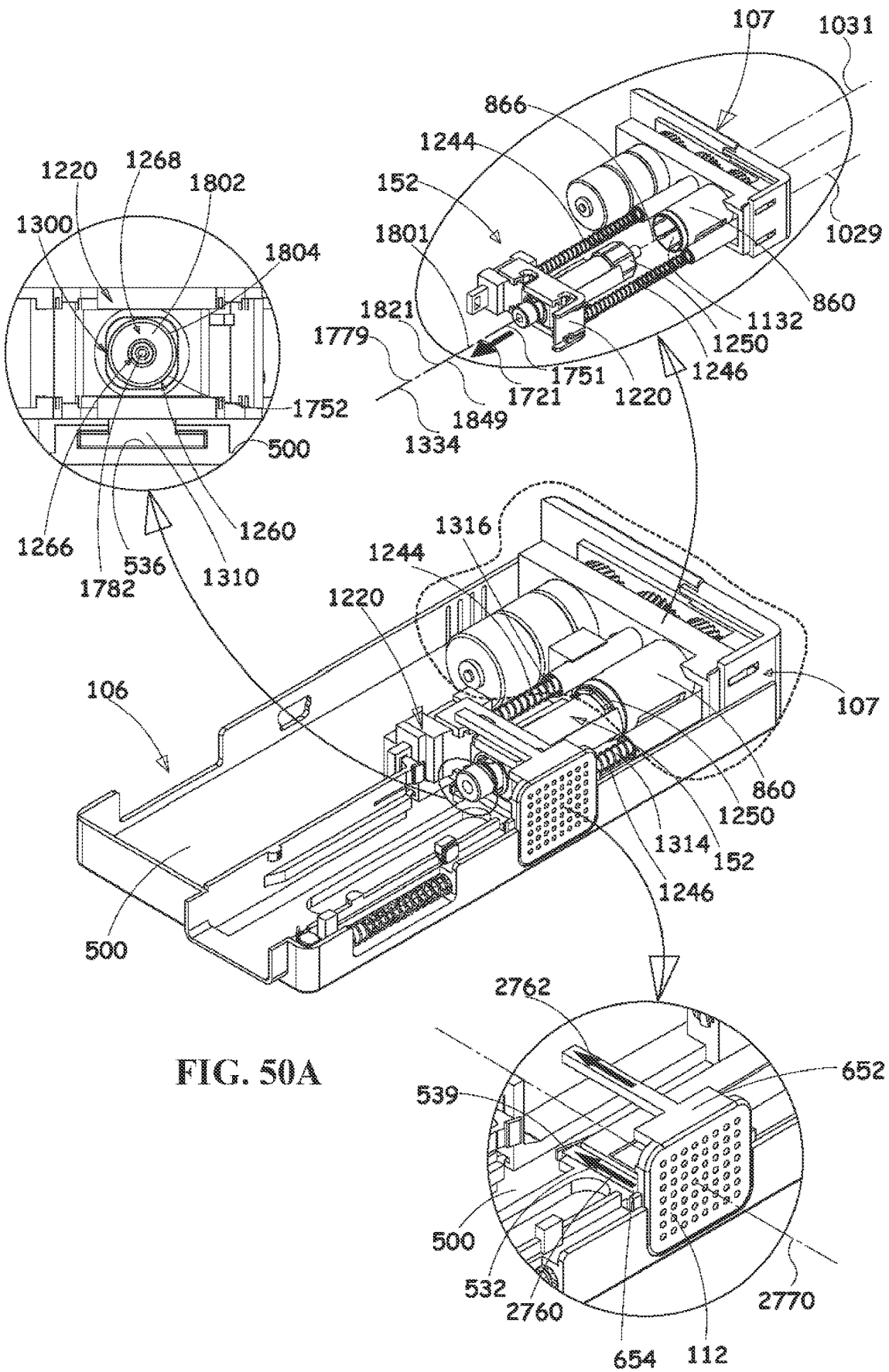
FIG. 50A is a simplified partially cut away illustration of the electronic automatic injection device of FIGS. 1A-2 seen from a first direction and showing in various enlargements the mounting of the multiple motion output subassembly and the injection module release button.
Figure 50B:
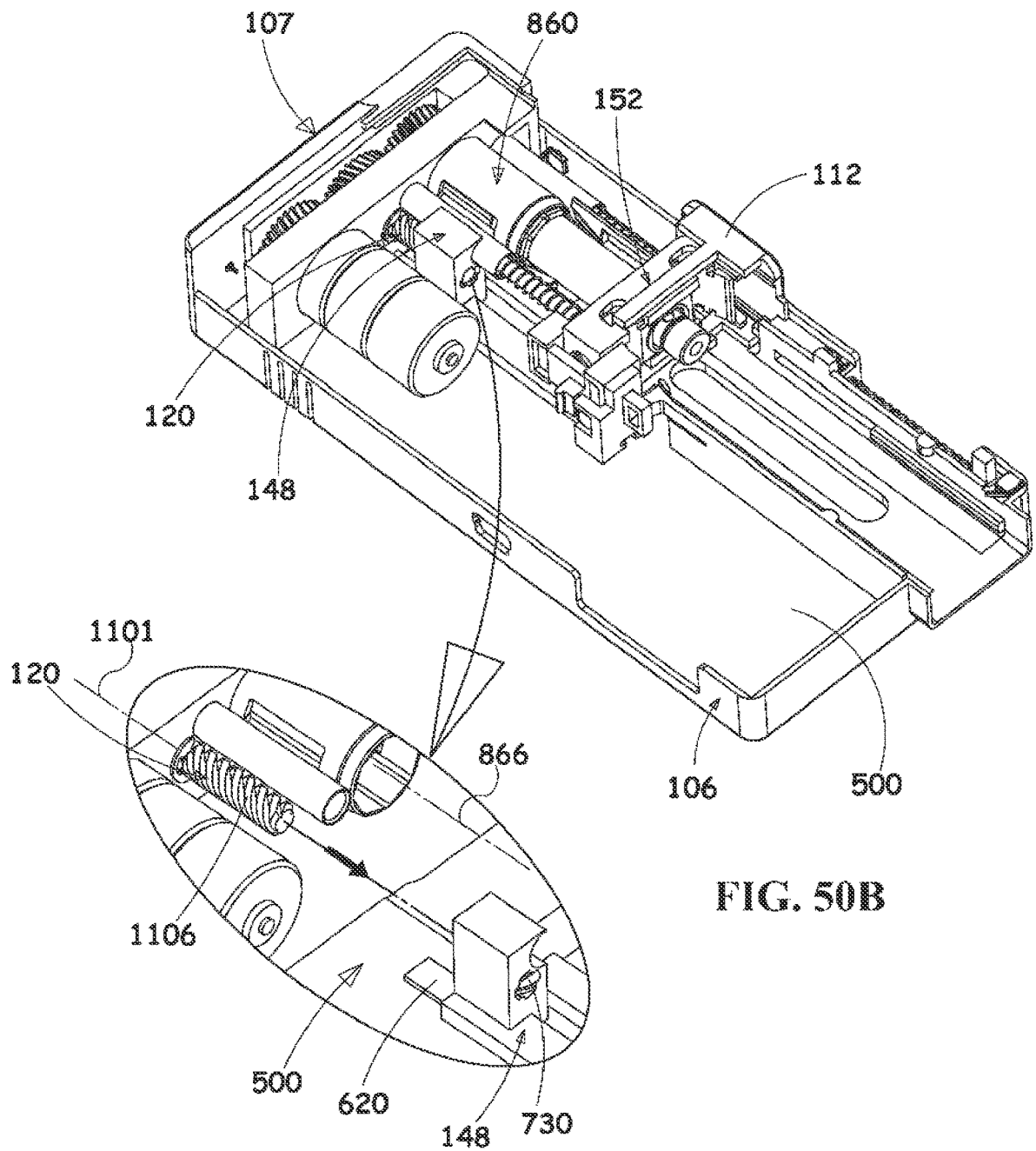
FIG. 50B is a simplified partially cut away illustration of the electronic automatic injection device of FIGS. 1A-2 seen from a second direction and showing in various enlargements the mounting of the injection depth selector travel track and locking of the injection module release button.

Reference is now made additionally to FIG. 50A, which is a simplified partially cut away illustration of the electronic automatic injection device of FIGS. 1A-2 seen from a first direction and showing in various enlargements the mounting of the multiple motion output subassembly 152 and the injection module release button and to FIG. 50B, which is a simplified partially cut away illustration of the electronic automatic injection device 100 of FIGS. 1A-2 seen from a second direction and showing in various enlargements the mounting of the injection depth selector travel track 148 and locking of the injection module release button 112.

It is noted that rearward driving screw 1250 is operatively seated in and drivingly engaged with throughgoing bore 1132 of multiple drive element 860 and that the mutual arrangement of the multiple motion output subassembly 152 and the end housing assembly 107 is such that axis 1334 of base element 1220 and axes 1721, 1751, 1779, 1801, 1821 and 1849 of elements of the rearward and forward plunger assemblies 1200 and 1210 all are coaxial with axis 866 of multiple drive element 860.

It is seen that compression springs 1244 and 1246 are seated over respective spring seating pins 1314 and 1316 which lie along respective axes 1029 and 1031.

It is specifically seen that bottom track following portion 1310 of base element 1220 of multiple motion output subassembly 152 slidingly engages parallel strip protrusion 536 of lower housing portion 500 of lower housing assembly 106, thereby permitting relative axial displacement of multiple motion output assembly 152 along axis 1334 relative to housing 102 (FIGS. 1A & 1B).

It is further seen that nut portion 1752 of intermediate screw 1260, nipple portion 1782 of forward driven element 1266, as well as forward facing surface 1802 and circular cylindrical surface 1804 of piston engaging element 1268 are all arranged symmetrically about axis 1334 are located within central wall portion 1300 of base element 1220.

It is additionally seen that T-shaped portions 652 and 654 are arranged for slidable engagement relative to the housing 102 along channel 532 formed in lower housing portion 500 for transverse displacement as indicated by an arrow 2760 and operative engagement with leaf spring 539. It is noted that T-shaped portion 652 is similarly arranged for slidable engagement relative to the housing 102 along channel 322 formed in upper housing portion 230 (FIG. 4D) for transverse displacement as indicated by an arrow 2762 and operative engagement with leaf spring 334 (FIGS. 3A & 3B). Arrows 2760 and 2762 extend parallel to a injection module release button travel axis 2770, which extends perpendicular to axis 866.

Referring specifically to FIG. 50B, it is seen that axis 1101 of threaded portion 1106 of injection depth selector 120 (FIG. 18) extends parallel to axis 866 and operatively engages threaded aperture 730 formed in injection depth selector travel track 148 (FIGS. 10A-10C), which in turn is slidably mounted on needle penetration depth adjusting element travel track 620 formed on lower housing portion 500.

Reference is now made to FIG. 50C, which is a simplified partially cut away illustration of the electronic automatic injection device of FIGS. 1A-2 seen from the first direction and showing in various enlargements the mounting of the electronic control assembly 134 and four microswitches and to FIG. 50D, which is a simplified partially cut away illustration of the electronic automatic injection device 100 of FIGS. 1A-2 seen from the second direction and showing in various enlargements the mounting of two additional microswitches.

As seen in FIGS. 50C & 50D, a microswitch 2800 is mounted on electronic control assembly 134 and indicates whether or not the multiple motion output subassembly 152 is in a fully retracted position.

A microswitch 2810 is mounted on microswitch support surface 1485 of base element 1220 and indicates whether or not an injection module 132 is fully inserted and locked with respect to multiple motion output subassembly 152.

A microswitch 2820 is mounted on outwardly facing surface 600 of lower housing portion 500 and indicates whether or not injection module 132 is its second operative orientation as shown in FIGS. 43C and 43D.

A microswitch 2830 is mounted on surface 601 of lower housing portion 500 and indicates whether or not RNS remover 108 engaged with the needle shield 147 (FIGS. 40A-40D).

A microswitch 2840 is mounted on side portion 508 of lower housing portion 500 and indicates whether or not injection actuation button 116 has been actuated.

A microswitch 2850 is mounted on corner cut out 726 of injection depth selector travel track 148 and indicates whether or not the multiple motion output subassembly 152 is in a fully extended position.

Reference is now made to FIGS. 51A & 51B, which are illustrations of the electronic automatic injection device of FIGS. 1A-2 in respective open and closed operative states. It is seen that when upper and lower housing assemblies 104 and 106 are assembled together with end housing assembly 107 T-shaped portion 652 is arranged for slidable engagement relative to the housing 102 along channel 322 formed in upper housing portion 230 (FIG. 4D) for transverse displacement as indicated by an arrow 2762 and operative engagement with leaf spring 334 (FIGS. 3A & 3B).

It is also seen that inner facing groove 378 of upper housing portion 230 (FIG. 4E) is engaged by a side of spring 812 (FIG. 12A).

The mutual arrangement of nut portion 1752 of intermediate screw 1260, nipple portion 1782 of forward driven element 1266, forward facing surface 1802 and circular cylindrical surface 1804 of piston engaging element 1268, which are all arranged symmetrically about axis 1334 and located within central wall portion 1300 of base element 1220, together with upper biasing assembly 144 (FIG. 2), lower biasing assembly 146 (FIG. 2) and injection module travel track protrusion 360, formed on upper housing portion 230 and injection module travel track protrusion 562, formed on lower housing portion 500.

Reference is now made to FIGS. 52A, 52B, 52C, 52D, 52E & 52F, which are simplified illustrations of the electronic automatic injection device of FIGS. 1A-51B employing a prefilled syringe injection module in a first illustrative operative state, which is a typical "out of the box" state. The first illustrative operative state is shown ex factory and prior to selection of injection depth by a physician or pharmacist and prior to presentation of the device to the user.

In the illustrated first illustrative operative state:
The multiple motion output subassembly 152 is in a fully extended operative orientation as shown in FIGS. 50A-50D, as indicated by the following:

Microswitch 2850 is in a closed state, resulting from engagement with microswitch engagement surface 1719 of protrusion 1712 of spring seat 1242.
Microswitch 2800 is in an open state because it is not engaged by microswitch engagement surface 1718 of spring seat 1242.
Engagement tooth portions 1360 are out of engagement with respective windows 1122 and 1124 in multiple drive element 860.
Octagonal cylindrical portion 1724 of rearward driving screw 1250 lies somewhat forwardly along axis 866 of inwardly tapered outer surface 1120 of multiple drive element 860.
Compression springs 1244 and 1246 are preloaded but not fully compressed.
Axis 1525 of locking element 1230 is coaxial with axis 2770 of injection module release button 112.
Central wall portion 1300 is forwardly spaced along axis 1334 from inwardly tapered outer surface 1120 of multiple drive element 860 by a first distance, indicated by A in FIG. 52A.

Rearward and forward plunger assemblies 1200 and 1210 are fully retracted.

Locking element 1230 lies adjacent injection module release button 112, as indicated by the following:
Edge surfaces 1546 and 1548 of locking element 1230 are spaced from side-facing surface 1480 of base element 1220.

Injection actuation button 116 has not yet been actuated as indicated by the following:
Microswitch 2840 is in an open state because it is not engaged by forward edge surface 1057 of injection actuation button 116.

Biasing assemblies 144 and 146 of the upper and lower housing assemblies 104 and 106 respectively are preloaded but not fully compressed as indicated by the following:
Forward-facing surface 792 of biasing element 768 abuts rearward-facing surface 608 of forward element 605 of lower housing portion 500.
Forward-facing surface 444 of biasing element 420 abuts rearward-facing surface 401 of spring enclosure 386 of upper housing portion 230.

No injection module 130 is engaged, as indicated, inter alia, by the following:
Microswitch 2810 is in an open state because it is not engaged.
Microswitch 2820 is in an open state because it is not engaged by rearwardly-facing surface 782 of biasing element 768.
Microswitch 2830 is in an open state because it is not engaged.
Flexible tab 570 of lower housing portion 500 is disposed at an initial released state. This is relevant for a case where a needleless cartridge injection module is employed.

Figure 53A:
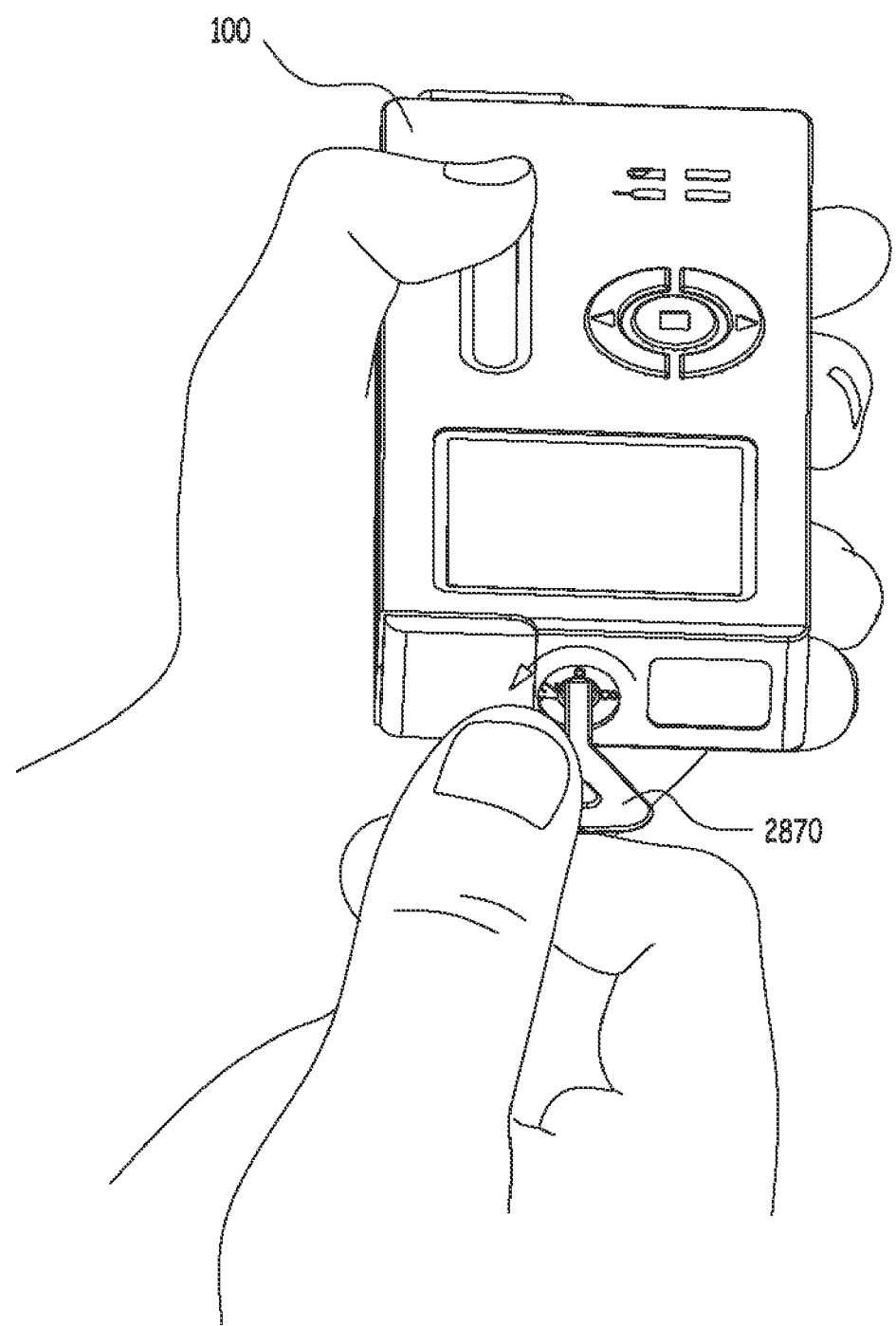
FIGS. 53A, 53B & 53C are simplified illustrations of the electronic automatic injection device of FIGS. 1A-51B in a second illustrative operative state, which is a typical injection depth adjustment state.
Figure 53B:
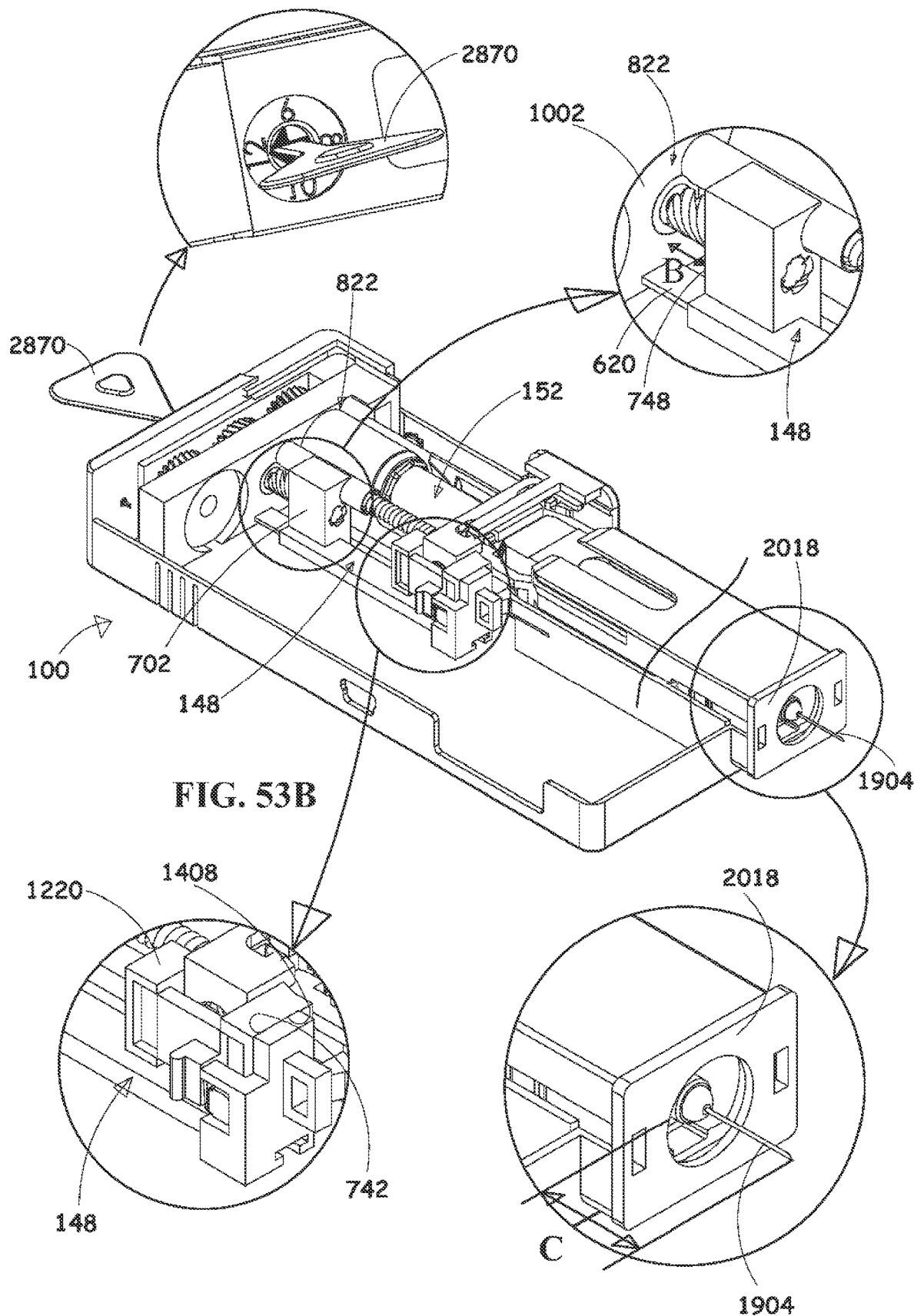
Figure 53C:
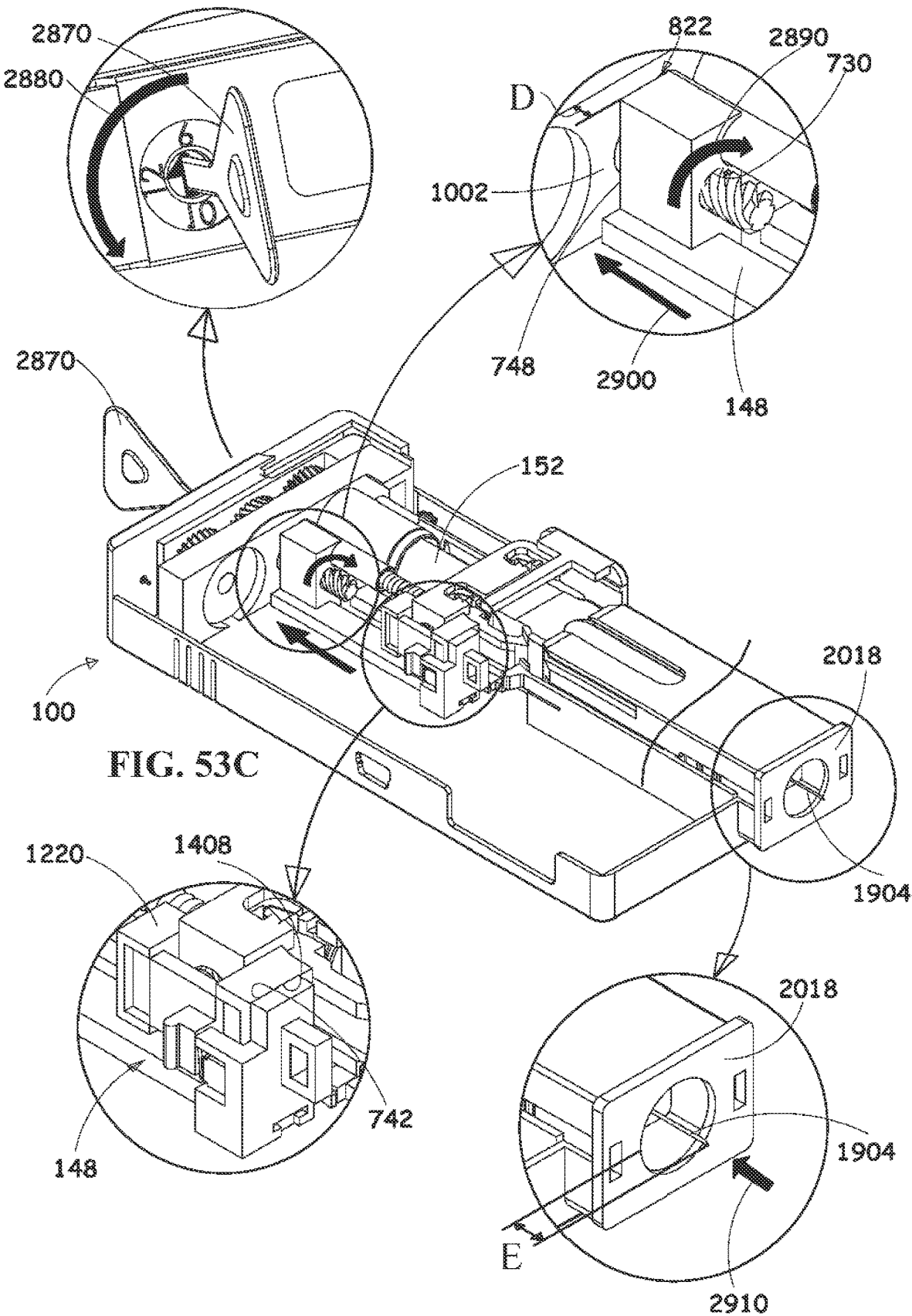

Reference is now made to FIGS. 53A, 53B & 53C, which are simplified illustrations of the electronic automatic injection device of FIGS. 1A-51B employing a prefilled syringe injection module in a second illustrative operative state, which is a typical "injection depth setting" state. The electronic automatic injection device of FIGS. 1A-51B in the second illustrative operative state is shown in the hands of a physician or pharmacist who is selecting an appropriate injection depth prior to presentation of the device to the user.

In this second illustrative operative state, prefilled syringe injection module 140 is not inserted into the electronic automatic injection device 100 and is shown in FIGS. 53A-53C for illustrative purposes only in order to indicate the position of the needle 1904.

In the illustrated second illustrative operative state, as compared with the first illustrative operative state:

The electronic automatic injection device 100 of FIGS. 1A-51B is initially set at a maximum injection depth, indicated by the numeral "12" as seen in FIGS. 53A & 53B. At this setting, injection depth selector travel track 148 is in a fully forwardly extended position, as indicated by the following:

Rearward facing surface 748 of injection depth selector travel track 148 is forwardly spaced from forward facing surface 1002 of forward support portion 822 by a distance "B" in FIG. 53B.

It is noted that in the fully forwardly extended position of the injection depth selector travel track 148, the multiple motion output subassembly 152 is positioned in the fully extended operative orientation and rearward facing surface 742 of injection depth selector travel track 148 lies against forward facing wall 1408 of base element 1220.

When the injection depth selector travel track 148 is in the fully forwardly extended position, the needle 1904 of PFS 140 is in a maximum exposure position, as indicated by distance "C" between the patient engagement plate 2018 of the needle shield 147 and the forward end of the needle 1904, as seen in FIG. 53B.

The electronic automatic injection device of FIGS. 1A-51B is subsequently set to a typical desired injection depth, here indicated by the numeral "6" as seen in FIG. 53C, as distinguished from the setting described above with respect to FIGS. 53A and 53B.

This subsequent setting is achieved by insertion of a key 2870 into operative engagement with injection depth selector 120 and rotation of the key 2870 in a direction indicated by arrow 2880. The rotation of key 2870 causes injection depth selector 120 to be threadably rotated within throughgoing threaded aperture 730 of injection depth selector travel track 148 in a direction indicated by an arrow 2890, producing axial rearward movement of injection depth selector travel track 148 in a direction indicated by an arrow 2900, such that injection depth selector travel track 148 assumes a fully retracted position, as indicated by the following:

As seen in FIG. 53C, rearward facing surface 748 of injection depth selector travel track 148 is spaced from forward facing surface 1002 of forward support portion 822, by a distance "D" which is less than distance B.

It is seen in an enlargement in FIG. 53C that in the fully retracted position of the injection depth selector travel track 148, the multiple motion output subassembly 152 is prevented from reaching its fully extended operative orientation by engagement of rearward facing surface 742 of injection depth selector travel track 148 with forward facing wall 1408 of base element 1220.

In the fully retracted position of the injection depth selector travel track 148, the needle 1904 of PFS 140 is axially displaced rearwardly in a direction indicated by an arrow 2910 to assume a minimal exposure position, as indicated by a distance "E" between the patient engagement plate 2018 of the needle shield 147 and the forward end of needle 1904. Distance E is less than distance C.

Figure 56:
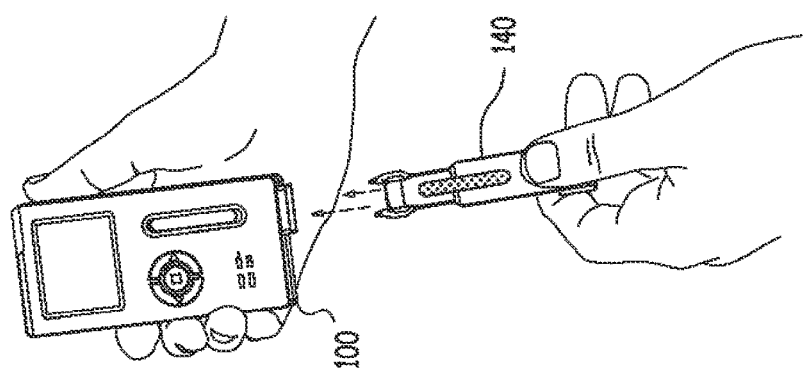
FIGS. 54, 55 and 56 are simplified pictorial illustrations of intermediate operational stages in the use of an embodiment of the electronic automatic injection device employing a prefilled syringe injection module.
Figure 55:
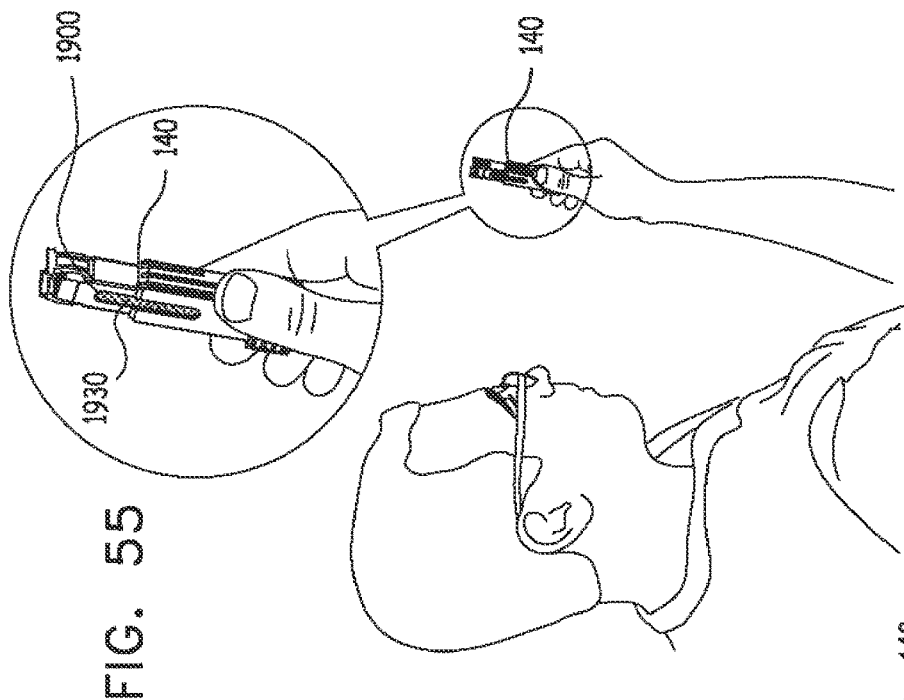
Figure 54:
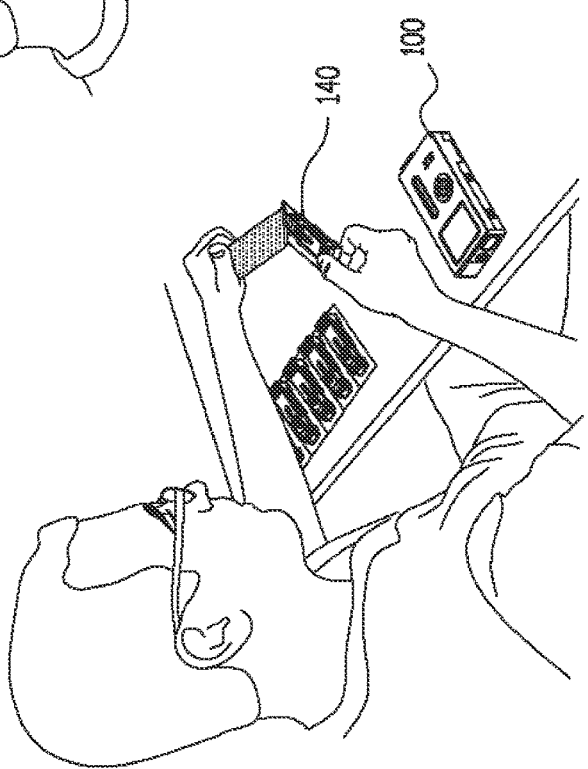

Reference is now made to FIGS. 54-56, which are simplified illustrations of the electronic automatic injection device of FIGS. 1A-51B employing a prefilled syringe injection module when it is ready to use, prior to insertion of the prefilled syringe injection module 140 into the electronic automatic injection device 100. The electronic automatic injection device 100 is shown in FIG. 54 on a table in front of a user, who is in the process of opening the package of one of the prefilled syringe injection modules.

FIG. 55 shows the prefilled syringe injection module 140 in the hands of a user who is in the process of inspecting the medication through window recess 1930 in the mounting element 1900. FIG. 56 shows the user about to insert the prefilled syringe injection module 140 into operative engagement with the electronic automatic injection device 100.

Figure 57A:
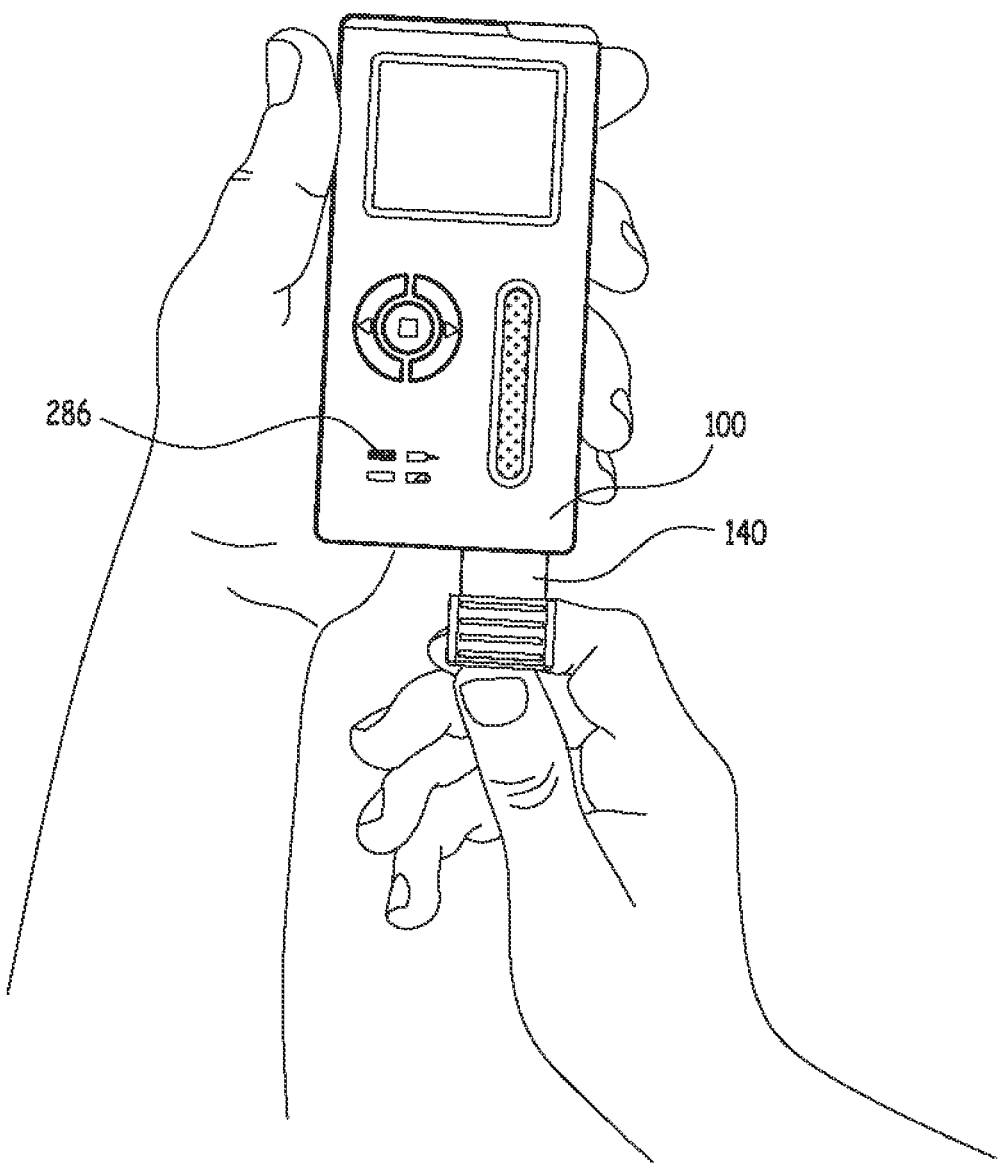

Reference is now made to FIGS. 57A, 57B, 57C & 57D, which are simplified illustrations of the electronic automatic injection device of FIGS. 1A-51B employing a prefilled syringe injection module in a third illustrative operative state, which is a typical "prefilled syringe injection module partial insertion" state. FIG. 57A shows a user who is in the process of inserting a prefilled syringe injection module into the electronic automatic injection device of FIGS. 1A-51B.

Figure 57C:
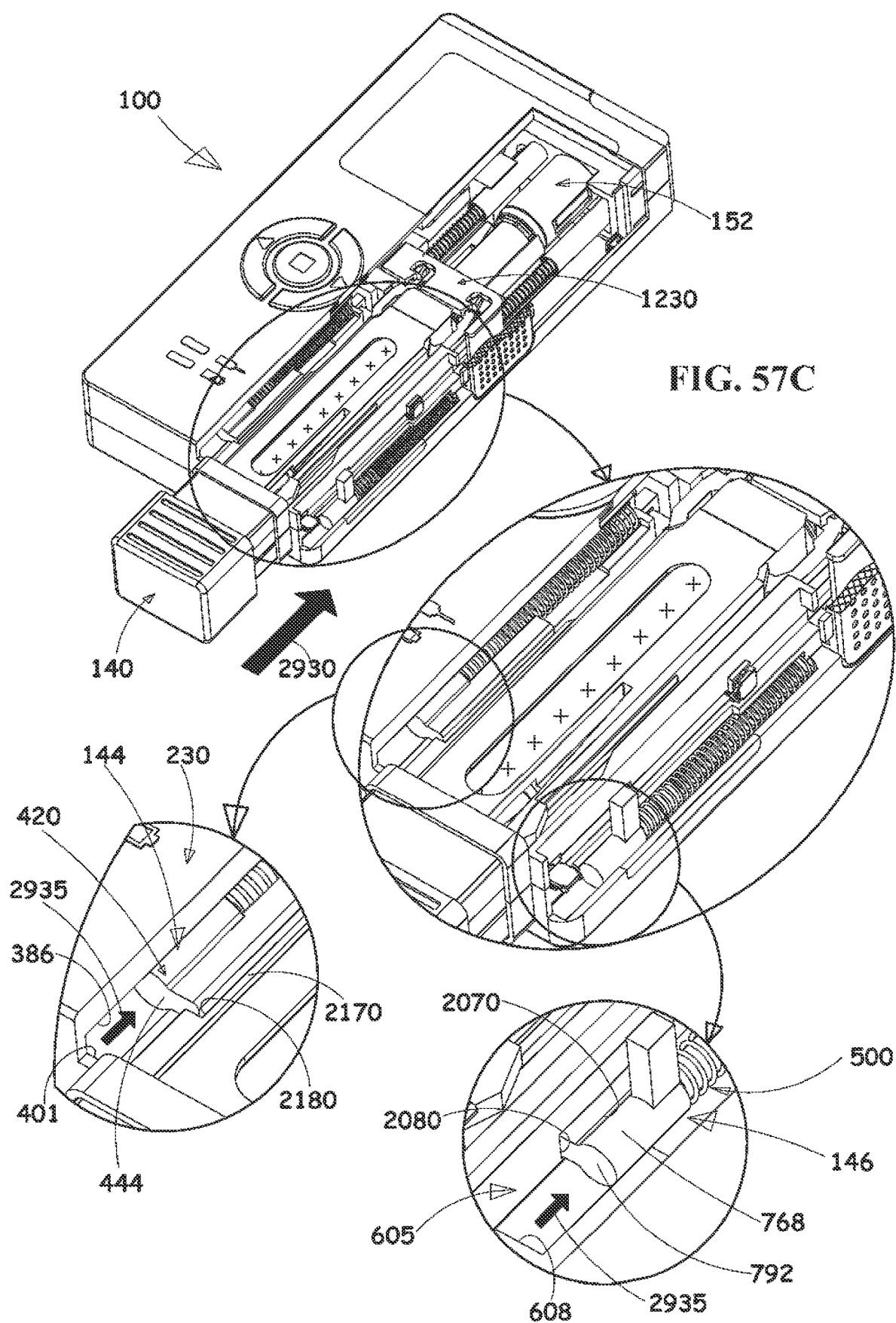
Figure 57D:
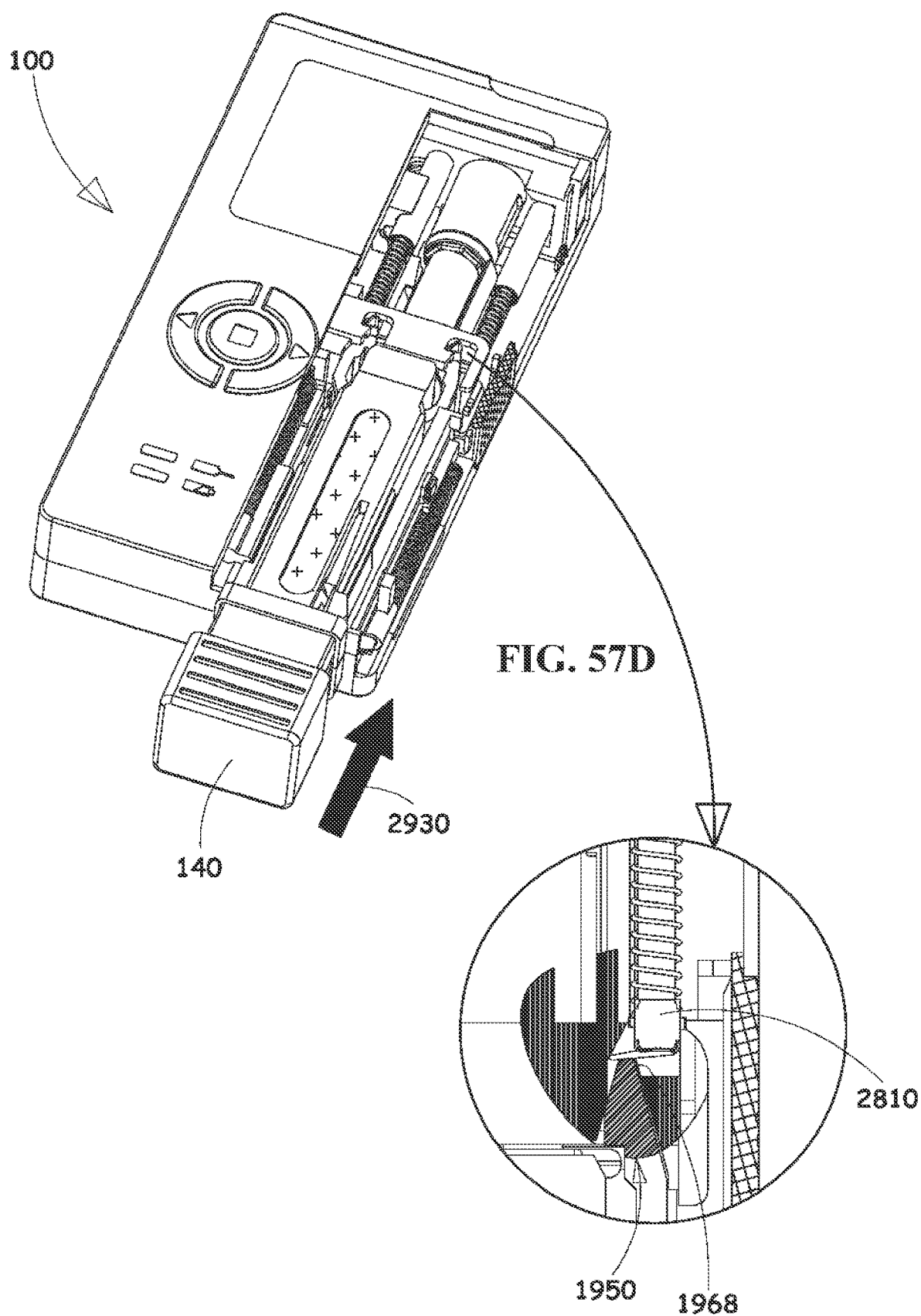

FIGS. 57B-57D show the electronic automatic injection device 100 of FIGS. 1A-51B following partial insertion therein of the prefilled syringe injection module 140. In this third state, as compared with the second operative state described above with respect to FIGS. 53A-53C:

The multiple motion output subassembly 152 remains in a fully extended operative orientation as shown in FIGS. 50A-50D.

Axis 1525 of locking element 1230 remains coaxial with axis 2770 of injection module release button 112.

Rearward and forward plunger assemblies 1200 and 1210 remain fully retracted.

Locking element 1230 now lies adjacent injection module release button 112 following sequential movement of the locking element 1230 first in a direction indicated by arrow 2910 and thereafter in a direction indicated by arrow 2920.

Displacement of the locking element 1230 along axis 1525 in the direction of arrow 2910 is caused by insertion of prefilled syringe injection module 140 into the automatic electronic injection device 100 as indicated by the following:

Engagement of inclined edge surface 1572 and inclined edge surface 1672 of locking element 1230 with rearwardly facing end tapered surface 1968 of arm 1950 of mounting element 1900 and engagement of inclined edge surface 1582 and inclined edge surface 1682 of locking element 1230 against rearwardly facing end tapered surface 1968 of arm 1952 of the mounting element 1900 against the force of the spring 1240.

Displacement of the locking element 1230 along axis 1525 in the direction of arrow 2920 is produced by urging of spring 1240 and resulting locking of the injection module 140 to the locking element 1230, as indicated by the following:

Engagement of forward facing shoulder surface 1988 of arm 1950 of mounting element 1900 with shoulder edge surface 1575 of locking element 1230 and engagement of forward facing shoulder surface 1990 of arm 1950 with shoulder edge surface 1675 of locking element 1230.

Engagement of forward facing shoulder surface 1988 of arm 1952 of mounting element 1900 with shoulder edge surface 1585 of locking element 1230 and engagement of forward facing shoulder surface 1990 of arm 1952 with shoulder edge surface 1685 of locking element 1230.

Needle shield 147 is rearwardly axially displaced in a direction indicated by an arrow 2930 against the force of the springs 462 and 812 of biasing assemblies 144 and 146 respectively, causing the biasing assemblies 144 and 146 of the upper and lower housing assemblies 104 and 106 respectively to be displaced rearwardly axially in a direction indicated by arrow 2935 and partially compressed, as indicated by the following:

Engagement between rearward facing forward end wall surface 2080 of recess 2070 of needle shield 147 and forward facing surface 792 of biasing element 768 and rearward facing forward end wall surface 2180 of recess 2170 engages forward facing surface 444 of biasing element 420.

Rearward movement of the needle shield 147 causes the following:

Forward-facing surface 792 of biasing element 786 becomes slightly rearwardly spaced from rearward-facing surface 608 of forward element 605 of lower housing portion 500.

Forward-facing surface 444 of biasing element 420 becomes slightly rearwardly spaced from rearward-facing surface 401 of spring enclosure 386 of upper housing portion 230.

Locking of prefilled syringe injection module 140 to locking element 1230 is as indicated inter alia by the following:

Microswitch 2810 is closed by engagement with rearwardly facing end tapered portion 1968 of arm 1950.

Microswitch 2820 remains in an open state because it is not engaged by rearwardly-facing surface 782 of biasing element 786.

Microswitch 2830 remains in an open state because it is not engaged.

Reference is now made to FIGS. 58A, 58B, 58C & 58D, which are simplified illustrations of the electronic automatic injection device of FIGS. 1A-51B employing a prefilled syringe injection module in a fourth illustrative operative state, which is a typical "prefilled syringe injection module full insertion" state. The electronic automatic injection device of FIGS. 1A-51B in the fourth illustrative operative state is shown in the hands of a user who is fully inserting a prefilled syringe injection module into the electronic automatic injection device of FIGS. 1A-51B.

Figure 58A:
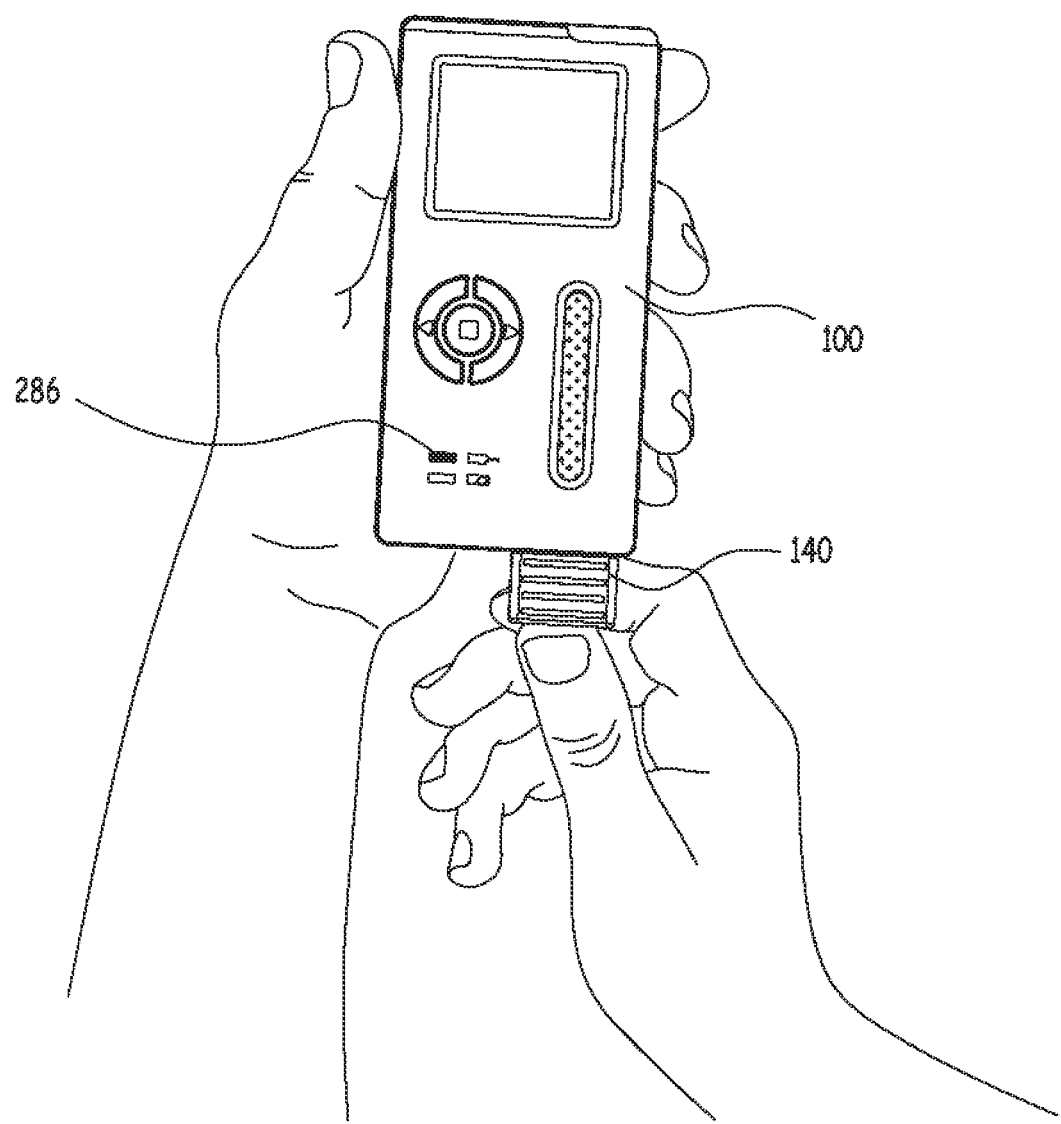

In FIG. 58A the user is seen fully inserting the prefilled syringe injection module into the electronic automatic injection device of FIGS. 1A-51B.

Figure 58B:
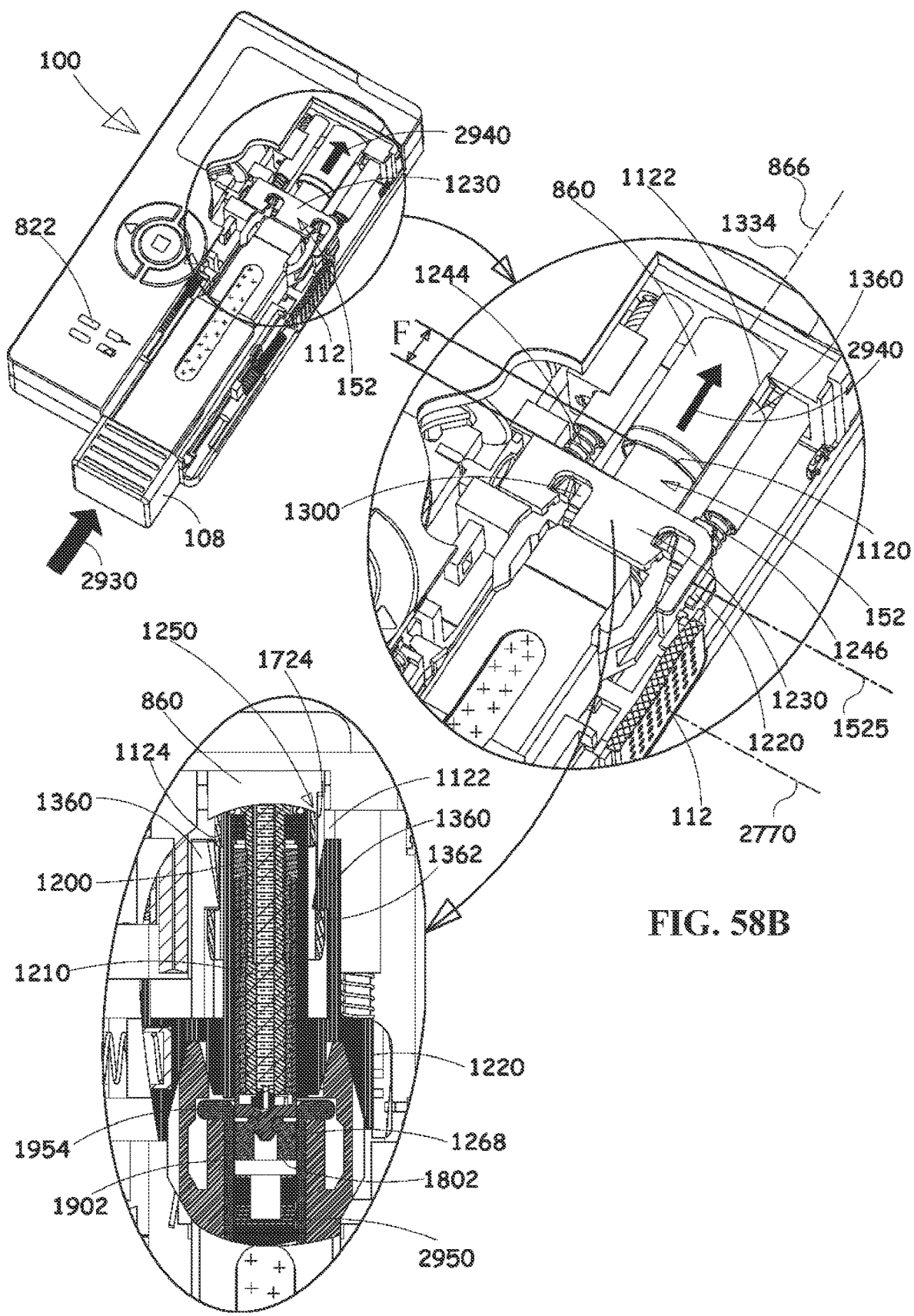
Figure 58C:
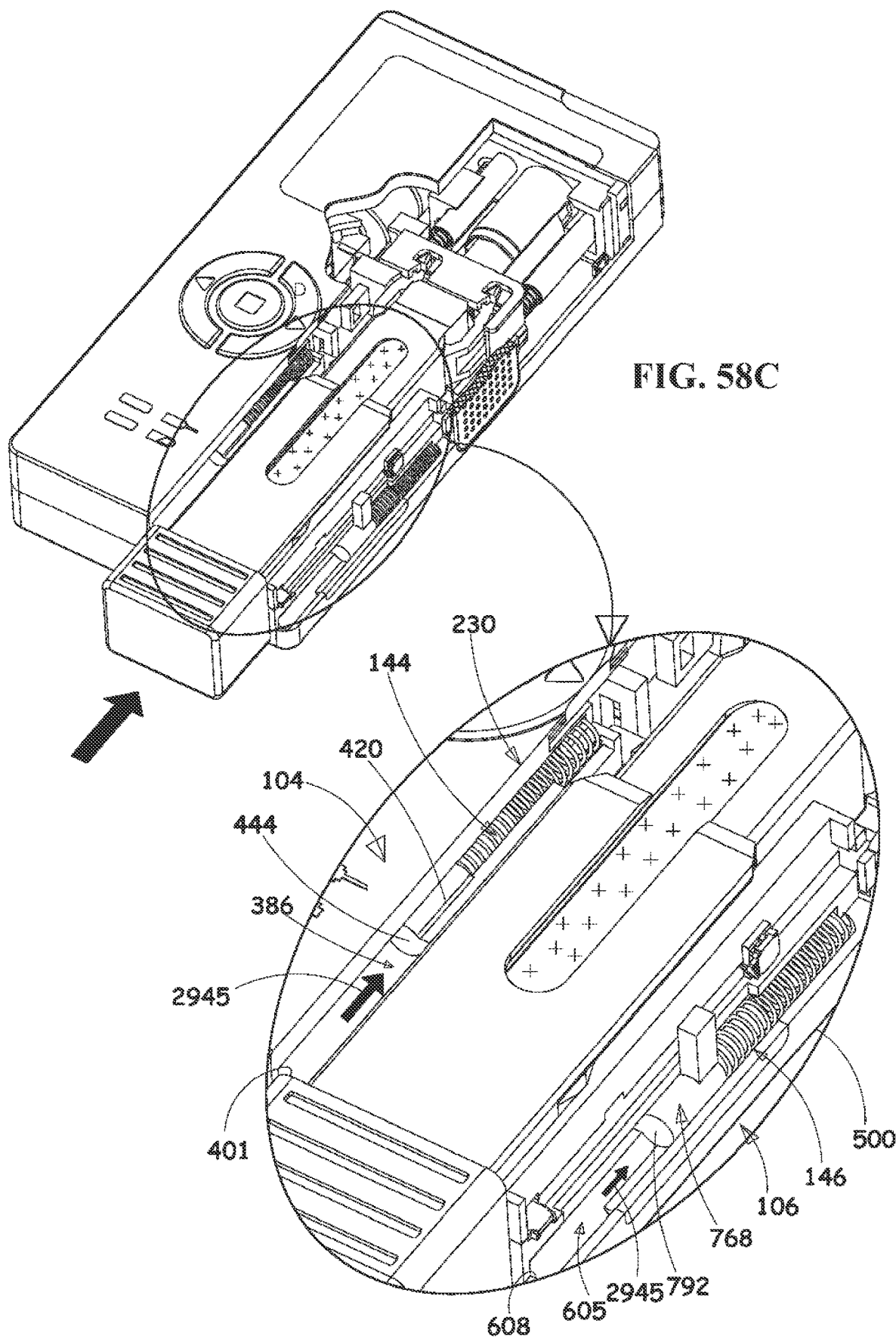

In FIGS. 58B-58D, the electronic automatic injection device of FIGS. 1A-51B is shown after the prefilled syringe injection module 140 has been fully inserted. In this operative state, as distinguished from the first state described above with respect to FIGS. 52A-52F and additionally with respect to the third state described above with respect to FIGS. 57A-57D:

The multiple motion output sub-assembly 152 is rearwardly displaced in a direction indicated by arrow 2940 and is positioned in a nearly fully retracted operative orientation, as indicated by the following:

Microswitch 2850 is in an open state as it is out of engagement with surface 1719 of protrusion 1712 of spring seat 1242;

Microswitch 2800 is in a closed state because it engages surface 1718 of spring seat 1242.

Tooth portions 1360 of base element 1220 are engaged with the forward ends of respective windows 1122 and 1124 in multiple drive element 860, specifically by engagement of radially inwardly facing inclined surface 1362 of engagement tooth portions 1360 with windows 1122 and 1124.

Octagonal cylindrical portion 1724 of rearward driving screw 1250 lies along axis 866 and fully within the multiple drive element 860.

Compression springs 1244 and 1246 are nearly fully compressed.

Axis 1525 of locking element 1230 lies axially rearwardly of injection module release button 112.

Central wall portion 1300 is forwardly spaced along axis 1334 from inwardly tapered outer surface 1120 of multiple drive element 860 by a distance "F" seen in FIG. 58B, which is substantially smaller than the corresponding distance "A" indicated in FIG. 52B.

Rearward and forward plunger assemblies 1200 and 1210 are fully retracted, as indicated by the following:

Forward facing surface 1802 of piston engaging element 1268 lies adjacent to and nearly touches a piston 2950 located near the flange 1954 of the prefilled syringe 1902.

Axis 1525 of locking element 1230 is spaced rearwardly from axis 2770 of injection module release button 112.

Injection actuation button 116 has not yet been actuated as indicated by the following:

Microswitch 2840 is in an open state because it is not engaged by forward edge surface 1057 of injection actuation button 116.

Biasing assemblies 144 and 146 of the upper and lower housing assemblies 104 and 106 respectively are further displaced rearwardly axially in a direction indicated by arrows 2945 and are further compressed as indicated by the following:

Forward-facing surface 792 of biasing element 786 is further rearwardly spaced from rearward-facing surface 608 of forward element 605 of lower housing portion 500.

Forward-facing surface 444 of biasing element 420 is slightly rearwardly spaced from rearward-facing surface 401 of spring enclosure 386 of upper housing portion 230.

Prefilled syringe injection module 140 is locked to the locking element 1230, as indicated inter alia by the following:

Microswitch 2810 is closed as indicated by engagement with rearwardly facing end tapered portion 1968 of arm 1952.

Microswitch 2820 is in an open state because it is not engaged by rearwardly-facing surface 782 of biasing element 786.

Microswitch 2830 is in a closed state because it is engaged by shaft 2330 of RNS remover 108.

Figure 59:
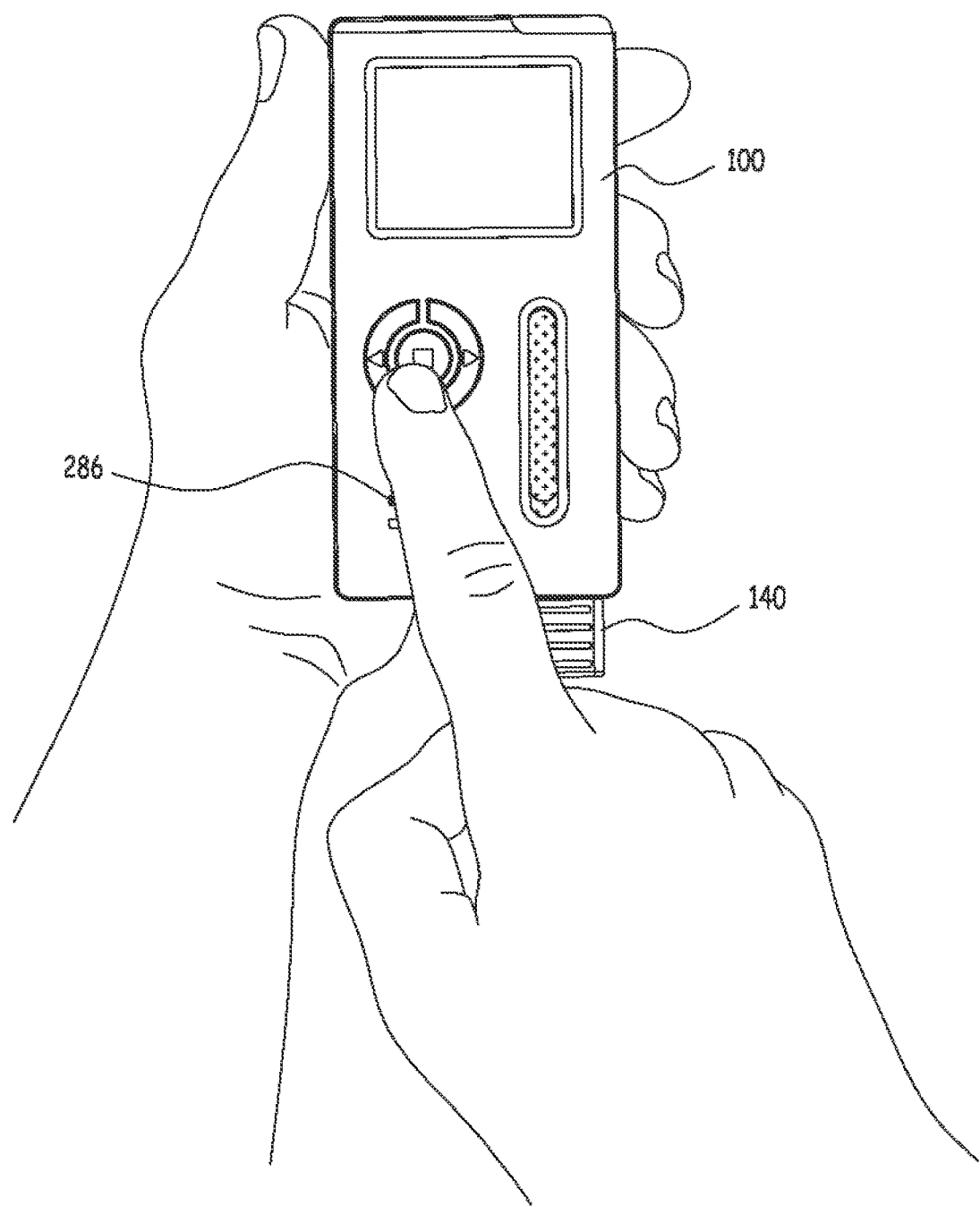
FIG. 59 is a simplified pictorial illustration of a data entry operation using an embodiment of the electronic automatic injection device employing a prefilled syringe injection module.

Reference is now made to FIG. 59, which is a simplified illustration of user data entry into the electronic automatic injection device of FIGS. 1A-51B with a pre-filled syringe. The various data entry functionalities of the system are described hereinbelow with reference to FIGS. 76A-76F.

Figure 60A:
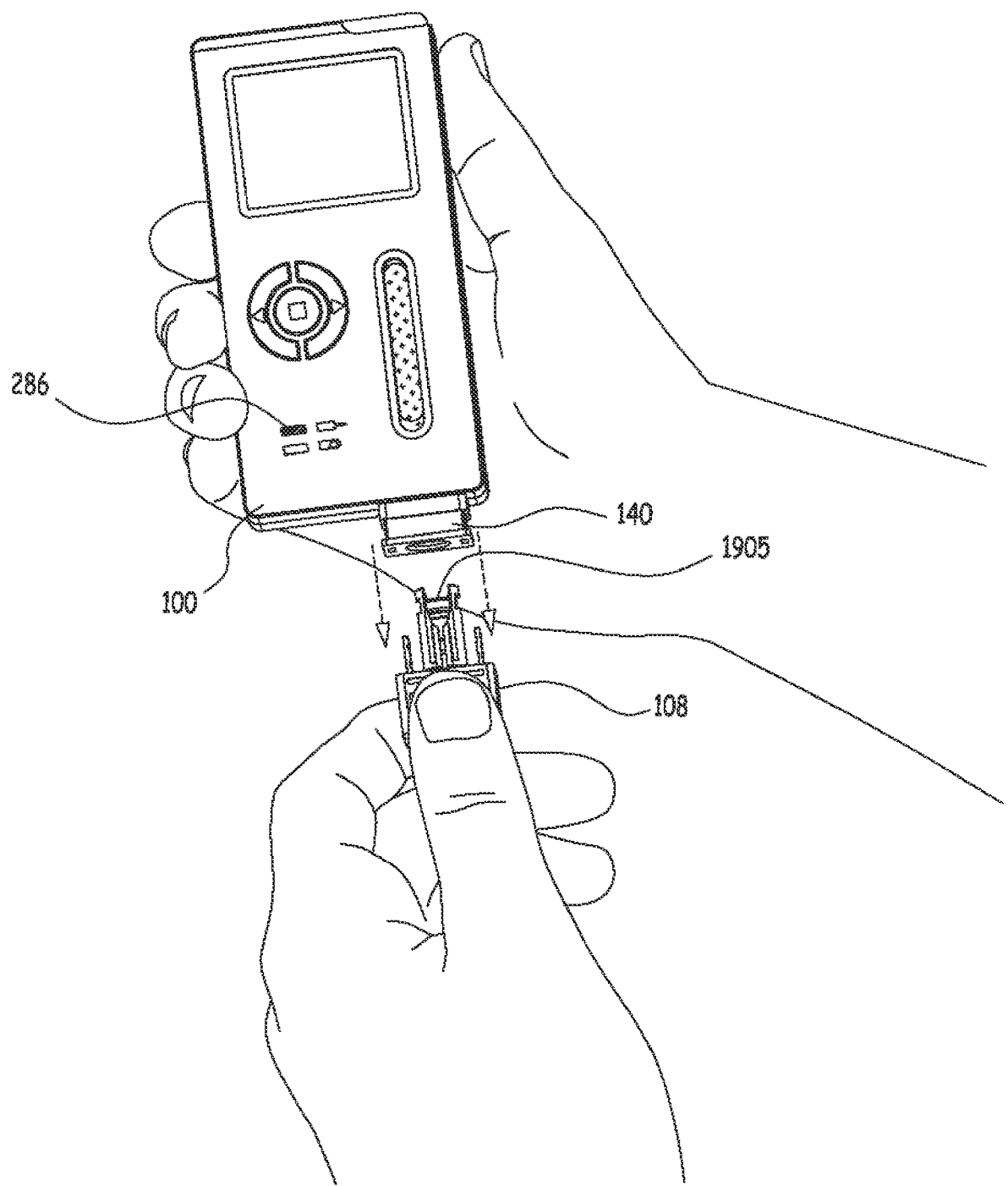
FIGS. 60A, 60B & 60C are simplified illustrations of the electronic automatic injection device employing a prefilled syringe injection module of FIGS. 1A-51B in a fifth illustrative operative state, which is a typical RNS removal state.
Figure 60B:
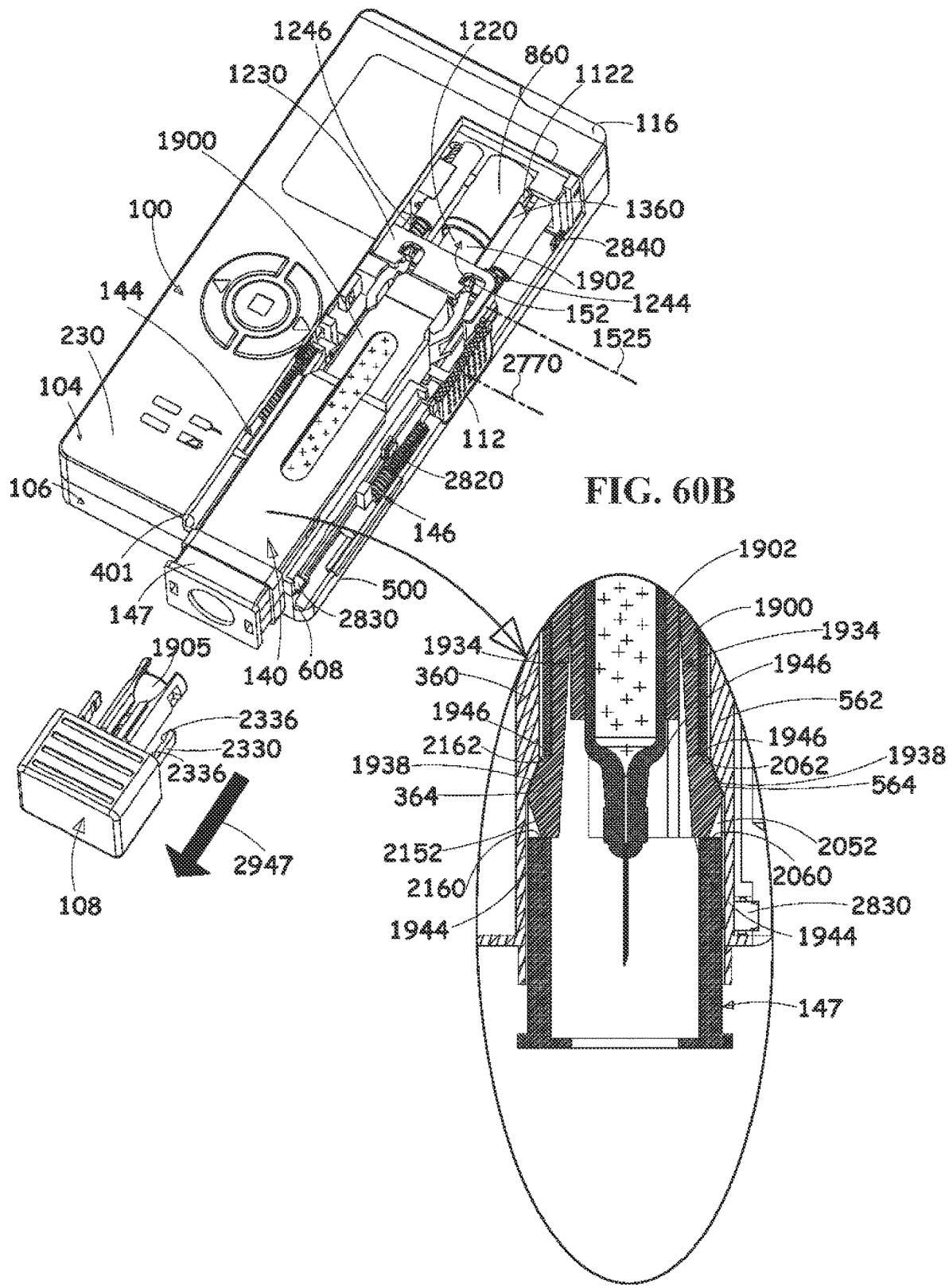
Figure 60C:
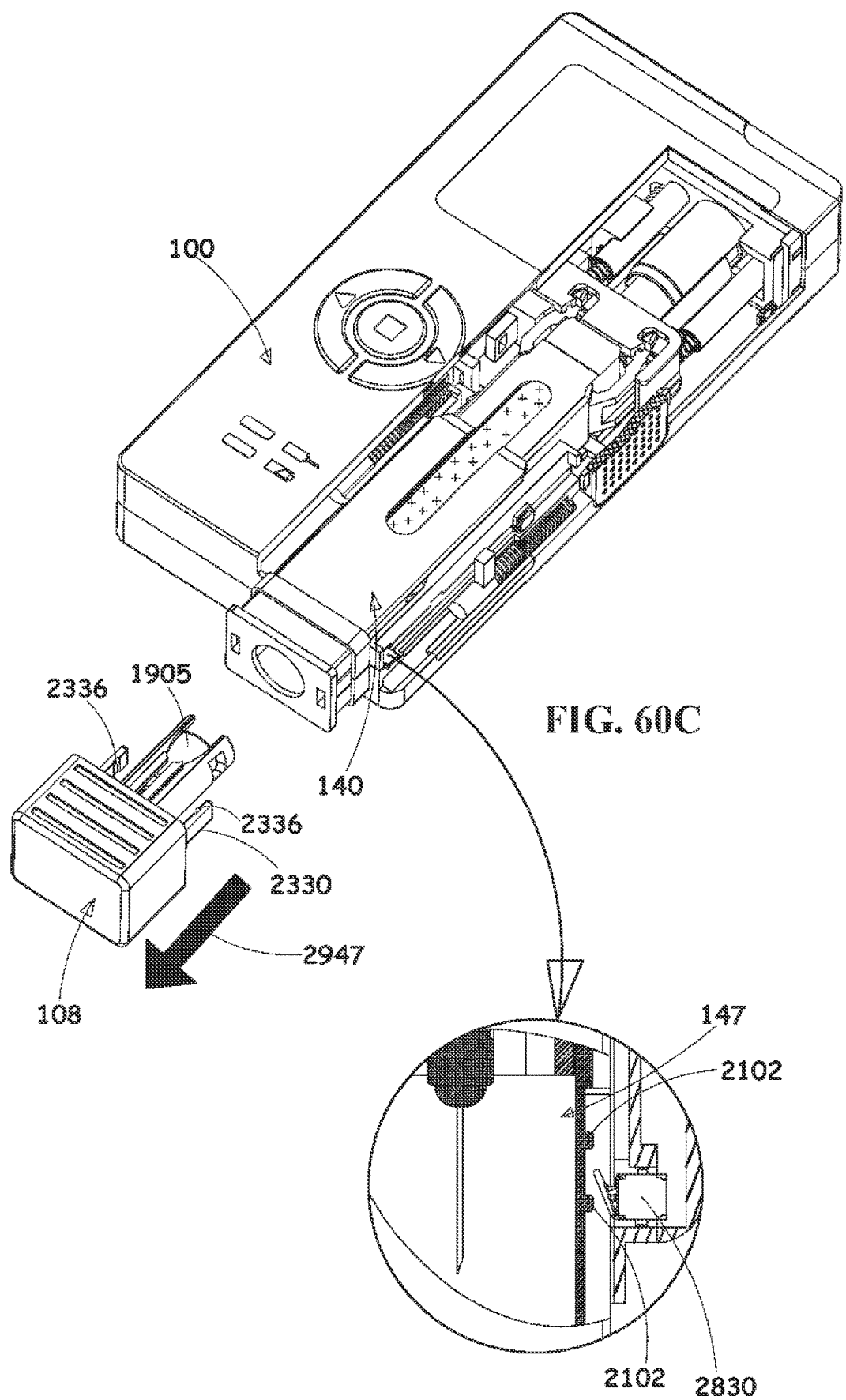

Reference is now made to FIGS. 60A-60C, which are simplified illustrations of the electronic automatic injection device of FIGS. 1A-51B employing a prefilled syringe injection module in a fifth illustrative operative state in which RNS 1905 and RNS remover 108 are together detached from the electronic automatic injection device 100.

FIG. 60A shows the user detaching the RNS remover 108 in a forward movement indicated by arrow 2947.

In this fifth illustrative operative state, as distinguished from the fourth illustrative operative state described above with respect to FIGS. 58A-58D and additionally with particular reference to FIGS. 42A-42D:

The multiple motion output sub-assembly 152 remains in a fully retracted operative orientation, as indicated by the following:

Engagement tooth portions 1360 of base element 1220 are engaged with the forward ends of respective windows 1122 and 1124 in multiple drive element 860.

Octagonal cylindrical portion 1724 of rearward driving screw 1250 lies along axis 866 and fully within the multiple drive element 860.

Compression springs 1244 and 1246 are nearly fully compressed.

Axis 1525 of locking element 1230 lies axially rearwardly of injection module release button 112 and parallel to axis 2770.

Central wall portion 1300 is forwardly spaced along axis 1334 from inwardly tapered outer surface 1120 of multiple drive element 860 by distance "F" seen in FIG. 58B.

Rearward and forward plunger assemblies 1200 and 1210 remain fully retracted.

Injection actuation button 116 has not yet been actuated as indicated by the following:

Microswitch 2840 is in an open state because it is not engaged by forward edge surface 1057 of injection actuation button 116.

Biasing assemblies 144 and 146 of the upper and lower housing assemblies 104 and 106 respectively are rearwardly spaced from surfaces 608 of lower housing portion 500 and 401 of upper housing portion 230 respectively.

Prefilled syringe injection module 140 remains locked to locking element 1230, as indicated inter alia by the following:

Microswitch 2810 is closed as indicated by engagement with rearwardly facing end tapered portion 1968 of arm 1952.

Microswitch 2820 remains in open state because it is not engaged by rearwardly-facing surface 782 of biasing element 786.

Microswitch 2830 is now in an open state because RNS remover 108 is forwardly displaced by the user in order to remove the RNS 1905 from the prefilled syringe 1902. As a result, microswitch 2830 is out of engagement with shaft 2330 of RNS remover 108, as indicated by disengagement of recesses 2336 of shafts 2330 from protrusions 2102 of the needle shield element 147 (FIG. 42C).

As seen in FIGS. 42A-42D, the prefilled syringe 1902 is securely retained within the mounting element 1900. Needle shield element 147 is axially retained in position relative to mounting element 1900 by engagement of flexible diagonally opposed needle shield engaging fingers 1934 of the mounting element 1900 in apertures 2152 and 2052, such that respective surfaces 1944 and 1946 of one of fingers 1934 engage corresponding respective surfaces 2060 and 2062 of aperture 2052 and respective surfaces 1944 and 1946 of the other of fingers 1934 engage corresponding respective surfaces 2160 and 2162 of aperture 2152.

It is further seen in FIG. 60B that in the fifth illustrative operative state, the rearward facing edge surface 1938 of one of the needle shield engaging fingers 1934 of mounting element 1900 lies against angled portion 364 of injection module travel track protrusion 360 of upper housing portion 230. Additionally, rearward facing edge surfaces 1938 of needle shield engaging fingers 1934 of mounting element 1900 lie against angled portions 564 of injection module travel track protrusion of 562 of lower housing portion 500.

Reference is now made to FIGS. 61A-61D, which are simplified illustrations of the electronic automatic injection device of FIGS. 1A-51B in a sixth illustrative operative state, in which the user pushes the needle shield 147 against the injection site.

Figure 61A:
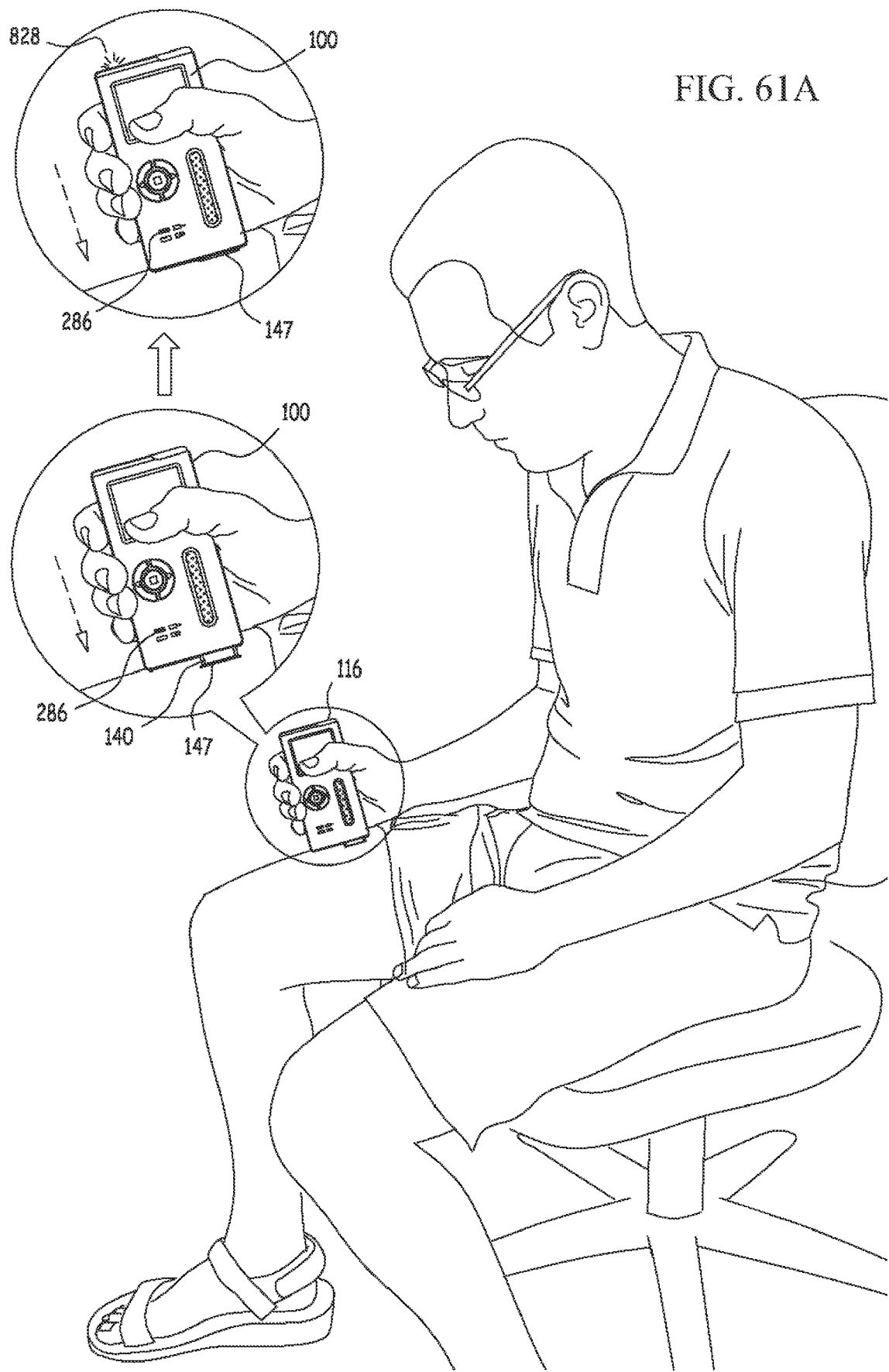
Figure 61B:
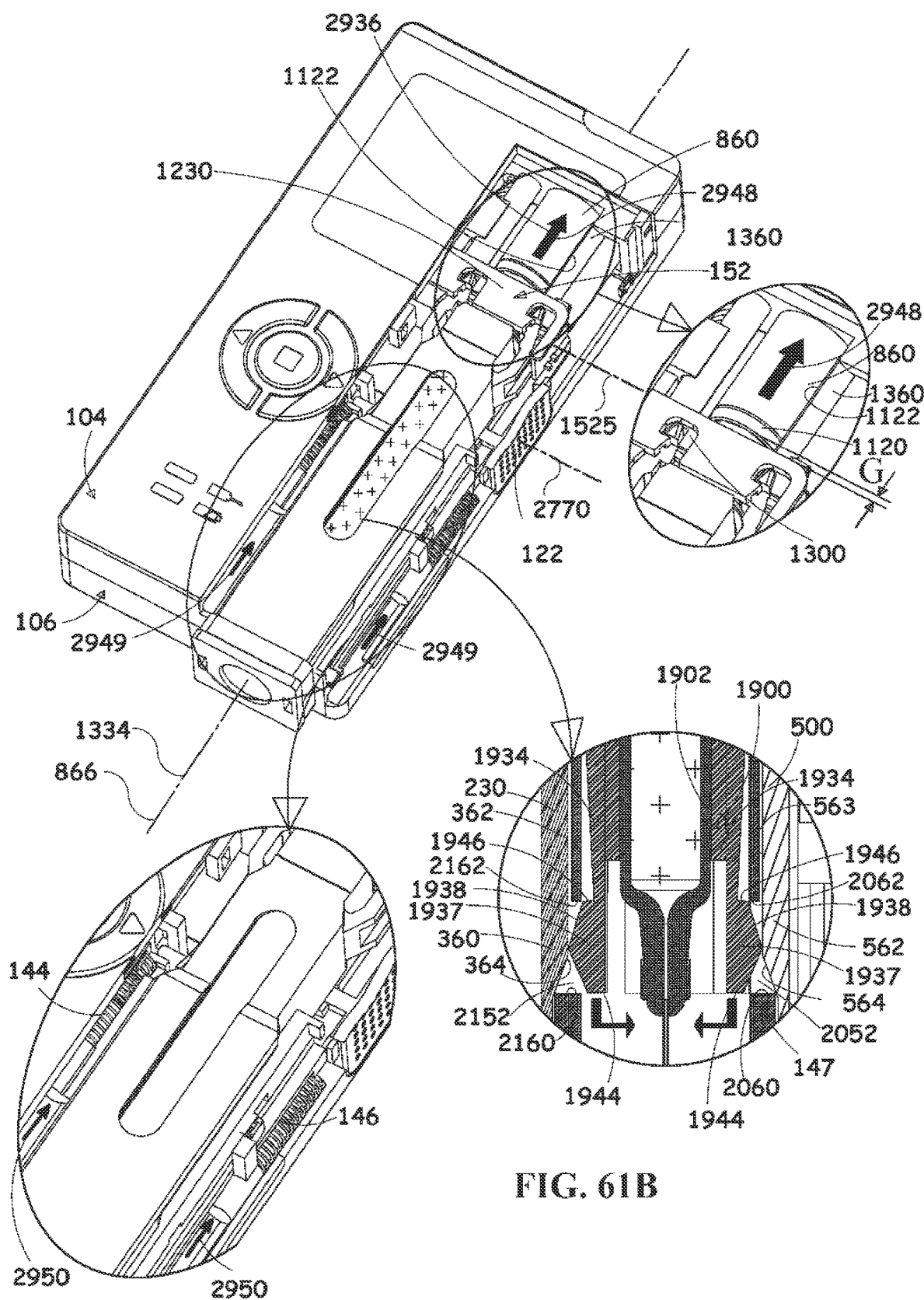

In this state, as distinguished from the fifth illustrative operative state described above with respect to FIGS. 60A-60C:

As seen in FIG. 61B, multiple motion output sub-assembly 152 is slightly further displaced rearwardly in a direction indicated by an arrow 2948 and assumes a fully retracted operative orientation, as indicated by the following:

Engagement tooth portions 1360 of base element 1220 are slightly displaced rearwardly to engage rearward ends of respective windows 1122 and 1124 of multiple drive element 860.

Octagonal cylindrical portion 1724 of rearward driving screw 1250 lies along axis 866 and fully within the multiple drive element 860.

Compression springs 1244 and 1246 are slightly rearwardly displaced and thus assume a fully compressed position.

Axis 1525 of locking element 1230 now lies axially rearwardly of injection module release button 112.

Central wall portion 1300 is now less forwardly spaced along axis 1334 from inwardly tapered outer surface 1120 of multiple drive element 860 by a third distance, "G". It is noted that distance "G" is substantially smaller than distance "F" as indicated in FIG. 60B.

Rearward and forward plunger assemblies 1200 and 1210 remain fully retracted.

Injection actuation button 116 has not yet been actuated as indicated by the following:

Microswitch 2840 is in an open state because it is not engaged by forward edge surface 1057 of injection actuation button 116.

Biasing assemblies 144 and 146 of the upper and lower housing assemblies 104 and 106 respectively are further displaced rearwardly axially in a direction indicated by arrows 2949 and further partially compressed as indicated by the following:

Forward-facing surface 792 of biasing element 786 is further rearwardly spaced from rearward-facing surface 608 of forward element 605 of lower housing portion 500.

Forward-facing surface 444 of biasing element 420 is further rearwardly spaced from rearward-facing surface 401 of spring enclosure 386 of upper housing portion 230.

Prefilled syringe injection module 140 remains locked to the locking element 1230 following removal of the RNS remover 108, as indicated inter alia by the following:

Microswitch 2810 is in a closed state due to engagement with rearwardly facing end tapered portion 1968 of arm 1952.

Microswitch 2820 remains in an open state because it is not engaged by rearwardly-facing surface 782 of biasing element 786.

Microswitch 2830 remains in an open state because RNS remover 108 has been removed.

The prefilled syringe 1902 remains securely retained within the mounting element 1900.

Needle shield element 147 is rearwardly displaced axially along with the mounting element 1900 relative to housing 102.

Flexible diagonally opposed needle shield engaging fingers 1934 of the mounting element 1900 are now disengaged from apertures 2152 and 2052, such that respective surfaces 1944 and 1946 of one of fingers 1934 lie adjacent corresponding respective surfaces 2060 and 2062 of aperture 2052 and respective surfaces 1944 and 1946 of the other of fingers 1934 lie adjacent corresponding respective surfaces 2160 and 2162 of aperture 2152.

It is further seen that due to rearward displacement of the needle shield element 147 and mounting element 1900 relative to housing 102, forward portions 1937 of fingers 1934 of mounting element 1900 are displaced rearwardly relative to the housing 102 and deflected radially inwardly due to their displacement along angled portions 364 of the upper housing portion 230 and 564 of the lower housing portion 500, as indicated by the following:

The rearward facing edge surface 1938 of one of the needle shield engaging fingers 1934 of mounting element 1900 lies rearwardly of the angled portion 364 of injection module travel track protrusion 360 of upper housing portion 230 and against elongate track portion 362 of injection module travel track protrusion 360 of upper housing portion 230.

Additionally, rearward facing edge surfaces 1938 of needle shield engaging fingers 1934 of mounting element 1900 lie rearwardly to angled portions 564 of injection module travel track protrusions of 562 of lower housing portion 500 and against elongate track portions 563 of injection module travel track protrusion 562 of lower housing portion 500.

Figure 61C:
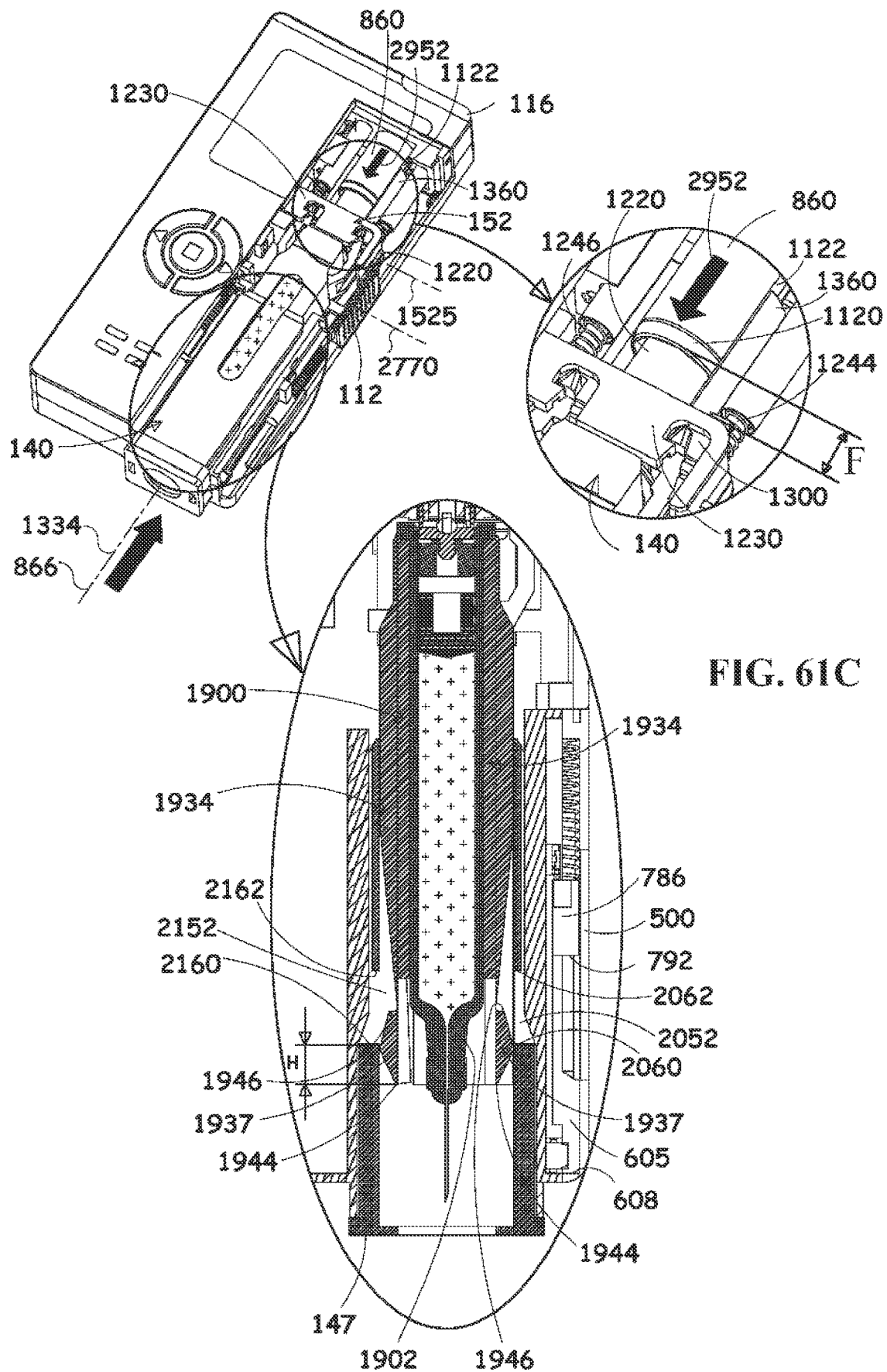

At this stage, as shown in FIGS. 61C & 61D, as distinguished from the stage shown in FIG. 61B, multiple motion output sub-assembly 152 is slightly displaced forwardly in a direction indicated by an arrow 2952, and assumes a nearly retracted operative orientation, as indicated by the following:

Engagement tooth portions 1360 of base element 1220 are slightly displaced forwardly to engage forward ends of respective windows 1122 and 1124 in multiple drive element 860.

Octagonal cylindrical portion 1724 of rearward driving screw 1250 lies along axis 866 and fully within the multiple drive element 860.

Compression springs 1244 and 1246 are slightly forwardly displaced and thus assume the nearly compressed position.

Axis 1525 of locking element 1230 lies rearwardly of injection module release button 112.

Central wall portion 1300 is more forwardly spaced along axis 1334 from inwardly tapered outer surface 1120 of multiple drive element 860 by distance F, seen in FIG. 61C. It is noted that distance "F" is substantially larger than distance "G" as indicated in FIG. 60B.

Rearward and forward plunger assemblies 1200 and 1210 remain fully retracted.

Injection actuation button 116 has not yet been actuated as indicated by the following:

Microswitch 2840 is in an open state because it is not engaged by forward edge surface 1057 of injection actuation button 116.

Biasing assemblies 144 and 146 of upper and lower housing assemblies 104 and 106 respectively remain fully compressed.

Prefilled syringe injection module 140 remains locked to the locking element 1230, as indicated inter alia by the following:

Microswitch 2810 is closed as indicated by engagement with rearwardly facing end tapered portion 1968 of arm 1952.

Microswitch 2820 is in a closed state because it is engaged by rearwardly-facing surface 782 of biasing element 768 following rearward displacement of the needle shield 147 relative to the housing 102.

Microswitch 2830 remains open because RNS remover 108 was previously removed.

The prefilled syringe 1902 remains securely retained within mounting element 1900.

Mounting element 1900 is displaced axially forwardly relative the needle shield 147, indicated by the following:

Flexible diagonally opposed needle shield engaging fingers 1934 of mounting element 1900 are further deflected radially inwardly and displaced forwardly with respect to apertures 2152 and 2052 by a distance H, seen in an enlargement in FIG. 61C, such that respective surfaces 1944 and 1946 of one of needle shield engaging fingers 1934 lie forwardly to corresponding respective surfaces 2060 and 2062 of aperture 2052 and respective surfaces 1944 and 1946 of the other of fingers 1934 lie forwardly corresponding respective surfaces 2160 and 2162 of aperture 2152 such that the forward portions 1937 of needle shield engaging fingers 1934 of mounting element 1900 partially lie against the inner circumferential surface of the needle shield 147.

Figure 62A:
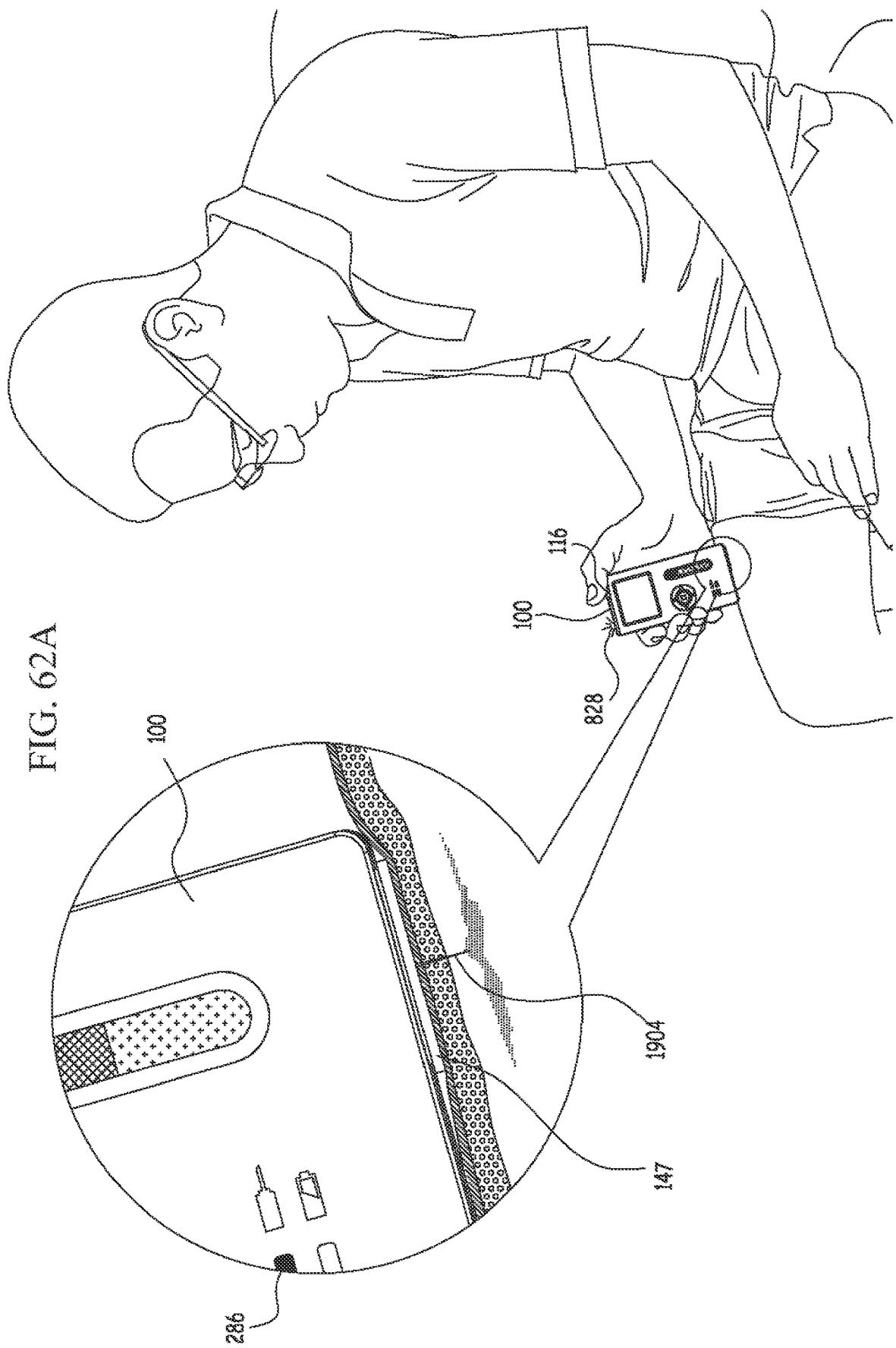
Figure 62C:
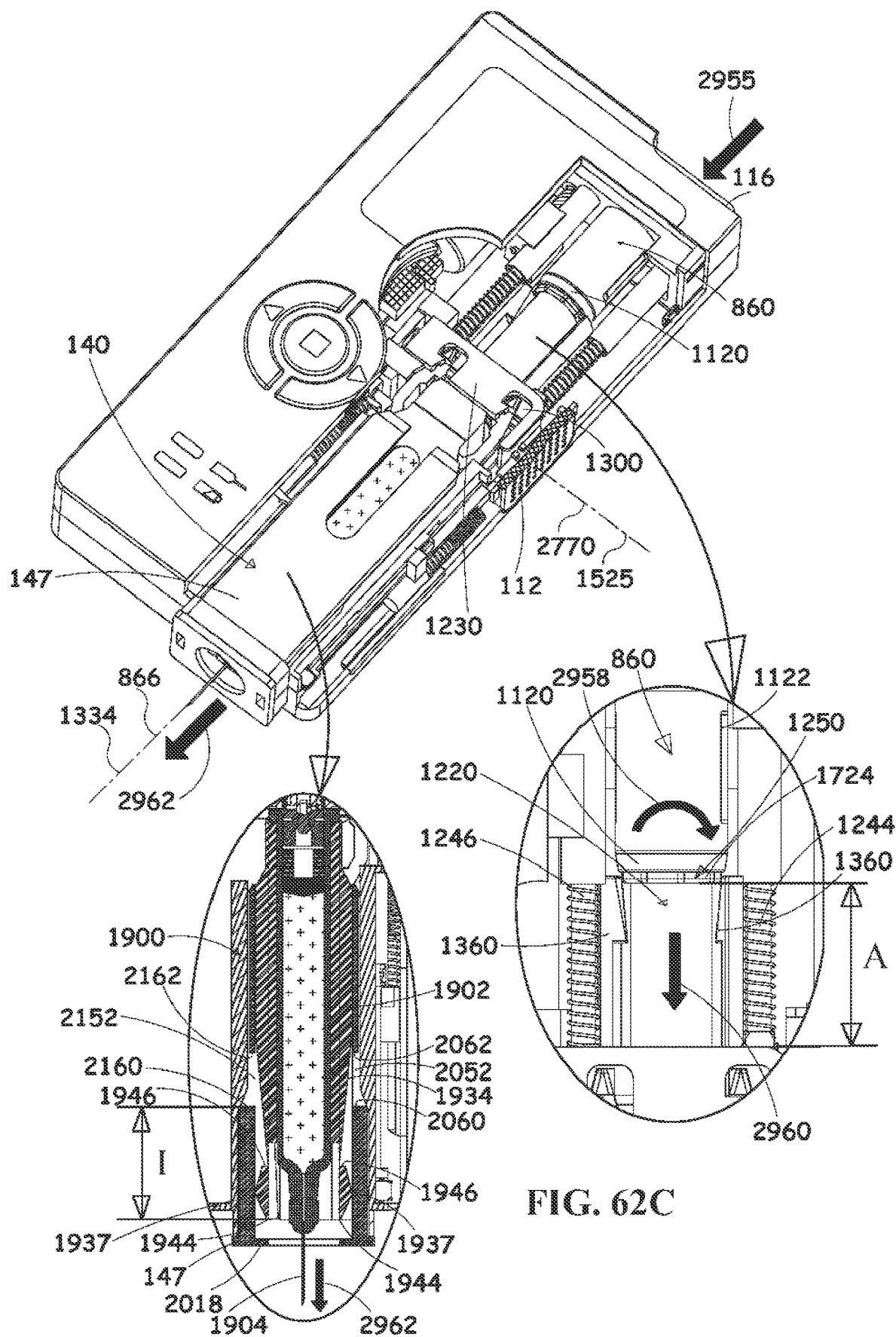
Figure 62D:
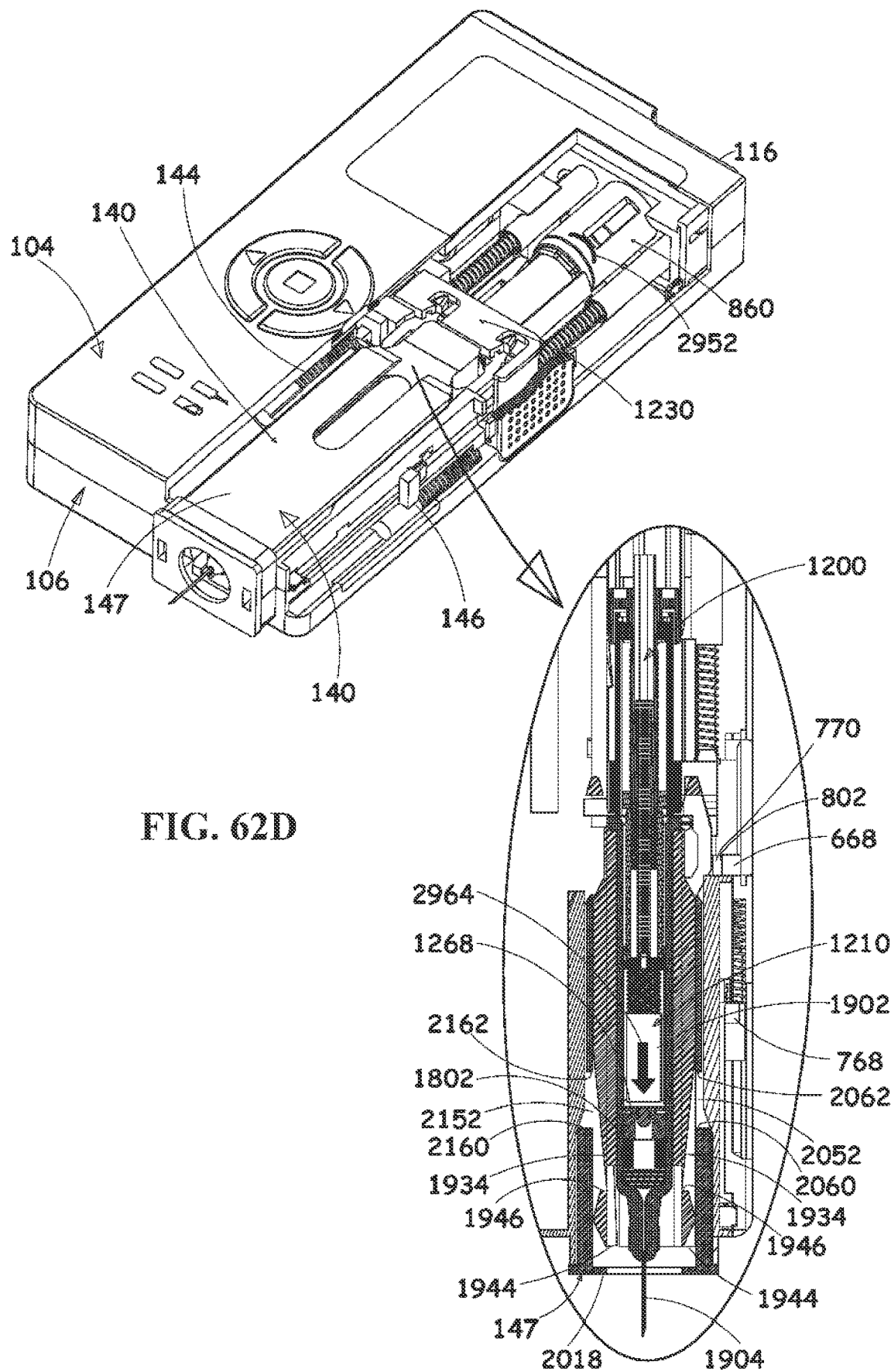
Figure 62E:
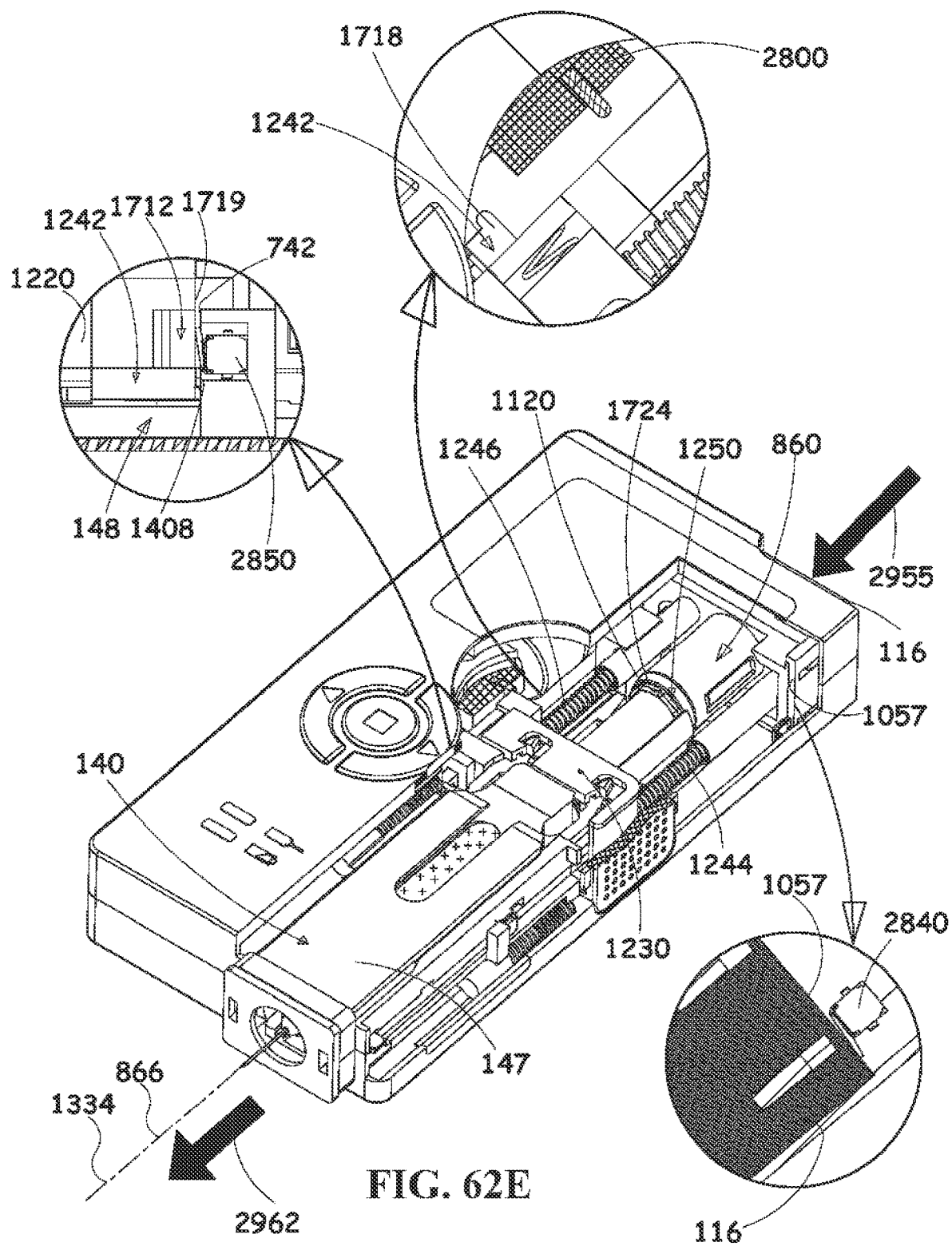

Reference is now made to FIGS. 62A-62C, which are simplified illustrations of the electronic automatic injection device of FIGS. 1A-51B employing a prefilled syringe injection module in a seventh illustrative operative state, which is a typical "needle penetration and injection" state. The electronic automatic injection device of FIGS. 1A-51B in the seventh illustrative operative state is seen while the user initially pushes the needle shield element 147 against the injection site and immediately thereafter presses the injection actuation button 116, thus causing the needle to extend into the injection site.

In this seventh state, as distinguished from the sixth state described above with respect to FIGS. 61A-61D and with particular reference to FIGS. 52A-52D and 53A-53C, the user presses injection actuation button 116, which initiates a sequence of sub-stages at which various elements are displaced with respect to each other.

In the first sub-stage, injection actuation button 116 is seen to have been actuated, in a direction indicated by an arrow 2955, as indicated by the following:

Microswitch 2840 is in a closed state because it is engaged by forward edge surface 1057 of injection actuation button 116. Closing of microswitch 2840 causes the electronic control assembly 134 to actuate electric motor 832. Rotational movement of the electric motor 832 in a clockwise direction produces corresponding rotation of the multiple drive element

860 in a direction indicated by an arrow 2958, by means of gears 838 and 846 which are registered with toothed surface 852 of the multiple drive element 860.

As the result of rotation of the multiple drive element 860, inwardly tapered side surfaces 1372 of engagement tooth portions 1360 of base element 1220 engage tapered longitudinal surfaces 1130 of slots 1122 and 1124 of multiple drive element 860 causing outward deflection of flexible engagement fingers 1324 and 1326 of base element 1220. As a result of this outward deflection, inwardly tapered side surfaces 1372 of engagement tooth portions 1360 of base element 1220 disengage from slots 1122 and 1124 of multiple drive element 860, thereby allowing axial forward displacement of multiple motion output sub-assembly 152.

In a second sub-stage, the multiple motion output sub-assembly 152 is displaced axially forwardly to assume a fully extended operative orientation and to cause needle penetration into the injection site in a direction indicated by an arrow 2960, as indicated by the following:

Microswitch 2850 is in a closed state, resulting from engagement with microswitch engagement surface 1719 of protrusion 1712 of spring seat 1242;

Microswitch 2800 is in an open state because it is not engaged by microswitch engagement surface 1718 of spring seat 1242.

Octagonal cylindrical portion 1724 of rearward driving screw 1250 now lies somewhat forwardly along axis 866 of inwardly tapered outer surface 1120 of multiple drive element 860.

Compression springs 1244 and 1246 are now released and assume their preloaded and not fully compressed state.

Axis 1525 of locking element 1230 becomes coaxial with axis 2770 of injection module release button 112.

Figure 52A:
Figure 52E:
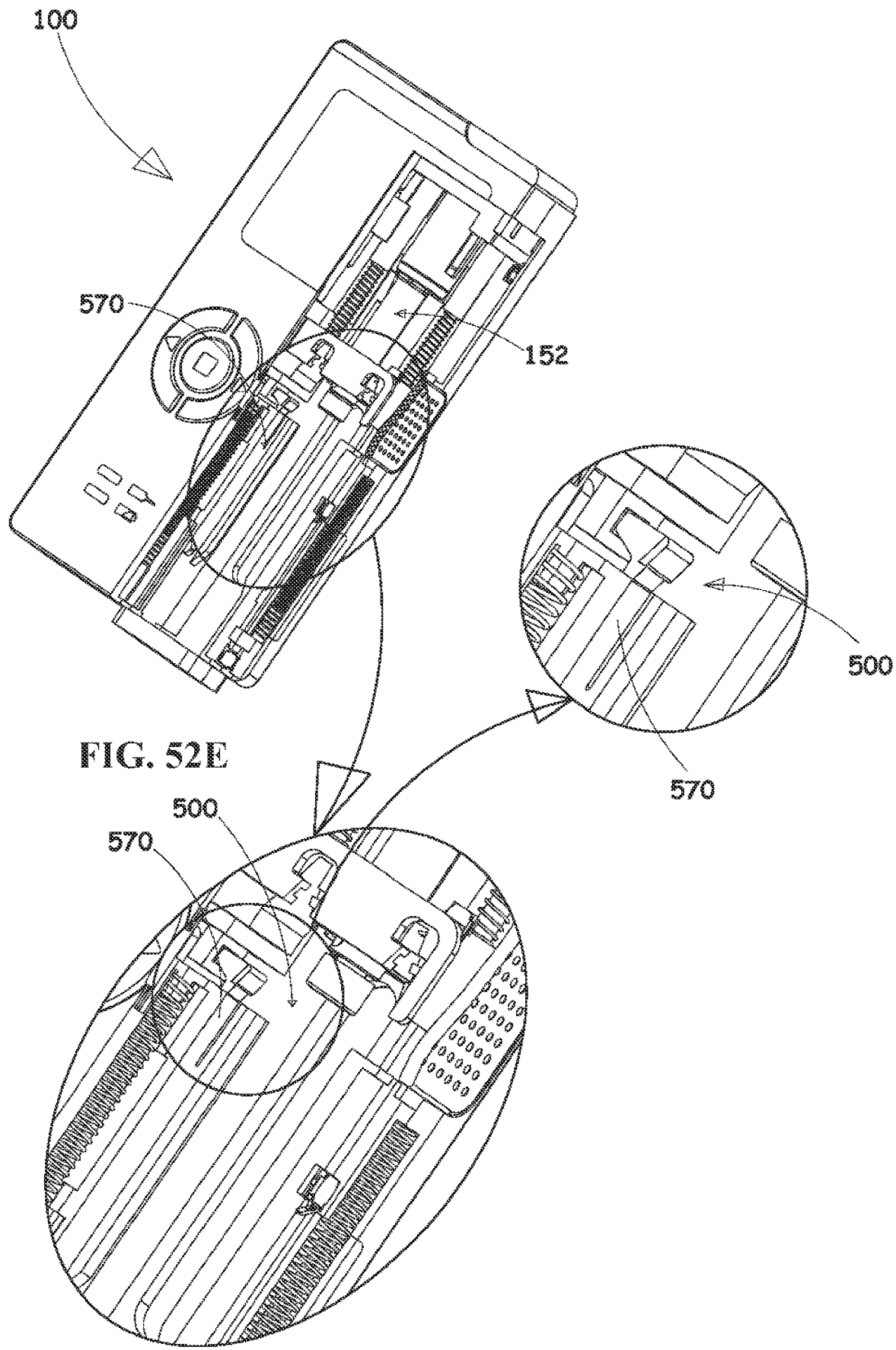
Figure 52F:
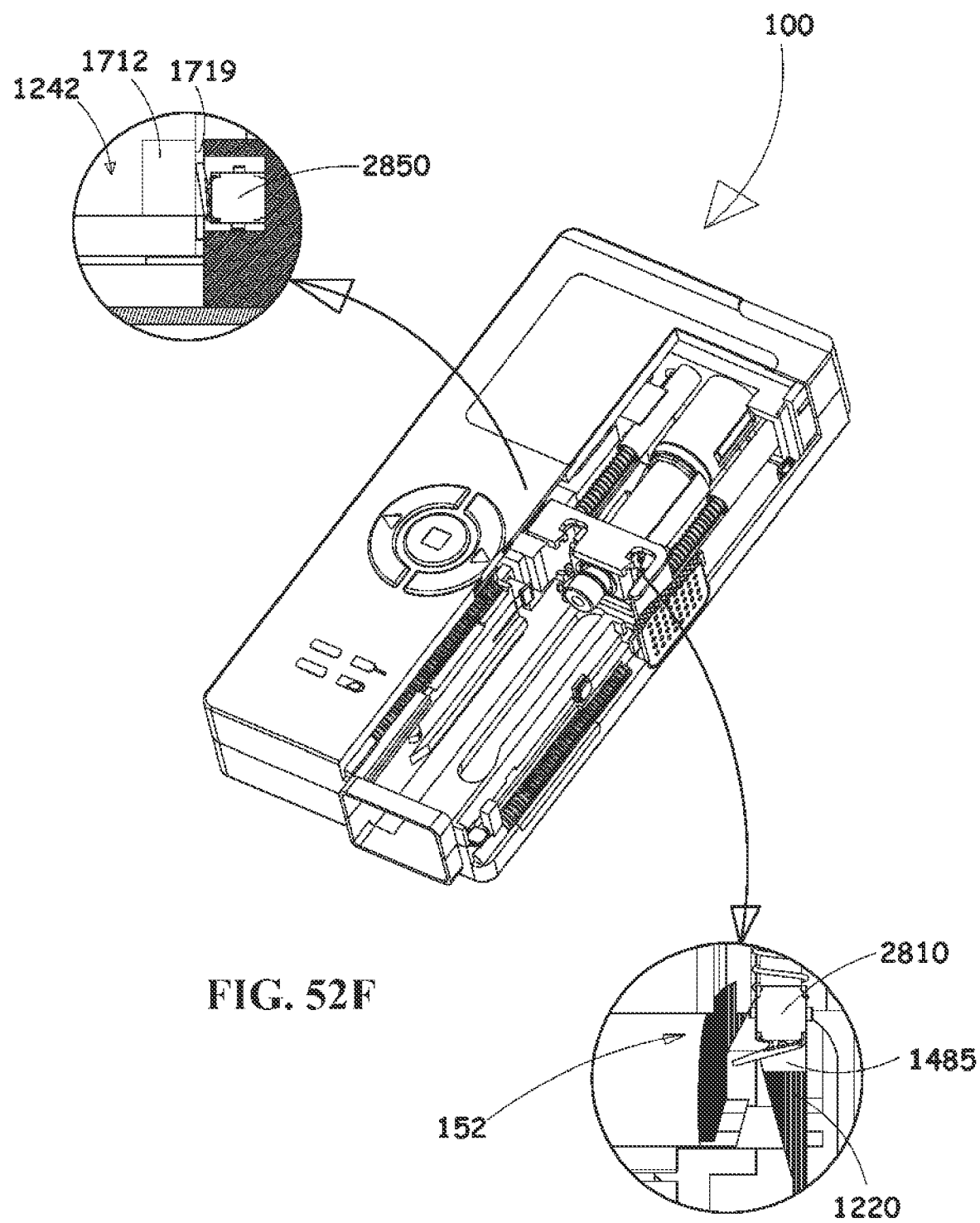

Central wall portion 1300 is forwardly displaced along axis 1334 from inwardly tapered outer surface 1120 of multiple drive element 860 to lie at distance A from surface 1120, as seen in FIG. 52A.

In accordance with the needle penetration depth setting, as described hereinabove with reference to FIGS. 53A-53C, in the fully extended operative orientation of the multiple motion output subassembly 152, rearward facing surface 742 of injection depth selector travel track 148 lies against forward facing wall 1408 of base element 1220 and thus defines the penetration depth of needle 1904 of the prefilled syringe 1902.

Locking element 1230 now lies adjacent injection module release button 112.

Biasing assemblies 144 and 146 of the upper and lower housing assemblies 104 and 106 respectively remain fully compressed.

Prefilled syringe injection module 140 remains locked to the locking element 1230, as indicated inter alia by the following:

Microswitch 2810 is closed as indicated by engagement with rearwardly facing end tapered portion 1968 of arm 1952.

Microswitch 2820 is in a closed state because it is engaged by rearwardly-facing surface 792 of biasing element 768 following rearward displacement of the needle shield 147 relative to the housing 102.

Microswitch 2830 remains open because RNS remover 108 was previously removed.

Prefilled syringe injection module 140 is prevented from being released by pressing the injection module release button 112, as indicated by the following:

Elongate surface 802 of elongate rod portion 770 of the biasing element 768 of the lower biasing assembly 146 lies against protrusion 668 of injection module release button 112 and prevents axial movement of injection module release button 112 along axis 2770.

The prefilled syringe 1902 remains securely retained within mounting element 1900. Mounting element 1900 is further displaced axially forwardly relative to the needle shield element 147, causing the needle 1904 of the prefilled syringe 1902 to protrude forwardly with respect to the patient engagement plate 2018 of the needle shield element 147 and thus penetrate the injection site, as indicated by the following:

Flexible diagonally opposed needle shield engaging fingers 1934 of the mounting element 1900 are further displaced forwardly with respect to apertures 2152 and 2052 by a distance "I", such that respective surfaces 1944 and 1946 of one of needle shield engaging fingers 1934 lie more forwardly with respect to corresponding respective surfaces 2060 and 2062 of aperture 2052. Respective surfaces 1944 and 1946 of the other of fingers 1934 lie more forwardly with respect to corresponding respective surfaces 2160 and 2162 of aperture 2152 such that the forward portions 1937 of needle shield engaging fingers 1934 of mounting element 1900 lie against the inner circumferential surface of the needle shield 147.

It is noted that distance "I" is substantially greater than distance "H" which is seen in FIGS. 61A-612C.

In the third sub-stage, due to continued rotational movement of the electric motor 832, rearward and forward plunger assemblies 1200 and 1210 extend forwardly as described in FIGS. 35 & 36 in a direction indicated by an arrow 2964, and cause ejection of medication contained within the prefilled syringe 1902 through the needle 1904, as indicated by:

Engagement between forward-facing surface 1802 of piston engaging element 1268 and the piston of the prefilled syringe 1902.

Figure 63A:
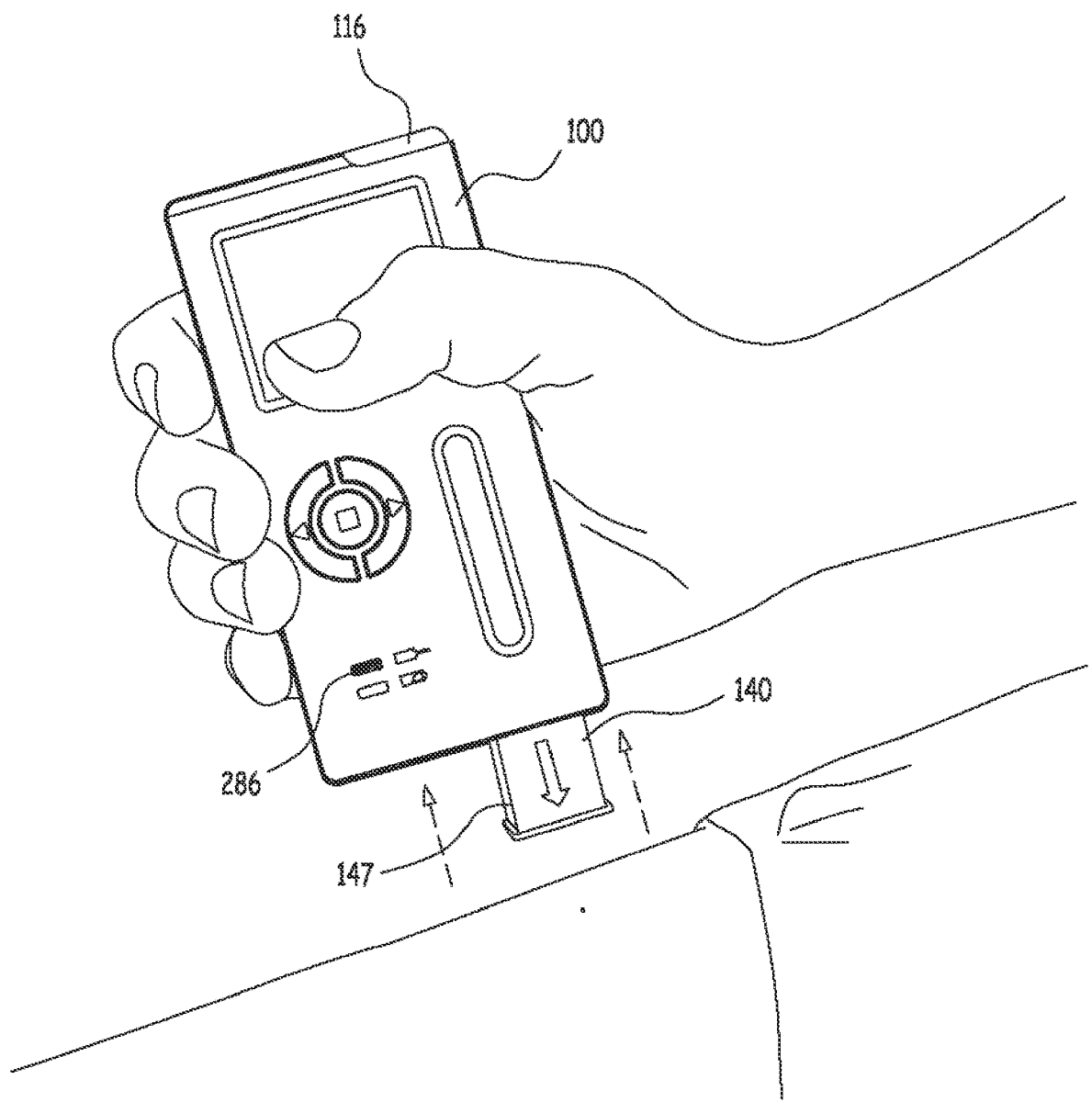
Figure 63C:
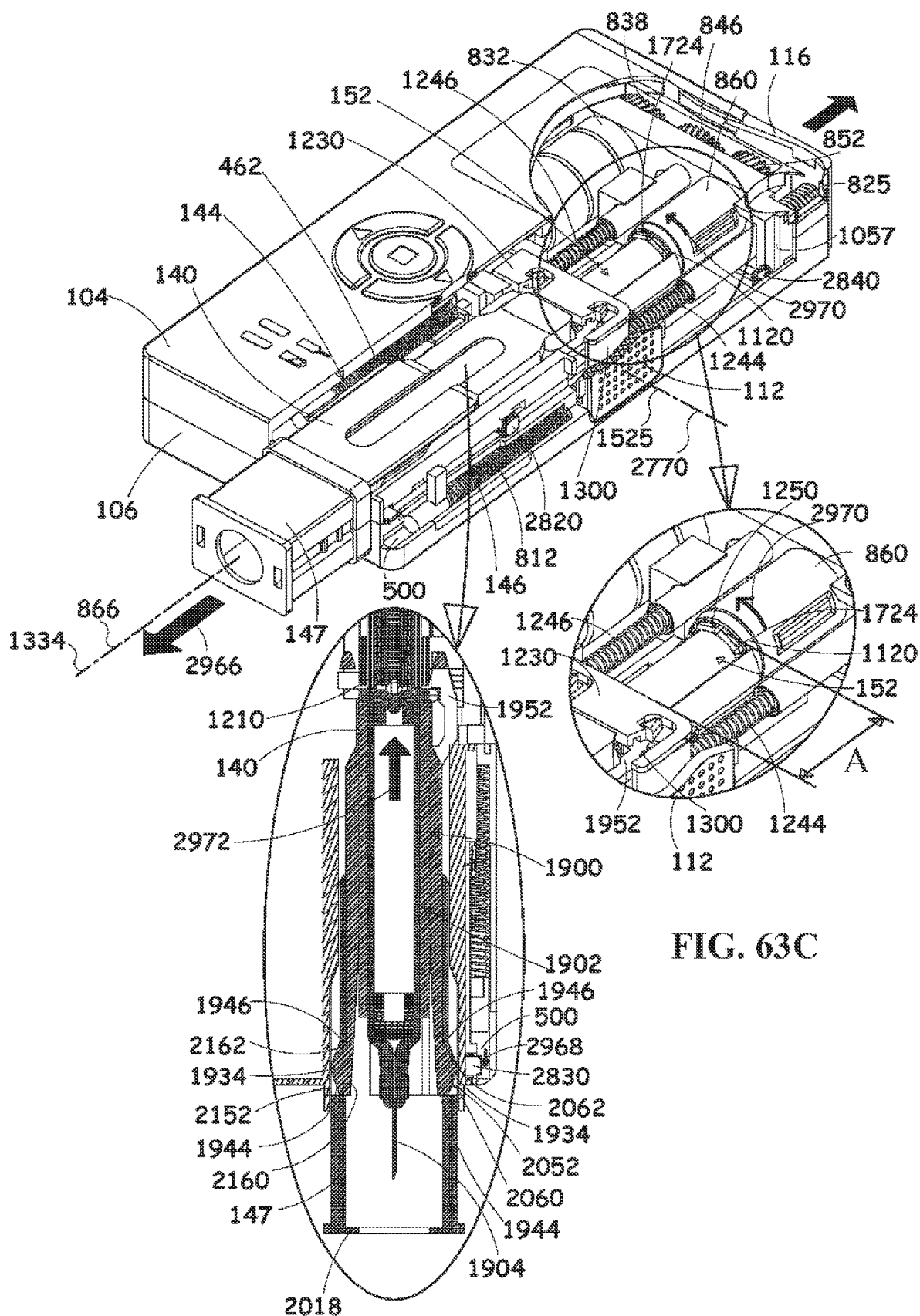
Figure 63D:
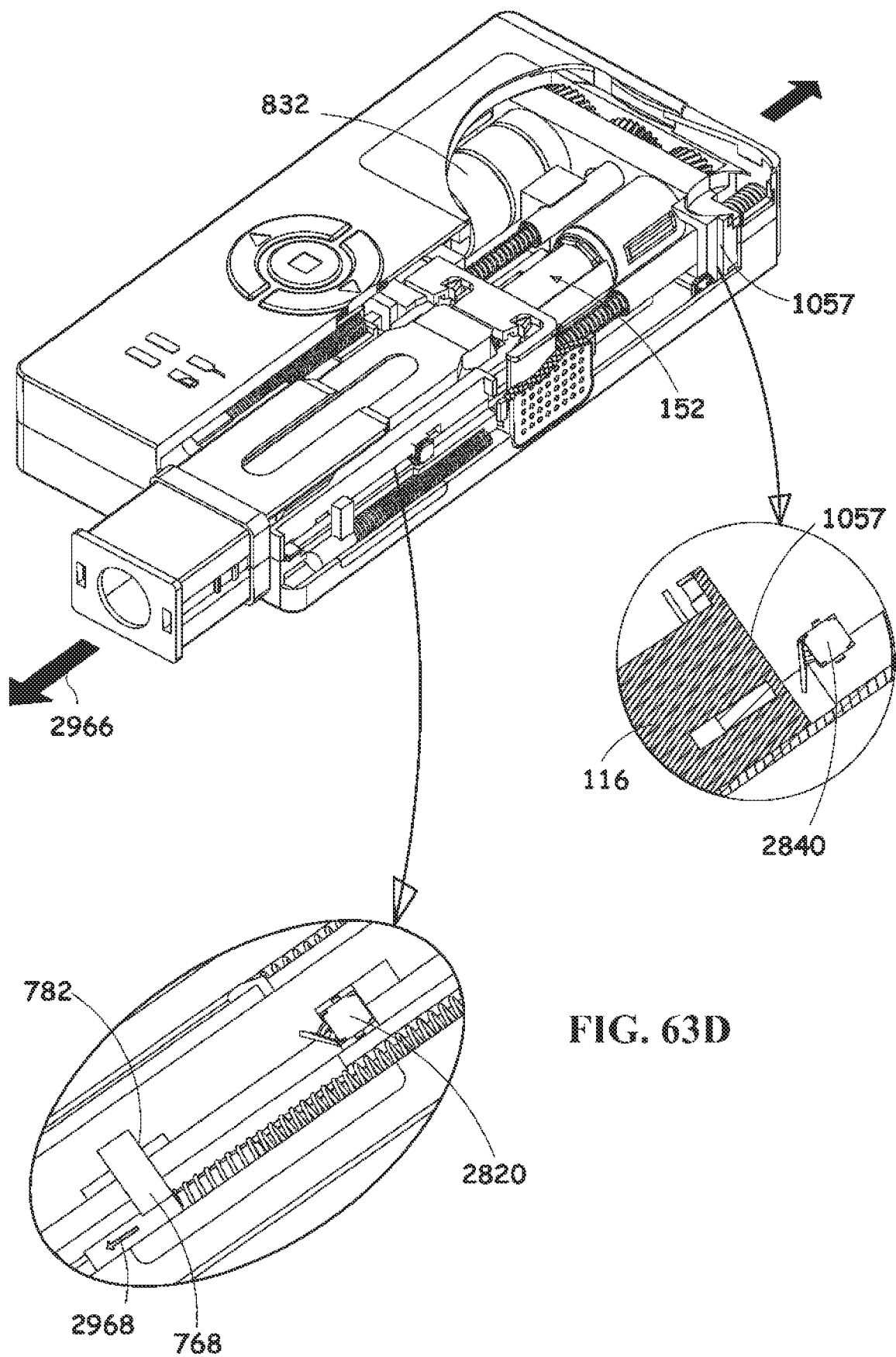
Figure 64A:
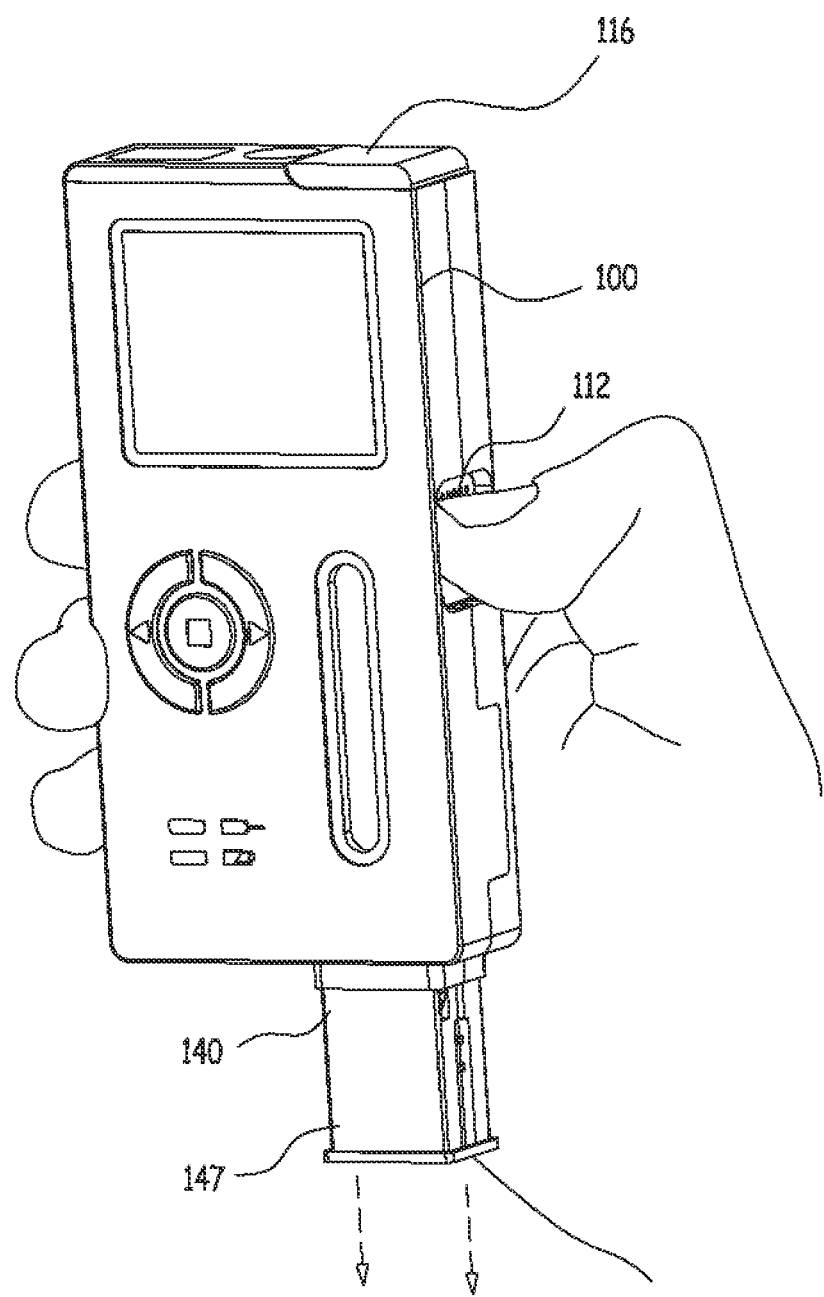
Figure 64C:
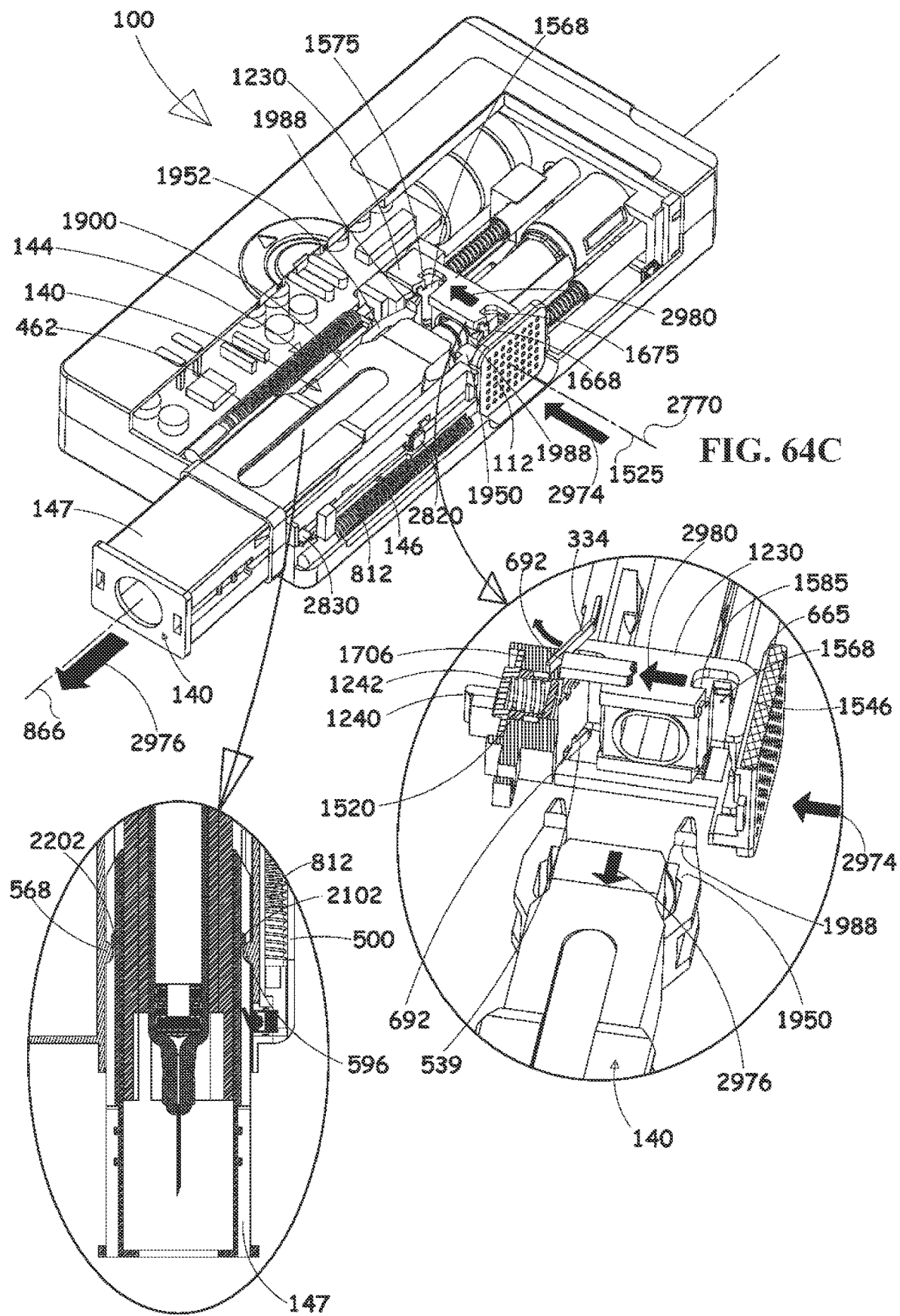
Figure 64D:
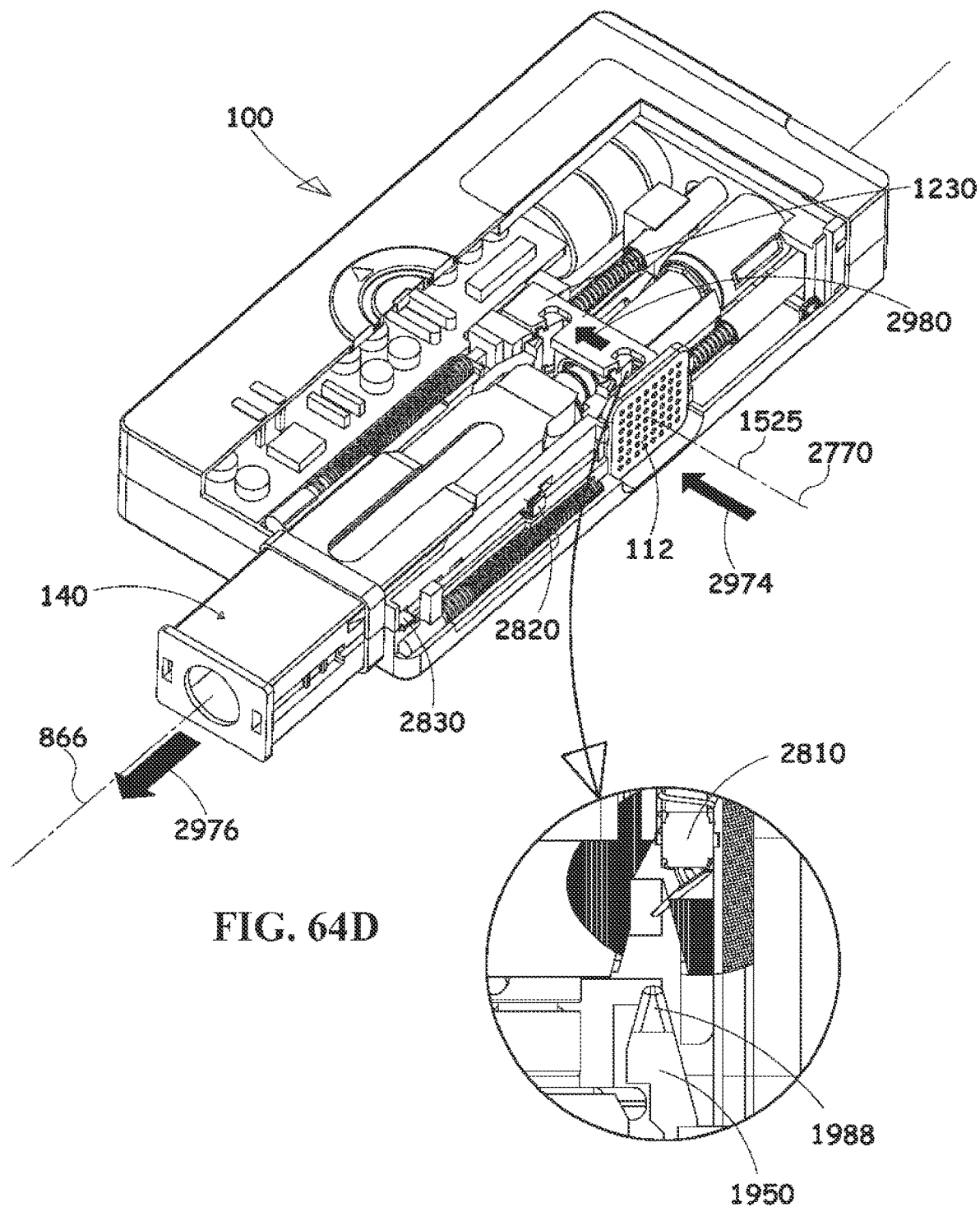

Reference is now made to FIGS. 63A-63D, which are simplified illustrations of the electronic automatic injection device of FIGS. 1A-51B employing a prefilled syringe injection module in an eighth illustrative operative state, in which the automatic electronic injection device is disengaged from the injection site. FIG. 63A shows the user pulling the automatic electronic injection device rearwardly out of engagement with the injection site.

In this eighth state, as distinguished from the seventh state described above with respect to FIGS. 62A-62E:

Injection actuation button 116 is released and returns to its initial position by the force of the spring 825, as indicated by the open state of microswitch 2840, which is no longer engaged by forward edge surface 1057 of injection actuation button 116.

The multiple motion output sub-assembly 152 remains in the fully extended operative orientation, as indicated by the following:

Microswitch 2850 remains in a closed state, resulting from engagement with microswitch engagement surface 1719 of protrusion 1712 of spring seat 1242;

Microswitch 2800 remains in an open state because it is not engaged by microswitch engagement surface 1718 of spring seat 1242.

Octagonal cylindrical portion 1724 of rearward driving screw 1250 remains somewhat forwardly along axis 866 of inwardly tapered outer surface 1120 of multiple drive element 860.

Compression springs 1244 and 1246 remain in their preloaded and not fully compressed state.

Axis 1525 of locking element 1230 remains coaxial with axis 2770 of injection module release button 112.

Central wall portion 1300 remains forwardly spaced along axis 1334 from inwardly tapered outer surface 1120 of multiple drive element 860 by distance A, as seen in FIG. 52A.

Locking element 1230 lies adjacent injection module release button 112.

Prefilled syringe injection module 140 remains locked to the locking element 1230, as indicated inter alia by the following:

Microswitch 2810 is closed as indicated by engagement with rearwardly facing end tapered portion 1968 of arm 1952.

Microswitch 2830 remains open because RNS remover 108 was previously removed.

The prefilled syringe 1902 remains securely retained within the mounting element 1900.

Needle shield element 147 is forwardly displaced in a direction indicated by an arrow 2966, following the removal of the automatic electronic injection device 100, by the force of the springs 462 and 812 of the biasing assemblies 144 and 146 respectively, as indicated by the following:

Engagement between rearward facing forward end wall surface 2080 of recess 2070 of needle shield element 147 and forward facing surface 792 of biasing element 768, as specifically seen in FIG. 57C.

Engagement between rearward facing forward end wall surface 2180 of recess 2170 and forward facing surface 444 of biasing element 420, as specifically seen in FIG. 57C.

As a result of this forward displacement of the needle shield element 147, biasing assemblies 144 and 146 of the upper and lower housing assemblies 104 and 106 respectively are displaced forwardly axially in a direction indicated by arrows 2968 and partially compressed, as indicated by the following:

Forward-facing surface 792 of biasing element 768 is slightly rearwardly spaced from rearward-facing surface 608 of forward element 605 of lower housing portion 500.

Forward-facing surface 444 of biasing element 420 is slightly rearwardly spaced from rearward-facing surface 401 of spring enclosure 386 of upper housing portion 230.

Following forward displacement of the biasing assemblies 144 and 146, microswitch 2820 is in an open state because it is disengaged from rearwardly-facing surface 782 of biasing element 768 following forward displacement of the needle shield element 147 relative to the housing 102.

Forward displacement of the needle shield element 147 causes covering of needle 1904 of prefilled syringe 1902, such that the patient engagement plate 2018 of needle shield element 147 is positioned forwardly of the forward end of the needle 1904, and additionally causes locking of the needle shield element 147 to mounting element 1900, as indicated by the following:

Flexible diagonally opposed needle shield engaging fingers 1934 of the mounting element 1900 are engaged within apertures 2152 and 2052, such that respective surfaces 1944 and 1946 of one of needle shield engaging fingers 1934 lie against respective surfaces 2060 and 2062 of aperture 2052 and respective surfaces 1944 and 1946 of the other of fingers 1934 lie against corresponding respective surfaces 2160 and 2162 of aperture 2152.

Electronic control assembly 134 senses that the microswitch 2820 is in an open state and in response causes the electronic control assembly 134 to transmit a signal to the electric motor 832 to rotate in a counter-clockwise direction, indicated by an arrow 2970. This rotational movement is transferred to the multiple drive element 860 by means of gears 838 and 846, which are registered with toothed surface 852 of the multiple drive element 860. Due to a non-rotatable connection between the multiple drive element 860 and the rearward driving screw 1250, rearward and forward plunger assemblies 1200 and 1210 are retracted axially rearwardly in a direction indicated by arrow 2972, to a position that is described hereinabove with reference to FIG. 34. At the end of this rotational movement, the multiple drive element 860 returns to the position described hereinabove with reference to FIGS. 52A-52F.

Reference is now made to FIGS. 64A-64D, which are simplified illustrations of the electronic automatic injection device of FIGS. 1A-51B employing a prefilled syringe in a ninth illustrative operative state in which the prefilled injection module 140 is released from the automatic electronic injection device 100, in response to the user pushing the injection module release button 112.

In this state, as distinguished from the state described above with respect to FIGS. 63A-63D:

The multiple motion output subassembly 152 remains in a fully extended operative orientation.

Axis 1525 of locking element 1230 remains coaxial with axis 2770 of injection module release button 112.

Rearward and forward plunger assemblies 1200 and 1210 remain fully retracted.

The user pushes the injection module release button 112, which in turn pushes the locking element 1230 against the force of the spring 1240 in a direction indicated by arrow 2974, as indicated by the following:

Elongated protrusions 665 of the injection module release button 112 engage edge surfaces 1546 and 1548 of the locking element 1230. The travel of the injection module release button 112 is limited by engagement of base wall portion 1520 of locking element 1230 with planar surface 1706 of spring seat 1242.

Spring engagement surfaces 692 of injection module release button 112 cause deflection of leaf springs 334 and 539.

The displacement of the locking element 1230 in the direction of arrow 2976 causes disengagement of the injection module 140 from the locking element 1230, as defined by the following:

Disengagement between forward facing shoulder surface 1988 of the arm 1950 of the mounting element 1900 from shoulder edge surface 1575 of the locking element 1230.

Disengagement of forward facing shoulder surface 1990 of arm 1950 from shoulder edge surface 1675 of locking element 1230.

Disengagement of forward facing shoulder surface 1988 of arm 1952 of mounting element 1900 from shoulder edge surface 1585 of the locking element 1230.

Disengagement of forward facing shoulder surface 1990 of arm 1952 from shoulder edge surface 1685 of the locking element 1230.

Following displacement of the locking element 1230 in the direction of arrow 2980, arms 1950 of the mounting element 1900 is permitted to move forwardly through narrow portions 1578 and 1678 of locking element 1230 and arm 1952 of the mounting element 1900 is permitted to move forwardly through narrow portions 1568 and 1668 of the locking element 1230.

Biasing assemblies 144 and 146 of the upper and lower housing assemblies 104 and 106 respectively are displaced axially forwardly by the force of the springs 462, 812 of the biasing assemblies 144 and 146 respectively, as indicated by the following:

Engagement between rearward facing forward end wall surface 2080 of recess 2070 of needle shield element 147 and forward facing surface 792 of biasing element 768, as specifically seen in FIG. 57C.

Rearward facing forward end wall surface 2180 of recess 2170 engages forward facing surface 444 of biasing element 420, as specifically seen in FIG. 57C.

This forward axial displacement in a direction indicated by arrows 2990 and results in the biasing assemblies 144 and 146 assuming a nearly-released position as indicated by the following:

Forward-facing surface 792 of biasing element 768 is less rearwardly spaced from rearward-facing surface 608 of forward element 605 of lower housing portion 500.

Forward-facing surface 444 of biasing element 420 is less rearwardly spaced from rearward-facing surface 401 of spring enclosure 386 of upper housing portion 230.

Forward displacement of the biasing assemblies 144 and 146 in the direction indicated by arrows 2990 urges forward axial displacement of the prefilled syringe injection module 140, as indicated by the following:

Springs 462 and 812 of the biasing assemblies 144 and 146 urge forward displacement of the prefilled syringe injection module 140 such that side facing rounded protrusion 2102 of the needle shield element 147 engages side-facing rounded protrusion 596 on the lower housing portion 500 and such that side facing rounded protrusion 2202 of the needle shield element 147 engages side-facing rounded protrusion 568 on the lower housing portion 500.

Microswitch 2810 is in an open state because it is disengaged from rearwardly facing end tapered portion 1968 of arm 1950.

Microswitch 2820 remains in an open state because it is not engaged by rearwardly-facing surface 782 of biasing element 768.

Microswitch 2830 remains in an open state because it is not engaged.

Figure 65B:
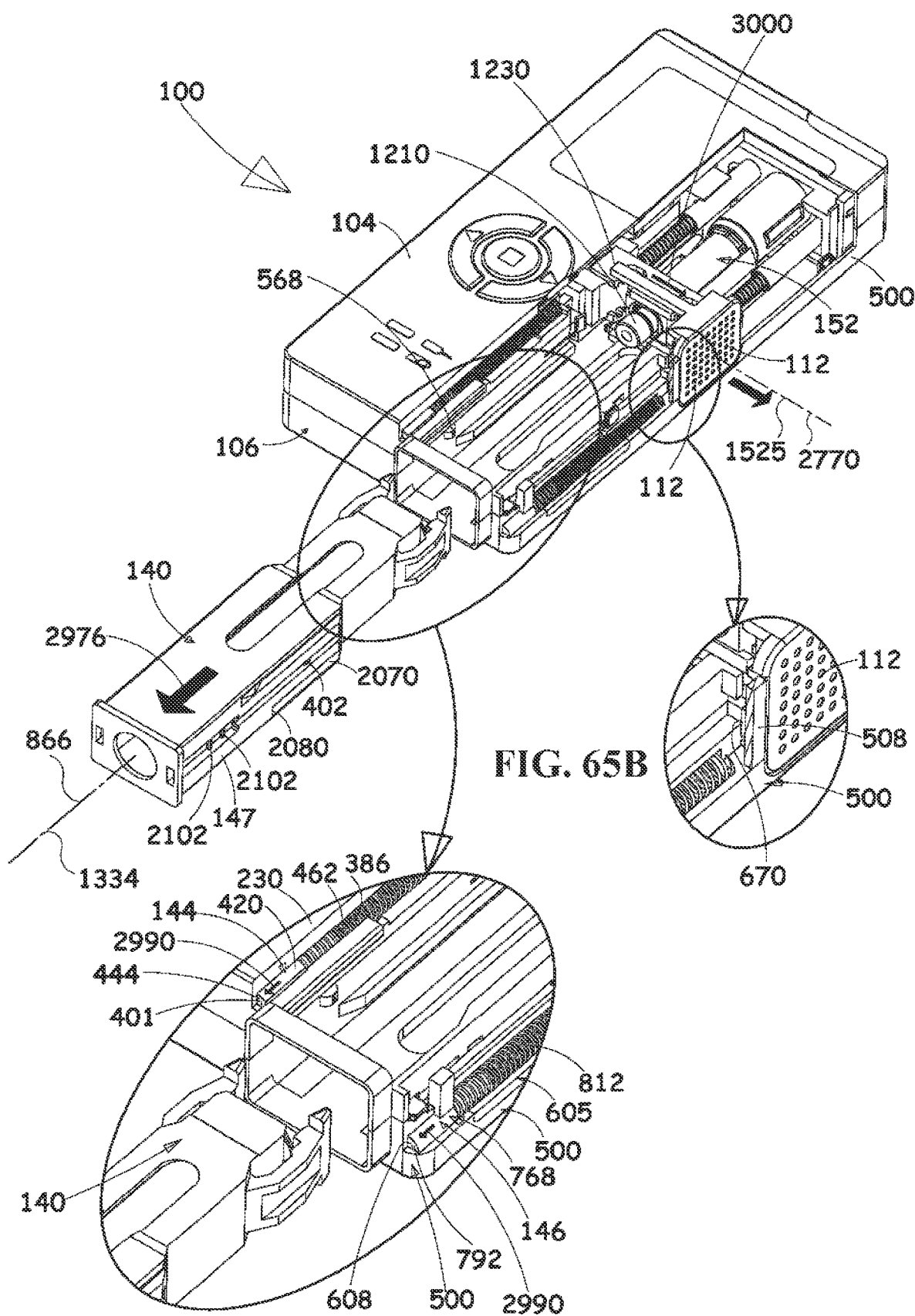
Figure 65C:
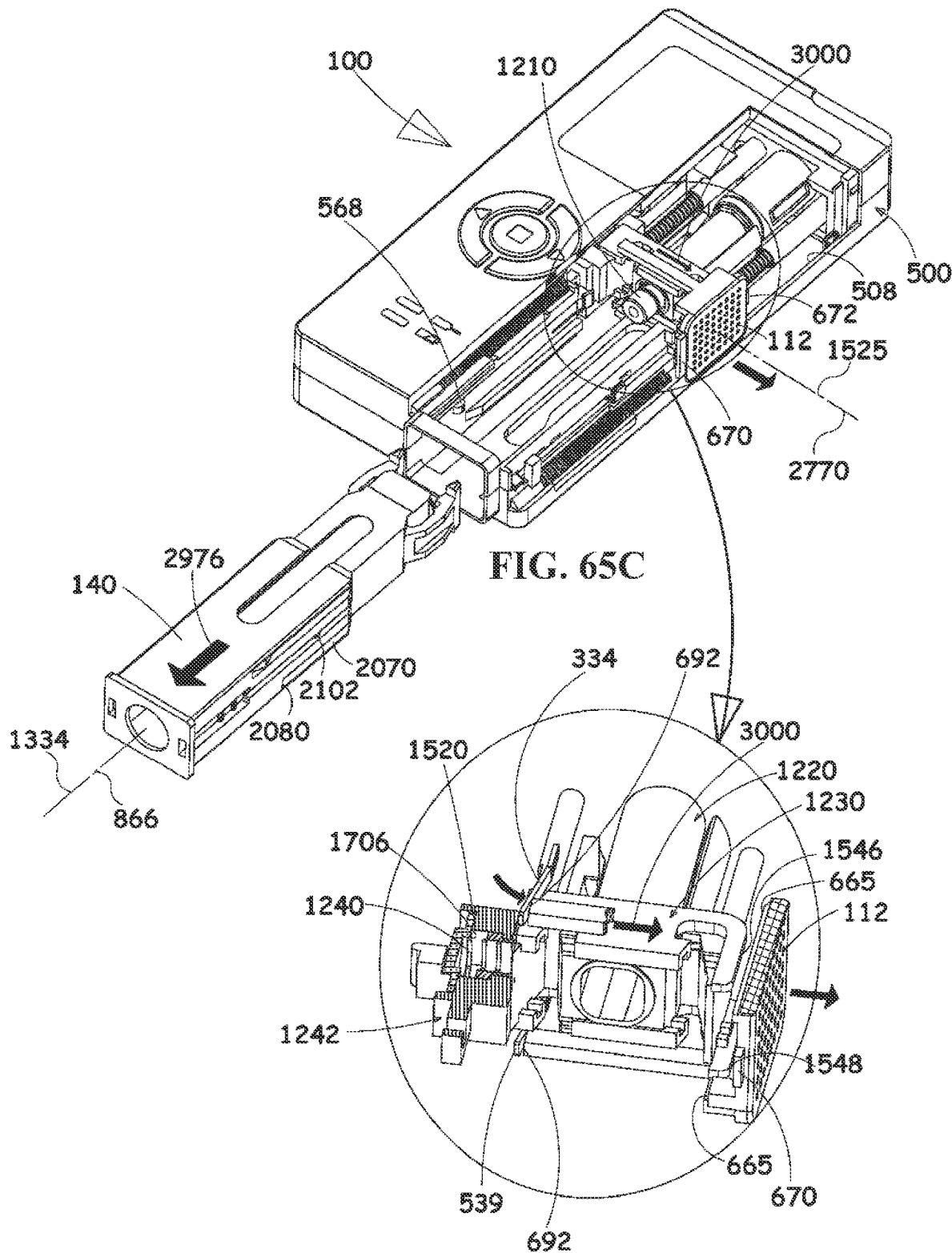

Reference is now made to FIGS. 65A-65C, which are simplified illustrations of the electronic automatic injection device of FIGS. 1A-51B employing a prefilled syringe injection module in a tenth illustrative operative state, in which the prefilled syringe injection module 140 is removed from the automatic electronic injection device 100.

In this tenth state, as distinguished from the ninth state described above with respect to FIGS. 64A-64C:

The multiple motion output subassembly 152 remains in a fully extended operative orientation.

Axis 1525 of locking element 1230 remains coaxial with axis 2770 of injection module release button 112.

Rearward and forward plunger assemblies 1200 and 1210 remain fully retracted.

The user releases the injection module release button 112, which causes the locking element 1230 to be displaced along axis 1525 in a direction indicated by 3000 by the force of the spring 1240, as indicated by the following:

Disengagement of base wall portion 1520 of locking element 1230 with planar surface 1706 of spring seat 1242.

Release of the injection module release button 112 permits displacement thereof along axis 2770 up to the initial state of the injection module release button 112, as specifically described in FIGS. 52A-52D. This displacement is urged by the force of the previously deflected leaf springs 334 and 539 exerted on spring engagement surfaces 692 of injection module release button 112, resulting in disengagement between elongated protrusions 665 of the injection module release button 112 and edge surfaces 1546 and 1548 of the locking element 1230.

Button travel stop protrusions 670 and 672 of the injection module release button 112 engage the side portion 508 of the lower housing portion 500.

Biasing assemblies 144 and 146 of the upper and lower housing assemblies 104 and 106 respectively are urged by the force of springs 462 and 812 to be forwardly axially displaced in a direction indicated by arrows 2990 following forward axial displacement of the prefilled syringe injection module 140 by the user and removal thereof from the automatic electronic injection device 100, as indicated by the following:

Following forward displacement of the prefilled injection module 140, side facing rounded protrusion 2102 of the needle shield element 147 disengages from side facing rounded protrusion 596 on the lower housing portion 500 and side facing rounded protrusion 2202 of the needle shield element 147 disengages from side-facing rounded protrusion 568 on the lower housing portion 500.

Additionally, rearward facing forward end wall surface 2080 of recess 2070 of needle shield 147 and forward facing surface 792 of biasing element 768 remain in mutual engagement and rearward facing forward end wall surface 2180 of recess 2170 remains in engagement with forward facing surface 444 of biasing element 420, as specifically seen in FIG. 57C.

The forward axial displacement of needle shield element 147 in a direction indicated by arrows 2990 proceeds until the biasing assemblies 144 and 146 assume their fully released position, as indicated by the following:

Forward-facing surface 792 of biasing element 768 lies against rearward-facing surface 608 of forward element 605 of lower housing portion 500.

Forward-facing surface 444 of biasing element 420 lies against rearward-facing surface 401 of spring enclosure 386 of upper housing portion 230.

Microswitch 2810 remains in an open state because it is disengaged from rearwardly facing end tapered portion 1968 of arm 1950.

Microswitch 2820 remains in open state because it is not engaged by rearwardly-facing surface 782 of biasing element 768.

Microswitch 2830 remains in open state because it is not engaged.

Figure 66:
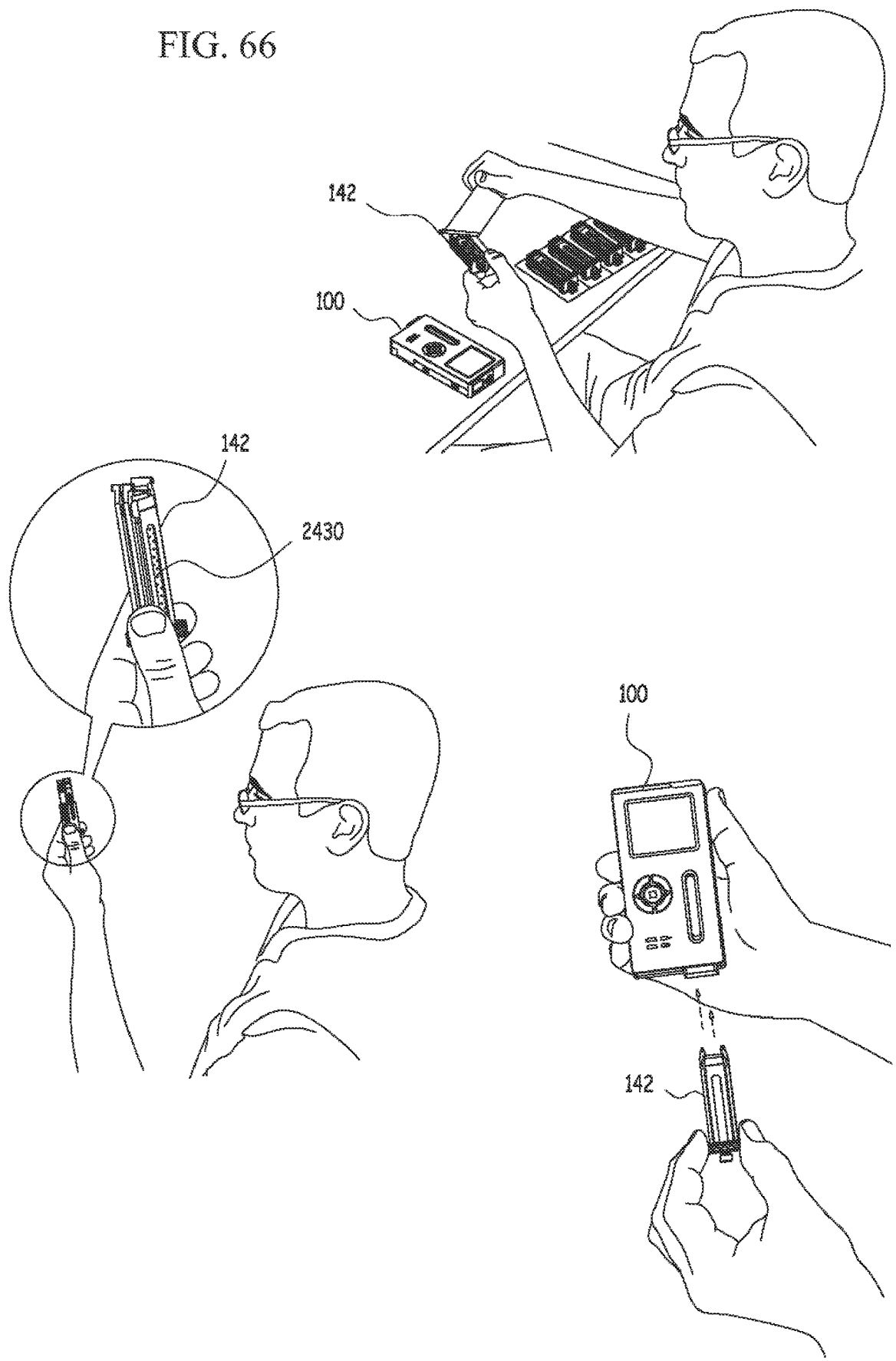
FIG. 66 is a simplified pictorial illustration of intermediate operational stages in the use of an embodiment of the electronic automatic injection device employing a needleless cartridge injection module.

Reference is now made to FIG. 66, which is a simplified illustration of the electronic automatic injection device of FIGS. 1A-51B employing a needleless cartridge injection module 142 when it is ready to use, prior to insertion of the needleless cartridge injection module 142 into the electronic automatic injection device 100. The electronic automatic injection device 100 is shown initially on a table in front of a user, who is in the process of opening the package of one of the needleless cartridge injection modules. FIG. 66 also shows the needleless cartridge injection module 142 in the hands of a user who is in the process of inspecting the medication through window recess 2430 in the mounting element 2400 and additionally shows the user about to insert the needleless cartridge injection module 142 into operative engagement with the electronic automatic injection device 100.

Figure 67A:
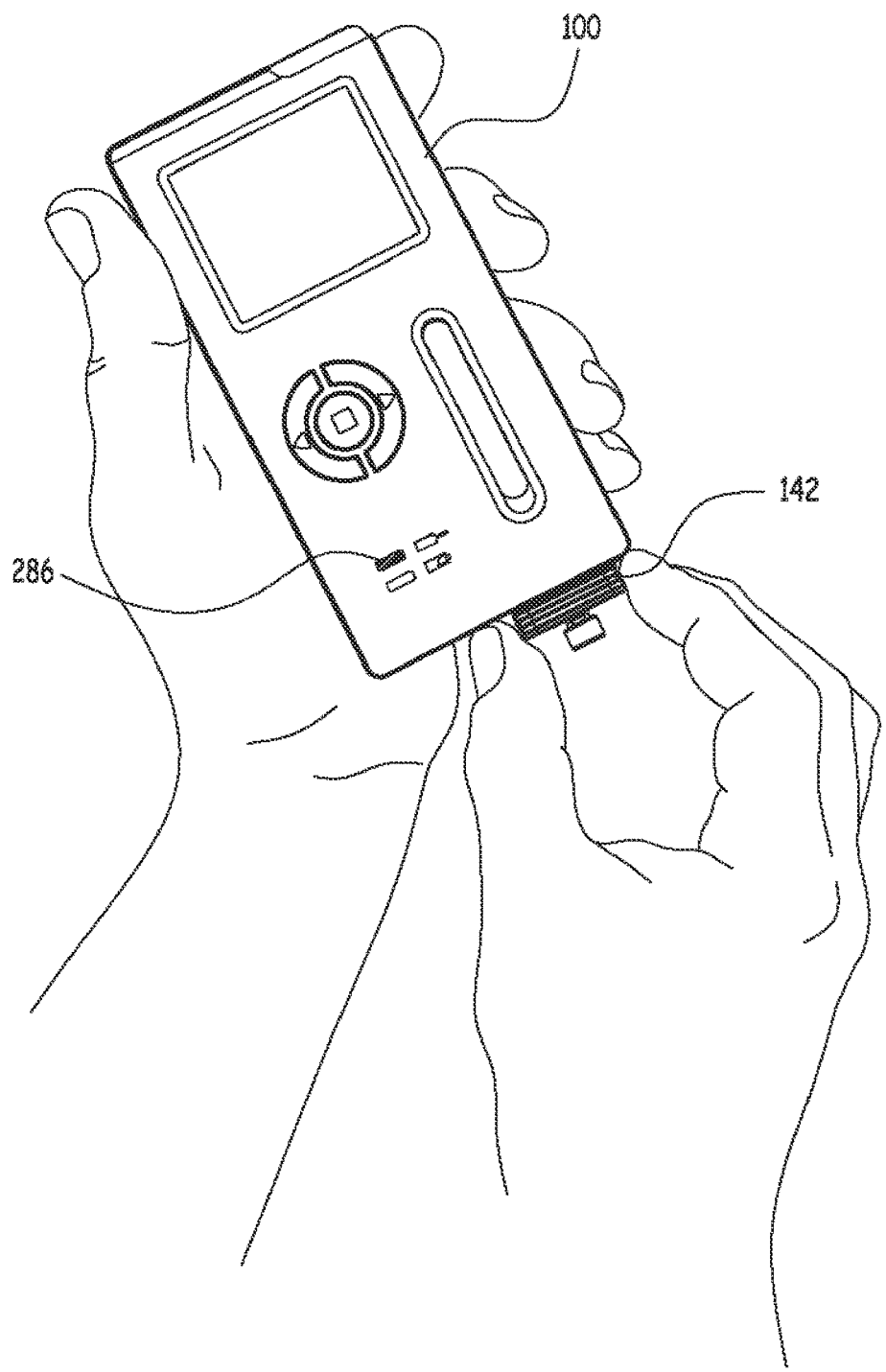
FIGS. 67A, 67B & 67C are simplified illustrations of the electronic automatic injection device employing a needleless cartridge of FIGS. 1A-51B in a second operative state, which is a typical "full insertion of needleless cartridge injection module" state, which corresponds to the fourth operative state shown in FIGS. 58A-58D, which is a "full insertion of a prefilled syringe injection module" state.
Figure 67B:
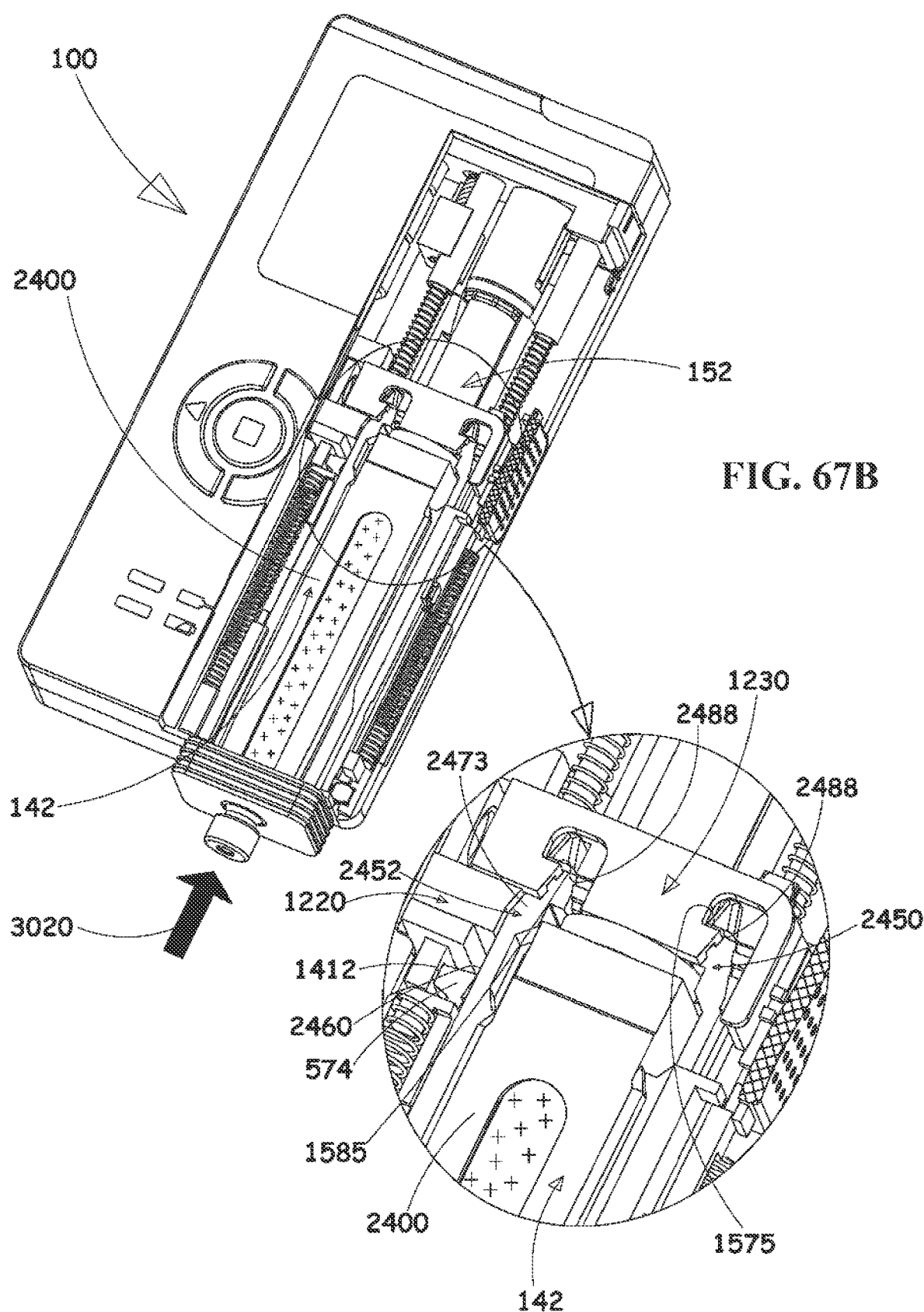
Figure 67C:
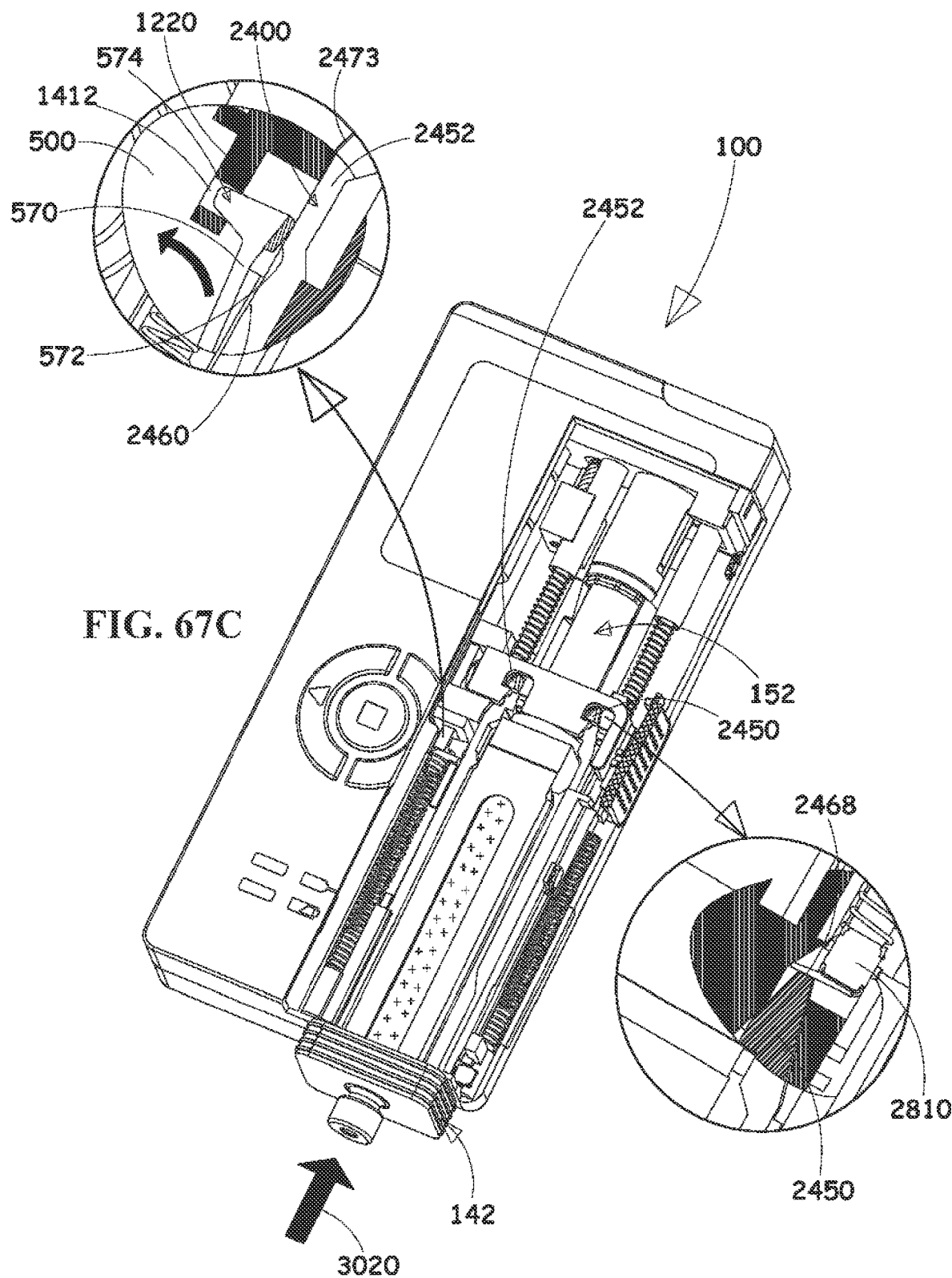

Reference is now made to FIGS. 67A, 67B & 67C, which are simplified illustrations of the electronic automatic injection device of FIGS. 1A-51B in a second illustrative operative state, which is a typical "needleless cartridge injection module insertion" state. FIG. 67A shows a user who is in the process of inserting a needleless cartridge injection module 142 into the electronic automatic injection device 100 of FIGS. 1A-51B.

Rearward displacement of the needleless cartridge injection module 142 in a direction indicated by arrow 3020 results in locking of the needleless cartridge injection module 142 with respect to multiple motion output subassembly 152, as indicated by the following:

Inwardly tapered outer surface 2473 of arm 2452 of mounting element 2400 of needleless cartridge injection module 142 engages protrusion 572 of flexible tab 570 (FIGS. 52A-52D) of lower housing portion 500 and results in outward deflection of the flexible tab 570. Following further rearward displacement of the needleless cartridge injection module 142, protrusion 572 of flexible tab 570 of lower housing portion 500 lies against outwardly directed portion 2460 of arm 2452 and in turn causes locking engagement of protrusion 574 of flexible tab 570 of lower housing portion 500 with aperture 1412 of base element 1220 of multiple motion output subassembly 152.

Engagement between forward facing shoulder surface 2488 of arms 2450 and 2452 and shoulder edge surfaces 1575 and 1585 of the locking element 1230;

Engagement between forward facing shoulder surface 2490 of arms 2450 and 2452 and shoulder edge surfaces 1675 and 1685 of the locking element; and Microswitch 2810 is in a closed state because it is engaged by rearwardly facing end tapered portion 2468 of arm 2450 of the needleless cartridge injection module 142.

Figure 68A:
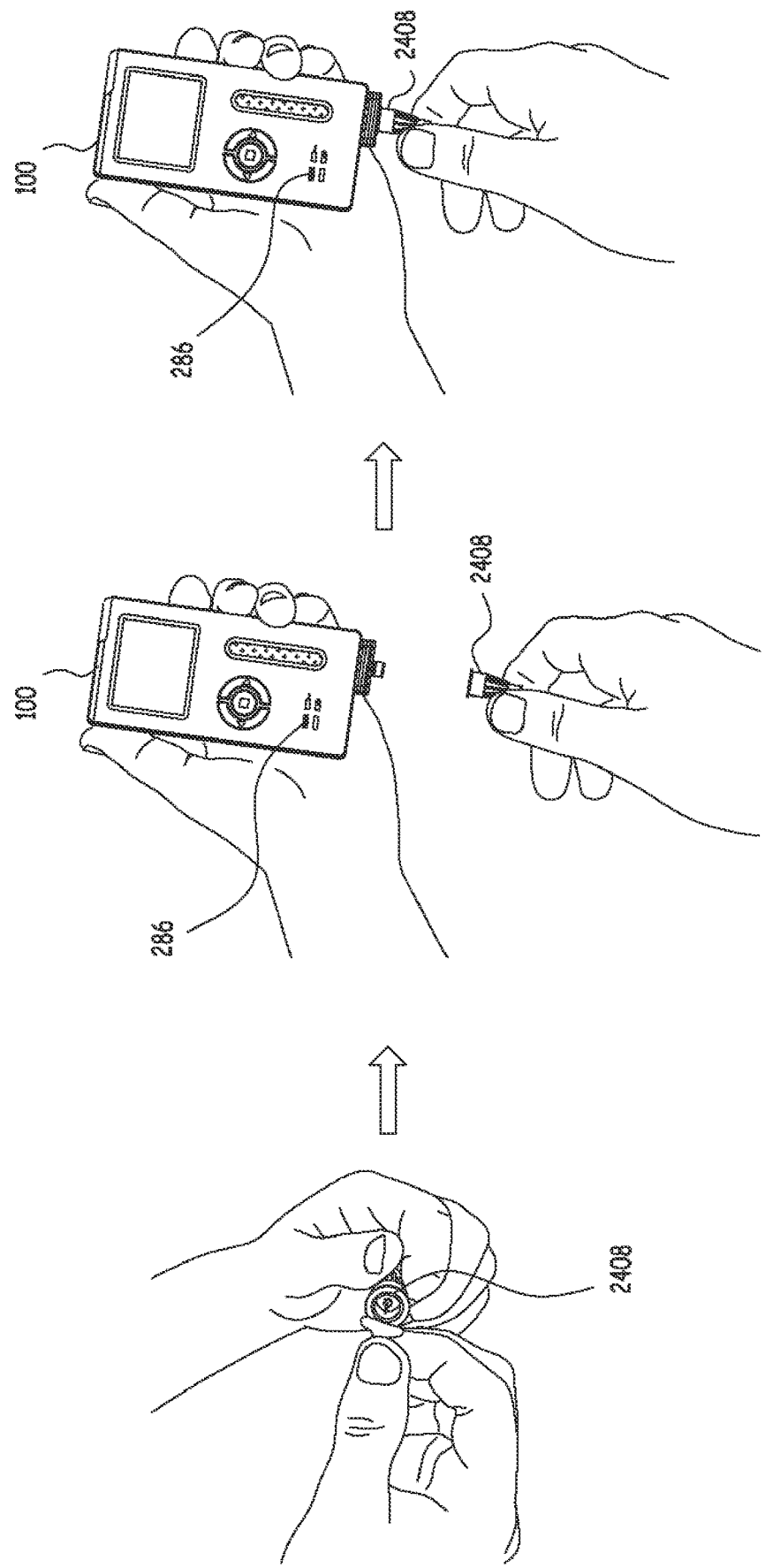

Reference is now made to FIGS. 68A & 68B, which are simplified illustrations of the electronic automatic injection device of FIGS. 1A-51B in a third illustrative operative state, in which a removable needle assembly is coupled to the needleless cartridge injection module. FIG. 68A shows a user who is in the process of preparing and coupling the needle to the needleless cartridge injection module.

Removable needle assembly 2408 is mounted on the needleless cartridge injection module 142, causing penetration of the septum 2405 of the needleless cartridge 2402 by the needle 2750.

Figure 69:
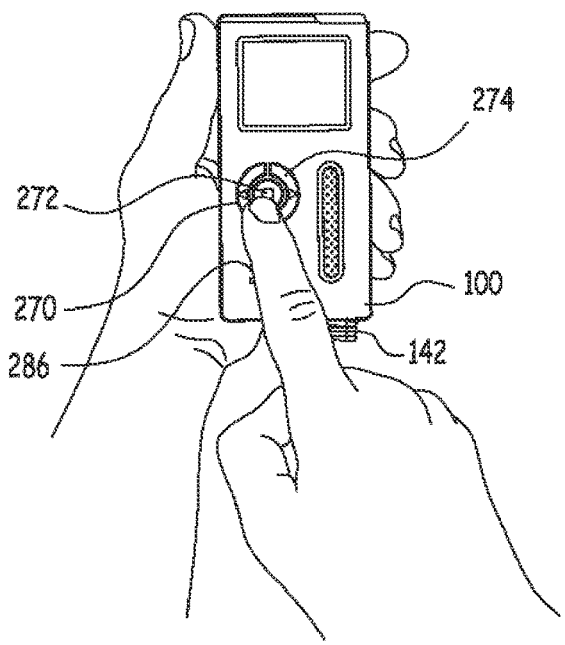
FIG. 69 is a simplified pictorial illustration of a dosage selection operation using an embodiment of the electronic automatic injection device employing a needleless cartridge injection module.

Reference is now made to FIG. 69, which is a simplified illustration of user data entry into the electronic automatic injection device of FIGS. 1A-51B employed with a needleless cartridge injection module 142. The various data entry functionalities of the system are described hereinbelow with reference to FIGS. 76A-76F.

Figure 70A:
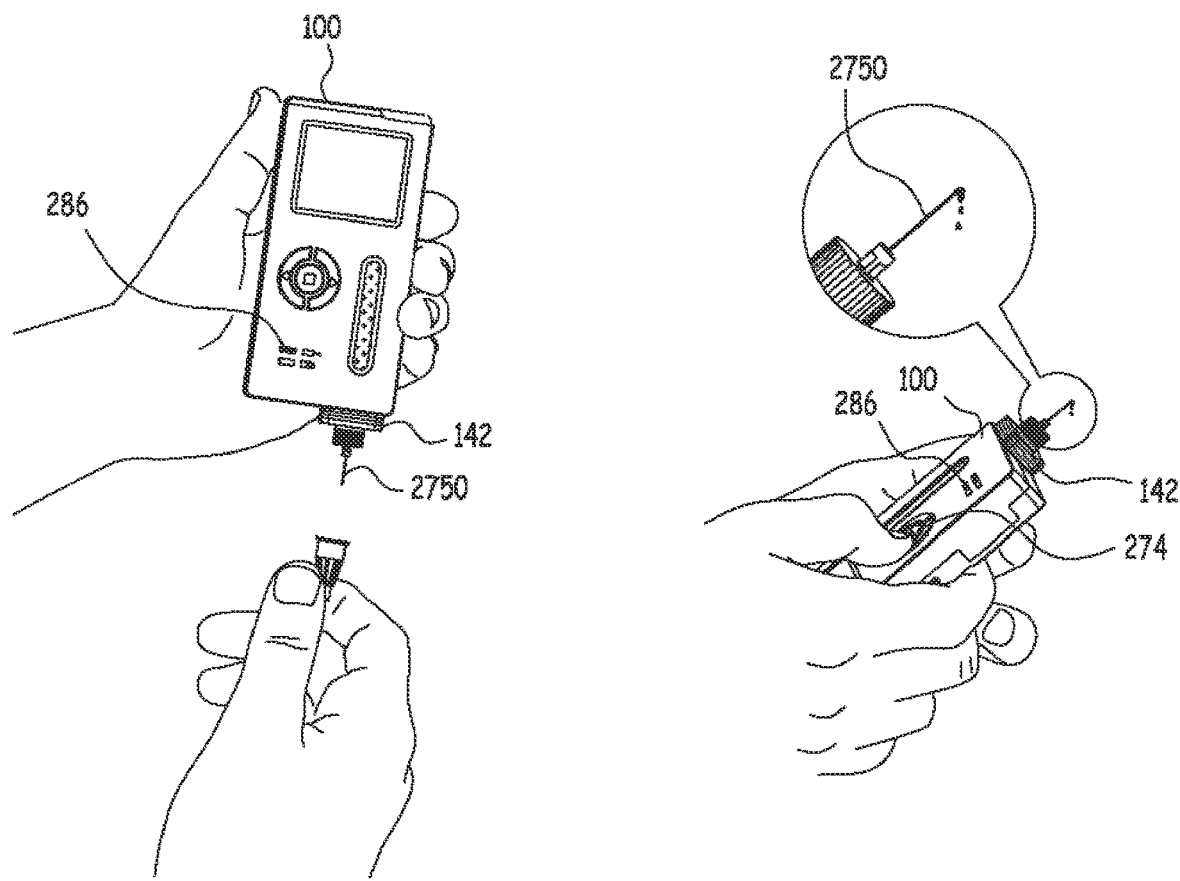
FIGS. 70A, 70B & 70C are simplified illustrations of the electronic automatic injection device employing a needleless cartridge of FIGS. 1A-51B in a fourth operative state, which is a typical "needle protector removal and priming" state.
Figure 70B:
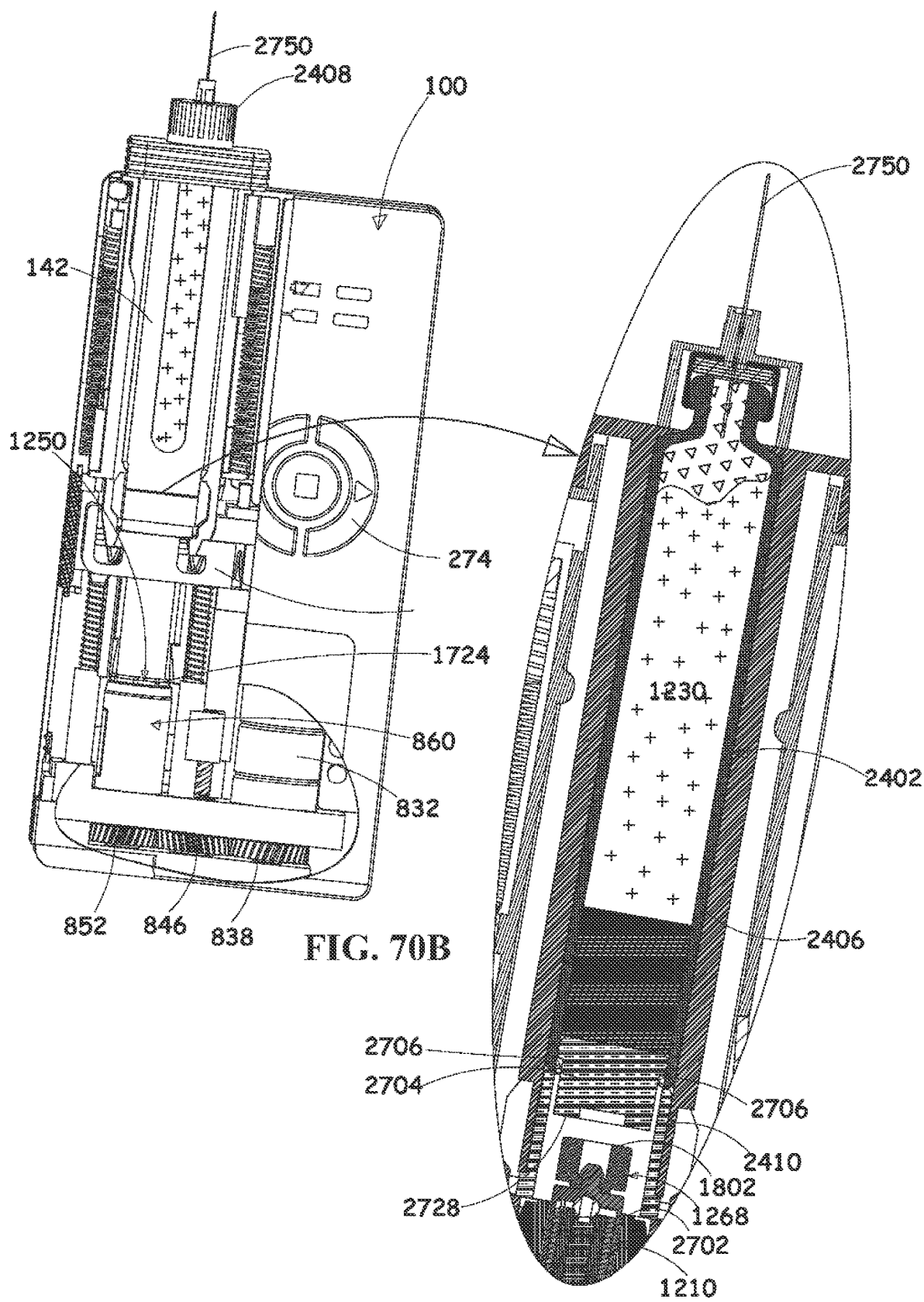
Figure 70C:
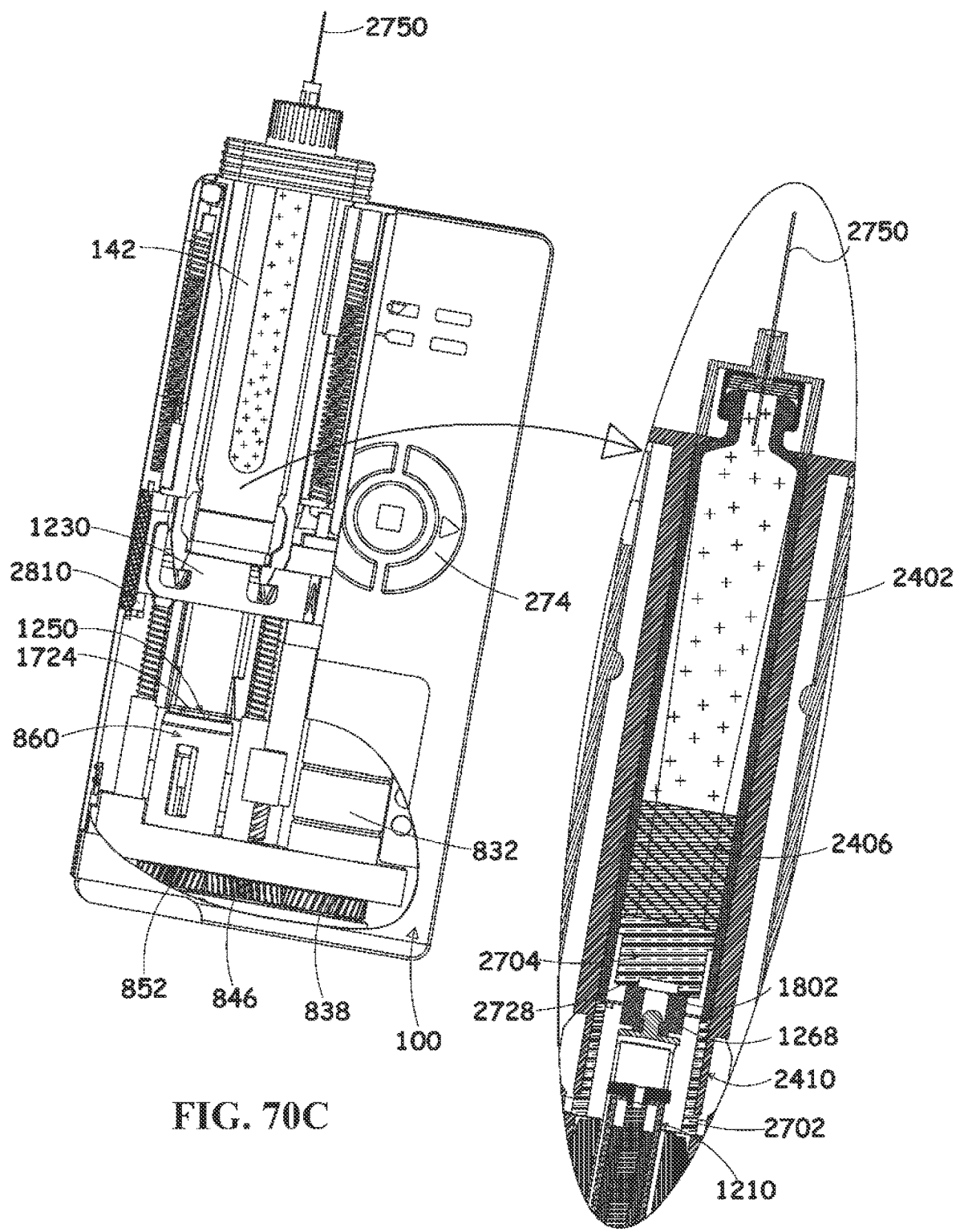

Reference is now made to FIGS. 70A, 70B & 70C, which are simplified illustrations of the electronic automatic injection device of FIGS. 1A-51B in a fourth illustrative operative state, which illustrates removal of a needle cover from a needle already mounted on the needleless cartridge and priming. FIG. 70A shows the user detaching the needle cover and performing priming of the needleless cartridge.

Needleless cartridge injection module 142 remains locked to the locking element 1230, as indicated, inter alia, by the following:

Microswitch 2810 is in a closed state due to engagement with rearwardly facing end tapered portion 2468 of arm 2450.

The user removes the cover of the removable needle assembly 2408 to expose the needle 2750.

Next, the user holds the automatic electronic injection device 100 such that the needle 2750 faces upwardly and performs priming for releasing trapped air bubbles from the needleless cartridge 2402, as specifically seen in FIG. 70B. The priming sequence is described hereinbelow with reference to FIGS. 76A-76F.

FIG. 70B shows the operative orientation of the electronic automatic injection device 100 prior to priming when rearward and forward plunger assemblies 1200 and 1210 are disposed in a fully retracted position, as indicated by the following:

Forward facing surface 1802 of piston engaging element 1268 is rearwardly spaced from rearward facing surface 2728 of piston engaging portion 2704 of piston extension element 2410.

Repeated pushing on the button 274 actuates the electric motor 832 and positions the automatic electronic injection device 100 in an operative state shown specifically in FIG. 70C.

Rotational movement of the electric motor 832 in a clockwise direction is transferred to the multiple drive element 860 by means of gears 838 and 846 which are registered with toothed surface 852 of the multiple drive element 860. Due to the non-rotatable relationship between the multiple drive element 860 and the octagonal portion 1724 of the rearward driving screw 1250, rotational movement of the electric motor 832 causes partial extension of rearward and forward plunger assemblies 1200 and 1210 as described hereinabove with reference to FIG. 35 and thus in turn causes ejection of the trapped air bubble from the needleless cartridge 2402 through the needle 2750 as described below.

Forward displacement of rearward and forward plunger assemblies 1200 and 1210 causes engagement between forward facing surface 1802 of piston engaging element 1268 with rearward facing surface 2728 of piston engaging portion 2704 of piston extension element 2410, which in turn causes forward displacement of the piston 2406 of the needleless cartridge 2402.

Further forward displacement of the piston engaging element 1268 provides for separation of piston engaging portion 2704 of the piston extension element 2410 from retaining portion 2702 by breaking frangible connection portions 2706 of piston extension element 2410. Further telescopic extension of the rearward and forward plunger assemblies 1200 and 1210 effectively displace piston 2406 forwardly within the needleless cartridge 2402 and eject trapped air bubbles therefrom until the user observes ejection of medication through needle 2750.

Reference is now made to FIGS. 71A, 71B & 71C, which are simplified illustrations of the electronic automatic injection device of FIGS. 1A-51B employing a needleless cartridge injection module in a fifth illustrative operative state in which needle penetration and injection operation takes place. FIG. 71A shows the user manually inserting the needle into the injection site and pushing the injection actuation button 116.

> Injection module 142 remains engaged to the locking element 1230, as indicated, inter alia, by the following:
> > Microswitch 2810 is closed as indicated by engagement with rearwardly facing end tapered portion 2468 of arm 2450.
>
> The user presses the injection actuation button 116, which actuates the electric motor 832, as indicated by the following:
> > Microswitch 2840 is in a closed state because it is engaged by forward edge surface 1057 of injection actuation button 116. The state of microswitch 2840 provides an injection actuation indication to the electronic control assembly 134, which in turn actuates the electric motor 832. The resulting rotational movement of the electric motor 832 in a clockwise direction is transferred to the multiple drive element 860 by means of gears 838 and 846, which are registered with toothed surface 852 of the multiple drive element 860.
>
> Due to non-rotatable relationship between the multiple drive element 860 and the octagonal portion 1724 of the rearward driving screw 1250, rotational movement of the electric motor 832 causes partial extension of rearward and forward plunger assemblies 1200 and 1210 as described in FIG. 35 and thus in turn causes ejection of a desired dosage of medication from the needleless cartridge 2402 through the needle 2750, as selected by the user in a manner described hereinbelow with reference to FIGS. 76A-76F as described hereinbelow.
>
> Engagement between forward facing surface 1802 of piston engaging element 1268 of plunger assemblies 1200 and 1210 with rearward facing surface 2728 of piston engaging portion 2704 of piston extension element 2410, provides forward displacement of the piston 2406 of the needleless cartridge 2402. Further extension of the rearward and forward plunger assemblies 1200 and 1210 effectively displaces the piston 2406 axially forwardly along axis 2411 within the needleless cartridge 2402 and ejects the desired dose of medication through needle 2750.

Reference is now made to FIGS. 72A, 72B & 72C, which are simplified illustrations of the electronic automatic injection device of FIGS. 1A-51B in a sixth illustrative operative state, in which the automatic electronic injection device is removed from the injection site, the needle 2750 is removed and discarded and the automatic electronic injection device including the already used needleless cartridge 2402 is used again. FIG. 72A shows the user removing the automatic electronic injection device from the injection site, removing and discarding the needle and mounting another needle onto the needleless cartridge injection module 142.

> Injection actuation button 116 is released by the user and returns to its initial position by the force of the spring 825, as indicated by the following:
> > Microswitch 2840 is in an open state because it is not engaged by forward edge surface 1057 of injection actuation button 116.
>
> Needleless cartridge injection module 142 remains locked to the locking element 1230, as indicated inter alia by the following:
> > Microswitch 2810 is in a closed state as indicated by engagement with rearwardly facing end tapered portion 2468 of arm 2450.

The operative states described in FIGS. 68A-72C, with the exception of priming may be repeated multiple times until the contents of the needleless cartridge 2402 are insufficient for further injection.

At this point electronic control assembly 134 transmits a signal to the electric motor 832 to rotate in a counter-clockwise direction. This rotational movement is transferred to the multiple drive element 860 by means of gears 838 and 846 which are registered with toothed surface 852 of the multiple drive element 860. Due to the non-rotatable connection between the multiple drive element 860 and the rearward driving screw 1250, rearward and forward plunger assemblies 1200 and 1210 retract rearwardly to a position that is described in FIG. 34. At the end of this rotational movement, the multiple drive element 860 returns to its original position, as described hereinabove with reference to FIG. 52A-52D.

Reference is now made to FIGS. 73A, 73B & 73C, which are simplified illustration of the electronic automatic injection device of FIGS. 1A-51B in a seventh illustrative operative state, in which the needleless cartridge injection module is released from the automatic electronic injection device in response to user actuation of the injection module release button 112. FIG. 73A shows the user pushing the injection module release button 112.

> In this seventh illustrative operative state:
> Axis 1525 of locking element 1230 remains coaxial with axis 2770 of injection module release button 112 and rearward and forward plunger assemblies 1200 and 1210 remain fully retracted.
>
> When the user pushes the injection module release button 112, this pushes the locking element 1230 against the force of the spring 1240 in a direction indicated by arrow 3040, as indicated by the following:
> > Elongated protrusions 665 of the injection module release button 112 engage edge surfaces 1546 and 1548 of the locking element 1230. The travel of the injection module release button 112 is limited by engagement of base wall portion 1520 of locking element 1230 with planar surface 1706 of spring seat 1242.
> > Spring engagement surfaces 692 of injection module release button 112 engage leave springs 334 and 539 and cause deflection thereof.
>
> The displacement of the locking element 1230 in the direction of arrows 3040 causes disengagement of the needleless cartridge injection module 142 from the locking element 1230, as indicated by the following:
> > Disengagement of forward facing shoulder surface 2488 of arms 2450 and 2452 and shoulder edge surfaces 1575 and 1585 of the locking element 1230.

Disengagement of forward facing shoulder surface 2490 of arms 2450 and 2452 and shoulder edge surfaces 1675 and 1685 of the locking element 1230.

Following displacement of the locking element 1230 in the direction of arrows 3040, arm 2450 of the mounting element 2400 is permitted to move forwardly through narrow portions 1578 and 1678 and arm 2452 of the mounting element 2400 is permitted to move forwardly through narrow portions 1568 and 1668 of the locking element 1230.

Microswitch 2810 is in an open state because it is disengaged from rearwardly facing end tapered portion 2468 of arm 2450.

Reference is now made to FIGS. 74A & 74B, which are simplified illustration of the electronic automatic injection device of FIGS. 1A-51B in an eighth illustrative operative state, in which the needleless cartridge injection module is removed from the automatic electronic injection device. FIG. 74A shows the user pulling the needleless cartridge injection module 142 forwardly.

In the eighth illustrative operative state, the multiple motion output subassembly 152 remains in a fully extended operative orientation and axis 1525 of locking element 1230 remains coaxial with axis 2770 of injection module release button 112.

Rearward and forward plunger assemblies 1200 and 1210 remain fully retracted.

When the user releases the injection module release button 112, this causes the locking element 1230 to be displaced along axis 1525 in a direction indicated by arrow 3060 by the force of the spring 1240, as indicated by the following:

Disengagement of base wall portion 1520 of locking element 1230 from planar surface 1706 of spring seat 1242.

Release of the injection module release button 112 permits displacement thereof along axis 2770 back to its initial state of the injection module release button 112, as specifically described hereinabove with reference to FIGS. 52A-52D. This displacement is urged by the force of the previously deflected leaf springs 334 and 539, which exerting force on spring engagement surfaces 692 of injection module release button 112, resulting in disengagement between elongated protrusions 665 of the injection module release button 112 and edge surfaces 1546 and 1548 of the locking element 1230.

Additionally, button travel stop protrusions 670 and 672 of the injection module release button 112 engage the side portion 508 of the lower housing portion 500.

Following forward axial displacement of the needleless cartridge injection module 142 in a direction indicated by arrow 3050, protrusion 574 of flexible tab 570 of lower housing portion 500 disengages from aperture 1412 of base element 1220 of multiple motion output subassembly 152.

Microswitch 2810 remains in an open state because it is disengaged from rearwardly facing end tapered portion 1968 of arm 1950.

Reference is now made to FIG. 75, which is a simplified functional block diagram illustration of the electronic control assembly 134 (FIG. 2) forming part of the electronic automatic injection device of FIGS. 1A-74B.

As seen in FIG. 75, the electronic control assembly 134 preferably comprises a microcontroller 3500, which preferably receives inputs as follows:

Mechanical status inputs from microswitches 2800, 2810, 2820, 2830, 2840 and 2850;

User interface inputs from injection actuation button 116 (FIGS. 1A-2), control buttons 270, 272 and 274;

A motor output shaft rotation status input from encoder 845; and

An injection module input from either of passive RF information transmitter assembly 1907 (FIG. 38) of a prefilled syringe injection module 140 or passive RF information transmitter assembly 2407 (FIG. 44) of a needleless cartridge injection module 142.

Microcontroller 3500 preferably provides outputs as follows:

Outputs to electric motor 832 preferably including direction of rotation outputs, steps per second, total steps and power.

Outputs to LEDs 286, 288 and 828;

A data output to connection port 122 (FIG. 1B);

A display data output to display 246 (FIGS. 3A & 3B); and

An audio output to transducer 613 (FIGS. 1D & 2).

Reference is now made to FIGS. 76A-76F, which are together a simplified flowchart illustrating operation of the electronic control assembly of FIG. 75.

Preferably, as shown in step 4000, operation of the electronic control assembly is initiated by the user pressing on button 272, which preferably causes transducer 613 to provide an audio indication to the user confirming initiation of operation, as shown in step 4002. As shown in step 4004, display 246 is automatically actuated and displays an introductory message, such as "HELLO, IF YOU ARE READY TO INJECT, PLEASE INSERT AN INJECTION MODULE".

As further shown in step 4006, a menu display select prompt preferably also appears on display 246 and may be actuated by the user pressing on button 270, as shown in step 4008. Preferably the menu includes the following selectable topics: User identification, time & date, injection schedule, injection duration selection, priming instruction, maximum permitting dosing and remaining drug volume. As shown in step 4010, the user can preferably program the electronic control assembly to provide audio and/or visual reminders that injections are due.

As shown in step 4020, the user can insert either a prefilled syringe injection module 140 or a needleless cartridge injection module 142. Once the user has inserted an injection module, an injection module input from either of passive RF information transmitter assembly 1907 (FIG. 38) of a prefilled syringe injection module 140 or passive RF information transmitter assembly 2407 (FIG. 44) of a needleless cartridge injection module 142 is received by the controller 3500 (step 4022). The injection module input typically includes authorized injection module verification data as well as information regarding the material to be injected, such as the allowed dosage, viscosity, expiry date, minimum injection duration, and specific manufacturing data.

As further shown in step 4024, controller 3500 verifies the authenticity and suitability of the injection module and its contents. If the injection module is not found to be authentic or suitable (step 4026), a suitable message is displayed on display 246 and the injection module may be released or ejected from the electronic automatic injection device 100.

If the injection module is found to be authentic and suitable (step 4030), LED 286 is typically illuminated to indicate successful insertion of a valid and suitable injection module. A prompt then preferably appears on display 246 inquiring whether the user wishes to proceed to inject (step 4032). The user may elect to proceed (step 4034), not to proceed (step 4036) or to view a menu (4038). The menu preferably includes the following selectable topics: User identification, time & date, injection schedule, injection duration selection, priming instruction, maximum permitting dosing and remaining drug volume.

If the user elects to proceed (step 4034), the electronic control assembly 134 enters an auto-inject mode automatically suitable for the injection module that was inserted, i.e. prefilled syringe injection module or needleless cartridge injection module, based on the information received from the passive RF information transmitter assembly 1907 or 2407.

If a prefilled syringe injection module 140 was inserted (step 4040), a message preferably appears on display 246 as follows: "PREFILLED SYRINGE INJECTION MODULE INSERTED—PLEASE REMOVE RNS" (step 4042).

Once the user removes the RNS remover (step 4044), as shown, for example, in FIG. 60A, a clock in the controller 3500 begins to run to measure elapsed exposure time of the needle (step 4046), and a message preferably appears on display 246 as follows: "RNS REMOVED—PLEASE PRESS PATIENT ENGAGEMENT PLATE AGAINST SKIN AT THE INJECTION SITE" (step 4048).

Once the user presses the patient engagement plate 2018 against his skin at the injection site (step 4050), the controller 3500 checks whether the elapsed exposure time of the needle 1904 has exceeded a predetermined maximum (step 4052). If the elapsed exposure time of the needle has exceeded the predetermined maximum (step 4054), a message preferably appears on display 246 as follows: "EXCESSIVE ELAPSED TIME BETWEEN RNS REMOVAL AND INJECTION—REPLACE INJECTION MODULE".

If the elapsed exposure time of the needle has not exceeded the predetermined maximum (step 4056), LED 828 is illuminated, indicating engagement of the patient engagement plate 2018 with the injection site and a message preferably appears on display 246 as follows: "PLEASE PRESS INJECTION ACTUATION BUTTON" (step 4058).

Once the user presses the injection actuation button 116 (step 4060) the following sequence of actions takes place:
LED 828 blinks, indicating that injection is taking place (step 4062);
Needle 1904 is caused to penetrate the injection site by virtue of rotation of electric motor 832, which allows springs 1244 & 1246 to force multiple motion output subassembly 152 axially forward along axis 1334 (step 4064).
Further rotation of the electric motor 832 produces telescopic extension of forward plunger assembly 1210 and rearward plunger assembly 1200, thereby forcing material, typically a drug, out from prefilled syringe 1902 through needle 1904 into the injection site (step 4066).

During injection a message preferably appears on display 246 which indicates the progress of the injection.

Upon completion of injection (step 4068), transducer 613 preferably provides an audio indication of completion of injection and LED 828 is turned off. A message preferably appears on display 246 as follows: "INJECTION COMPLETE—PLEASE REMOVE INJECTOR FROM INJECTION SITE".

Once the user disengages the electronic automatic injection device 100 from the injection site (step 4070), backward rotation of the electric motor 832 produces telescopic retraction of forward plunger assembly 1210 and rearward plunger assembly 1200 and a message preferably appears on display 246 as follows: "PLEASE PUSH THE INJECTION MODULE RELEASE BUTTON" (step 4072).

Once the user pushes the injection module release button 112 (step 4074), the prefilled syringe injection module is automatically released and may be pulled out by the user (step 4076). A message preferably appears on display 246 as follows: "PLEASE REMOVE AND DISPOSE OF THE INJECTION MODULE" (step 4078).

Once the user pulls the prefilled syringe injection module out of the electronic automatic injection device 100 (step 4080), a message preferably appears on display 246 as follows: "NEXT INJECTION SCHEDULED FOR . . . ," (step 4082) and the electronic automatic injection device 100 is automatically turned off (step 4084).

If a needleless cartridge injection module 142 was inserted (step 4100), LED 828 is illuminated (step 4102) and a message preferably appears on display 246 as follows: "NEEDLELESS CARTRIDGE INJECTION MODULE INSERTED—PLEASE SET DOSAGE AND MOUNT NEEDLE" (step 4104).

Once the user mounts the needle 2750, as shown, for example, in FIG. 44A (step 4106), a message preferably appears on display 246 as follows: "PLEASE REMOVE THE NEEDLE COVER AND PRIME THE INJECTOR" (step 4108).

Once the user has removed the needle cover (step 4110), a message preferably appears on display 246 as follows: "PLEASE ORIENT THE INJECTOR SO THAT THE NEEDLE FACES UPWARDLY" (step 4112).

Once the user has oriented the electronic automatic injection device 100 so that the needle 2750 faces upwardly (step 4114), a message preferably appears on display 246 as follows: "PLEASE PRESS THE INDICATED BUTTON MULTIPLE TIMES UNTIL LIQUID BEGINS TO EXIT THE TIP OF THE NEEDLE" (step 4116).

Each time the user presses button 274, this produces a short rotation of the electric motor 832, which slightly axially forwardly telescopically extends the forward plunger assembly 1210 and the rearward plunger assembly 1200, thus initially forcing air out of the needleless cartridge 2402 and the needle 2750. Once the user has pressed button 274 a sufficient number of times for all trapped air bubbles to have been forced out of the needleless cartridge 2402 and the needle 2750, priming is complete (step 4118).

Once the user has confirmed completion of priming of the electronic automatic injection device 100 (step 4119), a message preferably appears on display 246 as follows: "PLEASE PRESS NEEDLE AGAINST SKIN AT THE INJECTION SITE" (step 4120).

Once the user presses the needle 2750 against his skin at the injection site (step 4122), a message preferably appears on display 246 as follows: "PLEASE PRESS INJECTION ACTUATION BUTTON" (step 4124).

Once the user presses the injection actuation button 116 (step 4126), the following sequence of actions takes place:
LED 828 blinks, indicating that injection is taking place (step 4128);
Rotation of the electric motor 832 produces telescopic extension of forward plunger assembly 1210 and rearward plunger assembly 1200, thereby forcing material, typically a drug, out from needleless cartridge 2402 through needle 2750 into the injection site (step 4130).
During injection a message preferably appears on display 246 which indicates the progress of the injection.

Upon completion of injection, transducer 613 preferably provides an audio indication of completion of injection and LED 828 is turned off. A message preferably appears on display 246 as follows: "INJECTION COMPLETE—PLEASE REMOVE INJECTOR FROM INJECTION SITE" (step 4132).

Once the user disengages the electronic automatic injection device 100 from the injection site (step 4134), controller 3500 calculates whether the amount of drug remaining in the needleless cartridge 2402 is sufficient for a further dose as earlier selected (step 4136). If the amount of drug remaining is sufficient a message preferably appears on display 246 as follows: " . . . CCS OF THE DRUG REMAIN FOR USE—NEXT INJECTION SCHEDULED FOR . . . . PLEASE REMOVE AND DISCARD THE NEEDLE" (step 4138), and the electronic automatic injection device 100 is automatically turned off (step 4140).

If the amount of drug remaining in the needleless cartridge 2402 is insufficient for a further preselected dosage, the user is given the option of either selecting a lower dosage for which the amount of drug is sufficient or discarding the needleless cartridge injection module 142 (step 4142).

If the amount of drug remaining is not sufficient for the user indicated dosage (step 4144), backward rotation of the electric motor 832 produces telescopic retraction of forward plunger assembly 1210 and rearward plunger assembly 1200 and a message preferably appears on display 246 as follows: "PLEASE PUSH THE INJECTION MODULE RELEASE BUTTON" (step 4146).

Once the user pushes the injection module release button 112 (step 4148), the needleless cartridge syringe injection module 142 is automatically released and may be pulled out by the user (step 4150). A message preferably appears on display 246 as follows: "PLEASE REMOVE AND DISPOSE OF THE INJECTION MODULE" (step (4152).

Once the user pulls the needleless cartridge injection module 142 out of the electronic automatic injection device 100 (step (4154), a message preferably appears on display 246 as follows: "NEXT INJECTION SCHEDULED FOR . . . ," (step 4156), and the electronic automatic injection device 100 is automatically turned off (4158).

Should the user wish to use the previously used needleless cartridge injection module 142 (step 4160), the following sequence of actions preferably takes place:

The user presses button 277 to actuate the electronic automatic injection device 100 (step 4162). A message preferably appears on display 246 as follows: "NEEDLELESS CARTRIDGE INJECTION MODULE INSERTED—PLEASE MOUNT NEEDLE" (step 4164).

Once the user mounts the needle 2750, as shown, for example, in FIG. 44A (step 4166), a message preferably appears on display 246 as follows: "PLEASE REMOVE THE NEEDLE COVER" (step 4168).

Once the user has removed the needle cover (step 4170), a message preferably appears on display 246 as follows: PLEASE PRESS NEEDLE AGAINST SKIN AT THE INJECTION SITE" (step 4120).

Once the user presses the needle 2750 against his skin at the injection site (step 4122), a message preferably appears on display 246 as follows: "PLEASE PRESS INJECTION ACTUATION BUTTON" (step 4124).

Once the user presses the injection actuation button 116 (step 4126) the following sequence of actions takes place:

LED 828 blinks, indicating that injection is taking place (step 4128);

Rotation of the electric motor 832 produces telescopic extension of forward plunger assembly 1210 and rearward plunger assembly 1200, thereby forcing material, typically a drug, out from needleless cartridge 2402 through needle 2750 into the injection site (step 4130).

During injection a message preferably appears on display 246 which indicates the progress of the injection.

Upon completion of injection, transducer 613 preferably provides an audio indication of completion of injection and LED 828 is turned off. A message preferably appears on display 246 as follows: "INJECTION COMPLETE—PLEASE REMOVE INJECTOR FROM INJECTION SITE COVER THE NEEDLE AND DISCARD THE COVERED NEEDLE" (step 4132).

Once the user disengages the electronic automatic injection device 100 from the injection site (step 4134), controller 3500 calculates whether the amount of drug remaining in the needleless cartridge 2402 is sufficient for a further dose as earlier selected (step 4136). If the amount of drug remaining is sufficient a message preferably appears on display 246 as follows: " . . . CCS OF THE DRUG REMAIN FOR USE—NEXT INJECTION SCHEDULED FOR . . . ." (step 4138) and the electronic automatic injection device 100 is automatically turned off (step 4140).

If the amount of drug remaining in the needleless cartridge 2402 is insufficient for a further preselected dosage, the user is given the option of either selecting a lower dosage for which the amount of drug is sufficient or discarding the needleless cartridge injection module 142 (step 4142).

If the amount of drug remaining is not sufficient for the user indicated dosage (step 4144), backward rotation of the electric motor 832 produces telescopic retraction of forward plunger assembly 1210 and rearward plunger assembly 1200 and a message preferably appears on display 246 as follows: "PLEASE PUSH THE INJECTION MODULE RELEASE BUTTON" (step 4146).

Once the user pushes the injection module release button 112 (step 4148), the needleless cartridge syringe injection module 142 is automatically released and may be pulled out by the user (step 4150). A message preferably appears on display 246 as follows: "PLEASE REMOVE AND DISPOSE OF THE INJECTION MODULE" (step 4152).

Once the user pulls the prefilled syringe injection module out of the electronic automatic injection device 100 (step 4154), a message preferably appears on display 246 as follows: "NEXT INJECTION SCHEDULED FOR . . . ," (step 4156) and the electronic automatic injection device 100 is automatically turned off (step 4158).

The foregoing cycle is repeated until an insufficient amount of drug remains in the needleless cartridge 2402.

It will be appreciated by persons skilled in the art that the present invention is not limited by what has been particularly shown and described hereinabove. Rather the present invention includes both combinations and subcombinations of various features described herein and improvements and variations which would occur to persons skilled in the art upon reading the foregoing description and which are not in the prior art.

The invention claimed is:

1. An electronic automatic injection device comprising:
a housing configured to receive a prefilled syringe including a needle and containing a material to be injected;
an electric motor having a rotary drive output; at least one forward driving spring; and
a multifunctional electric motor driven drive assembly, connectable to said prefilled syringe;
a multiple drive element connectable to said multifunctional drive assembly,
said multifunctional electric motor driven drive assembly being responsive to said rotary drive output of said electric motor and being operative:

in an initial mode of operation to enable said at least one forward driving spring to displace said prefilled syringe in a forward direction in response to displacement of said multiple drive element, resulting from engagement of said multiple drive element with said multifunctional electric motor driven drive assembly; and in a subsequent mode of operation to eject said injectable liquid from said prefilled syringe through said needle, wherein said ejection is produced by operation of said electric motor.

2. An electronic automatic injection device according to claim 1 and also comprising a forward driving spring compression assembly operative in response to insertion of said prefilled syringe into said housing for automatically compressing said forward driving spring.

3. An electronic automatic injection device according to claim 1 and wherein in said initial mode of operation, said at least one forward driving spring drives said needle into injection engagement with a target subsequent to an actuation produced by operation of said electric motor.

4. An electronic automatic injection device comprising:
a housing having an injection module, containing a material to be injected, received therein, said injection module including a mounting element and a needle shield, said needle shield being configured to be displaceable relative to said mounting element, and said needle shield being configured to remain mounted onto the mounting element during injection of said material;
a multifunctional drive assembly, driven at least by an electric motor, connectable to said mounting element of said injection module; and
a multiple drive element configured to engage said multifunctional drive assembly, said needle shield is mounted onto the mounting element and is axially retained in position relative to said mounting element before engagement of said multifunctional drive assembly with said multiple drive element and said needle shield being displaceable relative to said mounting element only following engagement of said multifunctional drive assembly with said multiple drive element and prior to actuation of said electric motor, before injection of said material.

5. An electronic automatic injection device according to claim 4 and also comprising a computerized controller for governing the operation of at least said electric motor.

6. An electronic automatic injection device according to claim 5 and wherein said injection module includes at least one machine readable message and said computerized controller is responsive at least partially to said at least one machine readable message.

7. An electronic automatic injection device according to claim 5 and also comprising wireless communications functionality associated with said computerized controller.

8. An electronic automatic injection device according to claim 5 and also comprising defective injection alarm functionality associated with said computerized controller.

9. An electronic automatic injection device according to claim 5 and also comprising encoder functionality cooperating with said computerized controller for indicating quantities of ejected liquid.

10. An electronic automatic injection device according to claim 9 and wherein said electric motor cooperates with an encoder to provide a validated indication of quantity of ejected liquid.

11. An electronic automatic injection device according to claim 1 and also comprising at least one microswitch communicating an electronic output indication to a computerized controller.

12. An injection module containing a material to be injected using an injection device, said injection module including:
a mounting element having at least one arm formed thereon and a rearwardly facing surface forwardly spaced from said at least one arm;
a prefilled syringe fixedly retained in said mounting element and restrained from rearward displacement relative to said mounting element by engagement of said prefilled syringe with said at least one arm and restrained from forward displacement relative to said mounting element by engagement of a rearward flange of said prefilled syringe with said rearwardly facing surface, said retention causing said prefilled syringe to be displaced together with said mounting element; and
a needle shield located outside of said mounting element and arranged in slidable relationship therewith, and said needle shield being configured to remain nonreleasably mounted onto the mounting element both during and after injection of said material;
and
said needle shield having formed on at least one elongate surface thereof at least one travel track suitable for slidable engagement along a longitudinal axis of said injection device.

13. An injection module according to claim 12 and also comprising a wireless transmitter and data storage assembly mounted on said needle shield and containing information to be displayed to a user of said injection module.

14. An injection module according to claim 12 and wherein at least three travel tracks are provided on each of at least two opposite-facing elongate surfaces of said needle shield.

15. An electronic automatic injection device according to claim 1 and also comprising a computerized controller for governing the operation of at least said electric motor.

16. An electronic automatic injection device according to claim 15 and wherein said injection module includes at least one machine readable message and said computerized controller is responsive at least partially to said at least one machine readable message.

17. An electronic automatic injection device according to claim 15 and also comprising wireless communications functionality associated with said computerized controller.

18. An electronic automatic injection device according to claim 15 and also comprising encoder functionality cooperating with said computerized controller for indicating quantities of ejected liquid.

* * * * *